: US 7,217,528 B2

United States Patent
Ruben et al.

(10) Patent No.: US 7,217,528 B2
(45) Date of Patent: May 15, 2007

(54) ANTIBODIES TO HFXJW48 POLYPEPTIDE

(75) Inventors: Steven M. Ruben, Brookeville, MD (US); Craig A. Rosen, Laytonsville, MD (US); Charles Florence, Rockville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 157 days.

(21) Appl. No.: 10/866,831

(22) Filed: Jun. 15, 2004

(65) Prior Publication Data

US 2005/0095612 A1    May 5, 2005

Related U.S. Application Data

(60) Division of application No. 10/144,929, filed on May 15, 2002, now Pat. No. 6,881,823, which is a continuation of application No. 09/716,128, filed on Nov. 17, 2000, now abandoned, which is a continuation of application No. 09/251,329, filed on Feb. 17, 1999, now abandoned, which is a continuation-in-part of application No. PCT/US98/17044, filed on Aug. 18, 1998.

(60) Provisional application No. 60/092,956, filed on Jul. 15, 1998, provisional application No. 60/089,510, filed on Jun. 16, 1998, provisional application No. 60/056,555, filed on Aug. 19, 1997, provisional application No. 60/056,556, filed on Aug. 19, 1997, provisional application No. 60/056,535, filed on Aug. 19, 1997, provisional application No. 60/056,369, filed on Aug. 19, 1997, provisional application No. 60/056,628, filed on Aug. 19, 1997, provisional application No. 60/056,728, filed on Aug. 19, 1997, provisional application No. 60/056,368, filed on Aug. 19, 1997, provisional application No. 60/056,726, filed on Aug. 19, 1997.

(51) Int. Cl.
G01N 33/53 (2006.01)
C12P 21/08 (2006.01)
C07K 16/00 (2006.01)
C07K 16/46 (2006.01)
C07K 16/18 (2006.01)

(52) U.S. Cl. .............. 435/7.1; 435/70.21; 530/387.1; 530/387.3; 530/388.1

(58) Field of Classification Search .................... None
See application file for complete search history.

(56) References Cited

FOREIGN PATENT DOCUMENTS

WO    WO 98/06846 A    2/1998
WO    WO 00/73454 A1   12/2000
WO    WO 01/68848 A2   9/2001

OTHER PUBLICATIONS

GenBank Accession No. NM006811, Bossolasco et al., "Homo sapiens tumor differentially expressed 1 (TDE1), mRNA" (Jul. 20, 1999).
GenBank Accession No. Z97053, Ho, S., "Human DNA sequence from clone RP1-179M20 on chromosome 20 Contains a 3' end of a novel gene similar to cellular retinaldehyde-binding protein, the TDE1 gene (Tumour differentially expressed 1), the PKIG gene encoding protein kinase (cAMP-dependent, catalytic) inhibitor gamma, the 3' end of the ADA gene encoding adenosine deaminase, a putative novel gene, 2 CpG islands, ESTs, STSs and GSSs, complete sequence" (Apr. 9, 2001).
GenBank Accession No. AF164794, Gu et al., Homo sapiens Diff33 protein homolog mRNA, complete cds (Jul. 2, 1999).
Swissport Locus Q13530, Bossolasco et al., Tumor differentially expressed protein 1 (Transmembrane protein SBBI99) (Jul. 20, 1999).
Nimmrich et al., "Seven genes that are differentially transcribed in colorectal tumor cell lines," *Cancer Letters* 160(1):37-43 (Nov. 10, 2000).
Hu et al., "Gene expression profiling in the human hypothalamus-pituitary-adrenal axis and full-length cDNA cloning," *PNAS* 97(17):9543-9548 (Aug. 15, 2000).
Bossolasco et al., "The Human *TDE* Gene Homologue: Localization to 20q13.1-13.3 and Variable Expression in Human Tumor Cell Lines and Tissue," *Molec. Carcinogenesis* 26:189-200 (1999).
GenBank Accession No. AL137261, Koehrer et al., "Homo sapiens mRNA; cDNA DKFZp434H0413 (from clone DKFZp434H0413); partial cds" (Feb. 18, 2000).
GenBank Accession No. BC033029, Strausberg, R., Homo sapiens, KIAA 1253 protein, clone MGC:33018 Image:4831122, mRNA, complete cds (Jun. 24, 2002.
GenBank Accession No. U49188, Dakour et al., "Human placenta (Diff33) mRNA, complete cds" (Feb. 14, 1996).
Mungall, et al., EMBL Database Accession No. HSPA15D11.
Supplementary Partial European Search Report in European Application No. 98 94 0950.

*Primary Examiner*—James Martinell

(57) ABSTRACT

The present invention relates to novel human secreted proteins and isolated nucleic acids containing the coding regions of the genes encoding such proteins. Also provided are vectors, host cells, antibodies, and recombinant methods for producing human secreted proteins. The invention further relates to diagnostic and therapeutic methods useful for diagnosing and treating disorders related to these novel human secreted proteins.

22 Claims, No Drawings

SEQUENCE LISTING

<160> NUMBER OF SEQ ID NOS: 257

<210> SEQ ID NO 1
<211> LENGTH: 733
<212> TYPE: DNA
<213> ORGANISM: Homo sapiens

<400> SEQUENCE: 1

```
gggatccgga gcccaaatct tctgacaaaa ctcacacatg cccaccgtgc ccagcacctg      60
aattcgaggg tgcaccgtca gtcttcctct tccccccaaa acccaaggac accctcatga     120
tctcccggac tcctgaggtc acatgcgtgg tggtggacgt aagccacgaa gaccctgagg     180
tcaagttcaa ctggtacgtg gacggcgtgg aggtgcataa tgccaagaca aagccgcggg     240
aggagcagta caacagcacg taccgtgtgg tcagcgtcct caccgtcctg caccaggact     300
ggctgaatgg caaggagtac aagtgcaagg tctccaacaa agccctccca accccatcg     360 agaaaaccat ctccaaagcc aaagggcagc ccgagaacc acaggtgtac accctgcccc     420
catcccggga tgagctgacc aagaaccagg tcagcctgac ctgcctggtc aaaggcttct     480
atccaagcga catcgccgtg gagtgggaga gcaatgggca gccggagaac aactacaaga     540
ccacgcctcc cgtgctggac tccgacggct ccttcttcct ctacagcaag ctcaccgtgg     600
acaagagcag gtggcagcag gggaacgtct tctcatgctc cgtgatgcat gaggctctgc     660
acaaccacta cacgcagaag agcctctccc tgtctccggg taaatgagtg cgacggccgc     720
gactctagag gat                                                        733
```

<210> SEQ ID NO 2
<211> LENGTH: 5
<212> TYPE: PRT
<213> ORGANISM: Homo sapiens
<220> FEATURE:
<221> NAME/KEY: Site
<222> LOCATION: (3)
<223> OTHER INFORMATION: Xaa equals any of the twenty naturally ocurring L-amino acids

<400> SEQUENCE: 2

Trp Ser Xaa Trp Ser
 1               5

```
<210> SEQ ID NO 3
<211> LENGTH: 86
<212> TYPE: DNA
<213> ORGANISM: Homo sapiens

<400> SEQUENCE: 3
gcgcctcgag atttccccga aatctagatt tccccgaaat gatttcccg aaatgatttc     60 cccgaaatat ctgccatctc aattag                                        86

<210> SEQ ID NO 4
<211> LENGTH: 27
<212> TYPE: DNA
<213> ORGANISM: Homo sapiens

<400> SEQUENCE: 4
gcggcaagct ttttgcaaag cctaggc                                       27

<210> SEQ ID NO 5
<211> LENGTH: 271
<212> TYPE: DNA
<213> ORGANISM: Homo sapiens

<400> SEQUENCE: 5
ctcgagattt ccccgaaatc tagatttccc cgaaatgatt tccccgaaat gatttccccg    60
aaatatctgc catctcaatt agtcagcaac catagtcccg cccctaactc cgcccatccc   120
gcccctaact ccgcccagtt ccgcccattc tccgcccat ggctgactaa ttttttttat   180
ttatgcagag gccgaggccg cctcggcctc tgagctattc cagaagtagt gaggaggctt   240
ttttggaggc ctaggctttt gcaaaaagct t                                  271

<210> SEQ ID NO 6
<211> LENGTH: 32
<212> TYPE: DNA
<213> ORGANISM: Homo sapiens

<400> SEQUENCE: 6
gcgctcgagg gatgacagcg atagaacccc gg                                 32

<210> SEQ ID NO 7
<211> LENGTH: 31
<212> TYPE: DNA
<213> ORGANISM: Homo sapiens

<400> SEQUENCE: 7
gcgaagcttc gcgactcccc ggatccgcct c                                  31

<210> SEQ ID NO 8
<211> LENGTH: 12
<212> TYPE: DNA
<213> ORGANISM: Homo sapiens

<400> SEQUENCE: 8
ggggactttc cc                                                       12

<210> SEQ ID NO 9
<211> LENGTH: 73
<212> TYPE: DNA
<213> ORGANISM: Homo sapiens

<400> SEQUENCE: 9
gcggcctcga ggggactttc ccggggactt ccggggact ttccgggact ttccatcctg   60
```

```
ccatctcaat tag                                                              73

<210> SEQ ID NO 10
<211> LENGTH: 256
<212> TYPE: DNA
<213> ORGANISM: Homo sapiens

<400> SEQUENCE: 10
ctcgagggga ctttcccggg gactttccgg ggactttccg ggactttcca tctgccatct           60
caattagtca gcaaccatag tcccgcccct aactccgccc atcccgcccc taactccgcc          120
cagttccgcc cattctccgc cccatggctg actaattttt tttatttatg cagaggccga          180
ggccgcctcg gcctctgagc tattccagaa gtagtgagga ggcttttttg gaggcctagg          240
cttttgcaaa aagctt                                                          256

<210> SEQ ID NO 11
<211> LENGTH: 392
<212> TYPE: DNA
<213> ORGANISM: Homo sapiens

<400> SEQUENCE: 11
gaattcggca cgagcgctgt tgggtgtgtg tatgtttgcg ctgggcgcgc ttgccgtgcc           60
ggtgaccggt ttcggcagta tgcctgcgct ctcgatggcg ctgaccatgc tcggctgcta          120
cgcgatagcc atcctgctgt tcgtgacgct ggtgcgcaaa ccggcttaac gttacttgat          180
gacagacagg caaaaaaaaa cccgcttcgg cggktttttt aagaattcgg ytaaagtcag          240
atagcgataa cgttagcagc cgacgggcct ttggcaccat tggtgatttc gaactctacg          300
cgctggcctt cagcgagggt cttgaagccc tggctgaaaa tagcagagaa atgaacgaaa          360
acatctttgc tgccatcttc agggggtaatg aa                                       392

<210> SEQ ID NO 12
<211> LENGTH: 465
<212> TYPE: DNA
<213> ORGANISM: Homo sapiens
<220> FEATURE:
<221> NAME/KEY: SITE
<222> LOCATION: (357)
<223> OTHER INFORMATION: n equals a,t,g, or c
<220> FEATURE:
<221> NAME/KEY: SITE
<222> LOCATION: (395)
<223> OTHER INFORMATION: n equals a,t,g, or c
<220> FEATURE:
<221> NAME/KEY: SITE
<222> LOCATION: (440)
<223> OTHER INFORMATION: n equals a,t,g, or c

<400> SEQUENCE: 12
gaattcggca cgagctcact tgaaatccat gacactacat agaaaatgga ctctaaaatc           60
tgcctggcaa tgattctaca tttccctaat cccttcactt tcctactctc ccctactctc          120
ttagaatgtt ctgtatctcc ttatctttct tcaatctccc tgaatattct ccctgttcct          180
tgctttcagt tcaggaattg gtgccccaat ttttttatgt tgtttgattt ttttttttt           240 tttgagacag agtctggctc tgtcactggg gctggagtgc agtggtgcaa tcatggctca          300
ctgcaatctc tgcctcccag gctcgagagt attctagagc ggccgcgggc ccatcgnttt          360
tccaaccggg tggggtacca ggtaagtgta acccnattcg gcctatagtg agtccgtaat          420
taaaattcaa ctgggcggtn ggtttaaaaa cgtccgtgga actgg                          465
```

<210> SEQ ID NO 13
<211> LENGTH: 674
<212> TYPE: DNA
<213> ORGANISM: Homo sapiens

<400> SEQUENCE: 13

```
tgcccctgaa gagtaagaat gaatatgaca tgttgattct tgaagtggcc aaataaatca      60
cccgacggtg aagttctgca atggatgaag gtggcagtga aggaaagca gagagaatgc     120
agagacagga tcctaggcaa gaagacaaag gcctggacac agagaaggag atcaaagtgt    180
ggctctgggt acaaagtgag agtgagtgtg caggaagtga acaaggtcag tagaactagg    240
aaaagcmaaa ggtcaaggaa accagcattt ggagacagrt aatgatgtca cctttggacc    300
aagggagatt gaagcttctg taaggcraaa gtaaatgttc ctggttagta atccaggttc    360
ttggtaattg gtattaagtt tgtcatgtgc tgtggctcat gccaagtcca tccatataaa    420
gacaaccatg ttmgaataag aaagacaaag aactctcaga gtctgttcct gagatagagc    480
aggtcctgag aggcttatca aaagttcaga actaaggca aaattttggc catgatattc     540
acaaaattga agagaaacag catttaataa tacagccaag cataaaaaaa accaagacaa    600
cctaaaaccc caatgccatt tgtattgaag gtgagtgggg agctcaccgg tggtctcaag    660
aacttggcag atgc                                                      674
```

<210> SEQ ID NO 14
<211> LENGTH: 297
<212> TYPE: DNA
<213> ORGANISM: Homo sapiens

<400> SEQUENCE: 14

```
gaattcggca caggtctaaa tgagatggca cgggtatgct tctgttcttt ttctggacgt      60
tgtttagaga gtcagtagat cataataatt cagacacttt tttttckgga ccataaaata    120
tctgarscca yataataaca acatacagc acggtgaata agaacccaac ttttgagcca     180
gatcactttg catggaatcc ccattctatc attctatcat ttctgggctg tgggaacctc    240
agacaagtta cttaacttct tcaatgctca gattaaaaaa aaaaaaaaa aactcga        297
```

<210> SEQ ID NO 15
<211> LENGTH: 604
<212> TYPE: DNA
<213> ORGANISM: Homo sapiens

<400> SEQUENCE: 15

```
tcgacccacg cgtccgcagg gaaggaccct ttaagaggac atttactaaa atgcactttg      60
caacattaaa aagaagaccc tggaatacat ttctctcctt ctaagtgaaa tgctctcaaa    120
gagctctaag atggtgtcag ttaaacgggc tgacccgggg tctctgggtt tcactttctt    180
gctgtcctcc cttcccaagt gtacagtggg ggtctccaga ggccgcccca catgcaccag    240
ctgctctgat ggctgagata acgtctggca ttcccgttct tcaaattaaa cagaaacact    300
attcagtgtt ttcggttttta attaagaata cggtaaatat cagtcaatac agcccacatg    360
aacatggacc cctttggggt cctcaatgac ttcagaagtg attagtgctg aggtcagaaa    420
accggaggac aaaatcaatt acacgtcctg acaaggagct gagcctggca tcaactcaga    480
gaagggggttt gcagataaca gcattcacct gaggttccac taacacggaa taaagctgtg    540
gtataaaata aaaaaaaaaa aaaaaaaaa aaaaaaaaaa aaaaaaaaaa aaaaagggc      600
ggcc                                                                 604
```

<210> SEQ ID NO 16
<211> LENGTH: 1146
<212> TYPE: DNA
<213> ORGANISM: Homo sapiens
<220> FEATURE:
<221> NAME/KEY: SITE
<222> LOCATION: (1140)
<223> OTHER INFORMATION: n equals a,t,g, or c

<400> SEQUENCE: 16

| | | | | | |
|---|---|---|---|---|---|
| cttaattatt | aataagccaa | tgtgttatga | taccaatayc | tgttttaaaa | aactaaaacc | 60 |
| aaccatgctt | ctggcatgat | aaaatcatgg | aattaaatca | ggggtttaca | ttcttgtaga | 120 |
| gtgttcttga | acactctct | gcaccatttt | taaaacttga | gaatagtttt | agtatctctg | 180 |
| atattttttg | ccagaatcat | catgtcatgt | atgaatgtgt | tatccctatc | taaggaaaaa | 240 |
| ggtgaatatg | ttttttgtatg | aatgtttaac | tggaaatgtc | catggacttg | gctaatttat | 300 |
| atttactttt | tattgtacat | agatttctaa | tatttttcat | tcctgtatca | tttaaacttc | 360 |
| cttcatttga | gtaaattcac | taaatatttc | tattttttgc | tttttttaaat | tctgattta | 420 |
| tatgaattct | aattctttt | cactacatat | gttttaaaga | gttacataca | gtgatttaga | 480 |
| atggtttaca | gttaatgctg | atcttgtatt | ttaaattcca | acactttgtg | tcactacctc | 540 |
| ctctaatggt | tagtatgata | tgctagcaga | ctgtatgagg | tcttttttta | aaataccact | 600 |
| tttagtgtca | gtgaaccaaa | ttctggaatg | tcttaacagc | tctaaatctt | acttgtcttg | 660 |
| aaaatgattg | gggtttaata | ccactgctgg | tggttcacac | atcatcccat | ccttaatatg | 720 |
| cctgacaggc | atctgagcaa | aggtttttag | taattgaatt | tctctgcagt | agtccttcaa | 780 |
| gcacttgaat | gtaaaccttt | agcatttatt | cgtttaatga | ctactgatac | gaatctcaag | 840 |
| cagatttctt | gctcttaaaa | gttatgtttc | actgagttct | ggttttgtgt | agctatattt | 900 |
| tatatagcta | gatattcctc | acagtgaaca | tgaattgtaa | taattggtta | tttccttaag | 960 |
| tctttagatt | ataataattt | cagattattg | cacgtctgtg | atttgagagg | tgagttattt | 1020 |
| aagaggccag | ttttcaggac | atgggaattt | gaattgtaaa | cctgttatct | ctgtgaaact | 1080 |
| tttaacatga | taaaatataa | cctttctttg | tgcttaaaaa | aaaaaaaaa | aaaaaactcn | 1140 |
| aagggg | | | | | | 1146 |

<210> SEQ ID NO 17
<211> LENGTH: 678
<212> TYPE: DNA
<213> ORGANISM: Homo sapiens

<400> SEQUENCE: 17

| | | | | | |
|---|---|---|---|---|---|
| ggcacgaggc | ggaggtggag | acgcagagct | atatttggta | gactgtgaac | agactcacct | 60 |
| gcctagagca | gtgtattcac | attgggatta | ttagagtaaa | gtgtggacaa | gaggtataat | 120 |
| gcagaggtct | taatgtgtca | ggctggggaa | tgtacttagt | attctgtctc | tcatgtgtct | 180 |
| caaaccaggg | tcctcattca | cctgttggta | cttggtgaca | aggataaaaa | agctcctccc | 240 |
| tactctgcta | gttttacttc | aaataatgaa | gggaaactta | taattaattg | ataagtcatg | 300 |
| ttaaatatct | ctgtagcaac | ttaaatagga | aatatgatgc | tgaattttct | tgaattctta | 360 |
| aaataaggga | tttccaaata | atttgaagtt | attactgctc | ttttgagatt | gttttcaaac | 420 |
| tctgacaatc | actgatcatt | ctctctgcct | ttggaattct | tgagagacaa | agtgtggtta | 480 |
| tcacataagt | attagggagt | cattacaggt | tgatgcatag | aggaagagag | agccacgttt | 540 |

```
ctaataacac tcatacctga aatcattcca ttaccattct ttaatagttt cattctgact      600
tcattgtagc aactcttact ttattcttct taagttttta aggccaaatc atggtttcat      660
aaaaaaaaaa aaaaaaaa                                                    678
```

<210> SEQ ID NO 18
<211> LENGTH: 1305
<212> TYPE: DNA
<213> ORGANISM: Homo sapiens

<400> SEQUENCE: 18

```
cagcttgtgc agactccgag ccttcagtga caaaggcttt gctgtttgtc ctcttgacct       60
gtgtctgact tgctcctgga tgggcaccca cactcagagg ctacatatgg ccctagagca      120
ccaccttcct ctagggacac tggggctacc tacagacaac ttcatctaag tcctaactat      180
tacaatgatg gactcagcac ctccaaagca gttaattttt cactagaacc agtgagatct      240
ggaggaatgt gagaagcata tgctaaatgt acattttaat tttagactac ttgaaaaggc      300
ccctaataag gctagaggtc taagtccccc acccctttcc ccactcccct ctagtggtga      360
actttagagg aaaaggaagt aattgcacaa ggagtttgat tcttaccttt tctcagttac      420
agaggacatt aactggatca ttgcttcccc agggcaggag agcgcagagc tagggaaagt      480
gaaaggtaat gaagatggag cagaatgagc agatgcagat caccagcaaa gtgcactgat      540
gtgtgagctc ttaagaccac tcagcatgac gactgagtag acttgtttac atctgatcaa      600
agcactgggc ttgtccaggc tcataataaa tgctccattg aatctactat tcttgttttc      660
cactgctgtg gaaacctcct tgctactata gcgtcttatg tatggtttaa aggaaattta      720
tcaggtgaga gagatgagca acgttgtctt ttctctcaaa gctgtaatgt gggttttgtt      780
ttactgttta tttgtttgtt gttgtatcct tttctccttg ttatttgccc ttcagaatgc      840
acttgggaaa ggctggttcc ttagcctcct ggtttgtgtc ttttttttttt ttttttaaac      900 acagaatcac tctggcaatt gtctgcagct gccactggtg caaggcctta ccagccctag      960
cctctagcac ttctctaagt gccaaaaaca gtgtcattgt gtgtgttcct ttcttgatac     1020
ttagtcatgg gaggatatta caaaaaagaa atttaaattg tgttcatagt ctttcagagt     1080
agctcacttt agtcctgtaa ctttattggg tgatattttg tgttcagtgt aattgtcttc     1140
tctttgctga ttatgttacc atggtactcc taaagcatat gcctcacctg gttaaaaaag     1200
aacaaacatg tttttgtgaa agctactgaa gtgccttggg aaatgagaaa gttttaataa     1260
gtaaaatgat tttttaaata tcaaaaaaaa aaaaaaaaa ctcga                      1305
```

<210> SEQ ID NO 19
<211> LENGTH: 1060
<212> TYPE: DNA
<213> ORGANISM: Homo sapiens

<400> SEQUENCE: 19

```
gaattcggca cgagaatcaa tctacaccct caagcagttt gtagtctgct ggaatgacag       60
acttaaaaat gcttataact aaaatatttt atgtgcagga ctagggtttt taagctaaaa      120
ggctgctttt taaattgtga atataaagt acatgtagaa caatgcataa aacatgtcaa       180
cagttaaaca gatagttatg ggattatact ttgtgtatwt ttatgtttgc ttcttttatt      240
caacattctg tggttcatct gtgttgcttg tagcatcatc attactgtag catactttat      300
ttgttctact gttggtggac attactgttg cttccagttg ttggctatca ttaacaatga      360
tgctaagagt gttcttgatt atttgtcttg gtatgttttgt gcacgcacca ataatatata     420
```

-continued

```
tctaggaatg gaatcgttgg gtcatagaga atatacgtag cttttaagtt tactagataa      480
gtgattttcc aatttaaaaa gacctttgaa acgttttttct acattggtgg tttttaaagt      540
tatctatttt ctcatggaat ttggttttct catgagaata aggtaggaat ggttgtatgt      600
tgctaatatg tagttcaagt gcccttttcta cctaatctgg attgccagga atatgcttga     660
aatgccaaat catgacttag tattttmctg tggtaattgg agtagtcttt gacacatcag     720
gaagtatggg aatatgggaa agatctttga gagtggaaac tataccacag ttttgtttag     780
tgctaggtag gaaaggtgaa aaaaaaagcg cgagagtata ttaagtatac aaaaagctta     840
gtggttttaa aatgttaagc tcacatttgg aagtgtaatt ctattttaat ctctttccta     900
atggaggaag aaagatgact gatgtggtag ggtaatcttg tttgaaaaat tgacaactct     960
ggcatacggc ccagatctct tttcagattt tgtgtgaaaa agaaaaatgg cagcctctta    1020
gtgctattca ttggtgtaaa aaaaaaaaaa aaaactcga                            1060
```

<210> SEQ ID NO 20
<211> LENGTH: 1170
<212> TYPE: DNA
<213> ORGANISM: Homo sapiens

<400> SEQUENCE: 20

```
ggttaacatt tgtggatgac tgaagattga tggaatgcta ctatgccaaa ccttaattgt      60
gatattattt tcataactga attattttag aaatgtatca attgactgct gctcagcagt     120
aactaaaatt cctcaagtat ttgattaaac agaataatgt caaaatttaa accttccctt     180
aaaactttat acataagaca tttatgattg ttcaattttt ataatctatt tgtggatttt     240
gttaaaagat ttcacatgaa gatttattag ttgccattta aaattttat atgtttagtt      300 aaaagatttg acatgaaaat ttattagata ccatttaaaa attttatgtg ttatgtgttt     360
attctttgag aatgttacct tactgttgt aatagtgcta cattttttctg ctttcaggcc     420 tctgtatttt cacaaaacac caaaacagc atttaattat attatcatga gtgtgtttct     480
ggacacaaac ttctgcagta gaatgaccta acatgtcgtt ttcattgcag tcattatagg     540
attgaaatac gttcaaaata acctctctag gaaagtcttc tgctagaatt tctcccctct     600
attcattata atattctttg tttttaaagc cagtcaaata taatagtctt aataagatca     660
gaaactctcc aggagagtga gtctaccctc acgtccttgt aggatgatct tgattatagt     720
cttattatag gactataact gtattctcaa catttctcca gaaaggacct tgtaaaaagg     780
tcttttgtac cacagtattg gttttttccc ctctctcttc acttaaaaaa aaaaatagca     840
aggcagaaat agtgtattga aaagttgttc atctattatg aagtccttga gtggtgaaaa     900
atccgttgta catgagaaca tttctatgca tttaagccag aaacgaggta catggctgtg     960
tgctcttctg tcaaccaatg aaatgtgttt tcacatgtgt ggcagtgcaa gtaaataaca    1020
cattatttga ctgaatcagg catgatactg caccaaagtg ttggtacata ttcacggtag    1080
taaatcagta ccctgttaa aggatttatc ccattgcttc atattaataa aatggttaca     1140
atatatcaaa aaaaaaaaaa aaaactcga                                       1170
```

<210> SEQ ID NO 21
<211> LENGTH: 2084
<212> TYPE: DNA
<213> ORGANISM: Homo sapiens
<220> FEATURE:
<221> NAME/KEY: SITE
<222> LOCATION: (2075)

<223> OTHER INFORMATION: n equals a,t,g, or c
<220> FEATURE:
<221> NAME/KEY: SITE
<222> LOCATION: (2083)
<223> OTHER INFORMATION: n equals a,t,g, or c

<400> SEQUENCE: 21

| | | | | | |
|---|---|---|---|---|---:|
| ggcacgagga | gttgtgcaga | tacctggctg | agagctggct | caccttccag | attcacctgc | 60 |
| aggagctgct | gcagtacaag | aggcagaatc | agctcagtt | ctgcgttcga | gtctgctctg | 120 |
| gctgtgctgt | gttggctgtg | ttgggacact | atgttccagg | gattatgatt | tcctacattg | 180 |
| tcttgttgag | tatcctgctg | tggcccctgg | tggtttatca | tgagctgatc | cagaggatgt | 240 |
| acactcgcct | ggagcccctg | ctcatgcagc | tggactacag | catgaaggca | gaagccaatg | 300 |
| ccctgcatca | caaacacgac | aagaggaagc | gtcaggggaa | gaatgcaccc | caggaggtg | 360 |
| atgagccact | ggcagagaca | gagagtgaaa | gcgaggcaga | gctggctggc | ttctccccag | 420 |
| tggtggatgt | gaagaaaaca | gcattggcct | tggccattac | agactcagag | ctgtcagatg | 480 |
| aggaggcttc | tatcttggag | agtggtggct | ctccgtatc | ccgggccaca | actccgcagc | 540 |
| tgactgatgt | ctccgaggat | ttggaccagc | agagcctgcc | aagtgaacca | gaggagaccc | 600 |
| taagccggga | cctaggggag | ggagaggagg | gagagctggc | ccctcccgaa | gacctactag | 660 |
| gccgtcctca | agctctgtca | aggcaagccc | tggactcgga | ggaagaggaa | gaggatgtgg | 720 |
| cagctaagga | aaccttgttg | cggctctcat | ccccctcca | ctttgtgaac | acgcacttca | 780 |
| atggggcagg | gtcccccaa | gatggagtga | aatgctcccc | tggaggacca | gtggagacac | 840 |
| tgagccccga | gacagtgagt | ggtggcctca | ctgctctgcc | cggcaccctg | tcacctccac | 900 |
| tttgccttgt | tggaagtgac | ccagccccct | cccttccat | tctcccacct | gttcccagg | 960 |
| actcacccca | gccccctgcct | gccctgagg | aagaagaggc | actcaccact | gaggactttg | 1020 |
| agttgctgga | tcagggggag | ctggagcagc | tgaatgcaga | gctgggcttg | gagccagaga | 1080 |
| caccgccaaa | accccctgat | gctccacccc | tggggcccga | catccattct | ctggtacagt | 1140 |
| cagaccaaga | agctcaggcc | gtggcagagc | catgagccag | ccgttgagga | aggagctgca | 1200 |
| ggcacagtag | ggcttcttgg | ctaggagtgt | tgctgtttcc | tcctttgcct | accactctgg | 1260 |
| ggtggggcag | tgtgtgggga | agctggctgt | cggatggtag | ctattccacc | ctctgcctgc | 1320 |
| ctgcctgcct | gctgtcctgg | gcatggtgca | gtacctgtgc | ctaggattgg | ttttaaattt | 1380 |
| gtaaataatt | ttccatttgg | gttagtggat | gtgaacaggg | ctagggaagt | ccttcccaca | 1440 |
| gcctgcgctt | gcctccctgc | ctcatctcta | ttctcattcc | actatgcccc | aagccctggt | 1500 |
| ggtctggccc | tttctttttc | ctcctatcct | cagggacctg | tgctgctctg | ccctcatgtc | 1560 |
| ccacttggtt | gtttagttga | ggcactttat | aattttctc | ttgtcttgtg | ttcctttctg | 1620 |
| ctttatttcc | ctgctgtgtc | ctgtccttag | cagctcaacc | ccatcctttg | ccagctcctc | 1680 |
| ctatcccgtg | ggcactggcc | aagctttagg | gaggctcctg | gtctgggaag | taagagtaa | 1740 |
| acctggggca | gtgggtcagg | ccagtagtta | cactcttagg | tcactgtagt | ctgtgtaacc | 1800 |
| ttcactgcat | ccttgcccca | ttcagcccgg | cctttcatga | tgcaggagag | cagggatccc | 1860 |
| gcagtacatg | gcgccagcac | tggagttggt | gagcatgtgc | tctctcttga | gattaggagc | 1920 |
| ttccttactg | ctcctctggg | tgatccaagt | gtagtgggac | ccctactag | ggtyaggaag | 1980 |
| tggacactaa | catctgtgca | ggtgttgact | tgaaaaataa | agtgttgatt | ggctagaaaa | 2040 |
| aaaaaaaaaa | aaaaaaaaaa | actcgagggg | gggcnccggt | acnc | | 2084 |

```
<210> SEQ ID NO 22
<211> LENGTH: 643
<212> TYPE: DNA
<213> ORGANISM: Homo sapiens
<220> FEATURE:
<221> NAME/KEY: SITE
<222> LOCATION: (115)
<223> OTHER INFORMATION: n equals a,t,g, or c

<400> SEQUENCE: 22
gaattcggca cgagaaacta tctacaagga tgatgtttcc acaaagaact tctcacaagc     60
agaaatggga ggccaagaca cacatctaaa cagacctttc agaagcactt gcaangcaca    120
caggacatgt tgccgtacag cctgcctttt cacatttcct gtacttcttc tctgagccac    180
catcttcayc ctcatctgtt gtctctgttg ctttctttttt cgcctaaggg agtcacagct    240
gatgttaaaa tttcactgat gatggcaaaa tgactaagga tgaaggttca ctactgaaat    300
cacagctgag ttctaaacat gaaggtcaaa aacwtcatgg cagtaggtta gggatgacaa    360
tacagcaatt tcctggtgac tgcattgtgc aagtaattta ctaacttgct agagatatag    420
aaatagcatt ttaacaacag atgtctaagc caagaactaa attcatatga gtctttctta    480
gaaaaaagtg acatcagctg gtgtggtgg ctcatgcctg taatcccag cactttgggt    540 ggctgaggtg gaaggatcac ttaagctcag gagtccaaga ccagcctggg caacataccg    600
agacctcctc tctactaaaa aaaaaaaaaa aaaaaaaact cga                     643

<210> SEQ ID NO 23
<211> LENGTH: 647
<212> TYPE: DNA
<213> ORGANISM: Homo sapiens
<220> FEATURE:
<221> NAME/KEY: SITE
<222> LOCATION: (1)
<223> OTHER INFORMATION: n equals a,t,g, or c
<220> FEATURE:
<221> NAME/KEY: SITE
<222> LOCATION: (69)
<223> OTHER INFORMATION: n equals a,t,g, or c
<220> FEATURE:
<221> NAME/KEY: SITE
<222> LOCATION: (614)
<223> OTHER INFORMATION: n equals a,t,g, or c
<220> FEATURE:
<221> NAME/KEY: SITE
<222> LOCATION: (632)
<223> OTHER INFORMATION: n equals a,t,g, or c

<400> SEQUENCE: 23
nccaaagttc gaaattaccc ctcactaaag ggaaccaaaa gctggagctc caccgcgttg     60
gcggccgcnt ctagaactag tggatccccc gggctgcagg aattcggcac gagagctgcc    120
ttggctcggc ttggtctgcg gcctgtcaaa caggttcggg ttcagttctg tcccttcgag    180
aaaaacgtgg aatcgacgag gaccttcctg cagacggtga gcagtgagaa ggtccgctcc    240
actaatctca actgctcagt gattgcggac gtgaggcatg acggctccga gccctgcgtg    300
gacgtgctgt tcggagacgg gcatcgcctg attatgcgcg cgctcatct caccgctctg    360 gaaatgctca ccgccttcgc ctcccacatc cgggccaggg acgcggcggg cagcggggac    420
aagccgggcg ctgatactgg tcgctgcag cgccaaagag accaacaaga tgattttagc    480
gtggactagg acacttaacc taagaagagt ttcacttaat cattcaaatc actatctgaa    540
gggtcacgga gcgcaaaata aagtttaaaa ccctgctacc aaaaaaaaaa aaaaaaaaa    600 ctcgaggggg gggnccggta ccccaatttc gncctatagt ggagtcg                 647
```

```
<210> SEQ ID NO 24
<211> LENGTH: 825
<212> TYPE: DNA
<213> ORGANISM: Homo sapiens

<400> SEQUENCE: 24
gaattcggca cgagattaca cagcagtatg tgtttattgt agaaatgatt gaaatcgaaa      60
tgttaaaatt aaaaaataat ttctgttcta actcccaatt tgataaatag ctctctatcc     120
atatctctat atttatctat ttctctgtat ctatttgtgg tttttgtcca gttagatcat     180
gctatttaaa ctgttttta gcttgattct ttttcattt gttgtctcgt gcatcttttc      240
tgtatcaata aatattcccc tgtaaggaca tttgaaaagg ttttatagca ttctgtttat     300
ggacatacca taatttattg aatctaattt cttttgccaa acacttaagt tgttccaaat    360
ttctggttat tataaacagg gcttcacaac tctccttgtg catcattttg acattcattt    420
ctgattattt tcttatgaaa atttcccaat tttggtttta ctgagtcaga gtgtttccct    480
agaatattta aaaatatgtg gctgaaaaat gaacttattg ctgggtgcag tggcttatgc   540
ctgtgatact ggcaccttgg gaggctgagg tgggcaggtg gcttgaagtc aggagttcga   600
gaccagcctg gccaacatgg tgaaacccgt ctctactaaa aatacaaaaa gtagtcaggt   660
gtggtggcgc atgcctgtag tcccagctac tcaggaggct gaggcacgtg aatcacttga   720
gctagggaga cggaggttgc agtgagctga gatcgtgcca ctgcattcca gcctgggtga   780
cagagtgaga ctctgtttaa aaaaaaaaaa aaaaaaaaa ctcga                     825

<210> SEQ ID NO 25
<211> LENGTH: 541
<212> TYPE: DNA
<213> ORGANISM: Homo sapiens
<220> FEATURE:
<221> NAME/KEY: SITE
<222> LOCATION: (11)
<223> OTHER INFORMATION: n equals a,t,g, or c
<220> FEATURE:
<221> NAME/KEY: SITE
<222> LOCATION: (12)
<223> OTHER INFORMATION: n equals a,t,g, or c

<400> SEQUENCE: 25 ggaccccgg nncaggaatc ccccccccc cccccatct gtctctccag atcttaccca       60
tcttgtcctt ccacacgtcc ccgatgcctc tgaagatgcc attcatgttt ctctcccttc   120
cccgggacac attcctaatg ttggagttgg tgttaggtac tttcacttgc aatgggagtt   180
tctttattca caaagcctct tgagtgttgc tctcatacta ttttgtgtgt ccttccaggg   240
cagtgacctt gacagttatt tgtcttgttc tcccaagcgc gggtgctaag gacatagtct   300
gtgggcatgc agatgtgtgt gacttgttca cacgaactgt gaggatgagg acttggtgaa   360
tggtggaaat tcagatccaa actgtatctc cagggcatga tggcgcctgt ctgtagtgca   420
gttacttgag aacttgggag ggtgagttgg gaggatttct tgaggttcca ggagttcgag   480
accaacttgg gcaacatagc aagatcctgt ctctataaaa aaaaaaaaaa ggatccctcg   540
a                                                                   541

<210> SEQ ID NO 26
<211> LENGTH: 852
<212> TYPE: DNA
<213> ORGANISM: Homo sapiens
<220> FEATURE:
<221> NAME/KEY: SITE
```

<222> LOCATION: (719)
<223> OTHER INFORMATION: n equals a,t,g, or c
<220> FEATURE:
<221> NAME/KEY: SITE
<222> LOCATION: (834)
<223> OTHER INFORMATION: n equals a,t,g, or c
<220> FEATURE:
<221> NAME/KEY: SITE
<222> LOCATION: (840)
<223> OTHER INFORMATION: n equals a,t,g, or c

<400> SEQUENCE: 26

| | | | | | |
|---|---|---|---|---|---|
| gaattcggca | cgagaagtca | tggcggcgct | gtgtcggacc | cgtgctgtgg | ctgccgagag | 60 |
| ccattttctg | cgagtgtttc | tcttcttcag | gcccttcgg | ggtgtaggca | ctgagagtgg | 120 |
| atccgaaagt | ggtagttcca | atgccaagga | gcctaagacg | cgcgcaggcg | gtttcgcgag | 180 |
| cgcgttggag | cggcactcgg | agcttctaca | gaagggttct | ccaaaaaatg | tggaatcctt | 240 |
| tgcatctatg | ctgagacatt | ctcctcttac | acagatggga | cctgcaaagg | ataaactggt | 300 |
| cattggacgg | atctttcata | ttgtggagaa | tgatctgtac | atagattttg | gtggaaagtt | 360 |
| tcattgtgta | tgtagaagac | cagaagtgga | tggagagaaa | taccagaaag | gaaccagggt | 420 |
| ccggttgcgg | ctattagatc | ttgaacttac | gtctaggttc | ctgggagcaa | caacagatac | 480 |
| aactgtacta | gaggctaatg | cagttctctt | gggaatccag | gagagtaaag | actcaagatc | 540 |
| gaaagaagaa | catcatgaaa | aataaatgaa | ctttgcttag | tggattgact | cctttgctga | 600 |
| agtcagttat | tcatcaagaa | tgcaattaga | ctaattgtga | ataaatgatt | gaatgaagat | 660 |
| ataataaata | aaagctataa | ttatagataa | ctcttattag | aattttcttt | agcaatatnc | 720 |
| ccaccccca | ccccttgttt | tgctcttaat | ggttttttcc | ttgggtgggg | atagtataca | 780 |
| ctgtactaag | aaatgtcatt | caataaatac | gttttgagtg | ctgtctaaaa | aaanaaagan | 840 |
| ttggtggggg | gg | | | | | 852 |

<210> SEQ ID NO 27
<211> LENGTH: 4598
<212> TYPE: DNA
<213> ORGANISM: Homo sapiens
<220> FEATURE:
<221> NAME/KEY: SITE
<222> LOCATION: (948)
<223> OTHER INFORMATION: n equals a,t,g, or c

<400> SEQUENCE: 27

| | | | | | |
|---|---|---|---|---|---|
| tactgattgg | aacactttcc | tcctcttcct | tcctagcccc | agctattcac | tggggactgt | 60 |
| catagctggg | attctaaagg | tgccacattt | ttcagtttca | tctccactag | gttggttccc | 120 |
| gggcaggaag | tcaggcagca | gggaaggaca | cgggaacagc | aggtggagaa | ttcctacagt | 180 |
| ctttcttacc | ctgctagcaa | tagctctcag | tttcagaggc | acagtctttg | gagaccattc | 240 |
| agcactgaga | aagcaatatt | tagaacctat | tgcaaaactg | ggcctgagtt | aggcatggtg | 300 |
| atgaatgcat | cagcaaggaa | tagaaagttc | ttatcgtgaa | acccttcaac | ctcaactatg | 360 |
| ccttcataga | cacacacgtt | catgcacatg | taggcacatg | taccatctca | catcttcact | 420 |
| ttcccgagat | gccatataca | attacctaca | ttaataactg | tagcactatr | ccttttgagc | 480 |
| ccgagagg | gaattagtga | ctctaagtga | aggtcactga | cacagagaag | cagtatgtgt | 540 |
| ctggggcttc | caggacctgc | aggcccacta | gcgtgcactt | accagaatgg | catacacagg | 600 |
| acctgatcat | gaggaagacc | aggtttccag | tgtaaactac | tcttgttccc | accacctctg | 660 |
| gagcactcag | ggagccccat | acagtactta | caatgtcttt | aatggacttg | attctgttta | 720 |

```
attttttgtt ttatattagg cacactgtat taattttcca aaatgttata ccacactatg    780
ttcttggtcc tgacctattg ctctggagga aagagttgta taagaacgtg gctcatgtga    840
acttttgcta gcttcatttg aggacctgag aatcatgggg aaagggaagg taatgttttc    900
attgaaatca tcacagtgat ttttattccc tgggaacaca gcgtgtanct aaaaatacat    960
gagaaaatag catgtatatg aaagctattc tcaaaagtca cctgagctca ccatcttcat   1020
agccaaccct accagttata aagatggcag ctctatcact tgattaagtg ggaggtggtc   1080
aaatattttg gtgcctcatt ttcttcatct gtgagatggg aactgttatg cctggcttac   1140
taagagtctt gtgagagact gagaagttga ttttgttcat atccaatctg taaatgcgaa   1200
gtcaggggaa gtaatgtccc tgaaataaac gggttcatgc catctaggga caataaatgg   1260
ttttcttgtt gtaacttctg gttaatatca gtaccttgat gtcatcaccg tgatgacaaa   1320
gagaagagtt attgttgatc ttcttggttt tggtctgtct cttttcttag gataaagaaa   1380
aacttccaaa ctagaaaaac aggccctggt tcccttagtt tgcacttgaa cccaatatgt   1440
tgccttgtac atacttggtc cctgtcacat tgactgcttg ggaggcttcc agggagaagt   1500
atgagaccct gaggggtgag aatgggcagc tagcaagaac atggaaattc tgcttggcac   1560
tacagtcata aatagaaaac actgtgtgtg ctcaggggag caggggatgc cactgaagaa   1620
actcaaggga atgtgtattt gaaggaaatg caaaaactaa gtatttagca aaatgaaatt   1680
atgccttgat gactaaaagg cactagaaag gttgtgtcta ctaacttcag ccctaatcag   1740
aacagatgcc tagaaggagc attttttgtga caacttcata gtgattagaa tcagtggaga   1800
actccatctt agtggcagga atataatgaa actacccacg caagaacatg gttgaatcac   1860
atttgcttga cttagggcaa agtacgaaag agagacaaaa gggttctctt ggaaacaaga   1920
agagtkactc cagatgtggc ctgaataatt gccatgttaa gttaatgcaa aagatcagaa   1980
cagggctaca tttgcacagg cagtttctct ccgggccgta gttttcactg atgatcacct   2040
ttcacagcat tttccccaac cagcatttca cttagtcttc tctatacccca gcacctcccc   2100
cggcaccccc ggcaagccca ctatcacttc cgacttccaa cgtggcatcc gtgagatctg   2160
tccacattag gcgaagcagg agaacactga gagcagcagg atgggtttgg aaagagcatg   2220
cctctggaaa cacagcttcc tgggaattca catgaggcca gtcctacaga gagcaagatg   2280
caccccagga tttcttcatt ttctaataga tgtgggagtg ctccattttc cccgacagcg   2340
aatttcccct gagaaacgat actagaccct gggtttgccc accttgtaac tcttccttat   2400
ctcctccttt tcatccctaa ttcatcctcc ctctggcatg gaattgacgc ccgtgcagta   2460
catttgccaa gtggcacctt ctttcaattt atgttttatt ttgctatggt ggtgattctt   2520
tatttgctgg ttgtcttttc tcacacatct ttctctctgt ctctctcttt cctgctcttt   2580
gttttttctgc ccagaaaaac ctgacttcga taccaaaaaa gatgaaacta cagaaactca   2640
aatttaaaaa aaactttaaa agaaacaaaa aaatactcaa cgattctttc agctttatta   2700
acatttccca ttgtttcttg cgacttgtgt ctcgttcttt gtagtattga tgatgaacat   2760
ttgataatga atgttcttgt atattcagat aaagaaaaaa aaaccaaaa aagcggtctg   2820
aatttaatag tgtttataat aaaaatttta aaatgaccc tcatagcacg caaaacagga   2880
tggggaattt cccctcttct ttctgtgaca atgcgcatca ttcctgcatt agttttttaac   2940
accagactac ctacattcat catttccctc attttttcttt tattttcttg catttgtgaa   3000
ttagttcaag aatgctagaa aagtgtcgag ttgtgcacat ccatttcttg tttcacaatg   3060
tttaaaagtg acagtaattc attttgtaaa ctaaaaaaaa aaaaaaaaag gttggaatag   3120
```

-continued

```
tgagcataat aggtacaacc taacacatta ttatgtttat taactttgag acccagaaat      3180
aaattctttt cttttcttga ttcttgctct taaaaataca aaaaaaaaaa tgttttgttt      3240
tgtgttattt ttggtttgtt tattgggggg cttttttttaa ttgtcaggat tatgatcttg    3300
ctgtttttct tcaatatgta tacaaggtga tgtgaaaaga tgacttgggc agaggagtaa     3360
gaacaagtag gcttgttctt ctactttgct tcagaattca gttaatgcca aaagcgaaga     3420
tcaagcccat gttgatgtct cgttgctcac ctgcatttcc agagagtgtg acactcatgc     3480
agtccctgag aaaaataaaa tcagggacat acttctcctt ttagccttt aaaaattcaa      3540 aaacgtttag tccaagggaa cttttttatgc tatcaggaaa ggttttttgct gttttttgatt 3600 ctgattatca cagccaagta ctttgttttta ttctccctaa ttaataacta cattccatga    3660
ggcctcttcc aaccaaagag gccttttctt ccaggagagt cccgcagaga tgctggtatg     3720
atgggcacca ttggttaagt aaactacatg caggaagaag tccttggggc cagtctgcca    3780
gctgagtcct ggttttggat gaagagttaa tgagatattg ggccaggctc aatgctgtag   3840
ttttaatgct aagaggttac gtttacttca cagagtacac ctcttagtaa cctctgactt    3900
aggcagctgc ttaaagcaaa ttgcaaaact ggcttgattt ggaatgtttt tattagagga    3960
aaaaagaaag ccatattatc tggaaaaaaa ttcatttttaa ataccatcat tcaacaaatt  4020
atgttcagaa agtggtcaga acttaagcaa gaaaagtaaa gaaagaatgc agaattgtgg    4080
agcaatgctt taggaaatat ttctacctga acacttgtac tcttgaagtc acaacaaaat   4140
aatgatgagc ttttcacatc acctttatgg tttcaatccc tagctcaaag cttcctggaa    4200
tcttttattt tttgtaaact ttttttttctt ttgttaaaat aaataaaaca ttcaatgttt   4260
ttctcctttt ctctcttatt acttctttcc tttggcattt tcaatttgaa atgctttcct   4320
ttggttgttg gttttattct cccctaccc ctccccttt cttattattc agaatataaa      4380
cctgcaaagc tctgctctgt tttggttttg aaagtttaag cttttctgct tctgtgagag    4440
cacaggcttc tgtccctttt gattccaact gaacttttgt gttctctaat gatactaaca   4500
cggtgtaggt tttacagtct cctaatttgt actggtaatg catattccaa ataaatagtt   4560
tcttttgttg caaaaaaaaa aaaaaaaaa aaaaaaa                              4598

<210> SEQ ID NO 28
<211> LENGTH: 585
<212> TYPE: DNA
<213> ORGANISM: Homo sapiens

<400> SEQUENCE: 28
gaattcggca cgaggtgaag tggcatttct tataaagaaa aaaaagtcct ctagtattgt       60
ctatgggaaa ttcttccagg ctacaatacc tagtatgcaa gttttaatgc tggcacattt     120
tttgatcttg ctagaacatg ttcagggaag gtgttcagac aacaactagg actaatattc    180
cttcaagggt cattaaatgg ttgattaact gaaacatcaa gggattatag atcaggcatg    240
tgtaggcaat gacaactatg tcatgactgc tgtgtggcca acagtaattg aaggctgcca    300
tcaattataa gacacattcc atttcagaga tgttacagtg tggggtgggg gaaagtctgt    360
ctggaattag tagtaaggga cctgtcttat aataggcaga aaatgtgtgt aattgaatct    420
taagtatata acatctaaag aattataaga ttttagagcc aggaataaaa aaacacatgt    480
taccatccct tagaatctta gaaaatgtta ttggtgaaat aaactttagt gatgatcata    540
cagaaaaaaa aaaaaaaaaa aaaaaaaaaa aaaaaaaaa ctcga                     585
```

```
<210> SEQ ID NO 29
<211> LENGTH: 824
<212> TYPE: DNA
<213> ORGANISM: Homo sapiens
<220> FEATURE:
<221> NAME/KEY: SITE
<222> LOCATION: (759)
<223> OTHER INFORMATION: n equals a,t,g, or c
<220> FEATURE:
<221> NAME/KEY: SITE
<222> LOCATION: (791)
<223> OTHER INFORMATION: n equals a,t,g, or c
<220> FEATURE:
<221> NAME/KEY: SITE
<222> LOCATION: (792)
<223> OTHER INFORMATION: n equals a,t,g, or c

<400> SEQUENCE: 29
ggtcgaccca cgcgtccgag agactgggtt tcactgtgtt agcctggatg gtctcgattt      60
tctgatctta tgattcaccc acctctacct cccgaagtgc tgagattatg ggcgtgagca     120
ccgtgactgg cctgtttttt gtttctttaa caaaagtta tggggatttc tatgagtatt      180
gtgttgaatc taaatcacat tcggttatat aatcattgag caatactaat ttttccaatc    240
aatatggatt gtatgtgtat ttatatgttt ttaatcattt tgatcaatgt ttgtagattt    300
caaggtacaa acttctcacc tttatatgtt tattcctaaa tatttcttac tttaagctct    360
ttagcaaatg gaagtggttt ttaattttat tttaaaatta tttaatgtta atgtatggaa    420
attcaactaa tttttggtgc tattattcta ttctgcaaat acactgaata tgtttattag    480
ttccagttgt attttggttg actgtgatat tcttcacaga tcatgtcatc tacaaacaaa    540
taaaatttga cttctttctt tctgaaaaaa aaaaaaaaaa aaaaaaaaaa aaaaaaaaaa    600
aaaaaaaaaa gggcggccgc tctaaaggat ccaagcttac gtacgcgtgc atgcgacgtc    660
atagctctyc tatagtgtca cctaaattca attcactggc cgtcgtttta caacgtcgtg    720
actgggaaaa cctggcgtta cccaacttaa tcgccttgna gcacatcccc ctttcgccag    780
ctggggttat nncgaaaagg ccgcaccgat cggcccttcc ccaa                      824

<210> SEQ ID NO 30
<211> LENGTH: 751
<212> TYPE: DNA
<213> ORGANISM: Homo sapiens

<400> SEQUENCE: 30
ctcgcctcct tgctgcacga tggcctcgct ccgggtggag cgcgccggcg gcccgcgtct      60
ccctaggacc cgagtcgggc ggccggcagc gctccgcctc ctcctcctgc tgggcgctgt     120
cctgaatccc cacgaggccc tggctcagcc tcttcccacc acaggcacac cagggtcaga    180
agggggacg gtgaagaact atgagacagc tgtccaattt tgctggaatc attataagga    240
tcaaatggat cctatcgaaa aggattggtg cgactgggcc atgattagca ggccttatag    300
cacctgcga gattgcctgg agcactttgc agagttgttt gacctgggct tccccaatcc    360
cttggcagag aggatcatct ttgagactca ccagatccac tttgccaact gctccctggt    420
gcagcccacc ttctctgacc cccagagga tgtactcctg gccatgatca tagccccat     480
ctgcctcatc cccttcctca tcactcttgt agtatggagg agtaaagaca gtgaggccca    540
ggcctagggg gccacgagct tctcaacaac catgttactc cacttcccca ccccaccag    600
gcctccctcc tccctcccta ctcccttttc tcactctcat ccccaccaca gatccctgga    660
ttgctgggaa tggaagccag gtgggtcat ggcacaagtt ctgtaatctt caaaataaaa    720
```

```
cttttttttt gtaaaaaaaa aaaaaaaaaa a                              751

<210> SEQ ID NO 31
<211> LENGTH: 817
<212> TYPE: DNA
<213> ORGANISM: Homo sapiens

<400> SEQUENCE: 31
ggcacgaggg cgcctcttca gcttcctgta ccagagcagc cctgaccagg ttatagatgt   60
ggctcccgag cttctgcgta tctgcagcct cattctggca gagactattc agggcctggg  120
tgctgcctca gcccagtttg tgtctcggct gctccctgtg ctgttgagca ccgcccaaga  180
ggcagacccc gaggtgcgaa gcaatgccat cttcgggatg ggcgtgctgg cagagcatgg  240
gggccaccct gcccaggaac acttccccaa gctgctgggg ctccttttc ccctcctggc   300 gcgggagcga catgatcgtg tccgtgacaa catctgtggg gcacttgccc gcctgttgat  360
ggccagtccc accaggaaac cagagcccca ggtgctggct gccctactgc atgccctgcc  420
actgaaggag gacttggagg agtgggtcac cattgggcgc ctcttcagcc tcctgacgtt  480
cctggccaaa cagcacaccg acagctttca agcagctctg ggctcactgc ctgttgacaa  540
ggctcaggag ctccaggctg tactgggcct ctcctagact gcaggctgca gccagtccag  600
agagaataga gcctgcccag gccttaagac cacctctcag cccagttcag ttctgcctta  660
ccaaagattc tgagactcat acccatttgg agccagcccc acttgctgcc ttacagggct  720
gtccctgagg ctggatctgt tacaaatgag tcatgacatc atactgtaat aaaagcagct  780
tgttttctgc ttgaacaata aaaaaaaaa aaaaaaa                            817

<210> SEQ ID NO 32
<211> LENGTH: 1355
<212> TYPE: DNA
<213> ORGANISM: Homo sapiens
<220> FEATURE:
<221> NAME/KEY: SITE
<222> LOCATION: (7)
<223> OTHER INFORMATION: n equals a,t,g, or c
<220> FEATURE:
<221> NAME/KEY: SITE
<222> LOCATION: (12)
<223> OTHER INFORMATION: n equals a,t,g, or c
<220> FEATURE:
<221> NAME/KEY: SITE
<222> LOCATION: (111)
<223> OTHER INFORMATION: n equals a,t,g, or c
<220> FEATURE:
<221> NAME/KEY: SITE
<222> LOCATION: (113)
<223> OTHER INFORMATION: n equals a,t,g, or c
<220> FEATURE:
<221> NAME/KEY: SITE
<222> LOCATION: (1332)
<223> OTHER INFORMATION: n equals a,t,g, or c

<400> SEQUENCE: 32
ggaattngtg ancgattaca atttcaccac aggaaaccag ctatgaccat gattacgcaa   60
agctcgaaat taaccctcac taaagggaac maaagctgga ctccaccscg ntngcggccs  120
ctctagaact agtggatccc ccgsgctkca ggaattcggc acgagatttg ccgccctgtc  180
ttttcctggg ttgggggggtg gcatctgatg gtggcagagt gcctgttggt tcgccgtgg   240 gtctcatggt tcagacagag ggaggtggac ggcagggatc agggagccag gagcgcgcct  300
cagacttgca gcaaccattg tgatttgggt tgttcggaat atttaaatta ctgatcagaa  360
```

```
gatgaaagta gcttttctct tgggaagtct tgcagcccgt gggagtgata ccaggagcaa      420
cacagagctc agcagcggcg ccaaggtgtt ccctgtttcc tcagcacgtg agccttcacc      480
gcctgcttca ttcaggagcc agtgcagcag taatacagtc tatacattgt tctgttttca      540
aatttatcct gaggctttgt tgagcataaa tgattatacg ataaaggtat ccgttatttt      600
ggaactcatt tcagttggga tctcctgtat gcagagtgtt gcatttagag gtttgagtcc      660
catcttggtt tcttgccgtg ctgactgtag ccttcacctt gacttgaatg aaggtctgtg      720
gttggaatgt gtgaggagcc gctgaggtgt tcaggaggtg ctgcctggag gtcggtttct      780
tcctgggtgt tacgggcaac tgctcacaca gttgtttctc tgtgaacatt tccagtgttt      840
aatccaaaat gaaaacccac caatgctttt gctaacttca gtgcctttta taaatcattt      900
ttaaatttcc tgaacttgct ttttgaggat atacagggat attaagtaga cgcaggattg      960 ttttgtttg taaaaattct gaattgaaac tttgttttaa aaaaaggctt ctttctttca     1020
tatgacaaga gataggtcag gaatattgga atcaagattt aaatgttaaa attcgatttt     1080
gttacacagg gtgtgttcat ttgttttgta gcagacaaga tctagatccc agacagaaac     1140
aacacatgct attctaaaaa gccgcatttt aaaaggcacc ttggttctca aaagaaatca     1200
gaatatggat attcgtagtg atgatctgtt ttctctaaaa tcttaccata ttgtctgtat     1260
atggttgtaa attcaaatgg aaagtaaaac gttttggccc tgawaaaaaa aaaaaaaaaa     1320
aaaaaaaaaa tnactgcggt ccgtcaaggg aattc                                1355

<210> SEQ ID NO 33
<211> LENGTH: 536
<212> TYPE: DNA
<213> ORGANISM: Homo sapiens
<220> FEATURE:
<221> NAME/KEY: SITE
<222> LOCATION: (4)
<223> OTHER INFORMATION: n equals a,t,g, or c
<220> FEATURE:
<221> NAME/KEY: SITE
<222> LOCATION: (20)
<223> OTHER INFORMATION: n equals a,t,g, or c

<400> SEQUENCE: 33
cctngctaca aggagctggn agctccaccg cggtggacgg gccgctctag aactagtgga       60
tcccccgggc tgcaggaatt cggcacgagc tcaacatgtg gggattacaa ttcaagatga      120
gatttgggtc aggaaacaga gccaaaccat atcaagagcc tctggtaacc actgttctac      180
tcaatacttc tatgaggtga acttctttgg attccacata tgatcaagat catgaggaag      240
gaggagcaag tcttctttgt catgctatta agaaaatacc cagagtcaca gcaccatgat      300
ctccttgtga agcagaacaa gtaatataaa actgatctaa agaggcctcc cctctactct      360
tatctgtctg gtcgagtcat ttgggtccaa gtgggcacca ttgtggggagg gtgggaggac      420 tcatcactgg gggcccaggc atcattggca tgtggcctcc tgtgttagtt tgttctcatg      480
ctgcaaataa agacaacttg agactggata atttaaaaaa aaaaaaaaaa aaaaaa         536

<210> SEQ ID NO 34
<211> LENGTH: 1123
<212> TYPE: DNA
<213> ORGANISM: Homo sapiens
<220> FEATURE:
<221> NAME/KEY: SITE
<222> LOCATION: (78)
<223> OTHER INFORMATION: n equals a,t,g, or c
<220> FEATURE:
<221> NAME/KEY: SITE
```

<222> LOCATION: (79)
<223> OTHER INFORMATION: n equals a,t,g, or c

<400> SEQUENCE: 34

| | | | | | |
|---|---|---|---|---|---|
| aatccctatg | gtctctaatt | tcagctcttg | ctgtaaactg | caagccaaat | gctctttctc | 60 |
| agaaagagct | atattttnnt | cttcttacag | gcaacccaat | atttatttca | taaagtgtta | 120 |
| taaatattga | gaagatacac | tggggagata | gcatataaaa | atgatgctcc | aaaatgagaa | 180 |
| ttctatatgg | ggctttccct | aagaagaatc | catcccagca | catattttga | aaaggtgctg | 240 |
| aattaaaaag | tacaagagtt | tgctcatata | aatcaagttg | cccaggaaac | ctgaggtgat | 300 |
| gctatcattt | gtctcataat | ttagaaacgt | gatctcttga | gagagagact | acgcattgcc | 360 |
| tgggcacttt | cagattcctt | aggaagtgcc | cctttgatat | ttggaatgtg | gatatattta | 420 |
| taaaacaaat | ggattgttat | tccaaatcca | catggattta | taaccaagcc | ccagaagaat | 480 |
| aggcagcttt | gaaatagcta | gttcgtggaa | ttgaacagaa | ccttgatgga | atgcagttgc | 540 |
| ctgtgtgagg | acagaaaaca | aagaggctgc | ctcagaccas | atgcctatct | agagattaag | 600 |
| tggaatttgt | gagggacatt | ttgtggatgc | cttaaagatg | accagtggtg | ggttctgatg | 660 |
| ggaatatata | cactcatctg | gactaggcca | atggaagcag | tctctttcag | ttcacctccg | 720 |
| tacagcacaa | gttgttcctg | ctcatgacct | cattgaggaa | aatgagaatt | gtggtgctgg | 780 |
| tgactttcat | gtgtcttggg | aggttgaggt | gttcaacatc | gttaaggcac | tcccaaaacg | 840 |
| caaacctcct | tttttaaatg | ccaattgtac | atctacatta | attcatctat | gcaaacttgt | 900 |
| gttttcatgg | tttgttttttt | acactatatt | tctcattagg | ttctttaaac | atcaggttta | 960 |
| atattgatat | tatgaataat | ttttaaacca | aagtattcta | taagtctgtg | tgctttgttt | 1020 |
| tcctggatgg | tttgaccaag | gtaaacatca | gtcttgtcct | tctctcttaa | taaagtcatc | 1080 |
| catttgttaa | gaaaaaaaaa | aaaaaaaaa | aaaaaaact | cga | | 1123 |

<210> SEQ ID NO 35
<211> LENGTH: 587
<212> TYPE: DNA
<213> ORGANISM: Homo sapiens

<400> SEQUENCE: 35

| | | | | | |
|---|---|---|---|---|---|
| gaattcggca | cgagcttctt | tgcaggaagc | ccccccagga | gtttgcatag | tcaatctgtc | 60 |
| atttgaaatc | atttattcag | tttaaagcat | taccatcaga | gagtaagaag | gaatctgttt | 120 |
| ataaggagat | tttagataat | ggggaaaaat | ccagaaaaaa | aatttacaat | aatcttgcta | 180 |
| ctgattataa | catcatctct | tgctgacatt | tctttaaggg | gttagtctag | tatgtcaagc | 240 |
| atatgcagct | gcttggagct | cttgattttt | agaaatgaat | aatacaagag | aaccaactaa | 300 |
| tgttccttag | ctcttcaaac | cagtctagta | cctgcatgaa | aacattggtt | attttggtat | 360 |
| ccagttggag | agcacagggc | catgcagcag | gatttctgaa | atcaaagct | ctcttcctga | 420 |
| aatatatggc | cacaaaggat | gcatttctgg | gatctgatgt | ttcctggctt | attcaaataa | 480 |
| taatgatggt | gttaggaaac | ttttacaact | ataggcctct | tctttctttt | atgctcaatg | 540 |
| cctcgtgccg | aattcgatat | caagcttatc | gataccgtcg | acctcga | | 587 |

<210> SEQ ID NO 36
<211> LENGTH: 842
<212> TYPE: DNA
<213> ORGANISM: Homo sapiens
<220> FEATURE:
<221> NAME/KEY: SITE
<222> LOCATION: (823)

```
<223> OTHER INFORMATION: n equals a,t,g, or c
<220> FEATURE:
<221> NAME/KEY: SITE
<222> LOCATION: (826)
<223> OTHER INFORMATION: n equals a,t,g, or c
<220> FEATURE:
<221> NAME/KEY: SITE
<222> LOCATION: (831)
<223> OTHER INFORMATION: n equals a,t,g, or c
<220> FEATURE:
<221> NAME/KEY: SITE
<222> LOCATION: (832)
<223> OTHER INFORMATION: n equals a,t,g, or c
<220> FEATURE:
<221> NAME/KEY: SITE
<222> LOCATION: (838)
<223> OTHER INFORMATION: n equals a,t,g, or c

<400> SEQUENCE: 36
gttgttagtt gacatgtggt ttgataagtc atttagatac tattgaaggg aaatataagc      60
agcatataca gatttccttg ggaaatctgt ggtattaaat tctttccatg aagattaaaa     120
tcattaaaat gtattttatt tacttaaaat atattttatt gactccagga gtaggcatga     180
atgagacaag atagaatgaa aaacaaaaac agctagccct ctgtcctgtc ttttgctgag     240
gtcctctgac tctctctgag atggaaaagg tgaagggtca agcagcctag ttcaggcaca     300 cgagggact actaatatta catcagttaa aagtkgcaac atttccaagg agaattctac      360
acttagatca gaaaataggc aagagcaggg aakggycata gtttatttg kcacctcatt     420 tkgtccacaa ccaaatgaat ggataattgt ccatgtcggt gttctaagtg ctactcttaa     480
agagcagtta attcagagga gtgttgggtg gactgagata taccttaagt aactaaagca     540
cacctaggaa ccctgacatt cttctgcttt cctaggagaa ggagagtcag agctaacaaa     600
ttaattttaa aaaggctctg aacaagaatt ttatcaaatt accactttga ttttgcctgc     660
taggatgtca taacctagaa tctcatccct aatatataa cagtttagtt taaccgaggc      720 attttttcagc ctatgagacc gaagtgacat ctaacaaact ggtcttatta gaatttgcct    780
gtatgggagg cctcgtgccg ctcgtgccga attcgatatc aanttnaagc nnacctanta    840
ct                                                                   842

<210> SEQ ID NO 37
<211> LENGTH: 953
<212> TYPE: DNA
<213> ORGANISM: Homo sapiens
<220> FEATURE:
<221> NAME/KEY: SITE
<222> LOCATION: (952)
<223> OTHER INFORMATION: n equals a,t,g, or c

<400> SEQUENCE: 37
gaattcggca cgagaacaac ctctgccttg ccccttctcc accttcaggt cccccttccca    60 gatacaataa ttttttagctt tttatttta attattctgg ttgttaccta cataactctg    120
ggcaatatgg aaaagttatt gattttgtat attaatttca taatcagtta ccttgatgaa    180
ttctcttgtt tctagtagtt tttcttagg gttttaaagg gatacaatca taccatttgc     240
agttagtaac catttatctc ctcttatttc caacttcgta ctgttttctc ttgtctaatt    300 tgttttttaat tggtgggtac ttctagaaca aggttaaata aaagtggtgt tggtgggcgt   360
ccttatttct gatattaatg ggaatgagta taatgtataa atatataacc atgattttgg    420
tttttttcca agttttttatc agtaatgatt gctgagtttt atcaaaattt ttttggcatc   480
cattgagagg attatatatt actctttgac acattaatgt ggttaattaa agtaaccaac    540
```

| | |
|---|---|
| ttattaacct tgaaatagtc ttagttaaat aamccctact tgtcaatgct atatcattat | 600 |
| tttaatattg tactgaacat tttacaaagg tgtttcacca taaggcatat tgatctgtaa | 660 |
| tttttttttt tctgttgaac ttgctattgt caggttttgg tgtattatgt tggttttgga | 720 |
| gaataaattt aaaagtttcc tttatgttat ctatacattg cctgaaaaga gtttaaatag | 780 |
| cattgaaaat gatctcttct ttgaagattt aaccaatttc acctgtaaat ctgtctgtgc | 840 |
| tttgtaattt tggtgatact gttgactcaa attccaaaag cagtaaatgc agtgttttat | 900 |
| atttttctat taaaaatgta aaatcaaatt ataaaaaaaa aaaaaaaaaa cnc | 953 |

<210> SEQ ID NO 38
<211> LENGTH: 2211
<212> TYPE: DNA
<213> ORGANISM: Homo sapiens
<220> FEATURE:
<221> NAME/KEY: SITE
<222> LOCATION: (2181)
<223> OTHER INFORMATION: n equals a,t,g, or c

<400> SEQUENCE: 38

| | |
|---|---|
| ggcacaggaa agaagctgtc tccatcttgt ctgtatccgc tgctcttgtg acgttgtgga | 60 |
| gatggggagc gtcctggggc tgtgctccat ggcgagctgg ataccatgtt tgtgtggaag | 120 |
| tgccccgtgt ttgctatgcc gatgctgtcc tagtggaaac aactccactg taactagatt | 180 |
| gatctatgca ctttcttgc ttgttggagt atgtgtagct tgtgtaatgt tgataccagg | 240 |
| aatggaagaa caactgaata agattcctgg attttgtgag aatgagaaag gtgttgtccc | 300 |
| ttgtaacatt ttggttggct ataaagctgt atatcgtttg tgctttggtt tggctatgtt | 360 |
| ctatcttctt ctctctttac taatgatcaa agtgaagagt agcagtgatc ctagagctgc | 420 |
| agtgcacaat ggattttggt tctttaaatt tgctgcagca attgcaatta ttattggggc | 480 |
| attcttcatt ccagaaggaa cttttacaac tgtgtggttt tatgtaggca tggcaggtgc | 540 |
| cttttgtttc atcctcatac aactagtctt acttattgat tttgcacatt catggaatga | 600 |
| atcgtgggtt gaaaaaatgg aagaagggaa ctcgagatgt tggtatgcag ccttgttatc | 660 |
| agctacagct ctgaattatc tgctgtcttt agttgctatc gtcctgttct ttgtctacta | 720 |
| cactcatcca gccagttgtt cagaaaacaa ggcgttcatc agtgtcaaca tgctcctctg | 780 |
| cgttggtgct tctgtaatgt ctatactgcc aaaaatccaa gaatcacaac caagatctgg | 840 |
| tttgttacag tcttcagtaa ttacagtcta cacaatgtat ttgacatggt cagctatgac | 900 |
| caatgaacca gaaacaaatt gcaacccaag tctactaagc ataattggct acaatacaac | 960 |
| aagcactgtc ccaaaggaag ggcagtcagt ccagtggtgg catgctcaag gaattatagg | 1020 |
| actaattctc tttttgttgt gtgtatttta ttccagcatc cgtacttcaa acaatagtca | 1080 |
| ggttaataaa ctgactctaa caagtgatga atctacatta atagaagatg gtggagctag | 1140 |
| aagtgatgga tcactggagg atggggacga tgttcaccga gctgtagata tgaaaggga | 1200 |
| tggtgtcact tacagttatt ccttctttca cttcatgctt ttcctggctt cactttatat | 1260 |
| catgatgacc cttaccaact ggtacaggta tgaaccctct cgtgagatga aagtcagtg | 1320 |
| gacagctgtc tgggtgaaaa tctcttccag ttggattggc atcgtgctgt atgtttggac | 1380 |
| actcgtggca ccacttgttc ttacaaatcg tgattttgac tgagtgagac ttctagcatg | 1440 |
| aaagtcccac tttgattatt gcttatttga aaacagtatt cccaacttttt gtaaagttgt | 1500 |
| gtatgttttt gcttcccatg taacttctcc agtgttctgg catgaattag attttactgc | 1560 |

-continued

```
ttgtcatttt gttattttct taccaagtgc attgatatgt gaagtagaat gaattgcaga   1620
ggaaagtttt atgaatatgg tgatgagtta gtaaagtgg ccaytattgg gcttattctc    1680
tgctctatag ttgtgaaatg aagagtraaa acaaatttgt ttgactattt taaaattata   1740
ttagacctta agctgtttta gcaagcatta aagcaaatga atggctgcct tttgaaatat   1800
ttgatgtgtt gcctggcagg atactgcaaa gaacatggtt tattttaaaa ttttataaaca  1860 agtcacttaa atgccagttg tctgaaaaat cttataaggt tttaccccttg atacggaatt  1920 tacacaggta gggagtgttt agtggacaat agtgtaggtt atggatggag gtgtcggtac   1980
taaattgaat aacgagtaaa taatcttact tgggtagaga tggcctttgc caacaaagtg   2040
aactgttttg gttgttttaa actcatgaag tatgggttca gtggaaatgt ttggaactct   2100
gaaggattta gacaaggttt tgaaaaggat aatcatgggt tagaaggaag tgtttgaaag   2160
tcactttgaa agttagtttt ngggcccaca cggttggctc acccctgtaa t            2211
```

<210> SEQ ID NO 39
<211> LENGTH: 682
<212> TYPE: DNA
<213> ORGANISM: Homo sapiens

<400> SEQUENCE: 39

```
gaattcggca cgaggtgatt cgaaagtctt agaactggga gtgaaggccc acatgggatg    60
cactggctcg gaagggggtg gaggttgctg gagggtggag agaaggagct gccaacctgg   120
tcactgttgt tgctgtatcc aggttgcctc cagtcctgct ccaccacacc atggaccact   180
ccatcccaga tgcctgaagc cactggaggg cagggcaggc agggggggct tcccgccctc   240
ctgcagcaaa gggcaaccac cctcggatga tgggttgcag ccggcctgct gcttaaggtg   300
ggggctgcca tgaggggggc gtgtccagga gggtgaccat gggatggctt atacacacag   360
gcctccttgg agcctcagac tccaagctag gctgaggctc aggcagggcc cacaggcagc   420
cgattctctt gtgctgattt aaatgctgga cacggaggca ggctgtttaa acgctgctta   480
aagtcgcaac tgggccccctt tcaagaaatt ttgctctacc aggaaaacag ttacacattt   540
taagagaaca gagctacgtt ctttgtgaga gcttttcct tgscttgact tgctctttgt    600
cacagactgc ataagttgtc agccttgact atcttttgaa taaagatttg attttaaaca   660
aaaaaaaaaa aaaaaaactc ga                                           682
```

<210> SEQ ID NO 40
<211> LENGTH: 685
<212> TYPE: DNA
<213> ORGANISM: Homo sapiens

<400> SEQUENCE: 40

```
tcgacccacg cgtccgagca gacacaatgg taagaatggt gcctgtcctg ctgtctctgc    60
tgctgcttct gggtcctgct gtcccccagg agaaccaaga tggtcgttac tctctgacct   120
atatctacac tgggctgtcc aagcatgttg aagacgtccc cgcgtttcag gcccttggct   180
cactcaatga cctccagttc tttagataca acagtaaaga caggaagtct cagcccatgg   240
gactctggag acaggtggaa ggaatggagg attggaagca ggacagccaa cttcagaagg   300
ccagggagga catctttatg gagaccctga agacatygt ggagtattac aacgacagta   360
acgggtctca cgtattgcag ggaaggtttg gttgtgagat cgagaataac agaagcagcg   420
gagcattctg gaaatattac tatgatgaa aggactacat tgaattcaac aaagaaatcc   480
cagcctgggt ccccttcgac ccagcagccc agataaccaa gcagaagtgg gatgcctgtc   540
```

```
ttgagtagac ttggacccaa aaaatcatct caccttgagc ccacccccac cccattgtct      600
aatctgtaga agctaataaa taatcatccc tccttgccta gcaaaaaaaa aaaaaaaaa      660 aaaaaaaaaa aaaaaaaaaa aaaaa                                          685
```

<210> SEQ ID NO 41
<211> LENGTH: 550
<212> TYPE: DNA
<213> ORGANISM: Homo sapiens

<400> SEQUENCE: 41

```
gaattcggca cgagggttca gattagaatg ggtctgttta atcagtgtga ttacagtgat       60
ccaagtttgc agttagtttt tttttaatg gctctattcc acattttgtt ttcattaact       120
actttgatca tgtaaaccta taggttaata aatttctccc ccttactgtt cctctttcct      180
ctctaccact ttttttcata attggttttc attctagaat ggaaaagaaa atggtgtagt      240
aacatgagcc atggatttag gggcagaaat atttgggttc ctccgtttat tagtaaagtg      300
tctttggact attgtctcga cctttttaa aaaaaatagg ctatcatttt tactaagatt       360
gtggtgagat ttccatgaaa taatctaggg gaaagacttc atactgttct tcattcttgt      420
gctttactta tcctcaattt tgaaaaatgt ttttaaaaat aaattttatt ggctgggtgc      480
aggctcattg cattgcagcc tttgtgacaa gagcgagacc ctttctcaaa aaaaaaaaa      540 aaaaacacga                                                           550
```

<210> SEQ ID NO 42
<211> LENGTH: 602
<212> TYPE: DNA
<213> ORGANISM: Homo sapiens

<400> SEQUENCE: 42

```
tggatctcca ccgcggtggc ggccgctcta gaactagtgg atccccccggg ctgcaggaat     60 tcggcacgag attgtatcca ggaagtaact aacctgcttt tgattttaca ggctcatagg     120
tggaagggac ttgccttgtc tcagatgaga ctttagactg tggacttttg agttaatgct    180
gaaatgagtt aagactttgg gggactgtta gaaggcatg attggttttg aaatgcgaga    240
tcatgagatt tgggagggggc caggggcaga atgatatggt ttggctgtgt ccccatccga    300
atctcatctt gaatttctgt gtgttgtggg agggacaggt gggaggtcat tgaatgatgg    360
gggcaagtct tttctgtact gttccttgtga tagtgaataa gtctcatgag atctgatggt    420 tttaaaaga ggagtttccc tgctcaagtt ctctctcttt gcctgctgcc atccatgtaa     480
gatgtgactt gctcctcctt gccatctgcc atgatgtgag gcttcccag ccacgtggaa     540 ctgtaagtcc aattaaacct cttttctttg taaattaaaa aaaaaaaaa aaaaaactc       600 ga                                                                   602
```

<210> SEQ ID NO 43
<211> LENGTH: 1627
<212> TYPE: DNA
<213> ORGANISM: Homo sapiens
<220> FEATURE:
<221> NAME/KEY: SITE
<222> LOCATION: (618)
<223> OTHER INFORMATION: n equals a,t,g, or c
<220> FEATURE:
<221> NAME/KEY: SITE
<222> LOCATION: (627)
<223> OTHER INFORMATION: n equals a,t,g, or c

```
<400> SEQUENCE: 43
agctgtgaca gtgcgggcgg ccttgttccg ctccagtctg gccgagttca tttccgagcg      60
ggtggaggtg gtgtccccac tgagctcttg aagagagtg gttgaaggcc tttcactgtt     120
gggacttggg agtatctccg tattctggag cagtatttca tggaaactcc attaaataaa    180
tatacctctt tcatttccta attgactatg ctgaattggt gtttatgata actgrtgcac    240
tcactgctat tgcccctgtat tttgcaatcc aggacttcaa taaagttgtg tttaaaaagc    300
agaaactcct sctagaactg gaccagtatg ccccagatgt ggccgaactc atccggaccc    360
ctatggaaat gcgttacatc cctttgaaag tggccctgtt ctatctctta aatccttaca    420
cgattttgtc ttgtgttgcc aagtctacct gtgccatcaa caacaccctc attgctttct    480
tcattttgac tacgataaaa ggcagtgctt tcctcagtgc tatttttctt gccttagcga    540
cataccagtc tctgtaccca ctcaccttgt ttgtcccagg actcctctat ctcctccagc    600
ggcagtacat acctgtgnaa aatgaangag caaagccttc tggatctttt cttgggagta    660
tgccatgatg tatgtgggaa gcctagtggt aatcatttgc ctctccttct tccttctcag    720
ctcttgggat ttcatccccg cagtctatgg ctttatactt tctgttccag atctcactcc    780
aaacattggt cttttctggt acttcttttgc agagatgttt gagcacttca gcctcttctt    840
tgtatgtgtg tttcagatca acgtcttctt ctacaccatc cccttagcca taaagctaaa    900
ggagcacccc atcttcttca tgtttatcca gatcgctgtc atcgccatct ttaagtccta    960
cccgacagtg ggggacgtgg cgctctacat ggccttcttc cccgtgtgga accatctcta   1020
cagattcctg agaaacatct ttgtcctcac ctgcatcatc atcgtctgtt ccctgctctt   1080
ccctgtcctg tggcacctct ggatttatgc aggaagtgcc aactctaatt tcttttatgc   1140
catcacactg accttcaacg ttgggcagat cctgctcatc tctgattact tctatgcctt   1200
cctgcggcgg gagtactacc tcacacatgg cctctacttg accgccaagg atggcacaga   1260
ggccatgctc gtgctcaagt aggcctggct ggcacagggc tgcatggacc tcaggggggct   1320 gtggggccag aagctgggcc aagccctcca gccagagttg ccagcaggcg agtgcttggg   1380
cagaagaggt tcgagtccag ggtcacaagt ctctggtacc aaaagggacc catggctgac   1440
tgacagcaag gcctatgggg aagaactggg agctcccccaa cttggacccc caccttgtgc   1500
tctgcacacc aaggagcccc ctcccagaca ggaaggagaa gaggcaggtg agcagggctt   1560
gttagattgt ggctacttaa taaatgtttt ttgttatgaa gtctaaaaaa aaaaaaaag   1620 ggcggcc                                                              1627

<210> SEQ ID NO 44
<211> LENGTH: 1457
<212> TYPE: DNA
<213> ORGANISM: Homo sapiens
<220> FEATURE:
<221> NAME/KEY: SITE
<222> LOCATION: (879)
<223> OTHER INFORMATION: n equals a,t,g, or c
<220> FEATURE:
<221> NAME/KEY: SITE
<222> LOCATION: (1397)
<223> OTHER INFORMATION: n equals a,t,g, or c
<220> FEATURE:
<221> NAME/KEY: SITE
<222> LOCATION: (1425)
<223> OTHER INFORMATION: n equals a,t,g, or c
<220> FEATURE:
<221> NAME/KEY: SITE
<222> LOCATION: (1448)
<223> OTHER INFORMATION: n equals a,t,g, or c
```

```
<220> FEATURE:
<221> NAME/KEY: SITE
<222> LOCATION: (1455)
<223> OTHER INFORMATION: n equals a,t,g, or c

<400> SEQUENCE: 44
ctgatcccct gctcatcaat gacttcaagg atgtgacgca cacatgcccc agctgcaaag      60
ctacatctac acgtacaagc gcctgtgcta acggagctgg gactcgggac tccccgcct     120 gtcagtctgg cccctgtgc tttgctccct gygctcagtg gtcactttcc cgctcccact     180
tggggctggg agccgtgcca ccatccccta gaagtcctgt cctcttcacc ctgccctacc     240
tgagccgctg actcttctgg caaaaattct gttgggattt aaggccaagg gtcagtgggt     300 ggcaggggc tgrcaatgag cttgtgtgtt gttggtctgc ttggtgtgtg tgatcgggaa     360
gataagctgg gagggtctc ctgctgggt cctgatgcct ctgtttccaa acaaggtaca     420
ggttcagtcc agactctttc cccctgggac aacagcagc cagagcagtt agccagttag     480
tccccaggcc tgtggcacag gcgttttctg acctgctggg ccgagaatgg gtaagttgtc     540
tggagtcagg tgggcccacg taggacaggg tcacaaagcc tgggtttgtt tctgggtact     600
ttgcgcctct ggggtgctag aggtggggca tggtggctgg aagtaaaact gccaactytg     660
gccctcagaa ctctcaggta tagaagccca ggatgtctaa taccctgtcc cagtgcccga     720
ragctgcctg gtgtcaggta gagaggacac tgtacctggg tgaatgatca gaccctggta     780
gctaagaagg aacttgtccc tttgagtcag tgtgcagacc cccttcagg ccatgcctct     840 gtgaaccctg tattgctggg gccggaagga gcccctgang cctagcccct tcccgtctgc     900
cctgtgtcct cactgcgtgt gggtatgacc tctgcctggt ggctggtgta tcccaactgg     960
gcaagagatg gcagagggtc cccttgtgg gtgcgcttgg atgtgcagag ccttctccat    1020
ggattttctt ccctgtaagt gccgggcccc tcaccccagc tgacaggctg ttgctgtgcc    1080
tgctcacacc tgctcctgca ggcacactgg gctaggacg aggaaggagc agccacaagt    1140
ggtagaactg ccttggtgga caccagcctc gccctgtctt tatttcctga atggtttgtg    1200
aacttgctca cctggaccac tgtatcctgc cactgtcctt cctggtctcg cactgccact    1260
gcatggcctc ctgtcactgt gaatcgtggc ccagtctcag tttgtagttt ctcattaaat    1320 tggcccttc actccccgc aaaaaaaaa aaaaaaaac tcgagggggg gcccggtacc    1380
caatcgccct atatgantcg tattacaatt catggccgtc gtttnacaaa gtcgtgactg    1440
gggaaaanct ggcgnta                                                  1457

<210> SEQ ID NO 45
<211> LENGTH: 888
<212> TYPE: DNA
<213> ORGANISM: Homo sapiens

<400> SEQUENCE: 45
gaattcggca cgagacagag tgtgggatag atcatatatg catccacagg cactgtgtcc      60
atataaccat cttgaatagt aattgctcac ctgcattttg taacaagagg ggcatctgca     120
acaataaaca tcactgccat tgcaattatc tgtgggaccc tcccaactgc ctgataaaag     180
gctatggagg tagtgttgac agtggcccac cccctaagag aaagaagaaa agaagttct     240 gttatctgtg tatattgttg cttattgttt tgtttatttt attatgttgt ctttatcgac     300
tttgtaaaaa aagtaaacca wtaaaaaagc agcaagrtgt tcaaactcca tctgcaaaag     360
aagaggaaaa aattcagcgt cgacctcatg agttacctcc ccagagtcaa ccttgggtga     420
```

```
tgccttccca gagtcaacct cctgtgacgc cttcccagag tcatcctcag gtgatgcctt      480
cccagagtca acctcctgtg caccctccc agagtcaacc tcgggtgatg ccttctcaga       540
gtcaacctcc tgtgatgcct tcccagagtc atcctcagtt gacgccttcc cagagtcaac      600
ctcctgtgac accctcccag aggcaacctc agttgatgcc ttcccagagt caacctcctg      660
tgacgccctc ctagagccaa cctcagttga tgccttccca gagtcaacct cctgtgacgc      720
cctcccagag ccaacctcgg gtgacaccct cccagagtca acctcatgtg acaccttacc      780
ggagtaaaag tggtaaacaa aagcaatcag taccaattcc aaaaactgta tccagaaaag      840
gtacattaaa aaataattc ctaaaaaaaa aaaaaaaaa aaactcga                     888

<210> SEQ ID NO 46
<211> LENGTH: 752
<212> TYPE: DNA
<213> ORGANISM: Homo sapiens

<400> SEQUENCE: 46
gaattcggca cgaggaaaaa cccaaggaac cagatagaac cagtgtccct gtgactccac       60
ccactcatct ggccaccgtt gccctgacct gccaggagcc tggagaagat gaaggcatcc      120
gtggttctct ccctccttgg ctacctggtg gttccaagtg gtgcttacat cttggggcgt      180
tgcacagtgg ctaagaaact ccacgatgga ggcctggatt attttgaggg ctatagcctt      240
gagaactggg tgtgcctggc ctacttcgag agcaagttca accccatggc catctacgag      300
aacacacgtg agggctamac tggctttggc ctctttcaga tgcgtggcag tgactggtgt      360
ggcgaccatg gcaggaaccg ctgccatatg tcatgttccg ctttactgaa tcctaattta      420
gagaagacaa ttaaatgtgc caagaccatt gtaaaggaa agaagggat gggagcatgg       480 cccacctggt cccggtactg ccagtactcc gatacctgg cacggtggct ggatggttgc       540
aagctgtagc ckcctgcatg gccctgcag cactcaccag ttgcatcttg tgaatgaagg       600
tgcttttctg cttgctgctt cagtcaatcc ttttgatgat ctcaccactt taagagttcc      660
agatggaaaa agacaaaagt ttgcttcatc cggggatgca ggatgcagaa taaaccaaac      720
tagttactca aaaaaaaaa aaaaaactc ga                                      752

<210> SEQ ID NO 47
<211> LENGTH: 1788
<212> TYPE: DNA
<213> ORGANISM: Homo sapiens
<220> FEATURE:
<221> NAME/KEY: SITE
<222> LOCATION: (12)
<223> OTHER INFORMATION: n equals a,t,g, or c
<220> FEATURE:
<221> NAME/KEY: SITE
<222> LOCATION: (1490)
<223> OTHER INFORMATION: n equals a,t,g, or c

<400> SEQUENCE: 47
gtatgttcct gnattttatt ctctaaattg tactcaattt catggtaatt acatgaagaa       60
gttacctgca attattctta acactacatg gtaattcact gggtaattgt gggtcattta      120
tttcctgaag tcacgtgaaa tccttagctg gttgaatgtt gcacagtatt tgagaattac      180
ggtttgaagt gatttctgtg ggagggaatc attgcaatgt atattctaaa taagtcatc       240 taactattaa aaaaaaaaca cccttcctaa cccttctttt cttaaaattc cacattcatc      300
cacaatctca tccctttgta gaaattcttg cctgaattct caccaagttt tgaattccta      360
aggtagcccc gatctaggat gtgaaggctg cccagaaaaa gtttatggct ggaggagtat      420
```

```
catacagtgt ctacatatga tagtacttac agattaggtc ttkggatgct ttaacacaaa      480
agatttttgt tatccttatt agtcaaataa cgctattctt ttgtggttct agaccctggc      540
ttctatctcc ctgtgatttg ttttaatgct gaaatgactt ggctatccaa agcttctagt      600
ctagaggtct gttggttgaa ggcagacatt ccaagtttg ttgaaataat acgaagctga       660
ctagcttacg tgaatgatgt tgccctcatt tgttttgggt gaggactcat tactgcagta      720
tattgatctc ttcaccaaat gctttttcty tttctgaata aatgctgtat tagaggttct      780
atttatatat gatttttaaa actttggttt ccttctatcc accaaatact gtgaattgtt      840
tttccattta tttttcttag ctaatgtaac tttattcttc actttttttt agccctagac      900
ttcctagatt ttctgtggca ttctgtagga cattgtattg cttggaaaaa aaagatcaa       960 aatcattckg gggcaaakgc tctattatcc ttatttatga caagagaata atgaaattca     1020
taagaaatta ataacattca gatattgcta taaatgtact tgagtcattt tcatttgggg     1080
atagtaataa tggctgtggc agctttaatg gagaaacctg tgttggcctc tttttctggc     1140
attaggatct cttgtcatag aactattggt aaagtacagg tttgatagca gagttcctga     1200
attcagcata tcatcagaat ttccatttac cttttgtctt ttcttttat kgtattttt      1260 aacctttttg tttctattcc tacctcccat gagtaacatt gatttctgct gaagttagaa     1320
tttgtgttaa gaattgactt taaacttctg aaatagttga atattagaag tggcttcagt     1380
tgccatgaaa tgattgcttt tcttttttctt tttttttcct taaataaaaa taatgcagcc    1440
ttatatatgt ctcttcccct caagaatgtg aatttaggct gggcatagtn actcacgcct     1500
gtaatcccag acctttggga ggctgacacg ggaagattgc ttgagcccag gaatttcaga     1560
ccagcctggg caacacagga agactccatc tctacttaaa atattttgt tttttagcca      1620 ggtgtggtgg tatgtgcctg tagtcccagc tacttgggag gctgaggtgg gaggatcact     1680
tgaacccagg agtttgggt gcagtgagct atgattgcga cactgcactc cagcctgggc      1740
aacagagcaa gaccctgtct caaaaaaaaa aaaaaaaaa aaactcga                   1788
```

<210> SEQ ID NO 48
<211> LENGTH: 660
<212> TYPE: DNA
<213> ORGANISM: Homo sapiens
<220> FEATURE:
<221> NAME/KEY: SITE
<222> LOCATION: (393)
<223> OTHER INFORMATION: n equals a,t,g, or c
<220> FEATURE:
<221> NAME/KEY: SITE
<222> LOCATION: (401)
<223> OTHER INFORMATION: n equals a,t,g, or c

<400> SEQUENCE: 48

```
gaattcggca cgaggagatg cacatggccc tgaacaacca ggccaccggg ctcctgaacc       60
tcaagaagga catccggggc gtgctggacc agatggagga catccagctg gagattctca      120
gggagcgggc ccagtgccgc actcgagcca ggaaggagaa gcagatggca agcatgtcga      180
aagggaggcc aaagctggga agytccaagg gcctggcagg ccagctctgg ctgctgaccc      240
tgaggctgct gctgggcgcc ctgctggtct ggaccgytgc ctacgtgtac gtggtgaacc      300 ccacacctt cgagggctg gtgccamccc tgctgagccg tgccaccgty tggaagctcc       360
gggccctgct ggaccccttc ctgcgcctca aantgacgg nttcctgccc ttctaggcca      420
raggcccagc ggcccagca aggaggccag gcgaccagca ctgccccgga tgcccagtgg      480
```

```
ccgtgccagc cccctgcaca tggcaccact gtgcaccatc cttgccagaa gctgcagaga    540
agggtggagg tggggtctgt cctgagggct gggcctgtgg ctggacatag agtcatgaca    600
taaaaaaaaa aaaaaaaaaa aaaaaaaaaa aaaaaaaaaa aaaaaaaaaa aaaaactcga    660
```

<210> SEQ ID NO 49
<211> LENGTH: 1321
<212> TYPE: DNA
<213> ORGANISM: Homo sapiens

<400> SEQUENCE: 49

```
ccggatcacc aggtcaggag atcgagacca tcctagctaa cacagtgaaa tcctgtctct     60
actaaaaata caaaacttat ccaggcatgg tggtgcatgc ctgtaatccc agctactcag    120
gaggctgagg caggagaata gcttgaacct gggaggtgga gattgcaatg agatgacatc    180
gccccactgc actccagcct ggcgacagag caagactcca tctcaaaaaa agaaaaagt    240 catttggaag agatatgtgt agtgttgttc tgttaaaaga ctgtccactg ttttcttttt    300
cagtaattaa tggtcacaca ctgtgtttac ggctgttgct agaaattgca gacaacccgg    360
aggcggtcga tgtgaaagat gccaaaggac aaacaccact gatgcttgca gtagcatatg    420
gacatattga cgctgtttca ttgttacttg aaaaggaagc caacgtagac actgttgaca    480
tcctaggatg cacagcttta cacagagggg tatgtcatc tttctcagct ctagtcaagc    540
aattttttta atgagcttgt tttctttttt agcaaacaat tacaaagggc ctactttgat    600 tggatttta gcaaaaaatg tttagcaaaa attgtttcct aatacaacca attaaccttta   660 ttcagtccaa agaaattac aaaatccttg gcaaaggcaa ataatggaa ggttttgctc     720 ttaagatttc atgttagatt gtgataatag atgcatgaac acctactgct ggtgaaattg    780
gttctgcttt ctgactacaa aatacaagta tatcatagaa aatttgcaga atattttttt    840
ttaaagccca gagaagaaaa tcacaatcac cagtaatcat acctcctgga gataaccact    900
atttgatgta tattatctcc aatcttttttt ctatatatag atttgtttta gattttaaaa    960
agagaatact gaagatatca tttggattct gcttttttct cttagtatat caaggatctt   1020
ttttcatttc atttttttct gcatcatgat ttttaatgcc tcattgtgtt caagtgtcat   1080
agtttatttc aatgattacc tggttttcag tagttatgca atttctaatt gtttgtcctt   1140
acaaataatg ccaaaatatg tatcctgtgg gcaattattt gcacacatct gttgaagtgt   1200
ttggtttttt ttttttttaat ctcactctta tcacccaggt tgcagtgagc cgagatcaca   1260
ccactgcatt ccagcctggg tgacacagcg agactccatc tcaaaaaaaa aaaaaaaaaa   1320
a                                                                   1321
```

<210> SEQ ID NO 50
<211> LENGTH: 548
<212> TYPE: DNA
<213> ORGANISM: Homo sapiens
<220> FEATURE:
<221> NAME/KEY: SITE
<222> LOCATION: (10)
<223> OTHER INFORMATION: n equals a,t,g, or c
<220> FEATURE:
<221> NAME/KEY: SITE
<222> LOCATION: (14)
<223> OTHER INFORMATION: n equals a,t,g, or c
<220> FEATURE:
<221> NAME/KEY: SITE
<222> LOCATION: (27)
<223> OTHER INFORMATION: n equals a,t,g, or c
<220> FEATURE:
<221> NAME/KEY: SITE

```
<222> LOCATION: (68)
<223> OTHER INFORMATION: n equals a,t,g, or c
<220> FEATURE:
<221> NAME/KEY: SITE
<222> LOCATION: (533)
<223> OTHER INFORMATION: n equals a,t,g, or c
<220> FEATURE:
<221> NAME/KEY: SITE
<222> LOCATION: (539)
<223> OTHER INFORMATION: n equals a,t,g, or c

<400> SEQUENCE: 50
ctcgaaattn accntcacta aagggancaa aagctggagc tccaccgcgg tggcggccgc      60
tctagaanta gtggatcccc cgggctgcag gaattcggca cgagcggaat ttgcggcttt     120
ggcagattga aatcatggca ggtccagaaa gtgatgcgca ataccagttc actggtatta    180
aaaaatattt caactcttat actctcacag gtagaatgaa ctgtgtactg ccacatatg     240 gaagcattgc attgattgtc ttatatttca agtaaggtc caaaaaaact ccagctgtga     300
aagcaacata aatggatttt aaactgtcta cggttcttaa cctcatctgt taagttccca    360
tgcctggaga agctaatgcc aactcatcat gtgataattc aatttgtaca ataaattatg    420
aacctggaaa aaaaaaaaaa aaaaaactc gaggggggc ccsgtacccm attsgccctt    480
gkgrgkcgtt twccattcat ggcctsgttt tacaacgtcg tgactgggga aanccctggng   540 ttacccaa                                                              548

<210> SEQ ID NO 51
<211> LENGTH: 658
<212> TYPE: DNA
<213> ORGANISM: Homo sapiens

<400> SEQUENCE: 51
ggtcgaccca cgcgtccgtt ttctagtcta tgcataaact agaagaatgt gagaaaagac     60
tattttcagt tgctcatgtt tacctggatg aactagttta atttttgtct tttaaaacag    120
acatatttat tttaaaatta aaatagcttg aaattttaaa atacacccca agcaagatg     180 atcgtttaag ttaagttaaa caatacaatg aatggtcttt tattttggt gatgattgcc     240 aaaaacctct tgccttcagg aaataagcaa taaacctgat gaattgggca tagttgaggg    300
ggaaaataaa aatcaatggc ttctatttaa aaaacagt atgtaatatc taaaaaagaa    360
aggcattgtt tctgaattgg ggtgaatgta ccaaacatat accaaaagga aggcattttg    420
ttagaaaatt tgattaatta ttagaatctt cctgactgga gatgtaaatt atcttgtttt    480
aaatctaact cactctaatt tggttttaat gttgactgta atccaggctg tttctgggga    540
caacagaaca caatatacct ctttattcaa accacacaat cttggccagc tattccctac    600
tccagcctga atgacagaaa gagaccttgt ctcgaaaaaa aaaaaaaaa gggcggcc       658

<210> SEQ ID NO 52
<211> LENGTH: 622
<212> TYPE: DNA
<213> ORGANISM: Homo sapiens

<400> SEQUENCE: 52
ggtcgaccca cgcgtccgtt ctcatcatgt tatgggtgaa acaaggaga gaagagctgc      60 ggcccttcgg ggaaccgaga cctggaagct ccctgaggca gggctgtgac tccctctttg    120
gacctcttaa gttcctggag tctcaagctt ccagccgcca ccatgttccc tggtggcagc    180
tgtggaagct gcttctggtg tgcctggtcc agctgcagcc ttgcagagag ccggcaccca   240
```

```
tgcagacacc ttgtgctggc tgccccgctg cagcagctgg ggtgcctcac tgtgtgcagt    300
ggctggaccc catgctcact tgctcacaca cccctcactg ctccacacct ggcttgccgt    360
tggcagtgat gggatccagg ctggtagcgt gagctgagca cagcctgctc aagccaaatg    420
gatggaacaa acccagtggg ccagagcaga actcaggcaa aggtgccacc agccacagag    480
gcttctggsc agaaaagcaa caccctgagg atcctgcaac agtagtttta caaagtgttt    540
attttgtcat ataaaaatct ggttttttaat atttgcaaaa ataaaagtaa ggatgaaaaa    600
aaaaaaaaaa aaagggcgg cc                                              622
```

<210> SEQ ID NO 53
<211> LENGTH: 723
<212> TYPE: DNA
<213> ORGANISM: Homo sapiens

<400> SEQUENCE: 53

```
gggcgaccca cgcgtccgct cagcctttgt tgagagtgct gtgccccaaa tctggttggc     60
ttattctagg cattcgagtc tcttcccaaa taccaccttc tcaagtgcag cttttcctta    120
ctacttaatt ttatagtccc ccatcaatgt acgatgttac cctcttttcc ttcattgaga    180
gtgtttgtaa ttttttttttg tctgcttgtt tattgtcttt ttgccccata agtccaaggt    240
ttacatgaac agggaacttg tctgttttgt ttattactgt atcccctatg ctggcacata    300
ctatgtaata agtgtttgtt gagtgcatga gtgaataacc attctaaaaa actctgatgt    360
ttaaagccct ttgctttata taagaatttt acttggaacc ctggtatttt cgtttgtatt    420
tgtttgttaa taaatgtcaa gagttcagta gtaagatagg tttcagaaat gctaagttaa    480
acagaataaa gaaagaatat gtattacagg tcctggcaga gccttgaata tgctaacatt    540
tgacagtggg agtctttgag aattatcaca tgaagctgct gtacattaca acacattcta    600
ggaaatgctg tcttagacaa aaacctgtca tattagaatt ggggtaaggg gcacgatact    660
gaccgtgagg cagcagattc ctatggacta cattaaaaaa aaaaaaaaaa aaaagggcg    720 gcc                                                                  723
```

<210> SEQ ID NO 54
<211> LENGTH: 908
<212> TYPE: DNA
<213> ORGANISM: Homo sapiens
<220> FEATURE:
<221> NAME/KEY: SITE
<222> LOCATION: (361)
<223> OTHER INFORMATION: n equals a,t,g, or c

<400> SEQUENCE: 54

```
gaattcggca gaggggaggc ctgccctgcc cttcctcctg cagagagcca ggttcacagc     60
agggcgkcct gcaggacatt agcatgccta gtagatacac agtgtcgttg gggcgtgggc    120
attttgwttt ctgttccttc tttttcccta tttaactatc atgtttgggg acctttgcct    180
ctcaattttt aagagattaa aaaaaaatga grgcggcctt tattatacac tacatgtgtt    240
ttctcccagt ttgtcagttg tcttttgcct ttttggtaat tttgccaggt acttatgtca    300
acttgcatta agatgtcccc ttattaataa agtaatttg ctctcattgt atgcaattaa    360
nagaatacta aaatttctaa tgatcctacc acttaaagct gtataaacgc tgctaacata    420
ccaggtatcc cattccaggc ttgcttgtat gtgtatatat attaatattt atctgtagct    480
gtatgtctgk gacactctaa attattaaaa atttgtccca gtggcttaca aattttttt    540 tgtagtagca gcagctttta aaaaatacaa atcttagcat agttaacaga aaaaagagt    600
```

```
tgctccggtt aaggtagatt ctaatcccca ccagggcccc tgagacatgt ccttaaattg      660
ctacaaaatg tacaacaaac cactagtaaa gtttattcta tttgataact ctgtttgctt      720
ttaaaaactt catgtatagt gattattttc ctgttattct gtattcttca cctgcttcat      780
atttagtgac tgccaagtat tctattgtat gtttatgaca caagtaattt aactattttc      840
ttatcattga acatttacat ttgtatatac ttttactgtt ttgccaaaaa aaaaaaaaa       900 aaactcga                                                              908

<210> SEQ ID NO 55
<211> LENGTH: 822
<212> TYPE: DNA
<213> ORGANISM: Homo sapiens
<220> FEATURE:
<221> NAME/KEY: SITE
<222> LOCATION: (813)
<223> OTHER INFORMATION: n equals a,t,g, or c
<220> FEATURE:
<221> NAME/KEY: SITE
<222> LOCATION: (817)
<223> OTHER INFORMATION: n equals a,t,g, or c
<220> FEATURE:
<221> NAME/KEY: SITE
<222> LOCATION: (822)
<223> OTHER INFORMATION: n equals a,t,g, or c

<400> SEQUENCE: 55
tcgatccacg cgtccgcgga cgcgtggrgt tgaaaattca tagtaagatt gatatctata       60
aaatagatat aaattttaa gagaaagaat ttagtattat caaagggata agaaaaaaa        120 tactatttaa gatgtgaaaa ttacagtcca aaatactgtt ctttccaggc tatgtataaa      180
atacatagtg aaaattgttt agtgatatta catttattta tccagaaaac tgtgattca      240 ggagaaccta acatgctggt gaatattttc aacttttttcc ctcactaatt ggtactttta     300 aaacataac ataaattttt tgaagtcttt aataaatamc ccataattga agtgtataat      360
ataaaaaatt ttaaaaatct aagcagctta ttgtttctct gaaagtgtgt gtagttttac     420
tttcctaagg aattaccaag aatatccttt aaaatttaaa aggatggcaa gttgcatcag     480
aaagctttat tttgagatgt aaaaagattc ccaaacgtgg ttacattagc cattcatgta     540
tgtcagaagt gcagaattgg ggcacttaat ggtcaccttg taacagtttt gtgtaactcc     600
cagtgatgct gtacacatat ttgaagggtc tttctcaaag aaatattaag catgttttgt     660
tgctcagtgt ttttgtgaat tgcttggttg taattaaatt ctgagcctga tattgatatg     720
gttttaagaa gcagttgtac caagtgaaat tattttggag attataataa atatatacat     780
tcaaaaaaaa aaaaaaaaaa aaaaaaaaaa aanaagnaaa gn                        822

<210> SEQ ID NO 56
<211> LENGTH: 1951
<212> TYPE: DNA
<213> ORGANISM: Homo sapiens
<220> FEATURE:
<221> NAME/KEY: SITE
<222> LOCATION: (28)
<223> OTHER INFORMATION: n equals a,t,g, or c
<220> FEATURE:
<221> NAME/KEY: SITE
<222> LOCATION: (1636)
<223> OTHER INFORMATION: n equals a,t,g, or c
<220> FEATURE:
<221> NAME/KEY: SITE
<222> LOCATION: (1947)
<223> OTHER INFORMATION: n equals a,t,g, or c
<220> FEATURE:
```

<221> NAME/KEY: SITE
<222> LOCATION: (1951)
<223> OTHER INFORMATION: n equals a,t,g, or c

<400> SEQUENCE: 56

| | | | | |
|---|---|---|---|---|
| ggccctgggc | tcgcggcggt | gccgsggngg | atggcgggag | ccggagctgg | agccggagct | 60 |
| cgcggcggac | ggcggcgggg | gtcgaggctc | gagctcgcga | tccaccgccc | gcgcaccgcg | 120 |
| cacatcctcg | ccaccctcgg | cctgcggctc | agccctcggc | ccgcagatgg | atggcgggtc | 180 |
| aggggggcctg | gggtctgggg | acaacgcccc | gaccactgag | gctcttttcg | tggcactggg | 240 |
| cgcggccgtg | acggcgctca | gcatcccctg | ctctacgtga | agctgctcat | ccaggtgggt | 300 |
| catgagccga | tgcccccac | ccttgggacc | aatgtgctgg | ggaggaaggt | cctctatctg | 360 |
| ccgagcttct | tcacctacgc | caagtacatc | gtgcaagtgg | atggtaagat | agggctgttc | 420 |
| cgaggcctga | gtccccggct | gatgtccaac | gccctctcta | ctgtgactcg | gggtagcatg | 480 |
| aagaaggttt | tccctccaga | tgagattgag | caggtttcca | acaaggatga | tatgaagact | 540 |
| tccctgaaga | aagttgtgaa | ggagacctcc | tacgagatga | tgatgcagtg | tgtgtcccgc | 600 |
| atgttggccc | accccctgca | tgtcatctca | atgcgctgca | tggtccagtt | tgtgggacgg | 660 |
| gaggccaagt | acagtggtgt | gctgagctcc | attgggaaga | ttttcaaaga | ggaagggctg | 720 |
| ctgggattct | tcgttggatt | aatccctcac | ctcctgggcg | atgtggtttt | cttgtggggc | 780 |
| tgtaacctgc | tggcccactt | catcaatgcc | tacctggtgg | atgacagcgt | gagtgacacc | 840 |
| ccaggggggc | tgggaaacga | ccagaatcca | ggttcccagt | tcagccaggc | cctggccatc | 900 |
| cggagctata | ccaagttcgt | gatggggatt | gcagtgagca | tgctgaccta | ccccttcctg | 960 |
| ctagttggcg | acctcatggc | tgtgaacaac | tgcgggctgc | aagctgggct | cccccccttac | 1020 |
| tccccagtgt | tcaaatcctg | gattcactgc | tggaagtacc | tgagtgtgca | gggccagctc | 1080 |
| ttccgaggct | ccagcctgct | tttccgccgg | gtgtcatcag | gatcatgctt | tgccctggag | 1140 |
| taacctgaat | catctaaaaa | acacggtctc | aacctggcca | ccgtgggtga | ggcctgacca | 1200 |
| ccttgggaca | cctgcaagac | gactccaacc | caacaacaac | cagatgtgct | ccagcccagc | 1260 |
| cgggcttcag | ttccatattt | gccatgtgtc | tgtccagatg | tggggttgag | cggggtgggg | 1320 |
| gctgcaccca | gtggattggg | tcacccggca | gacctaggga | aggtgaggcg | aggtggggag | 1380 |
| ttggcagaat | ccccataccct | cgcagatttg | ctgagtctgt | cttgtgcaga | gggccagaga | 1440 |
| atggcttatg | ggggcccagg | ttggatgggg | aaaggctaat | ggggtcagac | cccacccgt | 1500 |
| ctaccctcc | agtcagccca | gcgcccatcc | tgcagctcag | ctgggagcat | cattctcctg | 1560 |
| ctttgtacat | agggtgtggt | cccctggcac | gtggccacca | tcatgtctag | gcctatgcta | 1620 |
| ggaggcaaat | ggccangctc | tgcctgtgtt | tttctcaaca | ctacttttct | gatatgaggg | 1680 |
| cagcacctgc | ctctgaatgg | gaaatcatgc | aactactcag | aatgtgtcct | cctcatctaa | 1740 |
| tgctcatctg | tttaatggtg | atgcctcgcg | tacaggatct | ggttacctgt | gcagttgtga | 1800 |
| atacccagag | gttgggcaga | tcagtgtctc | tagtcctacc | cagtttttaaa | gttcatggta | 1860 |
| agatttgacc | tcatctcccg | caaataaatg | tattggtgat | ttggaaaaaa | aaaaaaaaa | 1920 |
| aaaaaaaaaa | aaaaaaaaaa | gggggnccc | n | | | 1951 |

<210> SEQ ID NO 57
<211> LENGTH: 663
<212> TYPE: DNA
<213> ORGANISM: Homo sapiens
<220> FEATURE:
<221> NAME/KEY: SITE
<222> LOCATION: (43)
<223> OTHER INFORMATION: n equals a,t,g, or c
<220> FEATURE:
<221> NAME/KEY: SITE
<222> LOCATION: (64)
<223> OTHER INFORMATION: n equals a,t,g, or c

<400> SEQUENCE: 57

| | | | | | |
|---|---|---|---|---|---|
| ccaatcggct | aattcaactc | acatagtagg | gaaacgtggt | acnccctgca | ggtacccggt | 60 |
| ccgnaattcc | cgggtcgacc | cacgcgtccg | gctattgtaa | tcttttctac | ctatacttct | 120 |
| tcattggctc | agaatgaagc | aaggcatgtg | ctgctttctt | atatgtcatt | tatgccataa | 180 |
| atcccattgt | tagaaggtaa | tgcttctaac | ggattccatt | catgcttttg | agataaatgg | 240 |
| cattgacttt | catattgatc | acatggaaag | ctgttacctg | attcctttcc | tgagatcact | 300 |
| tccagcctaa | tgtgcatttg | gctggaatat | ggttgtctca | gaataacatc | atgcactcgg | 360 |
| gcttttatac | ttctgccttt | aggggactgt | ggcagcatgg | catgggtcaa | gaagtacttc | 420 |
| tccttcatct | tccttttgatg | tcggtaactc | atcctttctg | cactgcggga | gttgttaatg | 480 |
| cttttgtgtc | ctccagttca | catgctgatt | gctaagaaga | aaatgagcat | gagtgaaccc | 540 |
| aaagctgctg | aaacattctg | cgtttatgca | acttccttgc | cctctataca | aggaagatgg | 600 |
| tttcattgtc | ttgtctagag | aataaagtct | tttttaaaaa | taaaaaaaaa | aaaaaaggcg | 660 |
| gcc | | | | | | 663 |

<210> SEQ ID NO 58
<211> LENGTH: 778
<212> TYPE: DNA
<213> ORGANISM: Homo sapiens

<400> SEQUENCE: 58

| | | | | | |
|---|---|---|---|---|---|
| ggcagagtca | gctctgtgct | gagcctcctg | gcctggcccc | caccggtgca | tccgcccagt | 60 |
| gcgtccacct | gccctggcta | gcatgctgct | gggccacacc | ccaagatcag | gggccctggg | 120 |
| gacggcaagt | gaataaagca | catttccacc | caattttgtc | atccgagaga | gagcacaaac | 180 |
| tgcaggcccct | tgttgcagct | gaaggaagac | cctacagaga | atggaattga | gagtggagac | 240 |
| aggacacttc | acaggacact | tgagcacagt | caagatttta | ttcacacttt | tggttcctgt | 300 |
| gttttatatc | gaagacttag | ctatgaattg | ctatctaaat | ctcagagctt | agaagccaac | 360 |
| ccagtgacta | gaccttccag | tgaagaaagt | gatctcaaga | ggtccaggga | cttaacagcc | 420 |
| aagccacacc | acccgcacag | gttcttctgt | gacaccgaga | gatctaaccc | aaggcctggg | 480 |
| ttatgtctta | gtcgagacat | catcatctga | gaagcaccac | atcctttcag | acacatcctc | 540 |
| ggacacacat | gcggtccttg | gtgcccccag | gttcaatcct | gcgttagctc | ttttgatgag | 600 |
| aaggaaataa | accaaaccag | ccacttgcac | tatggcttcc | aagccaatgt | tattgactca | 660 |
| ataagtgctt | agcaattggc | ttcctctttt | gtcttcctat | tttcagctcc | atttaaacca | 720 |
| ggagttattt | ataaagacct | cttcctctca | aaaaaaaaaa | aaaaaaaaa | aaactcga | 778 |

<210> SEQ ID NO 59
<211> LENGTH: 982
<212> TYPE: DNA
<213> ORGANISM: Homo sapiens
<220> FEATURE:
<221> NAME/KEY: SITE
<222> LOCATION: (360)
<223> OTHER INFORMATION: n equals a,t,g, or c

<400> SEQUENCE: 59

| | |
|---|---:|
| gaattcggca cgagcatatg tccaagtgtt accttgtcta gcccccagga acacagtccc | 60 |
| caggaccatg ttttttgggg cacccacagc agggcagtg caggtctggt tgctcctgct | 120 |
| ctcacctgca gcatctcccg tagaggaatt gtcagttctg gttccctgtg ggcagtaaag | 180 |
| gtttccttgt aggtcactgg ggcattggcc agaaaaaggt tgtgaaaatc acatgctaat | 240 |
| ttctcaaaat tcctgctttc aatgttgatg tccaataaag atgttcataa tttcagctgg | 300 |
| atattcttaa taggatttcc tccaataccg atgctgtaaa gcatattgaa tggaacaggn | 360 |
| attcaaattt gaaactctct ctctagaagg gtccatgtgg gagatggtgg atcacttgag | 420 |
| gtcgggaatt cgagmccaga ctggscaaca tggtgaaccc ccatctgtac taaaaattac | 480 |
| aaaaaattgg ccaggagtct aggcatgtgc ctgtagtccc agytactcag gatgctgagc | 540 |
| ccrggrgaat tgcttgagcc caggaggcag atgttgcagt gagccgagat cactgccact | 600 |
| gtactccagc ctgggtgaca gaatgagact ccatctaaaa aatttttaa atttaaaaag | 660 |
| ttgacacact tttacaagct gcatcccatc tcagataagg aggtgatgta actgagttct | 720 |
| tttagatcca tctgctttca tcttatcttt ttgtaggtaa tattttgaca agcatgtttg | 780 |
| tacataaaga ttctccctatg gttgggattt taaaaattca tagactactc aggccaggtg | 840 |
| cggtgcctca agcctgtaat ctcaacacat tggaaggcca aggagggtgg attgtctgag | 900 |
| cccagaagtt caagaccagc ctgggcaaca tggcaaaatc ctgtctctac aaaaaataca | 960 |
| aaaaaaaaaa aaaaaaactc ga | 982 |

<210> SEQ ID NO 60
<211> LENGTH: 406
<212> TYPE: DNA
<213> ORGANISM: Homo sapiens

<400> SEQUENCE: 60

| | |
|---|---:|
| tcacacaacg ggtgatctca caaaactggt aagtttctta tgctcatgag ccctcccttt | 60 |
| tttttttaa tttggtgcct gcaactttct taacaatgat tctacttcct gggctatcac | 120 |
| attataatgc tcttggcctc tttttgctg ctgttttgct attcttaaac ttaggccaag | 180 |
| taccaatgtt ggctgttaga agggattctg ttcattcaac atgcaacttt agggaatgga | 240 |
| agtaagttca ttttaagtt gtgttgtcag taggtgcggt gtctagggta gtgaatcctg | 300 |
| taagttcaaa tttatgatta ggtgacgagt tgacattgag attgtccttt tccctgatca | 360 |
| aaaaatgaat aaagcctttt taaacaaaaa aaaaaaaaa aaaaaa | 406 |

<210> SEQ ID NO 61
<211> LENGTH: 813
<212> TYPE: DNA
<213> ORGANISM: Homo sapiens

<400> SEQUENCE: 61

| | |
|---|---:|
| gaattcggca cgagtctcag gtatgtttaa acccaatgtt tctttgttaa ttttctctct | 60 |
| agatgatcta attctgagag agagggaaaa tgaatatggg gaagtctaaa aaatgaaaaa | 120 |
| ggggaaaaat gaaggaatat gcctgctgtt tcctaatgaa tagctgaaag tcttcaacct | 180 |
| atgaagcctc ctggatcatc tgccaattgt tcaacacaac tcccaccccct gccttcatcc | 240 |
| tctttccctg attcacaccc tcatggcctc ttttcattac agtcaaggtc catcccagct | 300 |
| ttgacctcat gaatccatta tgccctcctc tgttactgct agacctgcag acccagtgtc | 360 |
| cacaaagatg ctcctatatt ctttattcct gcttctctgg aatggtttta atgccccta | 420 |
| aagcaccagc wtgtgaatcg acctttgtgt tcatatcatg gagtcctctt agctccttgg | 480 |

| | |
|---|---|
| tgcctccaag gccaagcttc catcacctgc caagacacag cgagctggac caatatttgt | 540 |
| gtggcaggtt gggtgtgaca tgaatgtcaa agccaccctg aattgaggga ttctgctccc | 600 |
| ctttgttgaa cttcctttgg gtggtaagcc agacattgtc attcagcaaa catggtttca | 660 |
| ataaatatct agatgcaatc aagagaaaca tgaaaatgac atggcctcag tcctccaaga | 720 |
| gttcaaatct aacagaaggg acaaaaagtg tcttagccta agatgattaa aaaaaaaaa | 780 |
| aaaaaactcg agggggggcc cgtaccctct cgc | 813 |

<210> SEQ ID NO 62
<211> LENGTH: 846
<212> TYPE: DNA
<213> ORGANISM: Homo sapiens

<400> SEQUENCE: 62

| | |
|---|---|
| gaattcggca cgagtctttc tgtttttaat gctttattac atatgcctag ttttgcttaa | 60 |
| gcttgtctaa atttatgac ggaactataa aaatgtatt tcacttttac gtgacatgtt | 120 |
| attggtgaat cttgtgtttg tatgtttttt tcttttttgaa aggagagtgc atttaaaatg | 180 |
| ctgaattgaa caggacatct tgagagaatg ttttaatttg agctcatgta tctgctgatc | 240 |
| gattctaagt gcaggatatt ttctgtttgt catagatatt tgaatggtgg tacttccata | 300 |
| agcatggcac atcttttatt gagcaagtat ctgtaagcca tttgcaacca ctgatgggag | 360 |
| gaacagagag cagcatttca gaaccaggtt ctccttcgag gaacagagaa atgaaaacca | 420 |
| gcagacagaa tttgtcaggt gactacttt ctaatgtgtt ttcagagctg tgtatttaag | 480 |
| attgagtttg gctctgggag atagaaaact caaaacagca gagtgctgtg gtgtgcatgt | 540 |
| ttgtgtttcc cccaaaattc taatcaccaa tgtgatgtta cgaggtaggg tctttgggag | 600 |
| gtgatcaggt catgagggca gtgccctcag ggatgtgatg aatgcccta tgagagaccc | 660 |
| cagagagctg cttgccactt ctaccgtggg aggacaccac gagaaggcgc cgtctgtgaa | 720 |
| ccagaaagca gaccctcacc agacaccaaa tttgttggta ccttggtcat agacttccca | 780 |
| gcctccagaa ctgttaaaaa taaatttata ctgtttataa tctaaaaaaa aaaaaaaaa | 840 |
| actcga | 846 |

<210> SEQ ID NO 63
<211> LENGTH: 1442
<212> TYPE: DNA
<213> ORGANISM: Homo sapiens
<220> FEATURE:
<221> NAME/KEY: SITE
<222> LOCATION: (933)
<223> OTHER INFORMATION: n equals a,t,g, or c

<400> SEQUENCE: 63

| | |
|---|---|
| catgaagatg tgaaaatatc atcttaacca gtttcattct atgaacataa tattctggca | 60 |
| rcttttttcta taactgmgaa tggtatatct ttttatacac tgcctaaatc agtactactg | 120 |
| ccagtcacct gaggtcaggt ctgcacaaca ctaaattggg caataacata gaacatctag | 180 |
| gcagtcttga cagtcaacca gtgtaatcac taggggaagr aaaagtaggc ctacccttt | 240 |
| acttattaac ttaagtaata aaaattgtat aaaaatatga atgttsgctg cagaggagcc | 300 |
| tttacatgca gataatttga agcagtcttt gaaaataaca aaaattattc catttaatga | 360 |
| agggtttgtt ttgtttagct tttctctttt attcagaaaa catacctgtg ccttttgaaa | 420 |
| gggcttaatc ccaaacaggt aatatgtgtg gatcaatcat ctctcctccc atgaaattaa | 480 |

```
tcattcatgg taatatatta aggctggaac gtagctctta gtgacttaaa acatgacagt    540
aagcatttac actgttggaa ggtaatttca ttgctatgtt attaaaatga tgggaatcct    600
atttatacat ttatttattt atttatttac agaagattgg ttccttccag ttcaatttaa    660
cagcttcagt gaagttagta taatgataag aaaaattgac tgtagctatt attccaagtg    720
aaaatcatgc agctgagtcc tgctgcatcc tgggagcaaa gcattaattc aaatgaggag    780
tagtcagtcc tagcactgta gacgccgact ttaccaacca agatattgta tgtgtgtgac    840
attcagctaa cattgatcta ggcacttag tttgctacca cattgttccc ttcatgattg     900
aaactgtaaa taacataaca cctttaaggca gcnaagcaaa tattttaata agccagaaag   960
gcaagatgtc agagaaaatc tgtatattca gctatttgga gaactcgtgt tttccacaaa    1020
ttaaactgga gatgtcattt gaatttttct tcccttaaac atgctgtcac aacatggatt    1080
ccttctcatg gatgtctttc taggcttata aatatatggt gtgattgcta taattttgtg    1140
aaattttatt cagcaattaa tagtgatttc agcaatatgt actaagattc caaggcagaa    1200
ataaatgtat aaaggatttg agcctgtatg tgtaagaaga aactctctct tcagtcatat    1260
ttcctaaatt cagtgtaagt acctcgctga tttagcactg gagttattcc ttgaatgtgt    1320
aaataatgat gttctattct gacctaatga attcctgtaa tgtgaatatt taaaataaaa    1380
gaattcaatt taaatgtata aaaaaaaaaa aaaaaaact cggaggggggg gcccggtacc    1440 ta                                                                   1442

<210> SEQ ID NO 64
<211> LENGTH: 1004
<212> TYPE: DNA
<213> ORGANISM: Homo sapiens

<400> SEQUENCE: 64
ccgggtcgac ccacgcgtcc ggggcgccca tgcatcacag ctgtgtccac aggatgcacg     60
atggccattg agaaatggat tttggagtca gaagacctgg gtgctgcatg cttaactcat    120
ctgggtcctt tggacaaatc acatcacctc tcatggcctc catatgttcc ttctgtgcat    180
gaaggatgat gttacttctt gcctctgcct tcctcatagg gacagtgtta ggatcaaaca    240
gatcatgtat gagtcagtgc tgtgggcacc ataaatcaca gaaagcccag aagcatcgt     300 catttattac agccccagtc aagtaaaagc ccatttaccc aggcacattg gttccaacag    360
taagcctttt tggctgatga agctgtgta aagtttggtc tctggagaga agctgtttta    420
tttttttaaa ccaagtctgt aaaaccttgg atgagaagct cttttagctc ttttatgttt    480
tgatcaataa tcaatgaagg cccaatataa gatctcctcc cccgaccgtg tatgcaacac    540
atttccaagg cccatccaca gcaactttgt tacttctgcc tgccgcatgc atggtttgaa    600
atttggcagc tcatattggt gtaaaaatca catatcactg taggctaaac ttacctctgc    660
acactcctcc atgtccactg agcatctgct gaagtctgct tttcttcat ttttatgga    720 atgtaaagct catccatgtg tacattattc atgcatttac ttttctgcca cctccaaagc    780
attcaattaa agcaggaatt aaggctcaac tatcttactt tagcacagtt ttggcagaga    840
tgttacagtg agatgatttt tttctgtctg tcaaagttgt ttcttcatgt tttccaagat    900
ggtctagaac atcatttaga gtaaattttc attttggagg aaatttttat gaaaagtctc    960
tgtaggtatc tcctgtgaat agaggtttta aaaaaaaaaa aaaa                     1004

<210> SEQ ID NO 65
<211> LENGTH: 1683
```

<212> TYPE: DNA
<213> ORGANISM: Homo sapiens

<400> SEQUENCE: 65

| | | | | | |
|---|---|---|---|---|---|
| tgctctttct | ggttccgctg | ctgtgggccc | cggctgcggt | ccgggccggc | ccagatgaag | 60 |
| accttagcca | ccggaacaaa | gaaccgccgg | cgccggccag | cagctgcagc | cgcagcctgt | 120 |
| gstgtgcagg | gccccgagcc | ggcccgggtc | gagaaaatat | ttacaccagc | agctccagtt | 180 |
| cataccaata | aagaagatcc | tgctacccaa | actaatttgg | gatttatcca | tgcatttgtc | 240 |
| gctgccatat | cagttattat | tgtatctgaa | ttgggtgata | agacattttt | tatagcagcc | 300 |
| atcatggcaa | tgcgctataa | ccgcctgacc | gtgctggctg | gtgcaatgct | tgccttggga | 360 |
| ctaatgacat | gcttgtcagt | tttgtttggc | tatgccacca | cagtcatccc | cagggtctat | 420 |
| acatactatg | tttcaactgt | attatttgcc | attttggca | ttagaatgct | tcgggaaggc | 480 |
| ttaaagatga | gccctgatga | gggtcaagag | gaactggaag | aagttcaagc | tgaattaaag | 540 |
| aagaaagatg | aagaatttca | acgaaccaaa | cttttaaatg | gaccgggaga | tgttgaaacg | 600 |
| ggtacaagca | taacagtacc | tcagaaaaag | tggttgcatt | ttatttcacc | cattttgtt | 660 |
| caagctctta | cattaacatt | cttagcagaa | tggggtgatc | gctctcaact | aactacaatt | 720 |
| gtattggcag | ctagagagga | cccctatggt | gtagccgtgg | gtggaactgt | ggggcactgc | 780 |
| ctgtgcacgg | gattggcagt | aattggagga | agaatgatag | cacagaaaat | ctctgtcaga | 840 |
| actgtgacaa | tcataggagg | catcgttttt | ttggcgtttg | cattttctgc | actatttata | 900 |
| agccctgatt | ctggttttta | acaagctgtt | tgttcatcta | tatttagttt | aaaataggta | 960 |
| gtattatctt | tctgtacata | gtgtacatta | caactaaaag | tgatggaaaa | atactgtatt | 1020 |
| ttgtagcact | gattttgtga | gtttgaccca | ttattatgtc | tgagatataa | tcattgattc | 1080 |
| tatttgtaac | aaggagtttt | aaaagaaacc | tgacttctaa | gtgtgggttt | ttcttctctc | 1140 |
| caacataatt | atgttaatat | ggtcctcatt | tttcttttgg | tgcagaaccg | ttgtgcagtg | 1200 |
| gggtctacca | tgcaattttc | tttcagcact | gaccccttt | taaggaatac | aaattttctc | 1260 |
| cttcatcact | taggtgtttt | aagatgttta | ccttaaagtt | tttcttgggg | aaagaatgaa | 1320 |
| ttaatttcta | tttcttaaaa | catttccctg | agccagtaaa | cagtagttta | atcattggtc | 1380 |
| ttttcaaaac | taggtgttta | aaaaagaga | catatatgat | attgctgtta | tatcaataac | 1440 |
| atggcacaac | aagaactgtc | tgccaggtca | ttcttcctct | ttttttttta | attgggtagg | 1500 |
| acacccaata | taaaaacagt | caatatttga | caatgtggaa | ttccaaaatt | aaaagagaat | 1560 |
| actatgaatg | tattcatatt | ttttctatat | tgaataaaca | atgtaacata | gataacaata | 1620 |
| taaataaaag | tggtatgacc | aaaaaaaaaa | aaaacaaaa | aaaaaaaaaa | aaaagggcg | 1680 |
| gcc | | | | | | 1683 |

<210> SEQ ID NO 66
<211> LENGTH: 1441
<212> TYPE: DNA
<213> ORGANISM: Homo sapiens
<220> FEATURE:
<221> NAME/KEY: SITE
<222> LOCATION: (1362)
<223> OTHER INFORMATION: n equals a,t,g, or c
<220> FEATURE:
<221> NAME/KEY: SITE
<222> LOCATION: (1364)
<223> OTHER INFORMATION: n equals a,t,g, or c
<220> FEATURE:
<221> NAME/KEY: SITE
<222> LOCATION: (1421)

<223> OTHER INFORMATION: n equals a,t,g, or c

<400> SEQUENCE: 66

| | | | | | |
|---|---|---|---|---|---|
| aagttggttt | cggctgcaga | ggggaaggcg | gctaccagtg | taaagccaga | gctgaggttc | 60 |
| ttgatagtcc | acaatgggtg | aaccacagca | agtgagtgca | cttccaccac | ctccaatgca | 120 |
| atatatcaag | gaatatacgg | atgaaaatat | tcaagaaggc | ttagctccca | agcctccccc | 180 |
| tccaataaaa | gacagttaca | tgatgtttgg | caatcagttc | caatgtgatg | atcttatcat | 240 |
| ccgcccttttg | gaaagtcagg | gcatcgaacg | gcttcatcct | atgcagtttg | atcacaagaa | 300 |
| agaactgaga | aaacttaata | tgtctatcct | tattaatttc | ttggaccttt | tagatatttt | 360 |
| aataaggagc | cctgggagta | taaaacgaga | agagaaacta | aagatcttta | agctgctttt | 420 |
| tgtacacgtg | catcatctta | taaatgaata | ccgaccccac | caagcaagag | agaccttgag | 480 |
| agtcatgatg | gaggtccaga | aacgtcaacg | gcttgaaaca | gctgagagat | tcaaaagca | 540 |
| cctggaacga | gtaattgaaa | tgattcagaa | ttgcttggct | tctttgcctg | atgatttgcc | 600 |
| tcattcagaa | gcaggaatgc | agagtaaaaa | ctgaaccaat | ggatgctgat | gatagcaaca | 660 |
| attgtactgg | acagaatgaa | catcaaagag | aaaattcagg | tcataggaga | gatcagatta | 720 |
| tagagaaaga | tgctgccttg | tgtgtcctaa | ttgatgagat | gaatgaaaga | ccatgaaaga | 780 |
| tgtttctttt | tctttttttc | cttttgataa | tagcatcata | tattagttca | ttttcttttg | 840 |
| gacagtctta | agagaagttt | cactaaaaat | gtaaacagct | ttaatcttga | ctccaaattt | 900 |
| ttcaattatg | agatgtcata | ggcagtaatt | tcgctgtata | acaagcatag | acaaatgagt | 960 |
| gtccctgcac | taagaagaat | cactttaaaa | agcaaagtgt | tagctgctgt | tgtatgggac | 1020 |
| attcctatgt | tttagagttg | cagtaaaact | ttgatgataa | cctcaataat | agcaaagttt | 1080 |
| tcgtctttga | aaagggggatt | tagcatttgc | tttaagaatg | atagataaat | ggatattaag | 1140 |
| ctctctacat | gtaaaactat | gaatctttta | gacttattcc | attaaaaatt | ttgcttaagc | 1200 |
| tccaaaaagt | agcataacat | gttgatagag | aggagcccag | tagagttata | aaatagaaac | 1260 |
| ttcatttttt | cctcatgact | gcttctgtaa | acccactagc | tcagtcttt | ctccctatcc | 1320 |
| tgaatggact | cttgcaggga | agtccccata | aatgttgttt | tntngccagt | cactccaggg | 1380 |
| gaataagtcc | tttggggcac | tttaaagtta | cagacattaa | ntttaagtaa | ttaagatggc | 1440 |
| c | | | | | | 1441 |

<210> SEQ ID NO 67
<211> LENGTH: 622
<212> TYPE: DNA
<213> ORGANISM: Homo sapiens

<400> SEQUENCE: 67

| | | | | | |
|---|---|---|---|---|---|
| gcaattcggc | acgaggggcc | ctctcctctg | ctgactcttg | ccattttttcc | aggcctcccc | 60 |
| tcagtgagga | gaccaggcga | tgggagacag | gcatggtgct | gcttctgctg | ctccagagaa | 120 |
| accctgggac | acctttgttc | tgcttggttt | tctgggctgg | gctcaggaaa | cctgcccagt | 180 |
| tcaggcctat | attgggtcca | agctgcccct | gtgctgcttc | tgtcaagcga | ggtgtggaca | 240 |
| ttccaagttc | gtaagcatga | acaaaagaaa | agaggaaccc | agcagatgta | acagaactga | 300 |
| ctccagttgt | gtagagtttt | gctaaactgt | ttatcccctt | ttgctgtggt | ttacattaat | 360 |
| ggcaatagtt | agccaggtgt | ggggaatgag | agtgcattgc | tcgatagggt | ctgatgaact | 420 |
| gggagtaacc | caccattgca | attggggatt | gttttgcaag | gaaatagtat | ttttatgtgg | 480 |
| gggaccagca | aaatctctac | attagtgtaa | aatttcaaat | agttgtttta | tcgttggttt | 540 |

```
ggtttaccaa caaaaaaaaa aaaaaaaaa aaaaaaaaa ctcgagggg ggcccgtacc    600 caatagccct ctcatgtatc gt                                           622
```

<210> SEQ ID NO 68
<211> LENGTH: 616
<212> TYPE: DNA
<213> ORGANISM: Homo sapiens
<220> FEATURE:
<221> NAME/KEY: SITE
<222> LOCATION: (2)
<223> OTHER INFORMATION: n equals a,t,g, or c

<400> SEQUENCE: 68

```
gncccaacgc aattaatggg rgttagctma cycattaggc acccaaggct ttaaacttta    60
tgcttccggc tcgtatgttg tgtggaattg tgagcggata acaatttcac acaggaaaca   120
gctatgacca tgattacgcc aagctcgaaa ttaaccctca ctaaagggaa caaaagctgg   180
agctccaccg cggtggcggc cgctctagaa ctagtggatc ccccgggctg caggaattcc   240
cccccccccc cccacacccc cttcagctat gcttttggag tcctggatgg gaatctgggg   300
ggagagagga aggacaggtc aggtctcccc cagccccttc tgctcctgtc tcctcgtgtc   360
cgcattgctg gagctccacc tccctcttgg tttctccgca cccgcccatt ttccttctgy   420
ctttacctgc ttcgtatcct ttccctgctg atgtggctga cccctctccc accctccct    480 gcaggcggct ggccaggtgg gcaggtgcca gccggagctg taaatagasc gtgcgctttt    540
gtgctggttt gtgcgtgtgc tgtatttctg tgttttgata gaagtcacac aaaaaaaaaa    600
aaaaaggatc cctcga                                                    616
```

<210> SEQ ID NO 69
<211> LENGTH: 1019
<212> TYPE: DNA
<213> ORGANISM: Homo sapiens
<220> FEATURE:
<221> NAME/KEY: SITE
<222> LOCATION: (884)
<223> OTHER INFORMATION: n equals a,t,g, or c
<220> FEATURE:
<221> NAME/KEY: SITE
<222> LOCATION: (922)
<223> OTHER INFORMATION: n equals a,t,g, or c
<220> FEATURE:
<221> NAME/KEY: SITE
<222> LOCATION: (939)
<223> OTHER INFORMATION: n equals a,t,g, or c
<220> FEATURE:
<221> NAME/KEY: SITE
<222> LOCATION: (965)
<223> OTHER INFORMATION: n equals a,t,g, or c
<220> FEATURE:
<221> NAME/KEY: SITE
<222> LOCATION: (1003)
<223> OTHER INFORMATION: n equals a,t,g, or c

<400> SEQUENCE: 69

```
ggcgtccagg tccgctcggt aaccgtttcc cgcgcgcccg gccccgactc cggggtaaag    60
agccccggag cggagcagcg ctggccgcgt gccgcctccg gagccggcag ccccatggc    120 tgggggttat ggagtgatgg gtgacgatgg ttctattgat tatactgttc acgaagcctg    180
gaatgaagcc accaatgttt acttgatagt tatccttgtt agcttcggtc tcttcatgta    240
tgccaaaagg aacaaaagga gaattatgag gatattcagt gtgccaccta cagaggaaac    300
tttgtcagag cccaactttt atgacacgat aagcaagatt cgtttaagac aacaactgga    360
```

| | |
|---|---|
| aatgtattcc atttcaagaa agtacgacta tcagcagcca caaaaccaag ctgacagtgt | 420 |
| gcaactctca ttggaatgaa acctcagaaa aagagcaaca gaagtaattg tttcaagctc | 480 |
| ctgattcttt ctactaaatc atgaacagct ttaaaaacat ttctgtctgc ataaaattat | 540 |
| tttacttgta acttttcccc aattgttctg tgcattgttt tgccttttta aattacatct | 600 |
| ccaagtggct caaaaggcct tgacacaggg aacctgcaca tatccaggat atgtgtaacc | 660 |
| agcgatggtg acttgacctt gccaagacct gtgattcctt caggatacaa tcagtgagaa | 720 |
| ataaaaacac atcttgggaa gtgggaatcc tggagtttat gccatttgca atattaaaaa | 780 |
| ataaaatgc aagttattat ttcaataata acttcctgtt tcattgtatt ctgtgagtga | 840 |
| taagtgtcag atcaataaca gattaatttg ttgttaacag ctcnttttttt tttttttttt | 900 |
| tttggagaca ggagtctggt tngcccagac ttggagtgnc agtgggccaa atcctctggc | 960 |
| tcaantggca aacttccaac ctccccgggg tttaaacgga ttnctccctg gccacagcc | 1019 |

<210> SEQ ID NO 70
<211> LENGTH: 831
<212> TYPE: DNA
<213> ORGANISM: Homo sapiens

<400> SEQUENCE: 70

| | |
|---|---|
| gaattcggca cgagaatttc ttatggctga ataatatttc attgtgtaga taaaccacat | 60 |
| tatttgtcag ataatagaca tttgggttat tgctgtcttt tggctattat gagtgttata | 120 |
| aatatttgtg cacaagtatt tgtgtagaca tgttttgcatt tctcttgggt atataccctag | 180 |
| gagtgaaatt gctggataat atgtttaact atttgaggac tgatagacta ctttgtaaag | 240 |
| tggccaacat gagtaagttt tcatcacatt tataaaatgt tagtgtactt acattagctt | 300 |
| gcaaagcatt taataagcag caagagttaa accacgttgg tccaagtgaa ctgaaagcag | 360 |
| acttctgtgt tacatgtgta tgagttactg aacatgttcc ataatacagg agtgtgagca | 420 |
| cactaacagg taagtgcagg aaamcaagaa gaaatatttt cagagtatag tcaaaagtac | 480 |
| actgagcatg ggagaattgt tttgacattt tgctcaaaac tatttctgaa gaaaattcaa | 540 |
| catttcttc acggaaagtt ttaggaacag gtaaatacaa ttatataaag tactggtaga | 600 |
| atatgttcgt tcagatgacc ttgaagtgtt ttttcagact tatctgaact tgagatctga | 660 |
| actgaatttt tattagaaac tgttaaagcc tctggcattg aaggttagtt cataattggt | 720 |
| gagttctgaa tcacttcatt tcckgcagtg gttcctgaga gaatcttagt tmaaaggact | 780 |
| gcccccgcca acccctgccc cgccaaaaaa aaaaaaaaaa aaaaaactcg a | 831 |

<210> SEQ ID NO 71
<211> LENGTH: 750
<212> TYPE: DNA
<213> ORGANISM: Homo sapiens
<220> FEATURE:
<221> NAME/KEY: SITE
<222> LOCATION: (734)
<223> OTHER INFORMATION: n equals a,t,g, or c

<400> SEQUENCE: 71

| | |
|---|---|
| gaattcggca cgagcgggaa ggctggggtc cgtggggatg ggcagggtct gtggggacac | 60 |
| gcagggtgtc ccacatgatg cagcctgtcc tcatatgggg actctgagct ctgagactcc | 120 |
| ctgtgtgaga tgtttgggtg cagagctgtg aagacacaga aggaaacgtt gccgtctgca | 180 |
| ccaggctccc caccgttggt ggccctgttt tccgtggccc tgtggcctgt ggccctgtct | 240 |
| aacgaggcca caccacattc atgtggacaa gcaccaggag ctccgggtca gatgagaaca | 300 |

```
ctgtttcctc cgacctgact gcctctttgc ctggcggttt ctaagccagc atccagccgg      360
cctcggtgag gatgacacca gcatcccctt gaccctccaa ggtctcctgt gacattgccc      420
cagaggctct tgctgtgggg ccgtccagtt tatgtggagt gacctgcacc ctgagcacag      480 cccaacakttt ggccacacct tgggggcccg aggggctgag ttctacccag agcggctgga     540
ggctcacaag ggattttccc accttggagg gagccaagtt ccctgggg gcaggtgggc        600 tgctcagctc tgaaagacct cagtgccgtg gagtgcgctc tggaggaagg gtactgagcc      660
gattccctga cagtgactgt aataaagatg gctaaataga gaaaaaaaaa aaaaaaaaa       720 aaaaaaaaaa tagnaggggg tcccgtaccg                                      750
```

<210> SEQ ID NO 72
<211> LENGTH: 714
<212> TYPE: DNA
<213> ORGANISM: Homo sapiens

<400> SEQUENCE: 72

```
gaattcggca cgaggaggag ttattcaggc ctccgccagc ttcaaggccc tggggatggt       60
ctttcacctc cctctttctg atctcttttt catgctcctc cttgctccaa agaaaagccg      120
gatggcaaaa gagcccagaa cctattggaa ctgacaaaat caagtcacgg cgcctacaaa      180
gatgaggggc agattctggc tgccttttaa tttcgtcctt cacctgatat ctgtgccaga      240
gaatgtggca tggttcagtc ttccaggagt tctgctacag agaagagagt aacccccatc      300
catcatggcc aaagcaccca gtcaggctcc gctctggatc cagcccgaca aatgcaaccc      360
ttgaataggg tttgtgcaag caaactggat gacgaccgaa gaaaccctgt cgcttctgag      420
aagcacccca atccaagaat gaaagcatca ggttcaatac ctaggaactc ctgtagaggg      480
tgttgtggaa tcttctttaa aagaacaaaa caaggtaaaa caaagtttaa tagggtagag      540
cagccaggtg tggtgggtca tgcctgtaat ctcagcaatt tgggaggcca aggcaggatc      600
tcagcaattt gggaggcgaa ggcaggcaga tcacttgagc ctaggagttc aagaccagct      660
tgggcaacat agcaagaccc tgcctatacc aaaaaaaaaa aaaaaaaact cgta           714
```

<210> SEQ ID NO 73
<211> LENGTH: 1405
<212> TYPE: DNA
<213> ORGANISM: Homo sapiens
<220> FEATURE:
<221> NAME/KEY: SITE
<222> LOCATION: (8)
<223> OTHER INFORMATION: n equals a,t,g, or c
<220> FEATURE:
<221> NAME/KEY: SITE
<222> LOCATION: (35)
<223> OTHER INFORMATION: n equals a,t,g, or c
<220> FEATURE:
<221> NAME/KEY: SITE
<222> LOCATION: (59)
<223> OTHER INFORMATION: n equals a,t,g, or c

<400> SEQUENCE: 73

```
ccctcctncc cttccttggt ccttccaacc ttaantcctt tttccaaaaa aaaaaagang       60
aactgtgaag aacccccaaa aaacttccca cttcctggga ggccagccca caggaacagg      120
gaacaatatt tatttgggtc tcttcagttc cccctttgag aacaacatta aatacatgtt      180
agctggggct cccagggcat tctccttccc acagtagtgc ggccaaattc ccagtctggc      240
cagtctcttt gttgagactg aatagaagga ctgcaggttt ttttgagga tgagataatt       300
```

```
tttcctcgca ggcattttc ccttgccttc cttatgcatg aatggtccct ttgaatatta      360
tttccaaaag tgagagctaa gacaaagtca tcaaaaagag aggataacag aaggtggggg      420
cgggggcggg gtgcagtggg gtagggttac ctgttaattg ctgagactca gatgaaagtc      480
cagctctccc tgggcaaccc tagagggcag cagaggaccc cagagctcat tcaggccttg      540
ctgcttgttc taaactacac cttaggattt tttcttcttt ccaaaacatt ccattgattt      600
tataaagact ttctatagag aggctttcac ttttgagttc tttgagttta aagattgctt      660
ttcttgaaac gctcttttt taatgtagaa aattttact ttttcaaata tgcatacaat       720
ttttaaaaca gtagaagcaa attcatttta atgaccatgt aaagagcgaa tgtcagacag      780
tattattacc agtttattca aattacatac atgttcctac caaggtggaa agaaattcaa      840
acctcatggt aaaacttaag cacgatttaa gataaaagca tagtatttct tcagtgtaga      900
cttattaagt gccttattga acaggatctt aacctgcttt ttctgttttt ttgaaagagt      960
taatgcaatt gttgaagctt ctaaccaaga aacaacttaa ggaattggga gacttggtcc     1020
cctcgttgtc agggtctgg ctataagtac ctccccacct ttgggttttc ttaaatatgc      1080
caaaaggaat tctagttttt ataaccaatg ggttttttg tttgtgtgct tatggatttg      1140
tgtaatcatt gatgcttaat gttgtggatt cataatataa aaagtggctc ctgtcccttta    1200 tatttattca tgtgctagaa atagtatgca ttatataaag agtatgaagt tttcataagc     1260
ctttatattt caagctcttt atttaaacat tgttggaata tgtggcataa gccttgtttc     1320
atttatttaa taaactggag taatatataa taataaaaaa aaaaaaaaaa aactcgaggg     1380
ggggcccggt acccaatcgc cctat                                          1405

<210> SEQ ID NO 74
<211> LENGTH: 907
<212> TYPE: DNA
<213> ORGANISM: Homo sapiens
<220> FEATURE:
<221> NAME/KEY: SITE
<222> LOCATION: (455)
<223> OTHER INFORMATION: n equals a,t,g, or c

<400> SEQUENCE: 74
gggtcgaccc acgcgtccgg caaagatcat ttcagtctcg ggcttcttcg tgggaacttg       60
acttgccggg tagctccccc tggggttcag atctctgttc attgtttctc ttcaagccct      120
gggaagtgcc atgttatctg gaaagctttc cctaacatgt tctgtctgca tttatacttc      180
acccatgtgc ccctcaacta ttcatcatag ccctagtccc accataatga aaatgtctct      240
cattattttt ctggctggcc cacgagcctg caagtcctta taggcgccaa ctaagtatca      300
ttcatccctg gatgctctcc cactagacgt ttattgaatg aagagtggag gaatgaatga      360
agcaacgatg gctttctctg tgctcatcct tccagtgttc tacgcacaga ttaggaacaa      420
gagtttcctt tgtcttttctg acattctycc attantcctc atcctcctct tttgatagac      480
tcaaggttta cccaattggt gaatctctct tctgagcctt ctcctaaact aatttgtccc      540
cagaatagca ccccttctcc ctctctgtcc ttaccaacac atgcttctga cagtccaggt      600
tccacctctg aaatgtcagc taaaactctt ctcattcagg cagtgttccc tgtccagaaa      660
agaggcagca ctttctctct tgctctattt gaattaaaca tgcagttgcc aggagtcacc      720
tgaattcaca ctctacagca tactctttct tcccccttga ttcaagcatg atgtaaaatg      780
ttatacattt tttttcaagt tgtaaaagta ttaattcatt tgcatcgatg acttatcttt      840
gtcttgtaaa tattttgata atatctaagg actcttctag ttctaaaaaa aaaaaaaaag      900
```

```
ggcggcc                                                              907
```

<210> SEQ ID NO 75
<211> LENGTH: 687
<212> TYPE: DNA
<213> ORGANISM: Homo sapiens
<220> FEATURE:
<221> NAME/KEY: SITE
<222> LOCATION: (461)
<223> OTHER INFORMATION: n equals a,t,g, or c
<220> FEATURE:
<221> NAME/KEY: SITE
<222> LOCATION: (481)
<223> OTHER INFORMATION: n equals a,t,g, or c
<220> FEATURE:
<221> NAME/KEY: SITE
<222> LOCATION: (534)
<223> OTHER INFORMATION: n equals a,t,g, or c

<400> SEQUENCE: 75

```
ggctgtgaac actgcatctt agatgtggga ttgttcttca ctgtagtgag agctaagaaa     60
agaggcagca cttggcaccc ttaatcaccc aaattaagca attattctga tcccccattc   120
gaaatgaatt ggtatcatga aacaaagag gcaacatgca attgccaaat atttggccta    180
tattttattg tttcctttct ttctccagta ctggcagcag cccatgatgc taagaaatat   240
cccgtttggt tatgaagtta atgtggagat taaaagtcat tccctgttct acccacaccc   300
ttttttcttgt gtatagcatg tgactgagct gattggaagg catatagccc agtggccaag   360
cacttgggcc tcagtgtgat ggctgacaca tgttctgac tctgtccatt tctatwttgt    420
tgtggacaag ccttggcttt ctcagctgtc aaatgggggt nacaacagct ctacatatag   480
ncctgtagca attaaatgaa agcatttagg gccaggcatg gtggcttatg gcgntggtcc   540
cagcacttag ggaggccaag gcaggacaaa gtgggctctt gtctttgagc cctagagttt   600
gagaccagcc tgggcaacat agtgaggccc tgtctctaaa aaaaaaaaaa aaaaaaaac    660
tcgaggggg gcccgtaccc aatcgcc                                       687
```

<210> SEQ ID NO 76
<211> LENGTH: 792
<212> TYPE: DNA
<213> ORGANISM: Homo sapiens

<400> SEQUENCE: 76

```
gaattcggca cgaggtgaag cacactcaca tactcaaatg cacacacact catacacaca    60
gccccacacg ctagcacata cactcccttc actccgcccc tcttgtaagg cgatttcttc   120
ttcccaggac aggagctaga ggtgcagcct gggaccactc agccaagaag ccaagggcca   180
ggcatgcccg ggcctggagc actttattca tcttttacgt ctttttatta cacattctcg   240
aatcaccagc tcctccttgc cttgcttctc ctgggtttca ttgcctcttg cagtttcttc   300
ctctctcgag tgtttctaac ttttttccacc caattatgga aaaagtaaga accgagaaca   360
gcgaaaacaa ccaaaacaaa atctatagct atttctcatt gaaatcctgg aagaattttg   420
ggtttyccct tcgatttctc tcacccactc acgcattcac caattatgta tttgtttact    480
caatgagtgc agctcaggcc gagggtgcca gcctccacgg gatgagggc tagacactct   540
gatttcaccc cgacacctgc tgggtgcaag scgctcagtc tgcagccagc tctaggtccc   600
gcccctttgc gttgggctgc gggtgggcgg ggctgcttgg cctgcccaga ctcgccagga   660
aagacatgct gctgcggacc aatcagagtg gcccaagctg ggaggaggcc ttgccccgcc   720
```

```
ctcccctgcc ccgcccactt ggcgctggga ataaccacgt ggaaacccaa ctccgaggtc      780
tctggcgctc ga                                                          792

<210> SEQ ID NO 77
<211> LENGTH: 756
<212> TYPE: DNA
<213> ORGANISM: Homo sapiens

<400> SEQUENCE: 77
tcgagtaccc tgaagtcctc ctgctgttgt ttccaaccaa gaaagttttc catgagtaag       60
tctgagcaat gccgagctgc ttcccagct gccctggagc aggagctatc actgggcagg      120
ggctggtggg ggtgggcaac agaagggata ggaagccaga ttcacccagt cagtccccca      180
gcatcaccaa agcaaagccc ctccctcctc caaagcatgt gggataggtg taatagttac      240
acacatggtt ctttgcagtg ggacagactg aggcctccac ctgttctgcc accttctatc      300
tacacaatca ggacatgttc tcaaaggtta tttgctgcag cccagtccty ttcctattct      360
catatgaatg tcagagggcc cctgatccag ccccacaaca cccagggccc ttttcttacc      420
ccaagcctct caagcctgct gttccaccag agcagcccca cytgcacact gtcagcytgg      480
cctctgtcta ggtacgccca gccaggctca gcgctgctga ccacaccacc aagactgcag      540
agaggctgag caaacagccc tgctgggggc tctcacacct catcaccact taccactttg      600
agggaccaag gcaggccagg agacatccat cttgagaaat gccaggcctg ggccaatcat      660
gtgacagcta ctttcccagt actctcccc cctctctcgc tctttcctct ctctccagaa      720
cttcttgagg agtacaaggc ccctcgtgcc gaattc                                756

<210> SEQ ID NO 78
<211> LENGTH: 751
<212> TYPE: DNA
<213> ORGANISM: Homo sapiens
<220> FEATURE:
<221> NAME/KEY: SITE
<222> LOCATION: (750)
<223> OTHER INFORMATION: n equals a,t,g, or c

<400> SEQUENCE: 78
gcggccatgg tgaccatggt gacagggtcc cagccagaaa ccacaatggg atggaaactc       60
ctggggctgc tgtcagcagc tgggagacac agcgctgggg gagaccaggc attccccagg      120
cccaagggag aagcagagtc ggcctcgcct gagccagacg caggccttgg gtttaccctc      180
catggaccag acgtaaagtc taatggtgac atgagatttt taatgtcttt acatctgcag      240
atgtacacgt cagcaaaatt gcatcacaca aacctcactg caggcccagg ctttcctctt      300
tccaggtttc accaacctcc tccctccgtc ttggctgcct gtccctccac caatcagctc      360
tcacctgccc caggtgaccc gcgttaacag tggcacatga atttctcaca ttcatacaca      420
cataaatgca cgtctcttca ggcaaataca catttggaaa ggattttcct cctggcttgt      480
cctatgaacg taagaacgtg atctgcacgt ttttctgaga gttgctcttt ctcctaaccc      540 actcctcccct gtgccccacc catgtggcca gcctccgtg tccaccatcc tctgctccct      600
sccagggctt tgctccagga acgaagtccc aggcagcctc ctaggacaca agtttctgtt      660
ccttctgctc ccttggggtt tcctcgtaga atgaagactc ccagtggagt tactgggtca      720
aagaagacct gtattttttag ttttccctcgn c                                  751

<210> SEQ ID NO 79
<211> LENGTH: 1411
```

```
<212> TYPE: DNA
<213> ORGANISM: Homo sapiens
<220> FEATURE:
<221> NAME/KEY: SITE
<222> LOCATION: (541)
<223> OTHER INFORMATION: n equals a,t,g, or c
<220> FEATURE:
<221> NAME/KEY: SITE
<222> LOCATION: (1324)
<223> OTHER INFORMATION: n equals a,t,g, or c
<220> FEATURE:
<221> NAME/KEY: SITE
<222> LOCATION: (1370)
<223> OTHER INFORMATION: n equals a,t,g, or c
<220> FEATURE:
<221> NAME/KEY: SITE
<222> LOCATION: (1395)
<223> OTHER INFORMATION: n equals a,t,g, or c

<400> SEQUENCE: 79
gaagattctt tcttctgaaa gccaagcacc acaaggaaaa aaaattatta atagctcagg      60
ttaaaaacac ccatttaaac aaaaacaaga gcatttgtaa taggaagtgt ttatacaaat    120
agcacatttg tgatatgttg aaaagcatct ctcttggcaa ccaatctatg tttgaggaag    180
attgggtaat gctgatgtgt tccattcatg aaactgtatt tgatacataa tcctattatt    240
aattcgtatg cttagtcaac ctaggaaatc aaaataatgt tttgaagttc ttatttgagc    300
aatatggcct tgacttggag ggtagtttta gttgttttgt ttttaagtga ctgtggttta    360
aagcacaaat gccccaaggt ggggagactt ctctctgtga ttattgttgc tattaaattc    420
tgaactgtat ccatatttta aggaaggagc taaaaatgga aattcatgaa acataaatgg    480
tatcaagaac tttatcagta tgctttgttg aaagcagaaa ttaagataat aattgagttc    540
naattcgcct ctccgcattg cctattgata cactttacta atcatgaaat tctaacctaa    600
aaggaaaaca ttttcctgct tgtcttagaa gaaagtggaa taattccact gattgtgata    660
atggtttcaa tttctacaca atataaatat ccagtataaa ggaaagcgtt aagtcggtaa    720
gctagaggat tgtraatatc ttttatgtcc tctagataaa acacccgatt aacagatgtt    780
aaaccttttta atgttttgat ttgctttaaa aatggcctttc ctacacatta gctccagcta    840
aaaagacaca ttggagagct tagaggataa gtctctggag magaatttat cacacacaaa    900
agttacacca acagaatacc aagcagaatg atgaggacct gtaaaatacc ttgtgcccta    960
ttaaaaaaaa aaaaaaaaaa aaaagccagt arctgaatcc attttgattt ttggttgagt   1020
ttcctacaca aagaagaaaa taactgagaa tctggaatgt tgtagtccat cctttaaaga   1080
gtaagaaagt agcagttaat gctagtaacc gtgaattagg caccactgaa agcacatccc   1140
gaatttcttt aacaacaaca ttttatagtg aacactacaa gtttttatat ttaaaawtta   1200
agactctgta tatccttaag gtgctctatg ctttaccmgt aattcacagg gtatttcaaa   1260
tggtagaatc attttagctt ctgtgcttcc tttttctaaa taatgcaact tgtaagagtt   1320
gacnatgtaa taagccttat aatagtataa ccgtccagga gatatatatn tatatatcca   1380
cccccccca cgggnacaca gattttacca a                                  1411

<210> SEQ ID NO 80
<211> LENGTH: 1775
<212> TYPE: DNA
<213> ORGANISM: Homo sapiens
<220> FEATURE:
<221> NAME/KEY: SITE
<222> LOCATION: (820)
<223> OTHER INFORMATION: n equals a,t,g, or c
```

```
<400> SEQUENCE: 80
gcggcgcggg tgggggttgt gcgttttacg caggctgtgg cagcgacgcg gtccccagcc      60
tgggtaaaga tggccccatg gcccccgaag ggcctagtcc cagctgtgct ctggggcctc     120
agcctcttcc tcaacctccc aggacctatc tggctccagc cctctccacc tccccagtct     180 tctccccgc ctcagcccca tccgtgtcat acctgccggg gactggttga cagctttaac      240
aagggcctgg agagaaccat ccgggacaac tttggaggtg gaaacactgc ctgggaggaa     300
gagaatttgt ccaaatacaa agacagtgag acccgcctgg tagaggtgct ggagggtgtg     360
tgcagcaagt cagacttcga gtgccaccgc ctgctggagc tgagtgagga gctggtggag     420
agctggtggt ttcacaagca gcaggaggcc ccggacctct tccagtggct gtgctcagat     480
tccctgaagc tctgctgccc cgcaggcacc ttcgggccct cctgccttcc ctgtcctggg     540
ggaacagaga ggccctgcgg tggctacggg cagtgtgaag gagaagggac acgaggggc      600 agcgggcact gtgactgcca agccggctac ggggtgaggg cctgtggcca gtgtggcctt     660
ggctactttg aggcagaacg caacgccagc catctggtat gttcggcttg ttttggcccc     720
tgtgcccgat gctcaggacc tgaggaatca aactgtttgc aatgcaagaa gggctgggcc     780
ctgcatcacc tcaagtgtgt agactgtgcc aaggcctgcn taggctgcat gggggcaggg     840
ccaggtcgct gtaagaagtg tagccctggc tatcagcagg tgggctccaa gtgtctcgat     900
gtggatgagt gtgagacaga ggtgtgtccg ggagagaaca agcagtgtga aaacaccgag     960
ggcggttatc gctgcatctg tgccgagggc tacaagcaga tggaaggcat ctgtgtgaag    1020
gagcagatcc cagagtcagc aggcttcttc tcagagatga cagaagacga gttggtggtg    1080
ctgcagcaga tgttctttgg catcatcatc tgtgcactgg ccacgctggc tgctaagggc    1140
gacttggtgt tcaccgccat cttcattggg gctgtggcgg ccatgactgg ctactggttg    1200
tcagagcgca gtgaccgtgt gctggagggc ttcatcaagg gcagataatc gcggccacca    1260
cctgtaggac ctcctcccac ccacgctgcc cccagagctt gggctgccct cctgctggac    1320
actcaggaca gcttggttta ttttgagag tggggtaagc ccctacct gccttacaga       1380 gcagcccagg tacccaggcc cgggcagaca aggcccctgg ggtaaaaagt agccctgaag    1440
gtggatacca tgagctcttc acctggcggg gactggcagg cttcacaatg tgtgaatttc    1500
aaaagttttt ccttaatggt ggctgctaga gctttggccc ctgcttagga ttaggtggtc    1560
ctcacagggg tggggccatc acagctccct cctgccagct gcatgctgcc agttcctgtt    1620
ctgtgttcac cacatcccca caccccattg ccacttattt attcatctca ggaaataaag    1680 aaggtcttg gaaagttaaa aaaaaaaaaa aaaaaaaaa aaaaaactcg agggggggcc      1740
cgtacccaat cgccctatga tgtagtcgta ttaca                               1775
```

<210> SEQ ID NO 81
<211> LENGTH: 2078
<212> TYPE: DNA
<213> ORGANISM: Homo sapiens
<220> FEATURE:
<221> NAME/KEY: SITE
<222> LOCATION: (1177)
<223> OTHER INFORMATION: n equals a,t,g, or c
<220> FEATURE:
<221> NAME/KEY: SITE
<222> LOCATION: (1187)
<223> OTHER INFORMATION: n equals a,t,g, or c
<220> FEATURE:
<221> NAME/KEY: SITE
<222> LOCATION: (2057)
<223> OTHER INFORMATION: n equals a,t,g, or c

<400> SEQUENCE: 81

```
ggcacgagga gttgtgcaga tacctggctg agagctggct caccttccag attcacctgc      60
aggagctgct gcagtacaag aggcagaatc cagctcagtt ctgcgttcga gtctgctctg     120
gctgtgctgt gttggctgtg ttgggacact atgttccagg gattatgatt tcctacattg     180
tcttgttgag tatcctgctg tggccccctgg tggtttatca tgagctgatc cagaggatgt    240
acactcgcct ggagcccctg ctcatgcagc tggactacag catgaaggca gaagccaatg    300
cyctgcatca caaacacgac aagaggaagc gtcaggggaa gaatgcaccc ccaggaggtg    360
atgagccact ggmagagaca gagagtgaaa gcgaggcaga gctggctggc ttctccccag    420
tggtggatgt gaagaaaaca gcattggcct tggccattta cagactcaga gctgtcagat    480
gaggaggctt ctatcttgga gagtggtggc ttctccgtat cccggccac aactccgcag     540
ctgactgatg tctccgagga tttgaccag cagagcctgc caagtgaacc agaggagacc     600
ctaagccggg acctagggga gggagaggag ggagagctgg cccctcccga agacctacta    660
ggccgtcctc aagctctgtc aaggcaagcc ctggactcgg aggaagagga agaggatgtg    720
gcagctaagg aaaccttgtt gcggctctca tccccctcc actttgtgaa cacgcacttc     780
aatggggcag ggtcccccm agatggagtg aaatgctccc ctggaggacc agtggagaca    840
ctgagccccg agacagtgag tggtggcctc actgctctgc ccggcaccct gtcacctcca    900
ctttgccttg ttggaagtga cccagccccc tcccttcca ttctcccacc tgttccccag     960
gactcacccc agccctgcc tgccctgag gaagaagagg cactcaccac tgaggacttt    1020
gagttgctgg atcagggga gctggagcag ctgaatgcag agctgggctt ggagccagag   1080
acaccgccaa aaccccctga tgctccaccc ctggggcccg acatccattc tytggtacat    1140
cagaccaaga agctcaggcc gtggcagagc catgagncca gccgttnagg aaggagctgc   1200
aggcacagta gggcttcttg gctaggagta ttgctgtttc ctccttttgcc taccactctg   1260
gggtggggca gtgtgtgggg aagctggctg tcggatggta gctattccac cctctgcctg   1320
cctgcctgcc tgctgtcctg ggcatggtgc agtacctgtg cctaggattg gttttaaatt    1380
tgtaaataat tttccatttg ggttagtgga tgtgaacagg gctagggaag tccttcccac    1440
agcctgcgct tgcctccctg cctcatctct attctcattc cactatgccc caagccctgg    1500
tggtctggcc ctttctttttt cctcctatcc tcagggacct gtgctgctct gccctcatgt    1560
cccacttggt tgtttagttg aggcacttta taattttct cttgtcttgt gttccttct    1620
gctttatttc cctgctgtgt cctgtccta gcagctcaac cccatccttt gccagctcct    1680
cctatcccgt gggcactggc caagcttag ggaggctcct ggtctgggaa gtaaagagta    1740
aacctggggc agtgggtcag gccagtagtt acactcttag gtcactgtag tctgtgtaac    1800
cttcactgca tccttgcccc attcagcccg gcctttcatg atgcaggaga gcagggatcc    1860
cgcagtacat ggcgccagca ctggagttgg tgagcatgtg ctctctcttg agattaggag    1920
cttccttact gctcctctgg gtgatccaag tgtagtggga cccctacta gggtcaggaa    1980
gtggacacta acatctgtgc aggtgttgac ttgaaaaata aagtgttgat tggctagaaa    2040
aaaaaaaaaa aaaattnctg cggtccgcaa gggaattc                          2078
```

<210> SEQ ID NO 82
<211> LENGTH: 773
<212> TYPE: DNA
<213> ORGANISM: Homo sapiens
<220> FEATURE:

```
<221> NAME/KEY: SITE
<222> LOCATION: (2)
<223> OTHER INFORMATION: n equals a,t,g, or c
<220> FEATURE:
<221> NAME/KEY: SITE
<222> LOCATION: (773)
<223> OTHER INFORMATION: n equals a,t,g, or c

<400> SEQUENCE: 82
gnagcgcgcc ggcggcccgc gtctccctag gacccgagtc gggcggccgg cagcgctccg    60
cctcctccty ctgctgggcg ctgtcctgaa tccccacgag gccctggctc agmctcttcc   120
caccacaggc acaccaggt cagaaggggg gacggtgaaa aactakgaga cagctgtcca   180
attttgctgg aatcattata aggatcaaat ggatcctatc gaaaaggatt ggtgcgactg   240
ggccatgatt agcaggcctt atagcaccct gcgagattgc ctggagcact ttgcagagtt   300
gtttgacctg ggcttcccca atcccttggc agagaggatc atctttgaga ctcaccagat   360
ccactttgcc aactgctccc tggtgcagcc caccttctct gacccccag aggatgtact    420
cctggccatg atcatagccc ccatctgcct catccccttc ctcatcactc ttgtagtatg   480
gaggagtaaa gacagtgagg cccaggccta gggggccacg agcttctcaa caaccatgtt   540
actccacttc cccaccccca ccaggcctcc ctcctcccct cctactccct tttctcactc   600
tcatccccac cacagatccc tggattgctg ggaatggaag ccaggtgggg tcatggcaca   660
agttctgtaa tcttcaaaat aaaacttttt ttttgtaaaa aaaaaaaaa aaaaaaaaa    720
aaaaaaaaa aaaaaaaaaa aaaaaaaaaa aaaaaaaaa aaaaaaaaaa aan           773

<210> SEQ ID NO 83
<211> LENGTH: 969
<212> TYPE: DNA
<213> ORGANISM: Homo sapiens
<220> FEATURE:
<221> NAME/KEY: SITE
<222> LOCATION: (36)
<223> OTHER INFORMATION: n equals a,t,g, or c
<220> FEATURE:
<221> NAME/KEY: SITE
<222> LOCATION: (123)
<223> OTHER INFORMATION: n equals a,t,g, or c
<220> FEATURE:
<221> NAME/KEY: SITE
<222> LOCATION: (347)
<223> OTHER INFORMATION: n equals a,t,g, or c
<220> FEATURE:
<221> NAME/KEY: SITE
<222> LOCATION: (525)
<223> OTHER INFORMATION: n equals a,t,g, or c

<400> SEQUENCE: 83
gggaggaaca tgatggtgtc cgtgacaaca tctgtngggc acttgcccgc ctgttgatgg    60
ccagtcccac caggaaacca gagccccagg tgctggctgc cctactgcat gccctgccac   120
tgnaaggagg acttggagga gtgggtcacc attgggcgcc tcttcagctt cctgtaccag   180
agcagccctg accaggttat agatgtggct cccgagcttc tgcgtatctg cagcctcatt   240
ctggcagaga ctattcaggg cctggtgct gcctcagccc agtttgtgtc tcggctgctc    300
cctgtgctgt tgagcaccgc ccaagaggca gaccccgagg tgcgaanaat gccatcttcg   360
ggatgggcgt gctggcagag catggggcc accctgccca ggaacacttc cccaagctgc    420
tggggctcct ttttcccctc ctggcgcggg agcgacatga tcgtgtccgt gacaacatct   480
gtggggcact tgcccgcctg ttgatggcca gtcccaccag gaaaccaga gccccaggtg    540
ctggctgccc tactgcatgc cctgccactg aaggaggact tggaggagtg ggtcaaccat   600
```

```
tgggcgcctc ttcagcctcc tgacgttcct ggccaaacag cacaccgaca gctttcaagc    660
agctctgggc tcactgcctg ttgacaaggc tcaggagctc caggctgtac tgggcctctc    720
ctagactgca ggctgcagcc agtccagaga aatagagcc  tgcccaggcc ttaagaccac    780
ctctcagccc agttcagttc tgccttacca agattctga  gactcatacc catttggagc    840 cagcccact  tgctgcctta cagggctgtc cctgaggctg atctgttac  aaatgagtca    900 tgacatcata ctgtaataaa agcagcttgt tttctgcttg aacaataaaa aaaaaaaaa    960 aaaactcga                                                            969
```

<210> SEQ ID NO 84
<211> LENGTH: 1064
<212> TYPE: DNA
<213> ORGANISM: Homo sapiens

<400> SEQUENCE: 84

```
gtgttgttct gttaaaagac tgtccactgt tttcttttc  agtaattaat ggtcacacac     60
tgtgtttacg gctgttgcta gaaattgcag acaacccgga ggcggtcgat gtgaaagatg    120
ccaaaggaca aacaccactg atgcttgcag tagcatatgg acatattgac gctgtttcat    180
tgttacttga aaaggaagcc aacgtrgaca ctgttgacat cctaggatgc acagctttac    240
acagaggggt atgtacatct ttctcagctc tagtcaagca attttttta  tgagctgttt    300 tcttttttag caaacaatta caagggcct  actttgattg gattttagc  aaaaaatgtt    360 tagcaaaaat tgtttcctaa tacaaccaat taaccttatt cagtccaaaa gaaattacaa    420
aatccttggc aaaggcaaaa taatggaagg ttttgctctt aagatttcat gttagattgt    480
gataatagat gcatgaacac ctactgctgg tgaaattggt tctgctttct gactacaaaa    540
tacaagtata tcatagaaaa tttgcagaat atttttttt  aaagcccaga gaagaaaatc    600
acaatcacca gtaatcatac ctcctggaga taaccactat ttgatgtata ttatctccaa    660
tcttttttct atatatagat ttgttttaga ttttaaaaag agaatactga agatatcatt    720
tggattctgc tttttctct  tagtatatca aggatctttt tcatttcat  ttttttctgc    780 atcatgattt taatgcctc  attgtgttca agtgtcatag tttatttcaa tgattacctg    840
gttttcagta gttatgcaat ttctaattgt ttgtccttac aaataatgcc aaaatatgta    900
tcctgtgggc aattatttgc acacatctgt tgaagtgttt ggtttttttt tttttaatct    960
cactcttatc acccaggttg cagtgagccg agatcacacc actgcattcc agcctgggtg   1020
acacagcgag actccatctc aaaaaaaaaa aaaaaaaac  tcga                    1064
```

<210> SEQ ID NO 85
<211> LENGTH: 1126
<212> TYPE: DNA
<213> ORGANISM: Homo sapiens

<400> SEQUENCE: 85

```
ggcacgagcg gcgccccggc tgcttctgct ctttctggtt ccgctgctgt gggccccggc     60
tgcggtccgg gccggcccag atgaagacct yagccaccgg aacaaagaac cgccggcgcc    120
ggcccagcag ctgcagccgc agcctgtggc tgtgcagggc cccagccggg cccgggtcga    180
ggacccctat ggtgtagccg tgggtggaac tgtggggcac tgcctgtgca cgggattggc    240
agtaattgga ggaagaatga tagcacagaa aatctctgtc agaactgtga caatcatagg    300
aggcatcgtt ttttttggcgt ttgcattttc tgcactattt ataagccctg attctggttt    360
```

-continued

| | |
|---|---|
| ttaacaagct gtttgttcat ctatatttag tttaaaatag gtagtattat ctttctgtac | 420 |
| atagtgtaca ttacaactaa aagtgatgga aaaatactgt attttgtagc actgattttg | 480 |
| tgagtttgac ccattattat gtctgagata taatcattga ttctatttgt aacaaggagt | 540 |
| tttaaaagaa acctgacttc taagtgtggg tttttcttct ctccaacata attatgttaa | 600 |
| tatggtcctc attttctttt tggtgcagaa ccgttgtgca gtgggtctac ccatgcaatt | 660 |
| ttctttcagc actgacccct ttttaaggaa tacaaatttt ctccttcatc acttaggtgt | 720 |
| tttaagatgt ttaccttaaa gttttcttg gggaagaat gaattaattt ctatttctta | 780 |
| aaacatttcc ctgagccagt aaacagtagt ttaatcattg gtcttttcaa aactaggtgt | 840 |
| ttaaaaaaag agacatatat gatattgctg ttatatcaat aacatggcac aacaagaact | 900 |
| gtctgccagg tcattcttcc tcttttttttt taattgggg aggacaccca atataaaaac | 960 |
| agtcaatatt tgacaatgtg gaattaccaa attaaagag aatactatga atgtattcat | 1020 |
| attttttcta tattgaataa acaatgtaac atagataaca atataaataa aagtggtatg | 1080 |
| accaaaaaaa aaaaaaaaca aaaaaaaaaa aaaaaaagg gcggcc | 1126 |

<210> SEQ ID NO 86
<211> LENGTH: 866
<212> TYPE: DNA
<213> ORGANISM: Homo sapiens
<220> FEATURE:
<221> NAME/KEY: SITE
<222> LOCATION: (14)
<223> OTHER INFORMATION: n equals a,t,g, or c
<220> FEATURE:
<221> NAME/KEY: SITE
<222> LOCATION: (27)
<223> OTHER INFORMATION: n equals a,t,g, or c
<220> FEATURE:
<221> NAME/KEY: SITE
<222> LOCATION: (33)
<223> OTHER INFORMATION: n equals a,t,g, or c
<220> FEATURE:
<221> NAME/KEY: SITE
<222> LOCATION: (105)
<223> OTHER INFORMATION: n equals a,t,g, or c

<400> SEQUENCE: 86

| | |
|---|---|
| cctggcttgc tggncaagcc ttggtgncca tgntgaacaa gttttgtgga agttctgggg | 60 |
| agactccaag aactaccagg aacagggata cgagtgccag gctgnatctc ttgctcctct | 120 |
| gcagagtcag caggcttctt ctcagagatg acagaagacg agttggtggt gctgcagcag | 180 |
| atgttctttg gcatcatcat ctgtgcactg gccacgctgg ctgctaaggg cgacttggtg | 240 |
| ttcaccgcca tcttcattgg ggctgtggcg gccatgactg gctactggtt gtcagagcgc | 300 |
| agtgaccgtg tgctggaggg cttcatcaag ggcagataat cgcggccacc acctgtagga | 360 |
| cctcctccca cccacgctgc ccccagagct tgggctgccc tcctgctgga cactcaggac | 420 |
| agcttggttt attttttgaga gtggggtaag caccctacc tgcctacag agcagcccag | 480 |
| gtacccaggc ccgggcagac aaggcccctg ggtaaaaag tagccctgaa ggtggatacc | 540 |
| atgagctctt cacctggcgg ggactggcag gcttcacaat gtgtgaattt caaaagtttt | 600 |
| tccttaatgg tggctgctag agctttggcc cctgcttagg attaggtggt cctcacaggg | 660 |
| gtggggccat cacagctccc tcctgccagc tgcatgctgc cagttcctgt tctgtgttca | 720 |
| ccacatcccc acaccccatt gccacttatt tattcatctc aggaaataaa gaaaggtctt | 780 |
| ggaaagttaa aaaaaaaaa aaaaaaaaa aaaaaactc gagggggggc ccgtacccaa | 840 |
| tcgccctatg atgtagtcgt attaca | 866 |

<210> SEQ ID NO 87
<211> LENGTH: 30
<212> TYPE: PRT
<213> ORGANISM: Homo sapiens
<220> FEATURE:
<221> NAME/KEY: SITE
<222> LOCATION: (30)
<223> OTHER INFORMATION: Xaa equals stop translation

<400> SEQUENCE: 87

Met Pro Ala Leu Ser Met Ala Leu Thr Met Leu Gly Cys Tyr Ala Ile
 1               5                  10                  15

Ala Ile Leu Leu Phe Val Thr Leu Val Arg Lys Pro Ala Xaa
            20                  25                  30

<210> SEQ ID NO 88
<211> LENGTH: 34
<212> TYPE: PRT
<213> ORGANISM: Homo sapiens
<220> FEATURE:
<221> NAME/KEY: SITE
<222> LOCATION: (34)
<223> OTHER INFORMATION: Xaa equals stop translation

<400> SEQUENCE: 88

Met Phe Cys Ile Ser Leu Ser Phe Phe Asn Leu Pro Glu Tyr Ser Pro
 1               5                  10                  15

Cys Ser Leu Leu Ser Val Gln Glu Leu Val Pro Gln Phe Phe Tyr Val
            20                  25                  30

Val Xaa

<210> SEQ ID NO 89
<211> LENGTH: 65
<212> TYPE: PRT
<213> ORGANISM: Homo sapiens
<220> FEATURE:
<221> NAME/KEY: SITE
<222> LOCATION: (55)
<223> OTHER INFORMATION: Xaa equals any of the naturally occurring
      L-amino acids

<400> SEQUENCE: 89

Met Lys Val Ala Val Arg Gly Lys Gln Arg Glu Cys Arg Asp Arg Ile
 1               5                  10                  15

Leu Gly Lys Lys Thr Lys Ala Trp Thr Gln Arg Arg Arg Ser Lys Cys
            20                  25                  30

Gly Ser Gly Tyr Lys Val Arg Val Ser Val Gln Glu Val Asn Lys Val
        35                  40                  45

Ser Arg Thr Arg Lys Ser Xaa Arg Ser Arg Lys Pro Ala Phe Gly Asp
    50                  55                  60

Arg
 65

<210> SEQ ID NO 90
<211> LENGTH: 27
<212> TYPE: PRT
<213> ORGANISM: Homo sapiens
<220> FEATURE:
<221> NAME/KEY: SITE
<222> LOCATION: (27)
<223> OTHER INFORMATION: Xaa equals stop translation

<400> SEQUENCE: 90

```
Met Leu Leu Phe Phe Phe Trp Thr Leu Phe Arg Glu Ser Val Asp His
 1               5                  10                  15

Asn Asn Ser Asp Thr Phe Phe Ser Gly Pro Xaa
                20                  25
```

<210> SEQ ID NO 91
<211> LENGTH: 49
<212> TYPE: PRT
<213> ORGANISM: Homo sapiens
<220> FEATURE:
<221> NAME/KEY: SITE
<222> LOCATION: (49)
<223> OTHER INFORMATION: Xaa equals stop translation

<400> SEQUENCE: 91

```
Met Leu Ser Lys Ser Ser Lys Met Val Ser Val Lys Arg Ala Asp Pro
 1               5                  10                  15

Gly Ser Leu Gly Phe Thr Phe Leu Ser Ser Leu Pro Lys Cys Thr
                20                  25                  30

Val Gly Val Ser Arg Gly Arg Pro Thr Cys Thr Ser Cys Ser Asp Gly
            35                  40                  45

Xaa
```

<210> SEQ ID NO 92
<211> LENGTH: 33
<212> TYPE: PRT
<213> ORGANISM: Homo sapiens
<220> FEATURE:
<221> NAME/KEY: SITE
<222> LOCATION: (33)
<223> OTHER INFORMATION: Xaa equals stop translation

<400> SEQUENCE: 92

```
Met Ser Met Asp Leu Ala Asn Leu Tyr Leu Leu Phe Ile Val His Arg
 1               5                  10                  15

Phe Leu Ile Phe Phe Ile Pro Val Ser Phe Lys Leu Pro Ser Phe Glu
                20                  25                  30

Xaa
```

<210> SEQ ID NO 93
<211> LENGTH: 23
<212> TYPE: PRT
<213> ORGANISM: Homo sapiens
<220> FEATURE:
<221> NAME/KEY: SITE
<222> LOCATION: (23)
<223> OTHER INFORMATION: Xaa equals stop translation

<400> SEQUENCE: 93

```
Met Tyr Leu Val Phe Cys Leu Ser Cys Val Ser Asn Gln Gly Pro His
 1               5                  10                  15

Ser Pro Val Gly Thr Trp Xaa
                20
```

<210> SEQ ID NO 94
<211> LENGTH: 55
<212> TYPE: PRT
<213> ORGANISM: Homo sapiens
<220> FEATURE:
<221> NAME/KEY: SITE
<222> LOCATION: (55)
<223> OTHER INFORMATION: Xaa equals stop translation

<400> SEQUENCE: 94

```
Met Ser Asn Val Val Phe Ser Leu Lys Ala Val Met Trp Val Leu Phe
 1               5                  10                  15

Tyr Cys Leu Phe Val Cys Cys Ile Leu Phe Ser Leu Leu Phe Ala
                 20                  25                  30

Leu Gln Asn Ala Leu Gly Lys Gly Trp Phe Leu Ser Leu Val Cys
             35                  40                  45

Val Phe Phe Phe Phe Phe Xaa
             50                  55
```

<210> SEQ ID NO 95
<211> LENGTH: 39
<212> TYPE: PRT
<213> ORGANISM: Homo sapiens
<220> FEATURE:
<221> NAME/KEY: SITE
<222> LOCATION: (16)
<223> OTHER INFORMATION: Xaa equals any of the naturally occurring
      L-amino acids
<220> FEATURE:
<221> NAME/KEY: SITE
<222> LOCATION: (39)
<223> OTHER INFORMATION: Xaa equals stop translation

<400> SEQUENCE: 95

```
Met Ser Thr Val Lys Gln Ile Val Met Gly Leu Tyr Phe Val Tyr Xaa
 1               5                  10                  15

Tyr Val Cys Phe Phe Tyr Ser Thr Phe Cys Gly Ser Ser Val Leu Leu
                 20                  25                  30

Val Ala Ser Ser Leu Leu Xaa
             35
```

<210> SEQ ID NO 96
<211> LENGTH: 53
<212> TYPE: PRT
<213> ORGANISM: Homo sapiens
<220> FEATURE:
<221> NAME/KEY: SITE
<222> LOCATION: (53)
<223> OTHER INFORMATION: Xaa equals stop translation

<400> SEQUENCE: 96

```
Met Cys Leu Phe Phe Glu Asn Val Thr Leu Leu Phe Val Ile Val Leu
 1               5                  10                  15

His Phe Ser Ala Phe Arg Pro Leu Tyr Phe His Lys Thr Pro Lys Thr
                 20                  25                  30

Ala Phe Asn Tyr Ile Ile Met Ser Val Phe Leu Asp Thr Asn Phe Cys
             35                  40                  45

Ser Arg Met Thr Xaa
         50
```

<210> SEQ ID NO 97
<211> LENGTH: 337
<212> TYPE: PRT
<213> ORGANISM: Homo sapiens
<220> FEATURE:
<221> NAME/KEY: SITE
<222> LOCATION: (337)
<223> OTHER INFORMATION: Xaa equals stop translation

<400> SEQUENCE: 97

```
Met Ile Ser Tyr Ile Val Leu Leu Ser Ile Leu Leu Trp Pro Leu Val
 1               5                  10                  15

Val Tyr His Glu Leu Ile Gln Arg Met Tyr Thr Arg Leu Glu Pro Leu
                 20                  25                  30
```

```
Leu Met Gln Leu Asp Tyr Ser Met Lys Ala Glu Ala Asn Ala Leu His
         35                  40                  45
His Lys His Asp Lys Arg Lys Arg Gln Gly Lys Asn Ala Pro Pro Gly
 50                  55                  60
Gly Asp Glu Pro Leu Ala Glu Thr Glu Ser Glu Ser Glu Ala Glu Leu
 65                  70                  75                  80
Ala Gly Phe Ser Pro Val Val Asp Val Lys Lys Thr Ala Leu Ala Leu
                 85                  90                  95
Ala Ile Thr Asp Ser Glu Leu Ser Asp Glu Glu Ala Ser Ile Leu Glu
                100                 105                 110
Ser Gly Gly Phe Ser Val Ser Arg Ala Thr Thr Pro Gln Leu Thr Asp
            115                 120                 125
Val Ser Glu Asp Leu Asp Gln Gln Ser Leu Pro Ser Glu Pro Glu Glu
            130                 135                 140
Thr Leu Ser Arg Asp Leu Gly Glu Gly Glu Glu Gly Glu Leu Ala Pro
145                 150                 155                 160
Pro Glu Asp Leu Leu Gly Arg Pro Gln Ala Leu Ser Arg Gln Ala Leu
                165                 170                 175
Asp Ser Glu Glu Glu Glu Asp Val Ala Ala Lys Glu Thr Leu Leu
            180                 185                 190
Arg Leu Ser Ser Pro Leu His Phe Val Asn Thr His Phe Asn Gly Ala
            195                 200                 205
Gly Ser Pro Gln Asp Gly Val Lys Cys Ser Pro Gly Gly Pro Val Glu
        210                 215                 220
Thr Leu Ser Pro Glu Thr Val Ser Gly Gly Leu Thr Ala Leu Pro Gly
225                 230                 235                 240
Thr Leu Ser Pro Pro Leu Cys Leu Val Gly Ser Asp Pro Ala Pro Ser
                245                 250                 255
Pro Ser Ile Leu Pro Pro Val Pro Gln Asp Ser Pro Gln Pro Leu Pro
                260                 265                 270
Ala Pro Glu Glu Glu Glu Ala Leu Thr Thr Glu Asp Phe Glu Leu Leu
                275                 280                 285
Asp Gln Gly Glu Leu Glu Gln Leu Asn Ala Glu Leu Gly Leu Glu Pro
            290                 295                 300
Glu Thr Pro Pro Lys Pro Pro Asp Ala Pro Pro Leu Gly Pro Asp Ile
305                 310                 315                 320
His Ser Leu Val Gln Ser Asp Gln Glu Ala Gln Ala Val Ala Glu Pro
                325                 330                 335
Xaa
```

<210> SEQ ID NO 98
<211> LENGTH: 49
<212> TYPE: PRT
<213> ORGANISM: Homo sapiens
<220> FEATURE:
<221> NAME/KEY: SITE
<222> LOCATION: (49)
<223> OTHER INFORMATION: Xaa equals stop translation

<400> SEQUENCE: 98

```
Met Leu Pro Tyr Ser Leu Pro Phe His Ile Ser Cys Thr Ser Ser Leu
 1               5                  10                  15
Ser His His Leu His Pro His Leu Leu Ser Leu Leu Leu Ser Phe Ser
                20                  25                  30
Pro Lys Gly Val Thr Ala Asp Val Lys Ile Ser Leu Met Met Ala Lys
```

<210> SEQ ID NO 99
<211> LENGTH: 38
<212> TYPE: PRT
<213> ORGANISM: Homo sapiens
<220> FEATURE:
<221> NAME/KEY: SITE
<222> LOCATION: (38)
<223> OTHER INFORMATION: Xaa equals stop translation

<400> SEQUENCE: 99

Met Arg Gly Ala His Leu Thr Ala Leu Glu Met Leu Thr Ala Phe Ala
 1               5                  10                  15

Ser His Ile Arg Ala Arg Asp Ala Ala Gly Ser Gly Asp Lys Pro Gly
            20                  25                  30

Ala Asp Thr Gly Arg Xaa
            35

<210> SEQ ID NO 100
<211> LENGTH: 29
<212> TYPE: PRT
<213> ORGANISM: Homo sapiens
<220> FEATURE:
<221> NAME/KEY: SITE
<222> LOCATION: (29)
<223> OTHER INFORMATION: Xaa equals stop translation

<400> SEQUENCE: 100

Met Leu Phe Lys Leu Phe Phe Ser Leu Ile Leu Phe Ser Phe Val Val
 1               5                  10                  15

Ser Cys Ile Phe Ser Val Ser Ile Asn Ile Pro Leu Xaa
            20                  25

<210> SEQ ID NO 101
<211> LENGTH: 36
<212> TYPE: PRT
<213> ORGANISM: Homo sapiens
<220> FEATURE:
<221> NAME/KEY: SITE
<222> LOCATION: (36)
<223> OTHER INFORMATION: Xaa equals stop translation

<400> SEQUENCE: 101

Met Pro Phe Met Phe Leu Ser Leu Pro Arg Asp Thr Phe Leu Met Leu
 1               5                  10                  15

Glu Leu Val Leu Gly Thr Phe Thr Cys Asn Gly Ser Phe Phe Ile His
            20                  25                  30

Lys Ala Ser Xaa
            35

<210> SEQ ID NO 102
<211> LENGTH: 182
<212> TYPE: PRT
<213> ORGANISM: Homo sapiens
<220> FEATURE:
<221> NAME/KEY: SITE
<222> LOCATION: (182)
<223> OTHER INFORMATION: Xaa equals stop translation

<400> SEQUENCE: 102

Met Ala Ala Leu Cys Arg Thr Arg Ala Val Ala Ala Glu Ser His Phe
 1               5                  10                  15

-continued

```
Leu Arg Val Phe Leu Phe Phe Arg Pro Phe Arg Gly Val Gly Thr Glu
                20                  25                  30

Ser Gly Ser Glu Ser Gly Ser Ser Asn Ala Lys Glu Pro Lys Thr Arg
            35                  40                  45

Ala Gly Gly Phe Ala Ser Ala Leu Glu Arg His Ser Glu Leu Leu Gln
 50                  55                  60

Lys Gly Ser Pro Lys Asn Val Glu Ser Phe Ala Ser Met Leu Arg His
 65                  70                  75                  80

Ser Pro Leu Thr Gln Met Gly Pro Ala Lys Asp Lys Leu Val Ile Gly
                85                  90                  95

Arg Ile Phe His Ile Val Glu Asn Asp Leu Tyr Ile Asp Phe Gly Gly
                100                 105                 110

Lys Phe His Cys Val Cys Arg Arg Pro Glu Val Asp Gly Glu Lys Tyr
            115                 120                 125

Gln Lys Gly Thr Arg Val Arg Leu Arg Leu Asp Leu Glu Leu Thr
130                 135                 140

Ser Arg Phe Leu Gly Ala Thr Thr Asp Thr Thr Val Leu Glu Ala Asn
145                 150                 155                 160

Ala Val Leu Leu Gly Ile Gln Glu Ser Lys Asp Ser Arg Ser Lys Glu
                165                 170                 175

Glu His His Glu Lys Xaa
                180

<210> SEQ ID NO 103
<211> LENGTH: 84
<212> TYPE: PRT
<213> ORGANISM: Homo sapiens
<220> FEATURE:
<221> NAME/KEY: SITE
<222> LOCATION: (84)
<223> OTHER INFORMATION: Xaa equals stop translation

<400> SEQUENCE: 103

Met Asn Val Leu Val Tyr Ser Asp Lys Glu Lys Asn Gln Lys Ser
 1               5                  10                  15

Gly Leu Asn Leu Ile Val Phe Ile Ile Lys Ile Leu Lys Met Thr Leu
                20                  25                  30

Ile Ala Arg Lys Thr Gly Trp Gly Ile Ser Pro Leu Leu Ser Val Thr
            35                  40                  45

Met Arg Ile Ile Pro Ala Leu Val Phe Asn Thr Arg Leu Pro Thr Phe
 50                  55                  60

Ile Ile Ser Leu Ile Phe Leu Leu Phe Ser Cys Ile Cys Glu Leu Val
 65                  70                  75                  80

Gln Glu Cys Xaa

<210> SEQ ID NO 104
<211> LENGTH: 25
<212> TYPE: PRT
<213> ORGANISM: Homo sapiens
<220> FEATURE:
<221> NAME/KEY: SITE
<222> LOCATION: (25)
<223> OTHER INFORMATION: Xaa equals stop translation

<400> SEQUENCE: 104

Met Gln Val Leu Met Leu Ala His Phe Leu Ile Leu Leu Glu His Val
 1               5                  10                  15

Gln Gly Arg Cys Ser Asp Asn Asn Xaa
                20                  25
```

```
<210> SEQ ID NO 105
<211> LENGTH: 32
<212> TYPE: PRT
<213> ORGANISM: Homo sapiens
<220> FEATURE:
<221> NAME/KEY: SITE
<222> LOCATION: (32)
<223> OTHER INFORMATION: Xaa equals stop translation

<400> SEQUENCE: 105

Met Asp Cys Met Cys Ile Tyr Met Phe Leu Ile Ile Leu Ile Asn Val
  1               5                  10                  15

Cys Arg Phe Gln Gly Thr Asn Phe Ser Pro Leu Tyr Val Tyr Ser Xaa
             20                  25                  30

<210> SEQ ID NO 106
<211> LENGTH: 175
<212> TYPE: PRT
<213> ORGANISM: Homo sapiens

<400> SEQUENCE: 106

Met Ala Ser Leu Arg Val Glu Arg Ala Gly Gly Pro Arg Leu Pro Arg
  1               5                  10                  15

Thr Arg Val Gly Arg Pro Ala Ala Leu Arg Leu Leu Leu Leu Leu Gly
             20                  25                  30

Ala Val Leu Asn Pro His Glu Ala Leu Ala Gln Pro Leu Pro Thr Thr
         35                  40                  45

Gly Thr Pro Gly Ser Glu Gly Gly Thr Val Lys Asn Tyr Glu Thr Ala
     50                  55                  60

Val Gln Phe Cys Trp Asn His Tyr Lys Asp Gln Met Asp Pro Ile Glu
 65                  70                  75                  80

Lys Asp Trp Cys Asp Trp Ala Met Ile Ser Arg Pro Tyr Ser Thr Leu
                 85                  90                  95

Arg Asp Cys Leu Glu His Phe Ala Glu Leu Phe Asp Leu Gly Phe Pro
            100                 105                 110

Asn Pro Leu Ala Glu Arg Ile Ile Phe Glu Thr His Gln Ile His Phe
        115                 120                 125

Ala Asn Cys Ser Leu Val Gln Pro Thr Phe Ser Asp Pro Pro Glu Asp
    130                 135                 140

Val Leu Leu Ala Met Ile Ile Ala Pro Ile Cys Leu Ile Pro Phe Leu
145                 150                 155                 160

Ile Thr Leu Val Val Trp Arg Ser Lys Asp Ser Glu Ala Gln Ala
                165                 170                 175

<210> SEQ ID NO 107
<211> LENGTH: 119
<212> TYPE: PRT
<213> ORGANISM: Homo sapiens

<400> SEQUENCE: 107

Met Gly Val Leu Ala Glu His Gly Gly His Pro Ala Gln Glu His Phe
  1               5                  10                  15

Pro Lys Leu Leu Gly Leu Leu Phe Pro Leu Leu Ala Arg Glu Arg His
             20                  25                  30

Asp Arg Val Arg Asp Asn Ile Cys Gly Ala Leu Ala Arg Leu Leu Met
         35                  40                  45

Ala Ser Pro Thr Arg Lys Pro Glu Pro Gln Val Leu Ala Ala Leu Leu
     50                  55                  60
```

His Ala Leu Pro Leu Lys Glu Asp Leu Glu Glu Trp Val Thr Ile Gly
 65                  70                  75                  80

Arg Leu Phe Ser Leu Leu Thr Phe Leu Ala Lys Gln His Thr Asp Ser
                 85                  90                  95

Phe Gln Ala Ala Leu Gly Ser Leu Pro Val Asp Lys Ala Gln Glu Leu
            100                 105                 110

Gln Ala Val Leu Gly Leu Ser
        115

<210> SEQ ID NO 108
<211> LENGTH: 128
<212> TYPE: PRT
<213> ORGANISM: Homo sapiens
<220> FEATURE:
<221> NAME/KEY: SITE
<222> LOCATION: (128)
<223> OTHER INFORMATION: Xaa equals stop translation

<400> SEQUENCE: 108

Met Lys Val Ala Phe Leu Leu Gly Ser Leu Ala Ala Arg Gly Ser Asp
  1               5                  10                  15

Thr Arg Ser Asn Thr Glu Leu Ser Ser Gly Ala Lys Val Phe Pro Val
                 20                  25                  30

Ser Ser Ala Arg Glu Pro Ser Pro Ala Ser Phe Arg Ser Gln Cys
             35                  40                  45

Ser Ser Asn Thr Val Tyr Thr Leu Phe Cys Phe Gln Ile Tyr Pro Glu
         50                  55                  60

Ala Leu Leu Ser Ile Asn Asp Tyr Thr Ile Lys Val Ser Val Ile Leu
 65                  70                  75                  80

Glu Leu Ile Ser Val Gly Ile Ser Cys Met Gln Ser Val Ala Phe Arg
                 85                  90                  95

Gly Leu Ser Pro Ile Leu Val Ser Cys Arg Ala Asp Cys Ser Leu His
            100                 105                 110

Leu Asp Leu Asn Glu Gly Leu Trp Leu Glu Cys Val Arg Ser Arg Xaa
        115                 120                 125

<210> SEQ ID NO 109
<211> LENGTH: 31
<212> TYPE: PRT
<213> ORGANISM: Homo sapiens
<220> FEATURE:
<221> NAME/KEY: SITE
<222> LOCATION: (31)
<223> OTHER INFORMATION: Xaa equals stop translation

<400> SEQUENCE: 109

Met Arg Lys Glu Glu Gln Val Phe Phe Val Met Leu Leu Arg Lys Tyr
  1               5                  10                  15

Pro Glu Ser Gln His His Asp Leu Leu Val Lys Gln Asn Lys Xaa
                 20                  25                  30

<210> SEQ ID NO 110
<211> LENGTH: 32
<212> TYPE: PRT
<213> ORGANISM: Homo sapiens
<220> FEATURE:
<221> NAME/KEY: SITE
<222> LOCATION: (32)
<223> OTHER INFORMATION: Xaa equals stop translation

<400> SEQUENCE: 110

```
Met Arg Ile Val Val Leu Val Thr Phe Met Cys Leu Gly Arg Leu Arg
1               5                   10                  15

Cys Ser Thr Ser Leu Arg His Ser Gln Asn Ala Asn Leu Leu Phe Xaa
                20                  25                  30
```

<210> SEQ ID NO 111
<211> LENGTH: 96
<212> TYPE: PRT
<213> ORGANISM: Homo sapiens

<400> SEQUENCE: 111

```
Met Phe Leu Ser Ser Ser Asn Gln Ser Ser Thr Cys Met Lys Thr Leu
1               5                   10                  15

Val Ile Leu Val Ser Ser Trp Arg Ala Gln Gly His Ala Ala Gly Phe
                20                  25                  30

Leu Lys Ile Lys Ala Leu Phe Leu Lys Tyr Met Ala Thr Lys Asp Ala
                35                  40                  45

Phe Leu Gly Ser Asp Val Ser Trp Leu Ile Gln Ile Met Met Val
        50                  55                  60

Leu Gly Asn Phe Tyr Asn Tyr Arg Pro Leu Leu Phe Phe Met Leu Asn
65                  70                  75                  80

Ala Ser Cys Arg Ile Arg Tyr Gln Ala Tyr Arg Tyr Arg Arg Pro Arg
                85                  90                  95
```

<210> SEQ ID NO 112
<211> LENGTH: 22
<212> TYPE: PRT
<213> ORGANISM: Homo sapiens
<220> FEATURE:
<221> NAME/KEY: SITE
<222> LOCATION: (22)
<223> OTHER INFORMATION: Xaa equals stop translation

<400> SEQUENCE: 112

```
Met Tyr Phe Ile Tyr Leu Lys Tyr Ile Leu Leu Thr Pro Gly Val Gly
1               5                   10                  15

Met Asn Glu Thr Arg Xaa
                20
```

<210> SEQ ID NO 113
<211> LENGTH: 46
<212> TYPE: PRT
<213> ORGANISM: Homo sapiens

<400> SEQUENCE: 113

```
Met Leu Val Leu Glu Asn Lys Phe Lys Ser Phe Leu Tyr Val Ile Tyr
1               5                   10                  15

Thr Leu Pro Glu Lys Ser Leu Asn Ser Ile Glu Asn Asp Leu Phe Phe
                20                  25                  30

Glu Asp Leu Thr Asn Phe Thr Cys Lys Ser Val Cys Ala Leu
                35                  40                  45
```

<210> SEQ ID NO 114
<211> LENGTH: 356
<212> TYPE: PRT
<213> ORGANISM: Homo sapiens
<220> FEATURE:
<221> NAME/KEY: SITE
<222> LOCATION: (356)
<223> OTHER INFORMATION: Xaa equals stop translation

<400> SEQUENCE: 114

```
Met Phe Tyr Leu Leu Leu Ser Leu Leu Met Ile Lys Val Lys Ser Ser
 1               5                  10                  15

Ser Asp Pro Arg Ala Ala Val His Asn Gly Phe Trp Phe Lys Phe
             20                  25                  30

Ala Ala Ala Ile Ala Ile Ile Gly Ala Phe Phe Ile Pro Glu Gly
         35                  40                  45

Thr Phe Thr Thr Val Trp Phe Tyr Val Gly Met Ala Gly Ala Phe Cys
     50                  55                  60

Phe Ile Leu Ile Gln Leu Val Leu Leu Ile Asp Phe Ala His Ser Trp
 65                  70                  75                  80

Asn Glu Ser Trp Val Glu Lys Met Glu Glu Gly Asn Ser Arg Cys Trp
                 85                  90                  95

Tyr Ala Ala Leu Leu Ser Ala Thr Ala Leu Asn Tyr Leu Leu Ser Leu
                100                 105                 110

Val Ala Ile Val Leu Phe Phe Val Tyr Tyr Thr His Pro Ala Ser Cys
             115                 120                 125

Ser Glu Asn Lys Ala Phe Ile Ser Val Asn Met Leu Leu Cys Val Gly
         130                 135                 140

Ala Ser Val Met Ser Ile Leu Pro Lys Ile Gln Glu Ser Gln Pro Arg
145                 150                 155                 160

Ser Gly Leu Leu Gln Ser Ser Val Ile Thr Val Tyr Thr Met Tyr Leu
                 165                 170                 175

Thr Trp Ser Ala Met Thr Asn Glu Pro Glu Thr Asn Cys Asn Pro Ser
             180                 185                 190

Leu Leu Ser Ile Ile Gly Tyr Asn Thr Thr Ser Thr Val Pro Lys Glu
         195                 200                 205

Gly Gln Ser Val Gln Trp Trp His Ala Gln Gly Ile Ile Gly Leu Ile
210                 215                 220

Leu Phe Leu Leu Cys Val Phe Tyr Ser Ser Ile Arg Thr Ser Asn Asn
225                 230                 235                 240

Ser Gln Val Asn Lys Leu Thr Leu Thr Ser Asp Glu Ser Thr Leu Ile
                 245                 250                 255

Glu Asp Gly Gly Ala Arg Ser Asp Gly Ser Leu Glu Asp Gly Asp Asp
             260                 265                 270

Val His Arg Ala Val Asp Asn Glu Arg Asp Gly Val Thr Tyr Ser Tyr
         275                 280                 285

Ser Phe Phe His Phe Met Leu Phe Leu Ala Ser Leu Tyr Ile Met Met
     290                 295                 300

Thr Leu Thr Asn Trp Tyr Arg Tyr Glu Pro Ser Arg Glu Met Lys Ser
305                 310                 315                 320

Gln Trp Thr Ala Val Trp Val Lys Ile Ser Ser Trp Ile Gly Ile
                 325                 330                 335

Val Leu Tyr Val Trp Thr Leu Val Ala Pro Leu Val Leu Thr Asn Arg
             340                 345                 350

Asp Phe Asp Xaa
        355

<210> SEQ ID NO 115
<211> LENGTH: 71
<212> TYPE: PRT
<213> ORGANISM: Homo sapiens
<220> FEATURE:
<221> NAME/KEY: SITE
<222> LOCATION: (71)
<223> OTHER INFORMATION: Xaa equals stop translation
```

-continued

```
<400> SEQUENCE: 115

Met His Trp Leu Gly Arg Gly Trp Arg Leu Leu Glu Gly Gly Glu Lys
 1               5                  10                  15

Glu Leu Pro Thr Trp Ser Leu Leu Leu Tyr Pro Gly Cys Leu Gln
            20                  25                  30

Ser Cys Ser Thr Thr Pro Trp Thr Thr Pro Ser Gln Met Pro Glu Ala
        35                  40                  45

Thr Gly Gly Gln Gly Arg Gln Gly Gly Leu Pro Ala Leu Leu Gln Gln
    50                  55                  60

Arg Ala Thr Thr Leu Gly Xaa
65                  70

<210> SEQ ID NO 116
<211> LENGTH: 171
<212> TYPE: PRT
<213> ORGANISM: Homo sapiens
<220> FEATURE:
<221> NAME/KEY: SITE
<222> LOCATION: (171)
<223> OTHER INFORMATION: Xaa equals stop translation

<400> SEQUENCE: 116

Met Val Pro Val Leu Ser Leu Leu Leu Leu Gly Pro Ala Val
 1               5                  10                  15

Pro Gln Glu Asn Gln Asp Gly Arg Tyr Ser Leu Thr Tyr Ile Tyr Thr
            20                  25                  30

Gly Leu Ser Lys His Val Glu Asp Val Pro Ala Phe Gln Ala Leu Gly
        35                  40                  45

Ser Leu Asn Asp Leu Gln Phe Phe Arg Tyr Asn Ser Lys Asp Arg Lys
    50                  55                  60

Ser Gln Pro Met Gly Leu Trp Arg Gln Val Glu Gly Met Glu Asp Trp
65                  70                  75                  80

Lys Gln Asp Ser Gln Leu Gln Lys Ala Arg Glu Asp Ile Phe Met Glu
                85                  90                  95

Thr Leu Lys Asp Ile Val Glu Tyr Tyr Asn Asp Ser Asn Gly Ser His
            100                 105                 110

Val Leu Gln Gly Arg Phe Gly Cys Glu Ile Glu Asn Asn Arg Ser Ser
        115                 120                 125

Gly Ala Phe Trp Lys Tyr Tyr Tyr Asp Gly Lys Asp Tyr Ile Glu Phe
    130                 135                 140

Asn Lys Glu Ile Pro Ala Trp Val Pro Phe Asp Pro Ala Ala Gln Ile
145                 150                 155                 160

Thr Lys Gln Lys Trp Asp Ala Cys Leu Glu Xaa
                165                 170

<210> SEQ ID NO 117
<211> LENGTH: 36
<212> TYPE: PRT
<213> ORGANISM: Homo sapiens
<220> FEATURE:
<221> NAME/KEY: SITE
<222> LOCATION: (36)
<223> OTHER INFORMATION: Xaa equals stop translation

<400> SEQUENCE: 117

Met Gly Leu Phe Asn Gln Cys Asp Tyr Ser Asp Pro Ser Leu Gln Leu
 1               5                  10                  15

Val Phe Phe Leu Met Ala Leu Phe His Ile Leu Phe Ser Leu Thr Thr
            20                  25                  30
```

-continued

```
Leu Ile Met Xaa
         35
```

<210> SEQ ID NO 118
<211> LENGTH: 14
<212> TYPE: PRT
<213> ORGANISM: Homo sapiens
<220> FEATURE:
<221> NAME/KEY: SITE
<222> LOCATION: (14)
<223> OTHER INFORMATION: Xaa equals stop translation

<400> SEQUENCE: 118

```
Met Arg Asp His Glu Ile Trp Glu Gly Pro Gly Ala Glu Xaa
  1               5                  10
```

<210> SEQ ID NO 119
<211> LENGTH: 156
<212> TYPE: PRT
<213> ORGANISM: Homo sapiens
<220> FEATURE:
<221> NAME/KEY: SITE
<222> LOCATION: (156)
<223> OTHER INFORMATION: Xaa equals stop translation

<400> SEQUENCE: 119

```
Met Phe Glu His Phe Ser Leu Phe Phe Val Cys Val Phe Gln Ile Asn
  1               5                  10                  15

Val Phe Phe Tyr Thr Ile Pro Leu Ala Ile Lys Leu Lys Glu His Pro
             20                  25                  30

Ile Phe Phe Met Phe Ile Gln Ile Ala Val Ile Ala Ile Phe Lys Ser
         35                  40                  45

Tyr Pro Thr Val Gly Asp Val Ala Leu Tyr Met Ala Phe Phe Pro Val
     50                  55                  60

Trp Asn His Leu Tyr Arg Phe Leu Arg Asn Ile Phe Val Leu Thr Cys
 65                  70                  75                  80

Ile Ile Ile Val Cys Ser Leu Leu Phe Pro Val Leu Trp His Leu Trp
                 85                  90                  95

Ile Tyr Ala Gly Ser Ala Asn Ser Asn Phe Phe Tyr Ala Ile Thr Leu
                100                 105                 110

Thr Phe Asn Val Gly Gln Ile Leu Leu Ile Ser Asp Tyr Phe Tyr Ala
            115                 120                 125

Phe Leu Arg Arg Glu Tyr Tyr Leu Thr His Gly Leu Tyr Leu Thr Ala
        130                 135                 140

Lys Asp Gly Thr Glu Ala Met Leu Val Leu Lys Xaa
145                 150                 155
```

<210> SEQ ID NO 120
<211> LENGTH: 39
<212> TYPE: PRT
<213> ORGANISM: Homo sapiens
<220> FEATURE:
<221> NAME/KEY: SITE
<222> LOCATION: (39)
<223> OTHER INFORMATION: Xaa equals stop translation

<400> SEQUENCE: 120

```
Met Val Cys Glu Leu Ala His Leu Asp His Cys Ile Leu Pro Leu Ser
  1               5                  10                  15

Phe Leu Val Ser His Cys His Cys Met Ala Ser Cys His Cys Glu Ser
             20                  25                  30
```

-continued

```
Trp Pro Ser Leu Ser Leu Xaa
            35

<210> SEQ ID NO 121
<211> LENGTH: 47
<212> TYPE: PRT
<213> ORGANISM: Homo sapiens
<220> FEATURE:
<221> NAME/KEY: SITE
<222> LOCATION: (46)
<223> OTHER INFORMATION: Xaa equals any of the naturally occurring
      L-amino acids
<220> FEATURE:
<221> NAME/KEY: SITE
<222> LOCATION: (47)
<223> OTHER INFORMATION: Xaa equals stop translation

<400> SEQUENCE: 121

Met Glu Val Val Leu Thr Val Ala His Pro Leu Arg Glu Arg Arg Lys
 1               5                  10                  15

Arg Ser Ser Val Ile Cys Val Tyr Cys Cys Leu Leu Phe Cys Leu Phe
            20                  25                  30

Tyr Tyr Val Val Phe Ile Asp Phe Val Lys Lys Val Asn Xaa Xaa
            35                  40                  45

<210> SEQ ID NO 122
<211> LENGTH: 147
<212> TYPE: PRT
<213> ORGANISM: Homo sapiens
<220> FEATURE:
<221> NAME/KEY: SITE
<222> LOCATION: (70)
<223> OTHER INFORMATION: Xaa equals any of the naturally occurring
      L-amino acids
<220> FEATURE:
<221> NAME/KEY: SITE
<222> LOCATION: (147)
<223> OTHER INFORMATION: Xaa equals stop translation

<400> SEQUENCE: 122

Met Lys Ala Ser Val Val Leu Ser Leu Leu Gly Tyr Leu Val Val Pro
 1               5                  10                  15

Ser Gly Ala Tyr Ile Leu Gly Arg Cys Thr Val Ala Lys Lys Leu His
            20                  25                  30

Asp Gly Gly Leu Asp Tyr Phe Glu Gly Tyr Ser Leu Glu Asn Trp Val
            35                  40                  45

Cys Leu Ala Tyr Phe Glu Ser Lys Phe Asn Pro Met Ala Ile Tyr Glu
        50                  55                  60

Asn Thr Arg Glu Gly Xaa Thr Gly Phe Gly Leu Phe Gln Met Arg Gly
 65                  70                  75                  80

Ser Asp Trp Cys Gly Asp His Gly Arg Asn Arg Cys His Met Ser Cys
                85                  90                  95

Ser Ala Leu Leu Asn Pro Asn Leu Glu Lys Thr Ile Lys Cys Ala Lys
            100                 105                 110

Thr Ile Val Lys Gly Lys Glu Gly Met Gly Ala Trp Pro Thr Trp Ser
            115                 120                 125

Arg Tyr Cys Gln Tyr Ser Asp Thr Leu Ala Arg Trp Leu Asp Gly Cys
            130                 135                 140

Lys Leu Xaa
145

<210> SEQ ID NO 123
<211> LENGTH: 44
```

-continued

```
<212> TYPE: PRT
<213> ORGANISM: Homo sapiens
<220> FEATURE:
<221> NAME/KEY: SITE
<222> LOCATION: (44)
<223> OTHER INFORMATION: Xaa equals stop translation

<400> SEQUENCE: 123
```

Met Tyr Leu Ser His Phe His Leu Gly Ile Val Ile Met Ala Val Ala
1               5                   10                  15

Ala Leu Met Glu Lys Pro Val Leu Ala Ser Phe Ser Gly Ile Arg Ile
            20                  25                  30

Ser Cys His Arg Thr Ile Gly Lys Val Gln Val Xaa
        35                  40

```
<210> SEQ ID NO 124
<211> LENGTH: 81
<212> TYPE: PRT
<213> ORGANISM: Homo sapiens
<220> FEATURE:
<221> NAME/KEY: SITE
<222> LOCATION: (35)
<223> OTHER INFORMATION: Xaa equals any of the naturally occurring
      L-amino acids
<220> FEATURE:
<221> NAME/KEY: SITE
<222> LOCATION: (52)
<223> OTHER INFORMATION: Xaa equals any of the naturally occurring
      L-amino acids
<220> FEATURE:
<221> NAME/KEY: SITE
<222> LOCATION: (74)
<223> OTHER INFORMATION: Xaa equals any of the naturally occurring
      L-amino acids
<220> FEATURE:
<221> NAME/KEY: SITE
<222> LOCATION: (81)
<223> OTHER INFORMATION: Xaa equals stop translation

<400> SEQUENCE: 124
```

Met Ser Lys Gly Arg Pro Lys Leu Gly Ser Ser Lys Gly Leu Ala Gly
1               5                   10                  15

Gln Leu Trp Leu Leu Thr Leu Arg Leu Leu Gly Ala Leu Leu Val
            20                  25                  30

Trp Thr Xaa Ala Tyr Val Tyr Val Val Asn Pro Thr Pro Phe Glu Gly
            35                  40                  45

Leu Val Pro Xaa Leu Leu Ser Arg Ala Thr Val Trp Lys Leu Arg Ala
        50                  55                  60

Leu Leu Asp Pro Phe Leu Arg Leu Lys Xaa Asp Gly Phe Leu Pro Phe
65                  70                  75                  80

Xaa

```
<210> SEQ ID NO 125
<211> LENGTH: 98
<212> TYPE: PRT
<213> ORGANISM: Homo sapiens

<400> SEQUENCE: 125
```

Met Cys Ser Val Val Leu Leu Lys Asp Cys Pro Leu Phe Ser Phe Ser
1               5                   10                  15

Val Ile Asn Gly His Thr Leu Cys Leu Arg Leu Leu Leu Glu Ile Ala
            20                  25                  30

Asp Asn Pro Glu Ala Val Asp Val Lys Asp Ala Lys Gly Gln Thr Pro
        35                  40                  45

```
Leu Met Leu Ala Val Ala Tyr Gly His Ile Asp Ala Val Ser Leu Leu
         50                  55                  60

Leu Glu Lys Glu Ala Asn Val Asp Thr Val Asp Ile Leu Gly Cys Thr
 65                  70                  75                  80

Ala Leu His Arg Gly Val Cys Thr Ser Phe Ser Ala Leu Val Lys Gln
                 85                  90                  95

Phe Phe

<210> SEQ ID NO 126
<211> LENGTH: 32
<212> TYPE: PRT
<213> ORGANISM: Homo sapiens
<220> FEATURE:
<221> NAME/KEY: SITE
<222> LOCATION: (32)
<223> OTHER INFORMATION: Xaa equals stop translation

<400> SEQUENCE: 126

Met Asn Cys Val Leu Ala Thr Tyr Gly Ser Ile Ala Leu Ile Val Leu
 1               5                  10                  15

Tyr Phe Lys Leu Arg Ser Lys Lys Thr Pro Ala Val Lys Ala Thr Xaa
                 20                  25                  30

<210> SEQ ID NO 127
<211> LENGTH: 22
<212> TYPE: PRT
<213> ORGANISM: Homo sapiens
<220> FEATURE:
<221> NAME/KEY: SITE
<222> LOCATION: (22)
<223> OTHER INFORMATION: Xaa equals stop translation

<400> SEQUENCE: 127

Met Asn Gly Leu Leu Phe Leu Val Met Ile Ala Lys Asn Leu Leu Pro
 1               5                  10                  15

Ser Gly Asn Lys Gln Xaa
                 20

<210> SEQ ID NO 128
<211> LENGTH: 121
<212> TYPE: PRT
<213> ORGANISM: Homo sapiens

<400> SEQUENCE: 128

Met Leu Trp Val Lys Thr Arg Arg Glu Glu Leu Arg Pro Phe Gly Glu
 1               5                  10                  15

Pro Arg Pro Gly Ser Ser Leu Arg Gln Gly Cys Asp Ser Leu Phe Gly
                 20                  25                  30

Pro Leu Lys Phe Leu Glu Ser Gln Ala Ser Ser Arg His His Val Ser
             35                  40                  45

Trp Trp Gln Leu Trp Lys Leu Leu Leu Val Cys Leu Val Gln Leu Gln
         50                  55                  60

Pro Cys Arg Glu Pro Ala Pro Met Gln Thr Pro Cys Ala Gly Cys Pro
 65                  70                  75                  80

Ala Ala Ala Ala Gly Val Pro His Cys Val Gln Trp Leu Asp Pro Met
                 85                  90                  95

Leu Thr Cys Ser His Thr Pro His Cys Ser Thr Pro Gly Leu Pro Leu
                100                 105                 110

Ala Val Met Gly Ser Arg Leu Val Ala
            115                 120
```

-continued

<210> SEQ ID NO 129
<211> LENGTH: 26
<212> TYPE: PRT
<213> ORGANISM: Homo sapiens
<220> FEATURE:
<221> NAME/KEY: SITE
<222> LOCATION: (26)
<223> OTHER INFORMATION: Xaa equals stop translation

<400> SEQUENCE: 129

Met Leu Pro Ser Phe Pro Ser Leu Arg Val Phe Val Ile Phe Phe Cys
 1               5                  10                  15

Leu Leu Val Tyr Cys Leu Phe Ala Pro Xaa
             20                  25

<210> SEQ ID NO 130
<211> LENGTH: 34
<212> TYPE: PRT
<213> ORGANISM: Homo sapiens

<400> SEQUENCE: 130

Met Arg Ala Ala Phe Ile Ile His Tyr Met Cys Phe Leu Pro Val Cys
 1               5                  10                  15

Gln Leu Ser Phe Ala Phe Leu Val Ile Leu Pro Gly Thr Tyr Val Asn
             20                  25                  30

Leu His

<210> SEQ ID NO 131
<211> LENGTH: 39
<212> TYPE: PRT
<213> ORGANISM: Homo sapiens
<220> FEATURE:
<221> NAME/KEY: SITE
<222> LOCATION: (39)
<223> OTHER INFORMATION: Xaa equals stop translation

<400> SEQUENCE: 131

Met Tyr Lys Ile His Ser Glu Asn Cys Leu Val Ile Leu His Leu Phe
 1               5                  10                  15

Ile Gln Lys Thr Val Ile Ser Gly Glu Pro Asn Met Leu Val Asn Ile
             20                  25                  30

Phe Asn Phe Phe Pro His Xaa
             35

<210> SEQ ID NO 132
<211> LENGTH: 74
<212> TYPE: PRT
<213> ORGANISM: Homo sapiens
<220> FEATURE:
<221> NAME/KEY: SITE
<222> LOCATION: (74)
<223> OTHER INFORMATION: Xaa equals stop translation

<400> SEQUENCE: 132

Met Gly Ile Ala Val Ser Met Leu Thr Tyr Pro Phe Leu Leu Val Gly
 1               5                  10                  15

Asp Leu Met Ala Val Asn Asn Cys Gly Leu Gln Ala Gly Leu Pro Pro
             20                  25                  30

Tyr Ser Pro Val Phe Lys Ser Trp Ile His Cys Trp Lys Tyr Leu Ser
             35                  40                  45

Val Gln Gly Gln Leu Phe Arg Gly Ser Ser Leu Leu Phe Arg Arg Val
             50                  55                  60

-continued

Ser Ser Gly Ser Cys Phe Ala Leu Glu Xaa
65                  70

<210> SEQ ID NO 133
<211> LENGTH: 55
<212> TYPE: PRT
<213> ORGANISM: Homo sapiens
<220> FEATURE:
<221> NAME/KEY: SITE
<222> LOCATION: (55)
<223> OTHER INFORMATION: Xaa equals stop translation

<400> SEQUENCE: 133

Met His Ser Gly Phe Tyr Thr Ser Ala Phe Arg Gly Leu Trp Gln His
1               5                   10                  15

Gly Met Gly Gln Glu Val Leu Leu His Leu Pro Leu Met Ser Val
            20                  25                  30

Thr His Pro Phe Cys Thr Ala Gly Val Val Asn Ala Phe Val Ser Ser
        35                  40                  45

Ser Ser His Ala Asp Cys Xaa
    50                  55

<210> SEQ ID NO 134
<211> LENGTH: 44
<212> TYPE: PRT
<213> ORGANISM: Homo sapiens
<220> FEATURE:
<221> NAME/KEY: SITE
<222> LOCATION: (44)
<223> OTHER INFORMATION: Xaa equals stop translation

<400> SEQUENCE: 134

Met Glu Leu Arg Val Glu Thr Gly His Phe Thr Gly His Leu Ser Thr
1               5                   10                  15

Val Lys Ile Leu Phe Thr Leu Leu Val Pro Val Phe Tyr Ile Glu Asp
            20                  25                  30

Leu Ala Met Asn Cys Tyr Leu Asn Leu Arg Ala Xaa
        35                  40

<210> SEQ ID NO 135
<211> LENGTH: 37
<212> TYPE: PRT
<213> ORGANISM: Homo sapiens
<220> FEATURE:
<221> NAME/KEY: SITE
<222> LOCATION: (37)
<223> OTHER INFORMATION: Xaa equals stop translation

<400> SEQUENCE: 135

Met Phe Phe Gly Ala Pro Thr Ala Gly Ala Val Gln Val Trp Leu Leu
1               5                   10                  15

Leu Leu Ser Pro Ala Ala Ser Pro Val Glu Glu Leu Ser Val Leu Val
            20                  25                  30

Pro Cys Gly Gln Xaa
        35

<210> SEQ ID NO 136
<211> LENGTH: 50
<212> TYPE: PRT
<213> ORGANISM: Homo sapiens
<220> FEATURE:
<221> NAME/KEY: SITE
<222> LOCATION: (50)
<223> OTHER INFORMATION: Xaa equals stop translation

<400> SEQUENCE: 136

Met Ile Leu Leu Pro Gly Leu Ser His Tyr Asn Ala Leu Gly Leu Phe
1               5                   10                  15

Phe Ala Ala Val Leu Leu Phe Leu Asn Leu Gly Gln Val Pro Met Leu
                20                  25                  30

Ala Val Arg Arg Asp Ser Val His Ser Thr Cys Asn Phe Arg Glu Trp
            35                  40                  45

Lys Xaa
    50

<210> SEQ ID NO 137
<211> LENGTH: 84
<212> TYPE: PRT
<213> ORGANISM: Homo sapiens

<400> SEQUENCE: 137

Met Asn Pro Leu Cys Pro Pro Leu Leu Leu Asp Leu Gln Thr Gln
1               5                   10                  15

Cys Pro Gln Arg Cys Ser Tyr Ile Leu Tyr Ser Cys Phe Ser Gly Met
                20                  25                  30

Val Leu Met Pro Pro Lys Ala Pro Ala Cys Glu Ser Thr Phe Val Phe
            35                  40                  45

Ile Ser Trp Ser Pro Leu Ser Ser Leu Val Pro Arg Pro Ser Phe
        50                  55                  60

His His Leu Pro Arg His Ser Glu Leu Asp Gln Tyr Leu Cys Gly Arg
65                  70                  75                  80

Leu Gly Val Thr

<210> SEQ ID NO 138
<211> LENGTH: 23
<212> TYPE: PRT
<213> ORGANISM: Homo sapiens
<220> FEATURE:
<221> NAME/KEY: SITE
<222> LOCATION: (23)
<223> OTHER INFORMATION: Xaa equals stop translation

<400> SEQUENCE: 138

Met Leu Leu Val Asn Leu Val Phe Val Cys Phe Phe Leu Phe Glu Arg
1               5                   10                  15

Arg Val His Leu Lys Cys Xaa
                20

<210> SEQ ID NO 139
<211> LENGTH: 45
<212> TYPE: PRT
<213> ORGANISM: Homo sapiens
<220> FEATURE:
<221> NAME/KEY: SITE
<222> LOCATION: (45)
<223> OTHER INFORMATION: Xaa equals stop translation

<400> SEQUENCE: 139

Met Met Gly Ile Leu Phe Ile His Leu Phe Ile Tyr Leu Phe Thr Glu
1               5                   10                  15

Asp Trp Phe Leu Pro Val Gln Phe Asn Ser Phe Ser Glu Val Ser Ile
                20                  25                  30

Met Ile Arg Lys Ile Asp Cys Ser Tyr Tyr Ser Lys Xaa
            35                  40                  45

```
<210> SEQ ID NO 140
<211> LENGTH: 47
<212> TYPE: PRT
<213> ORGANISM: Homo sapiens
<220> FEATURE:
<221> NAME/KEY: SITE
<222> LOCATION: (47)
<223> OTHER INFORMATION: Xaa equals stop translation

<400> SEQUENCE: 140

Met Met Leu Leu Leu Ala Ser Ala Phe Leu Ile Gly Thr Val Leu Gly
 1               5                  10                  15

Ser Asn Arg Ser Cys Met Ser Gln Cys Cys Gly His His Lys Ser Gln
            20                  25                  30

Lys Ala Gln Lys Thr Ser Ser Phe Ile Thr Ala Pro Val Lys Xaa
        35                  40                  45

<210> SEQ ID NO 141
<211> LENGTH: 288
<212> TYPE: PRT
<213> ORGANISM: Homo sapiens
<220> FEATURE:
<221> NAME/KEY: SITE
<222> LOCATION: (23)
<223> OTHER INFORMATION: Xaa equals any of the naturally occurring
      L-amino acids

<400> SEQUENCE: 141

Met Lys Thr Leu Ala Thr Gly Thr Lys Asn Arg Arg Arg Arg Pro Ala
 1               5                  10                  15

Ala Ala Ala Ala Ala Cys Xaa Val Gln Gly Pro Glu Pro Ala Arg Val
            20                  25                  30

Glu Lys Ile Phe Thr Pro Ala Ala Pro Val His Thr Asn Lys Glu Asp
        35                  40                  45

Pro Ala Thr Gln Thr Asn Leu Gly Phe Ile His Ala Phe Val Ala Ala
    50                  55                  60

Ile Ser Val Ile Ile Val Ser Glu Leu Gly Asp Lys Thr Phe Phe Ile
65                  70                  75                  80

Ala Ala Ile Met Ala Met Arg Tyr Asn Arg Leu Thr Val Leu Ala Gly
                85                  90                  95

Ala Met Leu Ala Leu Gly Leu Met Thr Cys Leu Ser Val Leu Phe Gly
            100                 105                 110

Tyr Ala Thr Thr Val Ile Pro Arg Val Tyr Thr Tyr Tyr Val Ser Thr
        115                 120                 125

Val Leu Phe Ala Ile Phe Gly Ile Arg Met Leu Arg Glu Gly Leu Lys
    130                 135                 140

Met Ser Pro Asp Glu Gly Gln Glu Glu Leu Glu Glu Val Gln Ala Glu
145                 150                 155                 160

Leu Lys Lys Lys Asp Glu Glu Phe Gln Arg Thr Lys Leu Leu Asn Gly
                165                 170                 175

Pro Gly Asp Val Glu Thr Gly Thr Ser Ile Thr Val Pro Gln Lys Lys
            180                 185                 190

Trp Leu His Phe Ile Ser Pro Ile Phe Val Gln Ala Leu Thr Leu Thr
        195                 200                 205

Phe Leu Ala Glu Trp Gly Asp Arg Ser Gln Leu Thr Thr Ile Val Leu
    210                 215                 220

Ala Ala Arg Glu Asp Pro Tyr Gly Val Ala Val Gly Gly Thr Val Gly
225                 230                 235                 240

His Cys Leu Cys Thr Gly Leu Ala Val Ile Gly Gly Arg Met Ile Ala
```

```
                        245                 250                 255
Gln Lys Ile Ser Val Arg Thr Val Thr Ile Ile Gly Gly Ile Val Phe
            260                 265                 270

Leu Ala Phe Ala Phe Ser Ala Leu Phe Ile Ser Pro Asp Ser Gly Phe
        275                 280                 285
```

<210> SEQ ID NO 142
<211> LENGTH: 24
<212> TYPE: PRT
<213> ORGANISM: Homo sapiens
<220> FEATURE:
<221> NAME/KEY: SITE
<222> LOCATION: (24)
<223> OTHER INFORMATION: Xaa equals stop translation

<400> SEQUENCE: 142

```
Met Phe Leu Phe Leu Phe Phe Leu Leu Ile Ile Ala Ser Tyr Ile Ser
 1               5                  10                  15

Ser Phe Ser Phe Gly Gln Ser Xaa
            20
```

<210> SEQ ID NO 143
<211> LENGTH: 54
<212> TYPE: PRT
<213> ORGANISM: Homo sapiens
<220> FEATURE:
<221> NAME/KEY: SITE
<222> LOCATION: (54)
<223> OTHER INFORMATION: Xaa equals stop translation

<400> SEQUENCE: 143

```
Met Val Leu Leu Leu Leu Gln Arg Asn Pro Gly Thr Pro Leu Phe
 1               5                  10                  15

Cys Leu Val Phe Trp Ala Gly Leu Arg Lys Pro Ala Gln Phe Arg Pro
            20                  25                  30

Ile Leu Gly Pro Ser Cys Pro Cys Ala Ala Ser Val Lys Arg Gly Val
        35                  40                  45

Asp Ile Pro Ser Ser Xaa
        50
```

<210> SEQ ID NO 144
<211> LENGTH: 61
<212> TYPE: PRT
<213> ORGANISM: Homo sapiens
<220> FEATURE:
<221> NAME/KEY: SITE
<222> LOCATION: (51)
<223> OTHER INFORMATION: Xaa equals any of the naturally occurring
      L-amino acids
<220> FEATURE:
<221> NAME/KEY: SITE
<222> LOCATION: (61)
<223> OTHER INFORMATION: Xaa equals stop translation

<400> SEQUENCE: 144

```
Met Leu Leu Glu Ser Trp Met Gly Ile Trp Gly Glu Arg Gly Arg Thr
 1               5                  10                  15

Gly Gln Val Ser Pro Ser Pro Phe Cys Ser Cys Leu Leu Val Ser Ala
            20                  25                  30

Leu Leu Glu Leu His Leu Pro Leu Gly Phe Ser Ala Pro Ala His Phe
        35                  40                  45

Pro Ser Xaa Phe Thr Cys Phe Val Ser Phe Pro Cys Xaa
    50                  55                  60
```

-continued

```
<210> SEQ ID NO 145
<211> LENGTH: 101
<212> TYPE: PRT
<213> ORGANISM: Homo sapiens
<220> FEATURE:
<221> NAME/KEY: SITE
<222> LOCATION: (101)
<223> OTHER INFORMATION: Xaa equals stop translation

<400> SEQUENCE: 145

Met Gly Asp Asp Gly Ser Ile Asp Tyr Thr Val His Glu Ala Trp Asn
 1               5                  10                  15

Glu Ala Thr Asn Val Tyr Leu Ile Val Ile Leu Val Ser Phe Gly Leu
                20                  25                  30

Phe Met Tyr Ala Lys Arg Asn Lys Arg Ile Met Arg Ile Phe Ser
            35                  40                  45

Val Pro Pro Thr Glu Thr Leu Ser Glu Pro Asn Phe Tyr Asp Thr
         50                  55                  60

Ile Ser Lys Ile Arg Leu Arg Gln Gln Leu Glu Met Tyr Ser Ile Ser
 65                  70                  75                  80

Arg Lys Tyr Asp Tyr Gln Gln Pro Gln Asn Gln Ala Asp Ser Val Gln
                85                  90                  95

Leu Ser Leu Glu Xaa
            100

<210> SEQ ID NO 146
<211> LENGTH: 42
<212> TYPE: PRT
<213> ORGANISM: Homo sapiens
<220> FEATURE:
<221> NAME/KEY: SITE
<222> LOCATION: (42)
<223> OTHER INFORMATION: Xaa equals stop translation

<400> SEQUENCE: 146

Met Phe Ala Phe Leu Leu Gly Ile Tyr Leu Gly Val Lys Leu Leu Asp
 1               5                  10                  15

Asn Met Phe Asn Tyr Leu Arg Thr Asp Arg Leu Leu Cys Lys Val Ala
                20                  25                  30

Asn Met Ser Lys Phe Ser Ser His Leu Xaa
            35                  40

<210> SEQ ID NO 147
<211> LENGTH: 63
<212> TYPE: PRT
<213> ORGANISM: Homo sapiens
<220> FEATURE:
<221> NAME/KEY: SITE
<222> LOCATION: (63)
<223> OTHER INFORMATION: Xaa equals stop translation

<400> SEQUENCE: 147

Met Phe Gly Cys Arg Ala Val Lys Thr Gln Lys Glu Thr Leu Pro Ser
 1               5                  10                  15

Ala Pro Gly Ser Pro Pro Leu Val Ala Leu Phe Ser Val Ala Leu Trp
                20                  25                  30

Pro Val Ala Leu Ser Asn Glu Ala Thr Pro His Ser Cys Gly Gln Ala
            35                  40                  45

Pro Gly Ala Pro Gly Gln Met Arg Thr Leu Phe Pro Pro Thr Xaa
         50                  55                  60
```

```
<210> SEQ ID NO 148
<211> LENGTH: 33
<212> TYPE: PRT
<213> ORGANISM: Homo sapiens
<220> FEATURE:
<221> NAME/KEY: SITE
<222> LOCATION: (33)
<223> OTHER INFORMATION: Xaa equals stop translation

<400> SEQUENCE: 148
```

Met Val Phe His Leu Pro Leu Ser Asp Leu Phe Met Leu Leu Leu
 1               5                  10                  15

Ala Pro Lys Lys Ser Arg Met Ala Lys Glu Pro Arg Thr Tyr Trp Asn
            20                  25                  30

Xaa

```
<210> SEQ ID NO 149
<211> LENGTH: 42
<212> TYPE: PRT
<213> ORGANISM: Homo sapiens
<220> FEATURE:
<221> NAME/KEY: SITE
<222> LOCATION: (42)
<223> OTHER INFORMATION: Xaa equals stop translation

<400> SEQUENCE: 149
```

Met Lys Val Gln Leu Ser Leu Gly Asn Pro Arg Gly Gln Gln Arg Thr
 1               5                  10                  15

Pro Glu Leu Ile Gln Ala Leu Leu Val Leu Asn Tyr Thr Leu Gly
            20                  25                  30

Phe Phe Leu Leu Ser Lys Thr Phe His Xaa
            35                  40

```
<210> SEQ ID NO 150
<211> LENGTH: 41
<212> TYPE: PRT
<213> ORGANISM: Homo sapiens
<220> FEATURE:
<221> NAME/KEY: SITE
<222> LOCATION: (35)
<223> OTHER INFORMATION: Xaa equals any of the naturally occurring
      L-amino acids
<220> FEATURE:
<221> NAME/KEY: SITE
<222> LOCATION: (41)
<223> OTHER INFORMATION: Xaa equals stop translation

<400> SEQUENCE: 150
```

Met Asn Glu Ala Thr Met Ala Phe Ser Val Leu Ile Leu Pro Val Phe
 1               5                  10                  15

Tyr Ala Gln Ile Arg Asn Lys Ser Phe Leu Cys Leu Ser Asp Ile Leu
            20                  25                  30

Pro Leu Xaa Leu Ile Leu Leu Phe Xaa
            35                  40

```
<210> SEQ ID NO 151
<211> LENGTH: 44
<212> TYPE: PRT
<213> ORGANISM: Homo sapiens
<220> FEATURE:
<221> NAME/KEY: SITE
<222> LOCATION: (44)
<223> OTHER INFORMATION: Xaa equals stop translation

<400> SEQUENCE: 151
```

Met Asn Trp Tyr His Glu Asn Lys Glu Ala Thr Cys Asn Cys Gln Ile

```
                1               5                   10                  15
            Phe Gly Leu Tyr Phe Ile Val Ser Phe Leu Ser Pro Val Leu Ala Ala
                            20                  25                  30

Ala His Asp Ala Lys Tyr Pro Val Trp Leu Xaa
                        35                  40

<210> SEQ ID NO 152
<211> LENGTH: 55
<212> TYPE: PRT
<213> ORGANISM: Homo sapiens
<220> FEATURE:
<221> NAME/KEY: SITE
<222> LOCATION: (55)
<223> OTHER INFORMATION: Xaa equals stop translation

<400> SEQUENCE: 152

Met Pro Gly Pro Gly Ala Leu Tyr Ser Ser Phe Thr Ser Phe Tyr Tyr
 1               5                  10                  15

Thr Phe Ser Asn His Gln Leu Leu Ala Leu Leu Leu Gly Phe
                20                  25                  30

Ile Ala Ser Cys Ser Phe Phe Leu Ser Arg Val Phe Leu Thr Phe Ser
            35                  40                  45

Thr Gln Leu Trp Lys Lys Xaa
        50                  55

<210> SEQ ID NO 153
<211> LENGTH: 165
<212> TYPE: PRT
<213> ORGANISM: Homo sapiens
<220> FEATURE:
<221> NAME/KEY: SITE
<222> LOCATION: (100)
<223> OTHER INFORMATION: Xaa equals any of the naturally occurring
      L-amino acids

<400> SEQUENCE: 153

Met Ser Lys Ser Glu Gln Cys Arg Ala Ala Cys Pro Ala Ala Leu Glu
 1               5                  10                  15

Gln Glu Leu Ser Leu Gly Arg Gly Trp Trp Gly Trp Ala Thr Glu Gly
                20                  25                  30

Ile Gly Ser Gln Ile His Pro Val Ser Pro Ala Ser Pro Lys Gln
            35                  40                  45

Ser Pro Ser Leu Leu Gln Ser Met Trp Asp Arg Cys Asn Ser Tyr Thr
        50                  55                  60

His Gly Ser Leu Gln Trp Asp Arg Leu Arg Pro Pro Val Leu Pro
 65                 70                  75                  80

Pro Ser Ile Tyr Thr Ile Arg Thr Cys Ser Gln Arg Leu Phe Ala Ala
                85                  90                  95

Ala Gln Ser Xaa Ser Tyr Ser His Met Asn Val Arg Gly Pro Leu Ile
            100                 105                 110

Gln Pro His Asn Thr Gln Gly Pro Phe Leu Thr Pro Ser Leu Ser Ser
        115                 120                 125

Leu Leu Phe His Gln Ser Ser Pro Ala Cys Thr Leu Ser Ala Trp Pro
130                 135                 140

Leu Ser Arg Tyr Ala Gln Pro Gly Ser Ala Leu Leu Thr Thr Pro Pro
145                 150                 155                 160

Arg Leu Gln Arg Gly
                165
```

<210> SEQ ID NO 154
<211> LENGTH: 114
<212> TYPE: PRT
<213> ORGANISM: Homo sapiens
<220> FEATURE:
<221> NAME/KEY: SITE
<222> LOCATION: (114)
<223> OTHER INFORMATION: Xaa equals stop translation

<400> SEQUENCE: 154

Met Gly Trp Lys Leu Leu Gly Leu Leu Ser Ala Ala Gly Arg His Ser
 1               5                  10                  15

Ala Gly Gly Asp Gln Ala Phe Pro Arg Pro Lys Gly Glu Ala Glu Ser
            20                  25                  30

Ala Ser Pro Glu Pro Asp Ala Gly Leu Gly Phe Thr Leu His Gly Pro
        35                  40                  45

Asp Val Lys Ser Asn Gly Asp Met Arg Phe Leu Met Ser Leu His Leu
    50                  55                  60

Gln Met Tyr Thr Ser Ala Lys Leu His His Thr Asn Leu Thr Ala Gly
65                  70                  75                  80

Pro Gly Phe Pro Leu Ser Arg Phe His Gln Pro Pro Ser Val Leu
                85                  90                  95

Ala Ala Cys Pro Ser Thr Asn Gln Leu Ser Pro Ala Pro Gly Asp Pro
            100                 105                 110

Arg Xaa

<210> SEQ ID NO 155
<211> LENGTH: 40
<212> TYPE: PRT
<213> ORGANISM: Homo sapiens
<220> FEATURE:
<221> NAME/KEY: SITE
<222> LOCATION: (40)
<223> OTHER INFORMATION: Xaa equals stop translation

<400> SEQUENCE: 155

Met Ala Leu Thr Trp Arg Val Val Leu Val Val Leu Phe Leu Ser Asp
 1               5                  10                  15

Cys Gly Leu Lys His Lys Cys Pro Lys Val Gly Arg Leu Leu Ser Val
            20                  25                  30

Ile Ile Val Ala Ile Lys Phe Xaa
        35                  40

<210> SEQ ID NO 156
<211> LENGTH: 392
<212> TYPE: PRT
<213> ORGANISM: Homo sapiens
<220> FEATURE:
<221> NAME/KEY: SITE
<222> LOCATION: (251)
<223> OTHER INFORMATION: Xaa equals any of the naturally occurring
      L-amino acids

<400> SEQUENCE: 156

Met Ala Pro Trp Pro Pro Lys Gly Leu Val Pro Ala Val Leu Trp Gly
 1               5                  10                  15

Leu Ser Leu Phe Leu Asn Leu Pro Gly Pro Ile Trp Leu Gln Pro Ser
            20                  25                  30

Pro Pro Pro Gln Ser Ser Pro Pro Gln Pro His Pro Cys His Thr
        35                  40                  45

Cys Arg Gly Leu Val Asp Ser Phe Asn Lys Gly Leu Glu Arg Thr Ile
    50                  55                  60

```
Arg Asp Asn Phe Gly Gly Gly Asn Thr Ala Trp Glu Glu Asn Leu
 65                  70                  75                  80

Ser Lys Tyr Lys Asp Ser Glu Thr Arg Leu Val Glu Val Leu Glu Gly
             85                  90                  95

Val Cys Ser Lys Ser Asp Phe Glu Cys His Arg Leu Leu Glu Leu Ser
            100                 105                 110

Glu Glu Leu Val Glu Ser Trp Trp Phe His Lys Gln Gln Glu Ala Pro
            115                 120                 125

Asp Leu Phe Gln Trp Leu Cys Ser Asp Ser Leu Lys Leu Cys Cys Pro
        130                 135                 140

Ala Gly Thr Phe Gly Pro Ser Cys Leu Pro Cys Pro Gly Gly Thr Glu
145                 150                 155                 160

Arg Pro Cys Gly Gly Tyr Gly Gln Cys Glu Gly Gly Thr Arg Gly
                165                 170                 175

Gly Ser Gly His Cys Asp Cys Gln Ala Gly Tyr Gly Gly Glu Ala Cys
            180                 185                 190

Gly Gln Cys Gly Leu Gly Tyr Phe Glu Ala Glu Arg Asn Ala Ser His
        195                 200                 205

Leu Val Cys Ser Ala Cys Phe Gly Pro Cys Ala Arg Cys Ser Gly Pro
210                 215                 220

Glu Glu Ser Asn Cys Leu Gln Cys Lys Lys Gly Trp Ala Leu His His
225                 230                 235                 240

Leu Lys Cys Val Asp Cys Ala Lys Ala Cys Xaa Gly Cys Met Gly Ala
            245                 250                 255

Gly Pro Gly Arg Cys Lys Lys Cys Ser Pro Gly Tyr Gln Gln Val Gly
            260                 265                 270

Ser Lys Cys Leu Asp Val Asp Glu Cys Glu Thr Glu Val Cys Pro Gly
        275                 280                 285

Glu Asn Lys Gln Cys Glu Asn Thr Glu Gly Gly Tyr Arg Cys Ile Cys
290                 295                 300

Ala Glu Gly Tyr Lys Gln Met Glu Gly Ile Cys Val Lys Glu Gln Ile
305                 310                 315                 320

Pro Glu Ser Ala Gly Phe Phe Ser Glu Met Thr Glu Asp Glu Leu Val
            325                 330                 335

Val Leu Gln Gln Met Phe Phe Gly Ile Ile Ile Cys Ala Leu Ala Thr
            340                 345                 350

Leu Ala Ala Lys Gly Asp Leu Val Phe Thr Ala Ile Phe Ile Gly Ala
        355                 360                 365

Val Ala Ala Met Thr Gly Tyr Trp Leu Ser Glu Arg Ser Asp Arg Val
370                 375                 380

Leu Glu Gly Phe Ile Lys Gly Arg
385                 390

<210> SEQ ID NO 157
<211> LENGTH: 118
<212> TYPE: PRT
<213> ORGANISM: Homo sapiens

<400> SEQUENCE: 157

Met Val Ala Ile Pro Pro Ser Ala Cys Leu Pro Ala Cys Cys Pro Gly
  1               5                  10                  15

His Gly Ala Val Pro Val Pro Arg Ile Gly Phe Lys Phe Val Asn Asn
             20                  25                  30

Phe Pro Phe Gly Leu Val Asp Val Asn Arg Ala Arg Glu Val Leu Pro
```

```
                    35                  40                  45
Thr Ala Cys Ala Cys Leu Pro Ala Ser Ser Leu Phe Ser Phe His Tyr
     50                  55                  60

Ala Pro Ser Pro Gly Gly Leu Ala Leu Ser Phe Ser Ser Tyr Pro Gln
 65                  70                  75                  80

Gly Pro Val Leu Leu Cys Pro His Val Pro Leu Gly Cys Leu Val Glu
                 85                  90                  95

Ala Leu Tyr Asn Phe Ser Leu Val Leu Cys Ser Phe Leu Leu Tyr Phe
             100                 105                 110

Pro Ala Val Ser Cys Pro
         115

<210> SEQ ID NO 158
<211> LENGTH: 28
<212> TYPE: PRT
<213> ORGANISM: Homo sapiens
<220> FEATURE:
<221> NAME/KEY: SITE
<222> LOCATION: (28)
<223> OTHER INFORMATION: Xaa equals stop translation

<400> SEQUENCE: 158

Met Ile Ile Ala Pro Ile Cys Leu Ile Pro Phe Leu Ile Thr Leu Val
 1               5                  10                  15

Val Trp Arg Ser Lys Asp Ser Glu Ala Gln Ala Xaa
                 20                  25

<210> SEQ ID NO 159
<211> LENGTH: 87
<212> TYPE: PRT
<213> ORGANISM: Homo sapiens
<220> FEATURE:
<221> NAME/KEY: SITE
<222> LOCATION: (55)
<223> OTHER INFORMATION: Xaa equals any of the naturally occurring
      L-amino acids
<220> FEATURE:
<221> NAME/KEY: SITE
<222> LOCATION: (87)
<223> OTHER INFORMATION: Xaa equals stop translation

<400> SEQUENCE: 159

Met Gly Val Leu Ala Glu His Gly Gly His Pro Ala Gln Glu His Phe
 1               5                  10                  15

Pro Lys Leu Leu Gly Leu Leu Phe Pro Leu Leu Ala Arg Glu Arg His
                 20                  25                  30

Asp Arg Val Arg Asp Asn Ile Cys Gly Ala Leu Ala Arg Leu Leu Met
             35                  40                  45

Ala Ser Pro Thr Arg Lys Xaa Arg Ala Pro Gly Ala Gly Cys Pro Thr
 50                  55                  60

Ala Cys Pro Ala Thr Glu Gly Leu Gly Gly Val Gly Gln Pro Leu
 65                  70                  75                  80

Gly Ala Ser Ser Ala Ser Xaa
             85

<210> SEQ ID NO 160
<211> LENGTH: 28
<212> TYPE: PRT
<213> ORGANISM: Homo sapiens
<220> FEATURE:
<221> NAME/KEY: SITE
<222> LOCATION: (28)
<223> OTHER INFORMATION: Xaa equals stop translation
```

-continued

<400> SEQUENCE: 160

Met His Ser Phe Thr Gln Arg Gly Met Tyr Ile Phe Leu Ser Ser Ser
1               5                   10                  15

Gln Ala Ile Phe Leu Met Ser Cys Phe Leu Phe Xaa
            20                  25

<210> SEQ ID NO 161
<211> LENGTH: 46
<212> TYPE: PRT
<213> ORGANISM: Homo sapiens
<220> FEATURE:
<221> NAME/KEY: SITE
<222> LOCATION: (46)
<223> OTHER INFORMATION: Xaa equals stop translation

<400> SEQUENCE: 161

Met Val Leu Ile Phe Leu Leu Val Gln Asn Arg Cys Ala Val Gly Ser
1               5                   10                  15

Thr Met Gln Phe Ser Phe Ser Thr Asp Pro Phe Leu Arg Asn Thr Asn
            20                  25                  30

Phe Leu Leu His His Leu Gly Val Leu Arg Cys Leu Pro Xaa
        35                  40                  45

<210> SEQ ID NO 162
<211> LENGTH: 64
<212> TYPE: PRT
<213> ORGANISM: Homo sapiens
<220> FEATURE:
<221> NAME/KEY: SITE
<222> LOCATION: (64)
<223> OTHER INFORMATION: Xaa equals stop translation

<400> SEQUENCE: 162

Met Thr Glu Asp Glu Leu Val Val Leu Gln Gln Met Phe Phe Gly Ile
1               5                   10                  15

Ile Ile Cys Ala Leu Ala Thr Leu Ala Ala Lys Gly Asp Leu Val Phe
            20                  25                  30

Thr Ala Ile Phe Ile Gly Ala Val Ala Ala Met Thr Gly Tyr Trp Leu
        35                  40                  45

Ser Glu Arg Ser Asp Arg Val Leu Glu Gly Phe Ile Lys Gly Arg Xaa
    50                  55                  60

<210> SEQ ID NO 163
<211> LENGTH: 51
<212> TYPE: PRT
<213> ORGANISM: Homo sapiens

<400> SEQUENCE: 163

Phe Ile Thr Pro Glu Asp Gly Ser Lys Asp Val Phe Val His Phe Ser
1               5                   10                  15

Ala Ile Ser Ser Gln Gly Phe Lys Thr Leu Ala Glu Gly Gln Arg Val
            20                  25                  30

Glu Phe Glu Ile Thr Asn Gly Ala Lys Gly Pro Ser Ala Ala Asn Val
        35                  40                  45

Ile Ala Ile
    50

<210> SEQ ID NO 164
<211> LENGTH: 26
<212> TYPE: PRT
<213> ORGANISM: Homo sapiens

```
<400> SEQUENCE: 164

Asn Ser Ala Arg Ala Leu Leu Gly Val Cys Met Phe Ala Leu Gly Ala
 1               5                  10                  15

Leu Ala Val Pro Val Thr Gly Phe Gly Ser
            20                  25

<210> SEQ ID NO 165
<211> LENGTH: 56
<212> TYPE: PRT
<213> ORGANISM: Homo sapiens

<400> SEQUENCE: 165

Lys Met Asp Ser Lys Ile Cys Leu Ala Met Ile Leu His Phe Pro Asn
 1               5                  10                  15

Pro Phe Thr Phe Leu Leu Ser Pro Thr Leu Glu Cys Ser Val Ser
            20                  25                  30

Pro Tyr Leu Ser Ser Ile Ser Leu Asn Ile Leu Pro Val Pro Cys Phe
        35                  40                  45

Gln Phe Arg Asn Trp Cys Pro Asn
    50                  55

<210> SEQ ID NO 166
<211> LENGTH: 65
<212> TYPE: PRT
<213> ORGANISM: Homo sapiens
<220> FEATURE:
<221> NAME/KEY: SITE
<222> LOCATION: (62)
<223> OTHER INFORMATION: Xaa equals any of the naturally occurring
      L-amino acids

<400> SEQUENCE: 166

Phe Phe Met Leu Phe Asp Phe Phe Phe Phe Glu Thr Glu Ser Gly
 1               5                  10                  15

Ser Val Thr Gly Ala Gly Val Gln Trp Cys Asn His Gly Ser Leu Gln
            20                  25                  30

Ser Leu Pro Pro Arg Leu Glu Ser Ile Leu Glu Arg Pro Arg Ala His
        35                  40                  45

Arg Phe Ser Asn Arg Val Gly Tyr Gln Val Ser Val Thr Xaa Phe Gly
    50                  55                  60

Leu
 65

<210> SEQ ID NO 167
<211> LENGTH: 16
<212> TYPE: PRT
<213> ORGANISM: Homo sapiens

<400> SEQUENCE: 167

Phe Leu Lys Trp Pro Asn Lys Ser Pro Asp Gly Glu Val Leu Gln Trp
 1               5                  10                  15

<210> SEQ ID NO 168
<211> LENGTH: 48
<212> TYPE: PRT
<213> ORGANISM: Homo sapiens

<400> SEQUENCE: 168

Val Lys Cys Ser Gln Arg Ala Leu Arg Trp Cys Gln Leu Asn Gly Leu
 1               5                  10                  15
```

```
Thr Arg Gly Leu Trp Val Ser Leu Ser Cys Cys Pro Pro Phe Pro Ser
            20                  25                  30

Val Gln Trp Gly Ser Pro Glu Ala Ala Pro His Ala Pro Ala Ala Leu
            35                  40                  45
```

<210> SEQ ID NO 169
<211> LENGTH: 46
<212> TYPE: PRT
<213> ORGANISM: Homo sapiens

<400> SEQUENCE: 169

```
Met Ala Glu Ile Thr Ser Gly Ile Pro Val Leu Gln Ile Lys Gln Lys
  1               5                  10                  15

His Tyr Ser Val Phe Ser Val Leu Ile Lys Asn Thr Val Asn Ile Ser
            20                  25                  30

Gln Tyr Ser Pro His Glu His Gly Pro Leu Trp Gly Pro Gln
            35                  40                  45
```

<210> SEQ ID NO 170
<211> LENGTH: 26
<212> TYPE: PRT
<213> ORGANISM: Homo sapiens

<400> SEQUENCE: 170

```
Cys Val Arg Leu Gly Asn Val Leu Ser Ile Leu Ser Leu Met Cys Leu
  1               5                  10                  15

Lys Pro Gly Ser Ser Phe Thr Cys Trp Tyr
            20                  25
```

<210> SEQ ID NO 171
<211> LENGTH: 23
<212> TYPE: PRT
<213> ORGANISM: Homo sapiens

<400> SEQUENCE: 171

```
Leu Val Thr Arg Ile Lys Lys Leu Leu Pro Thr Leu Val Leu Leu
  1               5                  10                  15

Gln Ile Met Lys Gly Asn Leu
            20
```

<210> SEQ ID NO 172
<211> LENGTH: 14
<212> TYPE: PRT
<213> ORGANISM: Homo sapiens

<400> SEQUENCE: 172

```
Arg Leu Met Tyr Gly Leu Lys Glu Ile Tyr Gln Val Arg Glu
  1               5                  10
```

<210> SEQ ID NO 173
<211> LENGTH: 53
<212> TYPE: PRT
<213> ORGANISM: Homo sapiens

<400> SEQUENCE: 173

```
Cys Gly Phe Cys Phe Thr Val Tyr Leu Phe Val Val Ser Phe Ser
  1               5                  10                  15

Pro Cys Tyr Leu Pro Phe Arg Met His Leu Gly Lys Ala Gly Ser Leu
            20                  25                  30

Ala Ser Trp Phe Val Ser Phe Phe Phe Phe Lys His Arg Ile Thr
            35                  40                  45
```

Leu Ala Ile Val Cys
    50

<210> SEQ ID NO 174
<211> LENGTH: 51
<212> TYPE: PRT
<213> ORGANISM: Homo sapiens

<400> SEQUENCE: 174

Ser Cys His Trp Cys Lys Ala Leu Pro Ala Leu Ala Ser Ser Thr Ser
 1               5                  10                  15

Leu Ser Ala Lys Asn Ser Val Ile Val Cys Val Pro Phe Leu Ile Leu
            20                  25                  30

Ser His Gly Arg Ile Leu Gln Lys Arg Asn Leu Asn Cys Val His Ser
        35                  40                  45

Leu Ser Glu
    50

<210> SEQ ID NO 175
<211> LENGTH: 90
<212> TYPE: PRT
<213> ORGANISM: Homo sapiens
<220> FEATURE:
<221> NAME/KEY: SITE
<222> LOCATION: (11)
<223> OTHER INFORMATION: Xaa equals any of the naturally occurring
      L-amino acids

<400> SEQUENCE: 175

Thr Asp Ser Tyr Gly Ile Ile Leu Cys Val Xaa Leu Cys Leu Leu Leu
 1               5                  10                  15

Leu Phe Asn Ile Leu Trp Phe Ile Cys Val Ala Cys Ser Ile Ile Ile
            20                  25                  30

Thr Val Ala Tyr Phe Ile Cys Ser Thr Val Gly Gly His Tyr Cys Cys
        35                  40                  45

Phe Gln Phe Leu Ala Ile Ile Asn Asn Asp Ala Lys Ser Val Leu Asp
    50                  55                  60

Tyr Leu Ser Trp Tyr Val Cys Ala Arg Thr Asn Asn Ile Tyr Leu Gly
65                  70                  75                  80

Met Glu Ser Leu Gly His Arg Glu Tyr Thr
                85                  90

<210> SEQ ID NO 176
<211> LENGTH: 54
<212> TYPE: PRT
<213> ORGANISM: Homo sapiens

<400> SEQUENCE: 176

His Glu Glu Leu Cys Arg Tyr Leu Ala Glu Ser Trp Leu Thr Phe Gln
 1               5                  10                  15

Ile His Leu Gln Glu Leu Leu Gln Tyr Lys Arg Gln Asn Pro Ala Gln
            20                  25                  30

Phe Cys Val Arg Val Cys Ser Gly Cys Ala Val Leu Ala Val Leu Gly
        35                  40                  45

His Tyr Val Pro Gly Ile
    50

<210> SEQ ID NO 177
<211> LENGTH: 31
<212> TYPE: PRT
<213> ORGANISM: Homo sapiens -continued

```
<220> FEATURE:
<221> NAME/KEY: SITE
<222> LOCATION: (28)
<223> OTHER INFORMATION: Xaa equals any of the naturally occurring
      L-amino acids

<400> SEQUENCE: 177

Cys Phe His Lys Glu Leu Leu Thr Ser Arg Asn Gly Arg Pro Arg His
  1               5                  10                  15

Thr Ser Lys Gln Thr Phe Gln Lys His Leu Gln Xaa Thr Gln Asp
             20                  25                  30

<210> SEQ ID NO 178
<211> LENGTH: 51
<212> TYPE: PRT
<213> ORGANISM: Homo sapiens
<220> FEATURE:
<221> NAME/KEY: SITE
<222> LOCATION: (29)
<223> OTHER INFORMATION: Xaa equals any of the naturally occurring
      L-amino acids

<400> SEQUENCE: 178

Asn Phe Thr Asp Asp Gly Lys Met Thr Lys Asp Glu Gly Ser Leu Leu
  1               5                  10                  15

Lys Ser Gln Leu Ser Ser Lys His Glu Gly Gln Lys Xaa His Gly Ser
             20                  25                  30

Arg Leu Gly Met Thr Ile Gln Gln Phe Pro Gly Asp Cys Ile Val Gln
         35                  40                  45

Val Ile Tyr
         50

<210> SEQ ID NO 179
<211> LENGTH: 30
<212> TYPE: PRT
<213> ORGANISM: Homo sapiens

<400> SEQUENCE: 179

Leu Cys Ala Ala Leu Ile Ser Pro Leu Trp Lys Cys Ser Pro Pro Ser
  1               5                  10                  15

Pro Pro Thr Ser Gly Pro Gly Thr Arg Arg Ala Ala Gly Thr
             20                  25                  30

<210> SEQ ID NO 180
<211> LENGTH: 48
<212> TYPE: PRT
<213> ORGANISM: Homo sapiens

<400> SEQUENCE: 180

Ser Arg Ala Leu Ile Leu Val Ala Asp Ser Ala Lys Glu Thr Asn Lys
  1               5                  10                  15

Met Ile Leu Ala Trp Thr Arg Thr Leu Asn Leu Arg Arg Val Ser Leu
             20                  25                  30

Asn His Ser Asn His Tyr Leu Lys Gly His Gly Ala Gln Asn Lys Val
         35                  40                  45

<210> SEQ ID NO 181
<211> LENGTH: 39
<212> TYPE: PRT
<213> ORGANISM: Homo sapiens

<400> SEQUENCE: 181

Gln Trp Glu Phe Leu Tyr Ser Gln Ser Leu Leu Ser Val Ala Leu Ile
```

```
                1               5                  10                   15
Leu Phe Cys Val Ser Phe Gln Gly Ser Asp Leu Asp Ser Tyr Leu Ser
                        20                  25                  30

Cys Ser Pro Lys Arg Gly Cys
            35

<210> SEQ ID NO 182
<211> LENGTH: 47
<212> TYPE: PRT
<213> ORGANISM: Homo sapiens

<400> SEQUENCE: 182

Asn Tyr Arg Asn Ser Asn Leu Lys Lys Thr Leu Lys Glu Thr Lys Lys
 1               5                  10                  15

Tyr Ser Thr Ile Leu Ser Ala Leu Leu Thr Phe Ser Ile Val Ser Cys
                20                  25                  30

Asp Leu Cys Leu Val Leu Cys Ser Ile Asp Asp Glu His Leu Ile
            35                  40                  45

<210> SEQ ID NO 183
<211> LENGTH: 31
<212> TYPE: PRT
<213> ORGANISM: Homo sapiens

<400> SEQUENCE: 183

Asn Ser Ala Arg Gly Glu Val Ala Phe Leu Ile Lys Lys Lys Lys Ser
 1               5                  10                  15

Ser Ser Ile Val Tyr Gly Lys Phe Phe Gln Ala Thr Ile Pro Ser
                20                  25                  30

<210> SEQ ID NO 184
<211> LENGTH: 141
<212> TYPE: PRT
<213> ORGANISM: Homo sapiens
<220> FEATURE:
<221> NAME/KEY: SITE
<222> LOCATION: (37)
<223> OTHER INFORMATION: Xaa equals any of the naturally occurring
      L-amino acids
<220> FEATURE:
<221> NAME/KEY: SITE
<222> LOCATION: (54)
<223> OTHER INFORMATION: Xaa equals any of the naturally occurring
      L-amino acids

<400> SEQUENCE: 184

Arg Ala Gly Gly Pro Arg Leu Pro Arg Thr Arg Val Gly Arg Pro Ala
 1               5                  10                  15

Ala Leu Arg Leu Leu Leu Leu Gly Ala Val Leu Asn Pro His Glu
                20                  25                  30

Ala Leu Ala Gln Xaa Leu Pro Thr Thr Gly Thr Pro Gly Ser Glu Gly
            35                  40                  45

Gly Thr Val Lys Asn Xaa Glu Thr Ala Val Gln Phe Cys Trp Asn His
     50                  55                  60

Tyr Lys Asp Gln Met Asp Pro Ile Glu Lys Asp Trp Cys Asp Trp Ala
 65                  70                  75                  80

Met Ile Ser Arg Pro Tyr Ser Thr Leu Arg Asp Cys Leu Glu His Phe
                85                  90                  95

Ala Glu Leu Phe Asp Leu Gly Phe Pro Asn Pro Leu Ala Glu Arg Ile
                100                 105                 110

Ile Phe Glu Thr His Gln Ile His Phe Ala Asn Cys Ser Leu Val Gln
```

```
                    115                 120                 125
Pro Thr Phe Ser Asp Pro Glu Asp Val Leu Leu Ala
        130                 135                 140

<210> SEQ ID NO 185
<211> LENGTH: 60
<212> TYPE: PRT
<213> ORGANISM: Homo sapiens

<400> SEQUENCE: 185

Cys Trp Asn His Tyr Lys Asp Gln Met Asp Pro Ile Glu Lys Asp Trp
  1               5                  10                  15

Cys Asp Trp Ala Met Ile Ser Arg Pro Tyr Ser Thr Leu Arg Asp Cys
             20                  25                  30

Leu Glu His Phe Ala Glu Leu Phe Asp Leu Gly Phe Pro Asn Pro Leu
         35                  40                  45

Ala Glu Arg Ile Ile Phe Glu Thr His Gln Ile His
     50                  55                  60

<210> SEQ ID NO 186
<211> LENGTH: 48
<212> TYPE: PRT
<213> ORGANISM: Homo sapiens

<400> SEQUENCE: 186

Phe Ala Asn Cys Ser Leu Val Gln Pro Thr Phe Ser Asp Pro Pro Glu
  1               5                  10                  15

Asp Val Leu Leu Ala Met Ile Ile Ala Pro Ile Cys Leu Ile Pro Phe
             20                  25                  30

Leu Ile Thr Leu Val Val Trp Arg Ser Lys Asp Ser Glu Ala Gln Ala
         35                  40                  45

<210> SEQ ID NO 187
<211> LENGTH: 10
<212> TYPE: PRT
<213> ORGANISM: Homo sapiens

<400> SEQUENCE: 187

Arg Ala Gly Gly Pro Arg Leu Pro Arg Thr
  1               5                  10

<210> SEQ ID NO 188
<211> LENGTH: 8
<212> TYPE: PRT
<213> ORGANISM: Homo sapiens

<400> SEQUENCE: 188

Asn Pro His Glu Ala Leu Ala Gln
  1               5

<210> SEQ ID NO 189
<211> LENGTH: 72
<212> TYPE: PRT
<213> ORGANISM: Homo sapiens

<400> SEQUENCE: 189

Ala Arg Gly Arg Leu Phe Ser Phe Leu Tyr Gln Ser Ser Pro Asp Gln
  1               5                  10                  15

Val Ile Asp Val Ala Pro Glu Leu Leu Arg Ile Cys Ser Leu Ile Leu
             20                  25                  30

Ala Glu Thr Ile Gln Gly Leu Gly Ala Ala Ser Ala Gln Phe Val Ser
```

-continued

```
                35                  40                  45
Arg Leu Leu Pro Val Leu Leu Ser Thr Ala Gln Glu Ala Asp Pro Glu
     50                  55                  60

Val Arg Ser Asn Ala Ile Phe Gly
 65                  70

<210> SEQ ID NO 190
<211> LENGTH: 49
<212> TYPE: PRT
<213> ORGANISM: Homo sapiens

<400> SEQUENCE: 190

Arg Gly Leu Pro Ser Thr Leu Ile Cys Leu Val Glu Ser Phe Gly Ser
 1               5                  10                  15

Lys Trp Ala Pro Leu Trp Glu Gly Gly Arg Thr His His Trp Gly Pro
             20                  25                  30

Arg His His Trp His Val Ala Ser Cys Val Ser Leu Phe Ser Cys Cys
         35                  40                  45

Lys

<210> SEQ ID NO 191
<211> LENGTH: 21
<212> TYPE: PRT
<213> ORGANISM: Homo sapiens

<400> SEQUENCE: 191

Gly Ile Leu Ile Cys Asn Phe Phe Ser Val Glu Leu Ala Ile Val
 1               5                  10                  15

Arg Phe Trp Cys Ile
             20

<210> SEQ ID NO 192
<211> LENGTH: 118
<212> TYPE: PRT
<213> ORGANISM: Homo sapiens

<400> SEQUENCE: 192

Ala Gln Glu Arg Ser Cys Leu His Leu Val Cys Ile Arg Cys Ser Cys
 1               5                  10                  15

Asp Val Val Glu Met Gly Ser Val Leu Gly Leu Cys Ser Met Ala Ser
             20                  25                  30

Trp Ile Pro Cys Leu Cys Gly Ser Ala Pro Cys Leu Leu Cys Arg Cys
         35                  40                  45

Cys Pro Ser Gly Asn Asn Ser Thr Val Thr Arg Leu Ile Tyr Ala Leu
     50                  55                  60

Phe Leu Leu Val Gly Val Cys Val Ala Cys Val Met Leu Ile Pro Gly
 65                  70                  75                  80

Met Glu Glu Gln Leu Asn Lys Ile Pro Gly Phe Cys Glu Asn Glu Lys
                 85                  90                  95

Gly Val Val Pro Cys Asn Ile Leu Val Gly Tyr Lys Ala Val Tyr Arg
             100                 105                 110

Leu Cys Phe Gly Leu Ala
         115

<210> SEQ ID NO 193
<211> LENGTH: 74
<212> TYPE: PRT
<213> ORGANISM: Homo sapiens
```

-continued

```
<400> SEQUENCE: 193

Ile Pro Cys Leu Cys Gly Ser Ala Pro Cys Leu Leu Cys Arg Cys Cys
1               5                   10                  15

Pro Ser Gly Asn Asn Ser Thr Val Thr Arg Leu Ile Tyr Ala Leu Phe
            20                  25                  30

Leu Leu Val Gly Val Cys Val Ala Cys Val Met Leu Ile Pro Gly Met
        35                  40                  45

Glu Glu Gln Leu Asn Lys Ile Pro Gly Phe Cys Glu Asn Glu Lys Gly
    50                  55                  60

Val Val Pro Cys Asn Ile Leu Val Gly Tyr
65                  70

<210> SEQ ID NO 194
<211> LENGTH: 95
<212> TYPE: PRT
<213> ORGANISM: Homo sapiens

<400> SEQUENCE: 194

Ala Arg Ser Asp Gly Ser Leu Glu Asp Gly Asp Val His Arg Ala
1               5                   10                  15

Val Asp Asn Glu Arg Asp Gly Val Thr Tyr Ser Tyr Ser Phe Phe His
            20                  25                  30

Phe Met Leu Phe Leu Ala Ser Leu Tyr Ile Met Met Thr Leu Thr Asn
        35                  40                  45

Trp Tyr Arg Tyr Glu Pro Ser Arg Glu Met Lys Ser Gln Trp Thr Ala
    50                  55                  60

Val Trp Val Lys Ile Ser Ser Ser Trp Ile Gly Ile Val Leu Tyr Val
65                  70                  75                  80

Trp Thr Leu Val Ala Pro Leu Val Leu Thr Asn Arg Asp Phe Asp
                85                  90                  95

<210> SEQ ID NO 195
<211> LENGTH: 28
<212> TYPE: PRT
<213> ORGANISM: Homo sapiens

<400> SEQUENCE: 195

Asn Glu Lys Gly Val Val Pro Cys Asn Ile Leu Val Gly Tyr Lys Ala
1               5                   10                  15

Val Tyr Arg Leu Cys Phe Gly Leu Ala Met Phe Tyr
            20                  25

<210> SEQ ID NO 196
<211> LENGTH: 19
<212> TYPE: PRT
<213> ORGANISM: Homo sapiens

<400> SEQUENCE: 196

Met Ile Lys Val Lys Ser Ser Ser Asp Pro Arg Ala Ala Val His Asn
1               5                   10                  15

Gly Phe Trp

<210> SEQ ID NO 197
<211> LENGTH: 21
<212> TYPE: PRT
<213> ORGANISM: Homo sapiens

<400> SEQUENCE: 197

Gly Met Ala Gly Ala Phe Cys Phe Ile Leu Ile Gln Leu Val Leu Leu
```

```
                 1               5                  10                  15

Ile Asp Phe Ala His
              20

<210> SEQ ID NO 198
<211> LENGTH: 24
<212> TYPE: PRT
<213> ORGANISM: Homo sapiens

<400> SEQUENCE: 198

Tyr Ala Ala Leu Leu Ser Ala Thr Ala Leu Asn Tyr Leu Leu Ser Leu
 1               5                  10                  15

Val Ala Ile Val Leu Phe Phe Val
              20

<210> SEQ ID NO 199
<211> LENGTH: 21
<212> TYPE: PRT
<213> ORGANISM: Homo sapiens

<400> SEQUENCE: 199

Pro Ser Leu Leu Ser Ile Ile Gly Tyr Asn Thr Thr Ser Thr Val Pro
 1               5                  10                  15

Lys Glu Gly Gln Ser
              20

<210> SEQ ID NO 200
<211> LENGTH: 22
<212> TYPE: PRT
<213> ORGANISM: Homo sapiens

<400> SEQUENCE: 200

Tyr Ser Ser Ile Arg Thr Ser Asn Asn Ser Gln Val Asn Lys Leu Thr
 1               5                  10                  15

Leu Thr Ser Asp Glu Ser
              20

<210> SEQ ID NO 201
<211> LENGTH: 20
<212> TYPE: PRT
<213> ORGANISM: Homo sapiens

<400> SEQUENCE: 201

Asp Asn Glu Arg Asp Gly Val Thr Tyr Ser Tyr Ser Phe Phe His Phe
 1               5                  10                  15

Met Leu Phe Leu
              20

<210> SEQ ID NO 202
<211> LENGTH: 18
<212> TYPE: PRT
<213> ORGANISM: Homo sapiens

<400> SEQUENCE: 202

Ile Val Leu Tyr Val Trp Thr Leu Val Ala Pro Leu Val Leu Thr Asn
 1               5                  10                  15

Arg Asp

<210> SEQ ID NO 203
<211> LENGTH: 13
<212> TYPE: PRT
<213> ORGANISM: Homo sapiens
```

-continued

```
<400> SEQUENCE: 203

Phe Glu Ser Leu Arg Thr Gly Ser Glu Gly Pro His Gly
 1               5                  10

<210> SEQ ID NO 204
<211> LENGTH: 11
<212> TYPE: PRT
<213> ORGANISM: Homo sapiens

<400> SEQUENCE: 204

Asp Pro Arg Val Arg Ala Asp Thr Met Val Arg
 1               5                  10

<210> SEQ ID NO 205
<211> LENGTH: 45
<212> TYPE: PRT
<213> ORGANISM: Homo sapiens

<400> SEQUENCE: 205

Gly Pro Ala Val Pro Gln Glu Asn Gln Asp Gly Arg Tyr Ser Leu Thr
 1               5                  10                  15

Tyr Ile Tyr Thr Gly Leu Ser Lys His Val Glu Asp Val Pro Ala Phe
                20                  25                  30

Gln Ala Leu Gly Ser Leu Asn Asp Leu Gln Phe Phe Arg
            35                  40                  45

<210> SEQ ID NO 206
<211> LENGTH: 21
<212> TYPE: PRT
<213> ORGANISM: Homo sapiens

<400> SEQUENCE: 206

Tyr Asn Ser Lys Asp Arg Lys Ser Gln Pro Met Gly Leu Trp Arg Gln
 1               5                  10                  15

Val Glu Gly Met Glu
            20

<210> SEQ ID NO 207
<211> LENGTH: 22
<212> TYPE: PRT
<213> ORGANISM: Homo sapiens

<400> SEQUENCE: 207

Phe Met Glu Thr Leu Lys Asp Ile Val Glu Tyr Tyr Asn Asp Ser Asn
 1               5                  10                  15

Gly Ser His Val Leu Gln
            20

<210> SEQ ID NO 208
<211> LENGTH: 20
<212> TYPE: PRT
<213> ORGANISM: Homo sapiens

<400> SEQUENCE: 208

Asn Arg Ser Ser Gly Ala Phe Trp Lys Tyr Tyr Asp Gly Lys Asp
 1               5                  10                  15

Tyr Ile Glu Phe
            20

<210> SEQ ID NO 209
<211> LENGTH: 71
```

```
<212> TYPE: PRT
<213> ORGANISM: Homo sapiens

<400> SEQUENCE: 209

Ile Arg His Glu Thr Glu Cys Gly Ile Asp His Ile Cys Ile His Arg
 1               5                  10                  15

His Cys Val His Ile Thr Ile Leu Asn Ser Asn Cys Ser Pro Ala Phe
             20                  25                  30

Cys Asn Lys Arg Gly Ile Cys Asn Asn Lys His His Cys His Cys Asn
         35                  40                  45

Tyr Leu Trp Asp Pro Pro Asn Cys Leu Ile Lys Gly Tyr Gly Gly Ser
     50                  55                  60

Val Asp Ser Gly Pro Pro Pro
 65                  70

<210> SEQ ID NO 210
<211> LENGTH: 11
<212> TYPE: PRT
<213> ORGANISM: Homo sapiens

<400> SEQUENCE: 210

Gly Ile Cys Asn Asn Lys His His Cys His Cys
 1               5                  10

<210> SEQ ID NO 211
<211> LENGTH: 145
<212> TYPE: PRT
<213> ORGANISM: Homo sapiens
<220> FEATURE:
<221> NAME/KEY: SITE
<222> LOCATION: (29)
<223> OTHER INFORMATION: Xaa equals any of the naturally occurring
      L-amino acids
<220> FEATURE:
<221> NAME/KEY: SITE
<222> LOCATION: (34)
<223> OTHER INFORMATION: Xaa equals any of the naturally occurring
      L-amino acids

<400> SEQUENCE: 211

Phe Cys Tyr Leu Cys Ile Leu Leu Ile Val Leu Phe Ile Leu Leu
 1               5                  10                  15

Cys Cys Leu Tyr Arg Leu Cys Lys Lys Ser Lys Pro Xaa Lys Lys Gln
             20                  25                  30

Gln Xaa Val Gln Thr Pro Ser Ala Lys Glu Glu Lys Ile Gln Arg
         35                  40                  45

Arg Pro His Glu Leu Pro Pro Gln Ser Gln Pro Trp Val Met Pro Ser
     50                  55                  60

Gln Ser Gln Pro Pro Val Thr Pro Ser Gln Ser His Pro Gln Val Met
 65                  70                  75                  80

Pro Ser Gln Ser Gln Pro Pro Val Thr Pro Ser Gln Ser Gln Pro Arg
             85                  90                  95

Val Met Pro Ser Gln Ser Gln Pro Pro Val Met Pro Ser Gln Ser His
            100                 105                 110

Pro Gln Leu Thr Pro Ser Gln Ser Gln Pro Val Thr Pro Ser Gln
        115                 120                 125

Arg Gln Pro Gln Leu Met Pro Ser Gln Ser Gln Pro Pro Val Thr Pro
    130                 135                 140

Ser
145
```

<210> SEQ ID NO 212
<211> LENGTH: 57
<212> TYPE: PRT
<213> ORGANISM: Homo sapiens

<400> SEQUENCE: 212

Ile Arg His Glu Glu Met His Met Ala Leu Asn Asn Gln Ala Thr Gly
1               5                   10                  15

Leu Leu Asn Leu Lys Lys Asp Ile Arg Gly Val Leu Asp Gln Met Glu
            20                  25                  30

Asp Ile Gln Leu Glu Ile Leu Arg Glu Arg Ala Gln Cys Arg Thr Arg
        35                  40                  45

Ala Arg Lys Glu Lys Gln Met Ala Ser
    50                  55

<210> SEQ ID NO 213
<211> LENGTH: 48
<212> TYPE: PRT
<213> ORGANISM: Homo sapiens

<400> SEQUENCE: 213

Trp Ile Pro Arg Ala Ala Gly Ile Arg His Glu Arg Asn Leu Arg Leu
1               5                   10                  15

Trp Gln Ile Glu Ile Met Ala Gly Pro Glu Ser Asp Ala Gln Tyr Gln
            20                  25                  30

Phe Thr Gly Ile Lys Lys Tyr Phe Asn Ser Tyr Thr Leu Thr Gly Arg
        35                  40                  45

<210> SEQ ID NO 214
<211> LENGTH: 28
<212> TYPE: PRT
<213> ORGANISM: Homo sapiens

<400> SEQUENCE: 214

Ala Phe Glu Ser Leu Pro Lys Tyr His Leu Leu Lys Cys Ser Phe Ser
1               5                   10                  15

Leu Leu Leu Asn Phe Ile Val Pro His Gln Cys Thr
            20                  25

<210> SEQ ID NO 215
<211> LENGTH: 43
<212> TYPE: PRT
<213> ORGANISM: Homo sapiens

<400> SEQUENCE: 215

Phe Phe Phe Val Cys Leu Phe Ile Val Phe Leu Pro His Lys Ser Lys
1               5                   10                  15

Val Tyr Met Asn Arg Glu Leu Val Cys Phe Val Tyr Tyr Cys Ile Pro
            20                  25                  30

Tyr Ala Gly Thr Tyr Tyr Val Ile Ser Val Cys
        35                  40

<210> SEQ ID NO 216
<211> LENGTH: 20
<212> TYPE: PRT
<213> ORGANISM: Homo sapiens

<400> SEQUENCE: 216

Arg Lys Lys Tyr Tyr Leu Arg Cys Glu Asn Tyr Ser Pro Lys Tyr Cys
1               5                   10                  15

-continued

Ser Phe Gln Ala
            20

<210> SEQ ID NO 217
<211> LENGTH: 234
<212> TYPE: PRT
<213> ORGANISM: Homo sapiens

<400> SEQUENCE: 217

Gly Ser Phe Arg Gly Thr Gly Arg Gly Arg Asp Gly Ala Gln His Pro
1               5                   10                  15

Leu Leu Tyr Val Lys Leu Leu Ile Gln Val Gly His Glu Pro Met Pro
            20                  25                  30

Pro Thr Leu Gly Thr Asn Val Leu Gly Arg Lys Val Leu Tyr Leu Pro
        35                  40                  45

Ser Phe Phe Thr Tyr Ala Lys Tyr Ile Val Gln Val Asp Gly Lys Ile
    50                  55                  60

Gly Leu Phe Arg Gly Leu Ser Pro Arg Leu Met Ser Asn Ala Leu Ser
65                  70                  75                  80

Thr Val Thr Arg Gly Ser Met Lys Lys Val Phe Pro Pro Asp Glu Ile
                85                  90                  95

Glu Gln Val Ser Asn Lys Asp Asp Met Lys Thr Ser Leu Lys Lys Val
            100                 105                 110

Val Lys Glu Thr Ser Tyr Glu Met Met Met Gln Cys Val Ser Arg Met
        115                 120                 125

Leu Ala His Pro Leu His Val Ile Ser Met Arg Cys Met Val Gln Phe
    130                 135                 140

Val Gly Arg Glu Ala Lys Tyr Ser Gly Val Leu Ser Ser Ile Gly Lys
145                 150                 155                 160

Ile Phe Lys Glu Glu Gly Leu Leu Gly Phe Phe Val Gly Leu Ile Pro
                165                 170                 175

His Leu Leu Gly Asp Val Val Phe Leu Trp Gly Cys Asn Leu Leu Ala
            180                 185                 190

His Phe Ile Asn Ala Tyr Leu Val Asp Asp Ser Val Ser Asp Thr Pro
        195                 200                 205

Gly Gly Leu Gly Asn Asp Gln Asn Pro Gly Ser Gln Phe Ser Gln Ala
    210                 215                 220

Leu Ala Ile Arg Ser Tyr Thr Lys Phe Val
225                 230

<210> SEQ ID NO 218
<211> LENGTH: 48
<212> TYPE: PRT
<213> ORGANISM: Homo sapiens

<400> SEQUENCE: 218

Gly Ser Phe Arg Gly Thr Gly Arg Gly Arg Asp Gly Ala Gln His Pro
1               5                   10                  15

Leu Leu Tyr Val Lys Leu Leu Ile Gln Val Gly His Glu Pro Met Pro
            20                  25                  30

Pro Thr Leu Gly Thr Asn Val Leu Gly Arg Lys Val Leu Tyr Leu Pro
        35                  40                  45

<210> SEQ ID NO 219
<211> LENGTH: 48
<212> TYPE: PRT
<213> ORGANISM: Homo sapiens

```
<400> SEQUENCE: 219

Ser Phe Phe Thr Tyr Ala Lys Tyr Ile Val Gln Val Asp Gly Lys Ile
 1               5                  10                  15

Gly Leu Phe Arg Gly Leu Ser Pro Arg Leu Met Ser Asn Ala Leu Ser
            20                  25                  30

Thr Val Thr Arg Gly Ser Met Lys Lys Val Phe Pro Pro Asp Glu Ile
        35                  40                  45

<210> SEQ ID NO 220
<211> LENGTH: 45
<212> TYPE: PRT
<213> ORGANISM: Homo sapiens

<400> SEQUENCE: 220

Glu Gln Val Ser Asn Lys Asp Asp Met Lys Thr Ser Leu Lys Lys Val
 1               5                  10                  15

Val Lys Glu Thr Ser Tyr Glu Met Met Met Gln Cys Val Ser Arg Met
            20                  25                  30

Leu Ala His Pro Leu His Val Ile Ser Met Arg Cys Met
        35                  40                  45

<210> SEQ ID NO 221
<211> LENGTH: 50
<212> TYPE: PRT
<213> ORGANISM: Homo sapiens

<400> SEQUENCE: 221

Val Gln Phe Val Gly Arg Glu Ala Lys Tyr Ser Gly Val Leu Ser Ser
 1               5                  10                  15

Ile Gly Lys Ile Phe Lys Glu Glu Gly Leu Leu Gly Phe Phe Val Gly
            20                  25                  30

Leu Ile Pro His Leu Leu Gly Asp Val Val Phe Leu Trp Gly Cys Asn
        35                  40                  45

Leu Leu
    50

<210> SEQ ID NO 222
<211> LENGTH: 43
<212> TYPE: PRT
<213> ORGANISM: Homo sapiens

<400> SEQUENCE: 222

Ala His Phe Ile Asn Ala Tyr Leu Val Asp Asp Ser Val Ser Asp Thr
 1               5                  10                  15

Pro Gly Gly Leu Gly Asn Asp Gln Asn Pro Gly Ser Gln Phe Ser Gln
            20                  25                  30

Ala Leu Ala Ile Arg Ser Tyr Thr Lys Phe Val
        35                  40

<210> SEQ ID NO 223
<211> LENGTH: 56
<212> TYPE: PRT
<213> ORGANISM: Homo sapiens

<400> SEQUENCE: 223

Leu Ile Leu Ser Ala Leu Arg Glu Leu Leu Met Leu Leu Cys Pro Pro
 1               5                  10                  15

Val His Met Leu Ile Ala Lys Lys Lys Met Ser Met Ser Glu Pro Lys
            20                  25                  30
```

```
Ala Ala Glu Thr Phe Cys Val Tyr Ala Thr Ser Leu Pro Ser Ile Gln
            35                  40                  45

Gly Arg Trp Phe His Cys Leu Val
 50                  55
```

<210> SEQ ID NO 224
<211> LENGTH: 19
<212> TYPE: PRT
<213> ORGANISM: Homo sapiens

<400> SEQUENCE: 224

```
Asp His Phe Gln Pro Asn Val His Leu Ala Gly Ile Trp Leu Ser Gln
 1               5                  10                  15

Asn Asn Ile
```

<210> SEQ ID NO 225
<211> LENGTH: 125
<212> TYPE: PRT
<213> ORGANISM: Homo sapiens

<400> SEQUENCE: 225

```
Ile Lys His Ile Ser Thr Gln Phe Cys His Pro Arg Glu Ser Thr Asn
 1               5                  10                  15

Cys Arg Pro Leu Leu Gln Leu Lys Glu Asp Pro Thr Glu Asn Gly Ile
                20                  25                  30

Glu Ser Gly Asp Arg Thr Leu His Arg Thr Leu Glu His Ser Gln Asp
            35                  40                  45

Phe Ile His Thr Phe Gly Ser Cys Val Leu Tyr Arg Arg Leu Ser Tyr
 50                  55                  60

Glu Leu Leu Ser Lys Ser Gln Ser Leu Glu Ala Asn Pro Val Thr Arg
 65                  70                  75                  80

Pro Ser Glu Glu Ser Asp Leu Lys Arg Ser Arg Asp Leu Thr Ala
                85                  90                  95

Lys Pro His His Pro His Arg Phe Phe Cys Asp Thr Glu Arg Ser Asn
                100                 105                 110

Pro Arg Pro Gly Leu Cys Leu Ser Arg Asp Ile Ile Ile
                115                 120                 125
```

<210> SEQ ID NO 226
<211> LENGTH: 43
<212> TYPE: PRT
<213> ORGANISM: Homo sapiens

<400> SEQUENCE: 226

```
Ile Lys His Ile Ser Thr Gln Phe Cys His Pro Arg Glu Ser Thr Asn
 1               5                  10                  15

Cys Arg Pro Leu Leu Gln Leu Lys Glu Asp Pro Thr Glu Asn Gly Ile
                20                  25                  30

Glu Ser Gly Asp Arg Thr Leu His Arg Thr Leu
            35                  40
```

<210> SEQ ID NO 227
<211> LENGTH: 41
<212> TYPE: PRT
<213> ORGANISM: Homo sapiens

<400> SEQUENCE: 227

```
Glu His Ser Gln Asp Phe Ile His Thr Phe Gly Ser Cys Val Leu Tyr
 1               5                  10                  15
```

```
Arg Arg Leu Ser Tyr Glu Leu Leu Ser Lys Ser Gln Ser Leu Glu Ala
            20                  25                  30

Asn Pro Val Thr Arg Pro Ser Ser Glu
            35                  40

<210> SEQ ID NO 228
<211> LENGTH: 41
<212> TYPE: PRT
<213> ORGANISM: Homo sapiens

<400> SEQUENCE: 228

Glu Ser Asp Leu Lys Arg Ser Arg Asp Leu Thr Ala Lys Pro His His
 1               5                  10                  15

Pro His Arg Phe Phe Cys Asp Thr Glu Arg Ser Asn Pro Arg Pro Gly
            20                  25                  30

Leu Cys Leu Ser Arg Asp Ile Ile Ile
            35                  40

<210> SEQ ID NO 229
<211> LENGTH: 22
<212> TYPE: PRT
<213> ORGANISM: Homo sapiens

<400> SEQUENCE: 229

Asn Ser Ala Arg Ala Tyr Val Gln Val Leu Pro Cys Leu Ala Pro Arg
 1               5                  10                  15

Asn Thr Val Pro Arg Thr
            20

<210> SEQ ID NO 230
<211> LENGTH: 21
<212> TYPE: PRT
<213> ORGANISM: Homo sapiens

<400> SEQUENCE: 230

Val Ser Tyr Ala His Glu Pro Ser Leu Phe Phe Asn Leu Val Pro
 1               5                  10                  15

Ala Thr Phe Leu Thr
            20

<210> SEQ ID NO 231
<211> LENGTH: 19
<212> TYPE: PRT
<213> ORGANISM: Homo sapiens

<400> SEQUENCE: 231

Phe Thr Pro Ser Trp Pro Leu Phe Ile Thr Val Lys Val His Pro Ser
 1               5                  10                  15

Phe Asp Leu

<210> SEQ ID NO 232
<211> LENGTH: 12
<212> TYPE: PRT
<213> ORGANISM: Homo sapiens

<400> SEQUENCE: 232

Arg Asn Tyr Lys Lys Cys Ile Ser Leu Leu Arg Asp
 1               5                  10

<210> SEQ ID NO 233
<211> LENGTH: 120
<212> TYPE: PRT
```

<213> ORGANISM: Homo sapiens

<400> SEQUENCE: 233

Ala Arg Ala Ala Pro Arg Leu Leu Leu Phe Leu Val Pro Leu Leu
1               5                   10                  15

Trp Ala Pro Ala Ala Val Arg Ala Gly Pro Asp Glu Asp Leu Ser His
                20                  25                  30

Arg Asn Lys Glu Pro Pro Ala Pro Ala Gln Gln Leu Gln Pro Gln Pro
            35                  40                  45

Val Ala Val Gln Gly Pro Glu Pro Ala Arg Val Glu Asp Pro Tyr Gly
    50                  55                  60

Val Ala Val Gly Gly Thr Val Gly His Cys Leu Cys Thr Gly Leu Ala
65                  70                  75                  80

Val Ile Gly Gly Arg Met Ile Ala Gln Lys Ile Ser Val Arg Thr Val
                85                  90                  95

Thr Ile Ile Gly Gly Ile Val Phe Leu Ala Phe Ala Phe Ser Ala Leu
            100                 105                 110

Phe Ile Ser Pro Asp Ser Gly Phe
        115                 120

<210> SEQ ID NO 234
<211> LENGTH: 70
<212> TYPE: PRT
<213> ORGANISM: Homo sapiens

<400> SEQUENCE: 234

Phe Arg Ile Ala Trp Leu Leu Cys Leu Met Ile Cys Leu Ile Gln Lys
1               5                   10                  15

Gln Glu Cys Arg Val Lys Thr Glu Pro Met Asp Ala Asp Ser Asn
            20                  25                  30

Asn Cys Thr Gly Gln Asn Glu His Gln Arg Glu Asn Ser Gly His Arg
        35                  40                  45

Arg Asp Gln Ile Ile Glu Lys Asp Ala Ala Leu Cys Val Leu Ile Asp
    50                  55                  60

Glu Met Asn Glu Arg Pro
65                  70

<210> SEQ ID NO 235
<211> LENGTH: 51
<212> TYPE: PRT
<213> ORGANISM: Homo sapiens

<400> SEQUENCE: 235

Arg Val Lys Thr Glu Pro Met Asp Ala Asp Asp Ser Asn Asn Cys Thr
1               5                   10                  15

Gly Gln Asn Glu His Gln Arg Glu Asn Ser Gly His Arg Arg Asp Gln
            20                  25                  30

Ile Ile Glu Lys Asp Ala Ala Leu Cys Val Leu Ile Asp Glu Met Asn
        35                  40                  45

Glu Arg Pro
    50

<210> SEQ ID NO 236
<211> LENGTH: 26
<212> TYPE: PRT
<213> ORGANISM: Homo sapiens

<400> SEQUENCE: 236

```
Gln Val Ser Ala Leu Pro Pro Pro Met Gln Tyr Ile Lys Glu Tyr
1               5                   10                  15

Thr Asp Glu Asn Ile Gln Glu Gly Leu Ala
                20                  25
```

<210> SEQ ID NO 237
<211> LENGTH: 24
<212> TYPE: PRT
<213> ORGANISM: Homo sapiens

<400> SEQUENCE: 237

```
Ser Gln Gly Ile Glu Arg Leu His Pro Met Gln Phe Asp His Lys Lys
1               5                   10                  15

Glu Leu Arg Lys Leu Asn Met Ser
                20
```

<210> SEQ ID NO 238
<211> LENGTH: 31
<212> TYPE: PRT
<213> ORGANISM: Homo sapiens

<400> SEQUENCE: 238

```
Leu Glu Thr Ala Glu Arg Phe Gln Lys His Leu Glu Arg Val Ile Glu
1               5                   10                  15

Met Ile Gln Asn Cys Leu Ala Ser Leu Pro Asp Asp Leu Pro His
                20                  25                  30
```

<210> SEQ ID NO 239
<211> LENGTH: 30
<212> TYPE: PRT
<213> ORGANISM: Homo sapiens

<400> SEQUENCE: 239

```
Asn Ser Ala Arg Gly Ala Leu Ser Ser Ala Asp Ser Cys His Phe Ser
1               5                   10                  15

Arg Pro Pro Leu Ser Glu Glu Thr Arg Arg Trp Glu Thr Gly
                20                  25                  30
```

<210> SEQ ID NO 240
<211> LENGTH: 154
<212> TYPE: PRT
<213> ORGANISM: Homo sapiens
<220> FEATURE:
<221> NAME/KEY: SITE
<222> LOCATION: (136)
<223> OTHER INFORMATION: Xaa equals any of the naturally occurring
      L-amino acids

<400> SEQUENCE: 240

```
Met Thr Met Ile Thr Pro Ser Ser Lys Leu Thr Leu Thr Lys Gly Asn
1               5                   10                  15

Lys Ser Trp Ser Ser Thr Ala Val Ala Ala Leu Glu Leu Val Asp
                20                  25                  30

Pro Pro Gly Cys Arg Asn Ser Pro Pro Pro His Thr Pro Phe Ser
            35                  40                  45

Tyr Ala Phe Gly Val Leu Asp Gly Asn Leu Gly Glu Arg Lys Asp
        50                  55                  60

Arg Ser Gly Leu Pro Gln Pro Leu Leu Leu Ser Pro Arg Val Arg
65                  70                  75                  80

Ile Ala Gly Ala Pro Pro Pro Ser Trp Phe Leu Arg Thr Arg Pro Phe
                85                  90                  95
```

```
Ser Phe Cys Leu Tyr Leu Leu Arg Ile Leu Ser Leu Leu Met Trp Leu
            100                 105                 110

Thr Pro Leu Pro Pro Leu Pro Ala Gly Gly Trp Pro Gly Gly Gln Val
        115                 120                 125

Pro Ala Gly Ala Val Asn Arg Xaa Cys Ala Phe Val Leu Val Cys Ala
    130                 135                 140

Cys Ala Val Phe Leu Cys Phe Asp Arg Ser
145                 150

<210> SEQ ID NO 241
<211> LENGTH: 28
<212> TYPE: PRT
<213> ORGANISM: Homo sapiens

<400> SEQUENCE: 241

Leu Thr Leu Thr Lys Gly Asn Lys Ser Trp Ser Ser Thr Ala Val Ala
  1               5                  10                  15

Ala Ala Leu Glu Leu Val Asp Pro Pro Gly Cys Arg
            20                  25

<210> SEQ ID NO 242
<211> LENGTH: 47
<212> TYPE: PRT
<213> ORGANISM: Homo sapiens

<400> SEQUENCE: 242

Ala Asp Asn Asn Phe Thr Gln Glu Thr Ala Met Thr Met Ile Thr Pro
  1               5                  10                  15

Ser Ser Lys Leu Thr Leu Thr Lys Gly Asn Lys Ser Trp Ser Ser Thr
            20                  25                  30

Ala Val Ala Ala Ala Leu Glu Leu Val Asp Pro Pro Gly Cys Arg
        35                  40                  45

<210> SEQ ID NO 243
<211> LENGTH: 49
<212> TYPE: PRT
<213> ORGANISM: Homo sapiens

<400> SEQUENCE: 243

Asn Ser Pro Pro Pro His Thr Pro Phe Ser Tyr Ala Phe Gly Val
  1               5                  10                  15

Leu Asp Gly Asn Leu Gly Gly Glu Arg Lys Asp Arg Ser Gly Leu Pro
            20                  25                  30

Gln Pro Leu Leu Leu Ser Pro Arg Val Arg Ile Ala Gly Ala Pro
        35                  40                  45

Pro

<210> SEQ ID NO 244
<211> LENGTH: 49
<212> TYPE: PRT
<213> ORGANISM: Homo sapiens

<400> SEQUENCE: 244

Pro Ser Trp Phe Leu Arg Thr Arg Pro Phe Ser Phe Cys Leu Tyr Leu
  1               5                  10                  15

Leu Arg Ile Leu Ser Leu Leu Met Trp Leu Thr Pro Leu Pro Pro Leu
            20                  25                  30

Pro Ala Gly Gly Trp Pro Gly Gly Gln Val Pro Ala Gly Ala Val Asn
        35                  40                  45
```

Arg

<210> SEQ ID NO 245
<211> LENGTH: 26
<212> TYPE: PRT
<213> ORGANISM: Homo sapiens

<400> SEQUENCE: 245

Arg Ala Pro Glu Arg Ser Ser Ala Gly Arg Val Pro Pro Glu Pro
 1               5                  10                  15

Ala Ala Pro Met Ala Gly Gly Tyr Gly Val
            20                  25

<210> SEQ ID NO 246
<211> LENGTH: 24
<212> TYPE: PRT
<213> ORGANISM: Homo sapiens

<400> SEQUENCE: 246

Thr Phe Gly Leu Leu Ser Phe Gly Tyr Tyr Glu Cys Tyr Lys Tyr
 1               5                  10                  15

Leu Cys Thr Ser Ile Cys Val Asp
            20

<210> SEQ ID NO 247
<211> LENGTH: 38
<212> TYPE: PRT
<213> ORGANISM: Homo sapiens

<400> SEQUENCE: 247

Glu His Cys Phe Leu Arg Pro Asp Cys Leu Phe Ala Trp Arg Phe Leu
 1               5                  10                  15

Ser Gln His Pro Ala Gly Leu Gly Glu Asp Thr Ser Ile Pro Leu
            20                  25                  30

Thr Leu Gln Gly Leu Leu
            35

<210> SEQ ID NO 248
<211> LENGTH: 153
<212> TYPE: PRT
<213> ORGANISM: Homo sapiens

<400> SEQUENCE: 248

Phe Arg Pro Ser Pro Asp Ile Cys Ala Arg Glu Cys Gly Met Val Gln
 1               5                  10                  15

Ser Ser Arg Ser Ser Ala Thr Glu Lys Arg Val Thr Pro Ile His His
            20                  25                  30

Gly Gln Ser Thr Gln Ser Gly Ser Ala Leu Asp Pro Ala Arg Gln Met
            35                  40                  45

Gln Pro Leu Asn Arg Val Cys Ala Ser Lys Leu Asp Asp Arg Arg
        50                  55                  60

Asn Pro Val Ala Ser Glu Lys Thr Pro Asn Pro Arg Met Lys Ala Ser
65                  70                  75                  80

Gly Ser Ile Pro Arg Asn Ser Cys Arg Gly Cys Gly Ile Phe Phe
                85                  90                  95

Lys Arg Thr Lys Gln Gly Lys Thr Lys Phe Asn Arg Val Glu Gln Pro
            100                 105                 110

Gly Val Val Gly His Ala Cys Asn Leu Ser Asn Leu Gly Gly Gln Gly
            115                 120                 125

```
Arg Ile Ser Ala Ile Trp Glu Ala Lys Ala Gly Arg Ser Leu Glu Pro
    130                 135                 140

Arg Ser Ser Arg Pro Ala Trp Ala Thr
145                 150
```

<210> SEQ ID NO 249
<211> LENGTH: 41
<212> TYPE: PRT
<213> ORGANISM: Homo sapiens

<400> SEQUENCE: 249

```
Phe Arg Pro Ser Pro Asp Ile Cys Ala Arg Glu Cys Gly Met Val Gln
 1               5                  10                  15

Ser Ser Arg Ser Ser Ala Thr Glu Lys Arg Val Thr Pro Ile His His
                20                  25                  30

Gly Gln Ser Thr Gln Ser Gly Ser Ala
            35                  40
```

<210> SEQ ID NO 250
<211> LENGTH: 39
<212> TYPE: PRT
<213> ORGANISM: Homo sapiens

<400> SEQUENCE: 250

```
Leu Asp Pro Ala Arg Gln Met Gln Pro Leu Asn Arg Val Cys Ala Ser
 1               5                  10                  15

Lys Leu Asp Asp Asp Arg Arg Asn Pro Val Ala Ser Glu Lys Thr Pro
                20                  25                  30

Asn Pro Arg Met Lys Ala Ser
            35
```

<210> SEQ ID NO 251
<211> LENGTH: 42
<212> TYPE: PRT
<213> ORGANISM: Homo sapiens

<400> SEQUENCE: 251

```
Gly Ser Ile Pro Arg Asn Ser Cys Arg Gly Cys Cys Gly Ile Phe Phe
 1               5                  10                  15

Lys Arg Thr Lys Gln Gly Lys Thr Lys Phe Asn Arg Val Glu Gln Pro
                20                  25                  30

Gly Val Val Gly His Ala Cys Asn Leu Ser
            35                  40
```

<210> SEQ ID NO 252
<211> LENGTH: 31
<212> TYPE: PRT
<213> ORGANISM: Homo sapiens

<400> SEQUENCE: 252

```
Asn Leu Gly Gly Gln Gly Arg Ile Ser Ala Ile Trp Glu Ala Lys Ala
 1               5                  10                  15

Gly Arg Ser Leu Glu Pro Arg Ser Arg Pro Ala Trp Ala Thr
                20                  25                  30
```

<210> SEQ ID NO 253
<211> LENGTH: 9
<212> TYPE: PRT
<213> ORGANISM: Homo sapiens

<400> SEQUENCE: 253

```
Gly Tyr Leu Leu Ile Ala Glu Thr Gln
 1               5
```

<210> SEQ ID NO 254
<211> LENGTH: 93
<212> TYPE: PRT
<213> ORGANISM: Homo sapiens
<220> FEATURE:
<221> NAME/KEY: SITE
<222> LOCATION: (3)
<223> OTHER INFORMATION: Xaa equals any of the naturally occurring
      L-amino acids
<220> FEATURE:
<221> NAME/KEY: SITE
<222> LOCATION: (5)
<223> OTHER INFORMATION: Xaa equals any of the naturally occurring
      L-amino acids

<400> SEQUENCE: 254

```
His Ser Xaa Ile Xaa Pro His Pro Pro Leu Leu Ile Asp Ser Arg Phe
 1               5                  10                  15

Thr Gln Leu Val Asn Leu Ser Ser Glu Pro Ser Pro Lys Leu Ile Cys
            20                  25                  30

Pro Gln Asn Ser Thr Pro Ser Pro Ser Leu Ser Leu Pro Thr His Ala
        35                  40                  45

Ser Asp Ser Pro Gly Ser Thr Ser Glu Met Ser Ala Lys Thr Leu Leu
    50                  55                  60

Ile Gln Ala Val Phe Pro Val Gln Lys Arg Gly Ser Thr Phe Ser Leu
65                  70                  75                  80

Ala Leu Phe Glu Leu Asn Met Gln Leu Pro Gly Val Thr
                85                  90
```

<210> SEQ ID NO 255
<211> LENGTH: 63
<212> TYPE: PRT
<213> ORGANISM: Homo sapiens
<220> FEATURE:
<221> NAME/KEY: SITE
<222> LOCATION: (29)
<223> OTHER INFORMATION: Xaa equals any of the naturally occurring
      L-amino acids

<400> SEQUENCE: 255

```
Lys Val Arg Thr Glu Asn Ser Glu Asn Asn Gln Asn Lys Ile Tyr Ser
 1               5                  10                  15

Tyr Phe Ser Leu Lys Ser Trp Lys Asn Phe Gly Phe Xaa Leu Arg Phe
            20                  25                  30

Leu Ser Pro Thr His Ala Phe Thr Asn Tyr Val Phe Val Tyr Ser Met
        35                  40                  45

Ser Ala Ala Gln Ala Glu Gly Ala Ser Leu His Gly Met Arg Gly
    50                  55                  60
```

<210> SEQ ID NO 256
<211> LENGTH: 17
<212> TYPE: PRT
<213> ORGANISM: Homo sapiens

<400> SEQUENCE: 256

```
Ser Ser Thr Leu Lys Ser Ser Cys Cys Cys Phe Gln Pro Arg Lys Phe
 1               5                  10                  15

Ser
```

<210> SEQ ID NO 257

```
-continued
<211> LENGTH: 15
<212> TYPE: PRT
<213> ORGANISM: Homo sapiens

<400> SEQUENCE: 257

Ala Ala Met Val Thr Met Val Thr Gly Ser Gln Pro Glu Thr Thr
 1               5                  10                  15
```

US 7,217,528 B2

ANTIBODIES TO HFXJW48 POLYPEPTIDE

CROSS-REFERENCE TO RELATED APPLICATIONS

This application is a divisional of U.S. patent application Ser. No. 10/144,929, filed May 15, 2002 now U.S. Pat. No. 6,881,823, which is a continuation of U.S. application Ser. No. 09/716,128 filed Nov. 17, 2000 now abandoned, which is a continuation of U.S. application Ser. No. 09/251,329 filed Feb. 17, 1999 now abandoned, which is a continuation-in-part of PCT International No. PCT/US98/17044, filed Aug. 18, 1998, which claims benefit under 35 U.S.C. § 119(e) based on U.S. Provisional Applications 60/056,555; 60/056,556; 60/056,535; 60/056,629; 60/056,369; 60/056,628; 60/056,728; 60/056,368; 60/056,726 (filed Aug. 19, 1997); and, 60/089,510 (filed Jun. 16, 1998); and, 60/092,956 (filed Jul. 15, 1998). Each of the above referenced patent applications is hereby incorporated by reference in its entirety.

FIELD OF THE INVENTION

This invention relates to newly identified polynucleotides and the polypeptides encoded by these polynucleotides, uses of such polynucleotides and polypeptides, and their production.

BACKGROUND OF THE INVENTION

Unlike bacterium, which exist as a single compartment surrounded by a membrane, human cells and other eucaryotes are subdivided by membranes into many functionally distinct compartments. Each membrane-bounded compartment, or organelle, contains different proteins essential for the function of the organelle. The cell uses "sorting signals," which are amino acid motifs located within the protein, to target proteins to particular cellular organelles.

One type of sorting signal, called a signal sequence, a signal peptide, or a leader sequence, directs a class of proteins to an organelle called the endoplasmic reticulum (ER). The ER separates the membrane-bounded proteins from all other types of proteins. Once localized to the ER, both groups of proteins can be further directed to another organelle called the Golgi apparatus. Here, the Golgi distributes the proteins to vesicles, including secretory vesicles, the cell membrane, lysosomes, and the other organelles.

Proteins targeted to the ER by a signal sequence can be released into the extracellular space as a secreted protein. For example, vesicles containing secreted proteins can fuse with the cell membrane and release their contents into the extracellular space—a process called exocytosis. Exocytosis can occur constitutively or after receipt of a triggering signal. In the latter case, the proteins are stored in secretory vesicles (or secretory granules) until exocytosis is triggered. Similarly, proteins residing on the cell membrane can also be secreted into the extracellular space by proteolytic cleavage of a "linker" holding the protein to the membrane.

Despite the great progress made in recent years, only a small number of genes encoding human secreted proteins have been identified. These secreted proteins include the commercially valuable human insulin, interferon, Factor VIII, human growth hormone, tissue plasminogen activator, and erythropoeitin. Thus, in light of the pervasive role of secreted proteins in human physiology, a need exists for identifying and characterizing novel human secreted proteins and the genes that encode them. This knowledge will allow one to detect, to treat, and to prevent medical disorders by using secreted proteins or the genes that encode them.

SUMMARY OF THE INVENTION

The present invention relates to novel polynucleotides and the encoded polypeptides. Moreover, the present invention relates to vectors, host cells, antibodies, and recombinant methods for producing the polypeptides and polynucleotides. Also provided are diagnostic methods for detecting disorders related to the polypeptides, and therapeutic methods for treating such disorders. The invention further relates to screening methods for identifying binding partners of the polypeptides.

DETAILED DESCRIPTION

Definitions

The following definitions are provided to facilitate understanding of certain terms used throughout this specification.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide.

In the present invention, a "secreted" protein refers to those proteins capable of being directed to the ER, secretory vesicles, or the extracellular space as a result of a signal sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage.

In specific embodiments, the polynucleotides of the invention are less than 300 kb, 200 kb, 100 kb, 50 kb, 15 kb, 10 kb, or 7.5 kb in length. In a further embodiment, polynucleotides of the invention comprise at least 15 contiguous nucleotides of the coding sequence, but do not comprise all or a portion of any intron. In another embodiment, the nucleic acid comprising the coding sequence does not contain coding sequences of a genomic flanking gene (i.e., 5' or 3' to the gene in the genome).

As used herein, a "polynucleotide" refers to a molecule having a nucleic acid sequence contained in SEQ ID NO:X or the cDNA contained within the clone deposited with the ATCC. For example, the polynucleotide can contain the nucleotide sequence of the full length cDNA sequence, including the 5' and 3' untranslated sequences, the coding region, with or without the signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO:X was often generated by overlapping sequences contained in multiple clones (contig analysis). A representative clone containing all or most of the sequence for SEQ ID NO:X was deposited with the American Type Culture Collection ("ATCC"). As shown in Table 1, each clone is identified by a cDNA Clone ID (Identifier) and the ATCC Deposit Number. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure.

A "polynucleotide" of the present invention also includes those polynucleotides capable of hybridizing, under stringent hybridization conditions, to sequences contained in SEQ ID NO:X, the complement thereof, or the cDNA within the clone deposited with the ATCC. "Stringent hybridization conditions" refers to an overnight incubation at 42° C. in a solution comprising 50% formamide, 5×SSC (750 mM NaCl, 75 mM sodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M $NaH_2PO_4$; 0.02M EDTA, pH 7.4), 0.5% SDS, 30% formamide, 100 ug/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone).

The polynucleotide of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992).)

"SEQ ID NO:X" refers to a polynucleotide sequence while "SEQ ID NO:Y" refers to a polypeptide sequence, both sequences identified by an integer specified in Table 1.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention.)

Polynucleotides and Polypeptides of the Invention

Features of Protein Encoded by Gene No: 1

The translation product of this gene shares sequence homology with DNA encoding allergens of *Cladosporium herbarum*, in addition to, the rat TSEP-1 protein (See Genbank Accession No.: W12827), which is thought to be important in the modulation of MHC Class I gene expression. As such, the translation product of this gene may be beneficial in the prevention and treatment of auto-immune diseases and transplant rejections.

When tested against myelogenous leukemia cell lines (AML-193), supernatants removed from cells containing this gene activated Calcium permeability. Thus, it is likely that this gene activates signal transduction pathways in myelogenous leukemia cells through intracellular calcium release. Binding of a ligand to a receptor is known to alter intracellular levels of small molecules, such as calcium, potassium, sodium, and pH, as well as alter membrane potential. Alterations in small molecule concentration can be measured to identify supernatants which bind to receptors of a particular cell.

In specific embodiments, polypeptides of the invention comprise the following amino acid sequence:

FITPEDGSKDVFVHFSAISSQGFKTLAE-GQRVEFEITNGAK GPSAANVIAI (SEQ ID NO:163) and/or NSARALLGVCMFALGALAVPVTGFGS (SEQ ID NO:164). Polynucleotides encoding these polypeptides are also encompassed by the invention.

This gene is expressed primarily in CD34-depleted white blood cells.

Therefore, polynucleotides and polypeptides of the invention are useful as reagents for differential identification of the tissue(s) or cell type(s) present in a biological sample and for diagnosis of diseases and conditions which include, but are not limited to, allergy caused by *Cladosporium herbarum*, hematopoietic and immune disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., blood cells, immune, hematopoietic, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in CD34-depleted white blood cells, and the homology to DNA encoding allergens of *Cladosporium herbarum*, indicates that polynucleotides and polypeptides corresponding to this gene are useful for the diagnosis and/or treatment of allergies caused by *Cladosporium herbarum*. Similarly, the tissue distribution in white blood cells, combined with the oberved calcium release activity in myelogenous leukemia cells, indicates that polynucleotides and polypeptides corresponding to this gene are useful for the diagnosis and/or treatment of a variety of immune system disorders. Expression of this gene product in immune cells indicates a role in the regulation of the proliferation; survival; differentiation; and/or activation of potentially all hematopoietic cell lineages, including blood stem cells.

This gene product may be involved in the regulation of cytokine production, antigen presentation, or other processes that may also suggest a usefulness in the treatment of cancer (e.g. by boosting immune responses). Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types.

The secreted protein can also be used to determine biological activity, to raise antibodies, as tissue markers, to isolate cognate ligands or receptors, to identify agents that modulate their interactions and as nutritional supplements. It may also have a very wide range of biological acitivities. Typical of these are cytokine, cell proliferation/differentiation modulating activity or induction of other cytokines; immunostimulating/immunosuppressant activities (e.g. for treating human immunodeficiency virus infection, cancer, autoimmune diseases and allergy); regulation of hematopoiesis (e.g. for treating anaemia or as adjunct to chemotherapy); stimulation or growth of bone, cartilage, tendons, ligaments and/or nerves (e.g. for treating wounds, stimulation of follicle stimulating hormone (for control of fertility); proteins involved in the proliferation and differentiation of cells. The gene encoding the disclosed cDNA is believed to reside on chromosome 2. Accordingly, polynucleotides related to this invention are useful as a marker in linkage analysis for chromosome 2.

In specific embodiments, polypeptides of the invention comprise the following amino acid sequence: KMD-SKICLAMILHFPNPFTFLLSPTLLECSVSPYLSSISLN ILPVPCFQFRNWCPN (SEQ ID NO:165), and/or FFM-LFDFFFFFETESGSVTGA GVQWCNHGSLQSLP-PRLESILERPRAHRFSNRVGYQVSVTXFGL (SEQ ID NO:166). Polynucleotides encoding these polypeptides are also encompassed by the invention.

This gene is expressed primarily in CD34 positive white blood cells.

Therefore, polynucleotides and polypeptides of the invention are useful as reagents for anti-tumor reagents. Similarly, polypeptides and antibodies directed to these polypeptides are useful in providing immunological probes for differential identification of the tissue(s) or cell type(s). For a number of disorders of the above tissues or cells, particularly of the immune and hematopoietic systems, expression of this gene at significantly higher or lower levels may be routinely detected in certain tissues or cell types (e.g., blood cells, immune, hematopoietic, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in CD34 positive cells, combined with its homology to the human HSF protein, in addition to the detected biological activity within leukemia cell lines, indicates that polynucleotides and polypeptides corresponding to this gene are useful for the treatment and/or diagnosis of hematopoietic related disorders such as anemia, pancytopenia, leukopenia, thrombocytopenia or leukemia. The uses include bone marrow cell ex vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types.

Furthermore, this gene product may be involved in the regulation of cytokine production, antigen presentation, or other processes that may also suggest a usefulness in the treatment of cancer (e.g. by boosting immune responses). Moreover, since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types.

The secreted protein can also be used to determine biological activity, to raise antibodies, as tissue markers, to isolate cognate ligands or receptors, to identify agents that modulate their interactions and as nutritional supplements. It may also have a very wide range of biological acitivities. Typical of these are cytokine, cell proliferation/differentiation modulating activity or induction of other cytokines; immunostimulating/immunosuppressant activities (e.g. for treating human immunodeficiency virus infection, cancer, autoimmune diseases and allergy); regulation of hematopoiesis (e.g. for treating anaemia or as adjunct to chemotherapy); stimulation or growth of bone, cartilage, tendons, ligaments and/or nerves (e.g. for treating wounds, stimulation of follicle stimulating hormone (for control of fertility); chemotactic and chemokinetic activities (e.g. for treating infections, tumors); hemostatic or thrombolytic activity (e.g. for treating haemophilia, cardiac infarction etc.); anti-inflammatory activity (e.g. for treating septic shock, Crohn's disease); as antimicrobials; for treating psoriasis or other hyperproliferative diseases; for regulation of metabolism, and behaviour. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:12 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 451 of SEQ ID NO:12, b is an integer of 15 to 465, where both a and b correspond to the positions of nucleotide residues shown in SEQ ID NO:12, and where b is greater than or equal to a+14.

Features of Protein Encoded by Gene No: 3

In specific embodiments, polypeptides of the invention comprise the following amino acid sequence: FLKWPNK-SPDGEVLQW (SEQ ID NO:167). Polynucleotides encoding these polypeptides are also encompassed by the invention.

This gene is expressed primarily in CD34 positive blood cells.

Therefore, polynucleotides and polypeptides of the invention are useful as reagents for differential identification of the tissue(s) or cell type(s) present in a biological sample and for diagnosis of diseases and conditions which include, but are not limited to, diseases of the immune and hematopoietic systems, especially those of CD34 positive blood cells. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., blood cells, immune, hematopoietic, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:89 as residues: Gly-7 to Asp-14, Ile-16 to Tyr-36, Lys-47 to Ser-54.

The tissue distribution in CD34 positive blood cells indicates that polynucleotides and polypeptides corresponding to this gene are useful for the treatment and/or diagnosis of hematopoetic related disorders such as anemia, pancytopenia, leukopenia, thrombocytopenia or leukemia. The uses include bone marrow cell ex vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types.

Furthermore, this gene product may be involved in the regulation of cytokine production, antigen presentation, or other processes that may also suggest a usefulness in the treatment of cancer (e.g. by boosting immune responses). Moreover, since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:13 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 660 of SEQ ID NO:13, b is an integer of 15 to 674, where both a and b correspond to the positions of nucleotide residues shown in SEQ ID NO:13, and where b is greater than or equal to a+14.

Features of Protein Encoded by Gene No: 4

This gene is expressed primarily in CD34 positive blood cells.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders, particularly diseases involving CD34 positive cells. Similarly, polypeptides and antibodies directed to these polypeptides are useful in providing immunological probes for differential identification of the tissue(s) or cell type(s). For a number of disorders of the above tissues or cells, particularly of the immune or hematopoietic systems, expression of this gene at significantly higher or lower levels may be routinely detected in certain tissues or cell types (e.g., blood cells, immune, hematopoietic, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:90 as residues: Glu-12 to Thr-21.

The tissue distribution in CD34 positive white blood cells indicates that polynucleotides and polypeptides corresponding to this gene are useful for the treatment and/or diagnosis of hematopoietic related disorders such as anemia, pancytopenia, leukopenia, thrombocytopenia or leukemia. The uses include bone marrow cell ex vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types.

Furthermore, this gene product may be involved in the regulation of cytokine production, antigen presentation, or other processes that may also suggest a usefulness in the treatment of cancer (e.g. by boosting immune responses). Moreover, since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:14 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 283 of SEQ ID NO:14, b is an integer of 15 to 297, where both a and b correspond to the positions of nucleotide residues shown in SEQ ID NO:14, and where b is greater than or equal to a+14.

Features of Protein Encoded by Gene No: 5

In specific embodiments, polypeptides of the invention comprise the following amino acid sequence: VKCSQRAL-RWCQLNGLTRGLWVSLSCCPPFPSVQWGSPE AAPHAPAAL (SEQ ID NO:168), and/or MAEITSGIPVL-QIKQKHYSVFSVLIKN TVNISQYSPHEHGPLWGPQ (SEQ ID NO:169). Polynucleotides encoding these polypeptides are also encompassed by the invention.

This gene is expressed primarily in Hodgkin's lymphoma tissues.

Therefore, polynucleotides and polypeptides of the invention are useful as reagents for differential identification of the tissue(s) or cell type(s) present in a biological sample and for diagnosis of diseases and conditions which include, but are not limited to, Hodgkin's lymphoma, or related immune or hematopoietic disorders. Similarly, polypeptides and antibodies directed to these polypeptides are useful in providing immunological probes for differential identification of the tissue(s) or cell type(s). For a number of disorders of the above tissues or cells, particularly of the immune or hematopoietic systems, expression of this gene at significantly higher or lower levels may be routinely detected in certain tissues or cell types (e.g., blood cells, immune, hematopoietic, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:91 as residues: Ser-36 to Cys-42.

The tissue distribution in Hodgkin's lymphoma tissues indicates that polynucleotides and polypeptides corresponding to this gene are useful for the diagnosis and/or treatment of a variety of immune system disorders. Expression of this gene product in Hodgkin's lymphoma indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses).

Moreover, Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:15 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 590 of SEQ ID NO:15, b is an integer of 15 to 604, where both a and b correspond to the positions of nucleotide residues shown in SEQ ID NO:15, and where b is greater than or equal to a+14.

Features of Protein Encoded by Gene No: 6

This gene is expressed primarily in placental and embryonic tissues, and to a lesser extent in tonsils and ovarian tissue.

Therefore, polynucleotides and polypeptides of the invention are useful as reagents for differential identification of the tissue(s) or cell type(s) present in a biological sample and for diagnosis of diseases and conditions which include, but are not limited to, diseases of the female reproductive system, or developing tissues. Similarly, polypeptides and antibodies directed to these polypeptides are useful in providing immunological probes for differential identification of the tissue(s) or cell type(s). For a number of disorders of the above tissues or cells, particularly of the female reproductive or immune systems, expression of this gene at significantly higher or lower levels may be routinely detected in certain tissues or cell types (e.g., developing, reproductive, immune, or cancerous and wounded tissues) or bodily fluids (e.g., amniotic fluid, lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in placental and embryonic tissue indicates that polynucleotides and polypeptides corresponding to this gene are useful for the diagnosis and/or treatment of cancer and other proliferative disorders, particularly of the female reproductive system. Similarly, expression within embryonic tissue and other cellular sources marked by proliferating cells indicates that this protein may play a role in the regulation of cellular division. Additionally, the expression in immune tissues indicates that this protein may play a role in the proliferation, differentiation, and/or survival of hematopoietic cell lineages. In such an event, this gene may be useful in the treatment of lymphoproliferative disorders, and in the maintenance and differentiation of various hematopoietic lineages from early hematopoietic stem and committed progenitor cells. Similarly, embryonic development also involves decisions involving cell differentiation and/or apoptosis in pattern formation. Thus this protein may also be involved in apoptosis or tissue differentiation and could again be useful in cancer therapy.

Likewise, the tissue distribution indicates that polynucleotides and polypeptides corresponding to this gene are useful for the diagnosis and/or treatment of disorders of the placenta. Specific expression within the placenta indicates that this gene product may play a role in the proper establishment and maintenance of placental function. Alternately, this gene product may be produced by the placenta and then transported to the embryo, where it may play a crucial role in the development and/or survival of the developing embryo or fetus. Expression of this gene product in a vascular-rich tissue such as the placenta also indicates that this gene product may be produced more generally in endothelial cells or within the circulation. In such instances, it may play more generalized roles in vascular function, such as in angiogenesis. It may also be produced in the vasculature and have effects on other cells within the circulation, such as hematopoietic cells. It may serve to promote the proliferation, survival, activation, and/or differentiation of hematopoietic cells, as well as other cells throughout the body.

Alternatively, expression within ovarian tissues indicates that the protein product of this gene is useful for the detection, treatment, and/or prevention of various endocrine disorders and cancers, particularly Addison's disease, Cushing's Syndrome, and disorders and/or cancers of the pancrease (e.g. diabetes mellitus), adrenal cortex, ovaries, pituitary (e.g., hyper-, hypopituitarism), thyroid (e.g. hyper-, hypothyroidism), parathyroid (e.g. hyper-, hypoparathyroidism), hypothallamus, and testes. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:16 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1132 of SEQ ID NO:16, b is an integer of 15 to 1146, where both a and b correspond to the positions of nucleotide residues shown in SEQ ID NO:16, and where b is greater than or equal to a+14.

Features of Protein Encoded by Gene No: 7

In specific embodiments, polypeptides of the invention comprise the following amino acid sequence: CVRLGNV-LSILSLMCLKPGSSFTCWY (SEQ ID NO:170), and/or LVTRIKKLLPTLLVLLQIMKGNL (SEQ ID NO:171). Polynucleotides encoding these polypeptides are also encompassed by the invention.

This gene is expressed primarily in embryonic tissues, and to a lesser extent in infant brain tissue.

Therefore, polynucleotides and polypeptides of the invention are useful as reagents for differential identification of the tissue(s) or cell type(s) present in a biological sample and for diagnosis of diseases and conditions which include, but are not limited to, developmental disorders, in addition to cancer and other disorders characterized by proliferating tissues. Similarly, polypeptides and antibodies directed to these polypeptides are useful in providing immunological probes for differential identification of the tissue(s) or cell type(s). For a number of disorders of the above tissues or cells, particularly of embryonic tissues, expression of this gene at significantly higher or lower levels may be routinely detected in certain tissues or cell types (e.g., developmental, proliferating, or cancerous and wounded tissues) or bodily fluids (e.g., lymph, amniotic fluid, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:93 as residues: Ser-11 to His-16.

The tissue distribution in embryonic tissues indicates that polynucleotides and polypeptides corresponding to this gene are useful for the diagnosis and/or treatment of cancer and other proliferative disorders. Expression within embryonic tissue and other cellular sources marked by proliferating cells indicates that this protein may play a role in the regulation of cellular division. Similarly, embryonic development also involves decisions involving cell differentiation and/or apoptosis in pattern formation. Thus this protein may also be involved in apoptosis or tissue differentiation and could again be useful in cancer therapy.

The secreted protein can also be used to determine biological activity, to raise antibodies, as tissue markers, to isolate cognate ligands or receptors, to identify agents that modulate their interactions and as nutritional supplements. It may also have a very wide range of biological acitivities. Typical of these are cytokine, cell proliferation/differentiation modulating activity or induction of other cytokines; immunostimulating/immunosuppressant activities (e.g. for treating human immunodeficiency virus infection, cancer, autoimmune diseases and allergy); regulation of hematopoiesis (e.g. for treating anaemia or as adjunct to chemotherapy); stimulation or growth of bone, cartilage, tendons, ligaments and/or nerves (e.g. for treating wounds, stimulation of follicle stimulating hormone (for control of fertility); chemotactic and chemokinetic activities (e.g. for treating infections, tumors); hemostatic or thrombolytic activity (e.g. for treating haemophilia, cardiac infarction etc.); anti-inflammatory activity (e.g. for treating septic shock, Crohn's disease); as antimicrobials; for treating psoriasis or other hyperproliferative diseases; for regulation of metabolism, and behaviour. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:17 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 664 of SEQ ID NO:17, b is an integer of 15 to 678, where both a and b correspond to the positions of nucleotide residues shown in SEQ ID NO:17, and where b is greater than or equal to a+14.

Features of Protein Encoded by Gene No: 8

In specific embodiments, polypeptides of the invention comprise the following amino acid sequence: RLMYGLKEIYQVRE (SEQ ID NO:172), CGFCFTVYLFVVV SFSPCYLPFRMHLGK- AGSLASWFVSFFFFFKHRITLAIVC (SEQ ID NO:173), and/or SCHWCKALPALASSTSLSAKNSVIVCVP- FLILSHGRILQKRNLNCVH SLSE (SEQ ID NO:174). Polynucleotides encoding these polypeptides are also encompassed by the invention. The gene encoding the disclosed cDNA is thought to reside on chromosome 5. Accordingly, polynucleotides related to this invention are useful as a marker in linkage analysis for chromosome 5.

This gene is expressed primarily in kidney tissue, and to a lesser extent in other human tissues.

Therefore, polynucleotides and polypeptides of the invention are useful as reagents for differential identification of the tissue(s) or cell type(s) present in a biological sample and for diagnosis of diseases and conditions which include, but are not limited to, diseases of the renal or urogenital systems. Similarly, polypeptides and antibodies directed to these polypeptides are useful in providing immunological probes for differential identification of the tissue(s) or cell type(s). For a number of disorders of the above tissues or cells, particularly of the renal and urinary systems, expression of this gene at significantly higher or lower levels may be routinely detected in certain tissues or cell types (e.g., urogenital, endocrine, kidney, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in kidney tissue indicates that this gene or gene product could be used in the treatment and/or detection of kidney diseases including renal failure, nephritus, renal tubular acidosis, proteinuria, pyuria, edema, pyelonephritis, hydronephritis, nephrotic syndrome, crush syndrome, glomerulonephritis, hematuria, renal colic and kidney stones, in addition to Wilms Tumor Disease, and congenital kidney abnormalities such as horseshoe kidney, polycystic kidney, and Falconi's syndrome. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:18 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1291 of SEQ ID NO:18, b is an integer of 15 to 1305, where both a and b correspond to the positions of nucleotide residues shown in SEQ ID NO:18, and where b is greater than or equal to a+14.

Features of Protein Encoded by Gene No: 9

In specific embodiments, polypeptides of the invention comprise the following amino acid sequence: TDSYGIIL- CVXLCLLLLFNILWFICVACSII- ITVAYFICSTVGGHYCCFQFLAI- INNDAKSVLDYLSWYVCARTNNIYLGMESLGHREYT (SEQ ID NO:175). Polynucleotides encoding these polypeptides are also encompassed by the invention.

This gene is expressed primarily in T-cell lymphoma, ovarian cancer tissues, lymphocytic leukemia, and embryonic tissues.

Therefore, polynucleotides and polypeptides of the invention are useful as reagents for differential identification of the tissue(s) or cell type(s) present in a biological sample and for diagnosis of diseases and conditions which include, but are not limited to, immune, developmental, or hematopoietic disorders, particularly T-cell lymphoma or other disorders characterized by proliferating tissues or cells. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., blood cells, rapidly proliferating tissues, immune, hematopoietic, developing, or cancerous and wounded tissues) or bodily fluids (e.g., lymph, amniotic fluid, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in cancerous tissues of such origins as the immune system and ovaries indicates that polynucleotides and polypeptides corresponding to this gene are useful for the diagnosis and/or treatment of a variety of immune system disorders and cancers, as well as cancers of other tissues where expression has been observed. Expression within embryonic tissue and other cellular sources marked by proliferating cells indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus this protein may also be involved in apoptosis or tissue differentiation and could again be useful in cancer therapy.

Alternatively, expression of this gene product in T-cell lymphoma indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:19 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1046 of SEQ ID NO:19, b is an integer of 15 to 1060, where both a and b correspond to the positions of nucleotide residues shown in SEQ ID NO:19, and where b is greater than or equal to a+14.

Features of Protein Encoded by Gene No: 10

This gene is expressed primarily in adipose tissue, and to a lesser extent in other human tissues.

Therefore, polynucleotides and polypeptides of the invention are useful as reagents for differential identification of the tissue(s) or cell type(s) present in a biological sample and for diagnosis of diseases and conditions which include, but are not limited to, metabolic disorders, particularly those involving anomalous lipid metabolism. Similarly, polypeptides and antibodies directed to these polypeptides are useful in providing immunological probes for differential identification of the tissue(s) or cell type(s). For a number of disorders of the above tissues or cells, particularly of adipose tissue or metabolic tissues, expression of this gene at significantly higher or lower levels may be routinely detected in certain tissues or cell types (e.g., adipose, metabolic, or cancerous and wounded tissues) or bodily fluids (e.g. bile, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:96 as residues: Tyr-25 to Thr-32.

The tissue distribution in adipose tissue indicates that polynucleotides and polypeptides corresponding to this gene are useful for the diagnosis, prevention, and/or treatment of various metabolic disorders such as Tay-Sachs disease, phenylkenonuria, galactosemia, hyperlipidemias, porphyrias, and Hurler's syndrome, as well as for the treatment of obesity and other metabolic and endocrine conditions or disorders. Furthermore, the protein product of this gene may show utility in ameliorating conditions which occur secondary to aberrant fatty-acid metabolism (e.g. aberrant myelin sheath development), either directly or indirectly. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:20 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1156 of SEQ ID NO:20, b is an integer of 15 to 1170, where both a and b correspond to the positions of nucleotide residues shown in SEQ ID NO:20, and where b is greater than or equal to a+14.

Features of Protein Encoded by Gene No: 11

In specific embodiments, polypeptides of the invention comprise the following amino acid sequence: HEELCRYLAESWLTFQIHLQELLQYKRQN-PAQFCVRVCSGCAVLAVLGHYVPGI (SEQ ID NO:176). Polynucleotides encoding these polypeptides are also encompassed by the invention. The gene encoding the disclosed cDNA is thought to reside on chromosome 2. Accordingly, polynucleotides related to this invention are useful as a marker in linkage analysis for chromosome 2.

This gene is expressed primarily in infant brain and adult cerebellum tissue, and to a lesser extent in human nine week old early stage tissue.

Therefore, polynucleotides and polypeptides of the invention are useful as reagents for differential identification of the tissue(s) or cell type(s) present in a biological sample and for diagnosis of diseases and conditions which include, but are not limited to, neural, neurodegenerative or developmental disorders. Similarly, polypeptides and antibodies directed to these polypeptides are useful in providing immunological probes for differential identification of the tissue(s) or cell type(s). For a number of disorders of the above tissues or cells, particularly of the central nervous or reproductive system, expression of this gene at significantly higher or lower levels may be routinely detected in certain tissues or cell types (e.g., brain, developing, neural, or cancerous and wounded tissues) or bodily fluids (e.g., lymph, amniotic fluid, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:97 as residues: Lys-50 to Asp-66, Pro-68 to Glu-77, Glu-102 to Glu-107, Glu-131 to Leu-146, Ala-175 to Glu-183, Phe-205 to Lys-216, Val-263 to Thr-281, Pro-304 to Ala-313. chemotactic and chemokinetic activities (e.g. for treating infections, tumors); hemostatic or thrombolytic activity (e.g. for treating haemophilia, cardiac infarction etc.); anti-inflammatory activity (e.g. for treating septic shock, Crohn's disease); as antimicrobials; for treating psoriasis or other hyperproliferative diseases; for regulation of metabolism, and behaviour. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:11 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 378 of SEQ ID NO:11, b is an integer of 15 to 392, where both a and b correspond to the positions of nucleotide residues shown in SEQ ID NO :11, and where b is greater than or equal to a+14.

Features of Protein Encoded by Gene No: 2

The translation product of this gene shares sequence homology with human histiocyte-secreted factor HSF, a tumor necrosis factor-related protein, which is thought to be important for its potential anti-tumor activity. When tested against K562 cell lines, supernatants removed from cells containing this gene activated the ISRE (interferon-sensitive responsive element ) pathway. Thus, it is likely that this gene activates leukemia cells through the Jaks-STAT signal transduction pathway. ISRE is a promoter element found upstream in many genes which are involved in the Jaks-STAT pathway.

The Jaks-STAT pathway is a large, signal transduction pathway involved in the differentiation and proliferation of cells. Therefore, activation of the Jaks-STATs pathway, reflected by the binding of the ISRE element, can be used to indicate The tissue distribution in infant brain and adult cerebellum tissues indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:21 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2070 of SEQ ID NO:21, b is an integer of 15 to 2084, where both a and b correspond to the positions of nucleotide residues shown in SEQ ID NO:21, and where b is greater than or equal to a+14.

Features of Protein Encoded by Gene No: 12

In specific embodiments, polypeptides of the invention comprise the following amino acid sequence: CFH-KELLTSRNGRPRHTSKQTFQKHLQXTQD (SEQ ID NO:177), and/or NFTDDGKMTKDEGSLLK-SQLSSKHEGQKXHGSRLGMTIQ QFPGDCIVQVIY (SEQ ID NO:178). Polynucleotides encoding these polypeptides are also encompassed by the invention.

This gene is expressed primarily in atrophic endometrium tissue.

Therefore, polynucleotides and polypeptides of the invention are useful as reagents for differential identification of the tissue(s) or cell type(s) present in a biological sample and for diagnosis of diseases and conditions which include, but are not limited to, atrophic endometriosis, or other disorders of the female reproductive system. Similarly, polypeptides and antibodies directed to these polypeptides are useful in providing immunological probes for differential identification of the tissue(s) or cell type(s). For a number of disorders of the above tissues or cells, particularly of the female reproductive system, expression of this gene at significantly higher or lower levels may be routinely detected in certain tissues or cell types (e.g., reproductive, uterine. or cancerous and wounded tissues) or bodily fluids (e.g., lymph, amniotic fluid, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in atrophic endometrial tissues indicates that polynucleotides and polypeptides corresponding to this gene are useful for diagnosis and/or treatment of atrophic endometriosis and related uterine disorders. Furthermore, the tissue distribution indicates that polynucleotides and polypeptides corresponding to this gene are useful for treating female infertility. The protein product is likely involved in preparation of the endometrium of implantation and could be administered either topically or orally. Alternatively, this gene could be transfected in gene-replacement treatments into the cells of the endometrium and the protein products could be produced. Similarly, these treatments could be performed during artificial insemination for the purpose of increasing the likelihood of implantation and development of a healthy embryo. In both cases this gene or its gene product could be administered at later stages of pregnancy to promote heathy development of the endometrium. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:22 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 629 of SEQ ID NO:22, b is an integer of 15 to 643, where both a and b correspond to the positions of nucleotide residues shown in SEQ ID NO:22, and where b is greater than or equal to a+14.

Features of Protein Encoded by Gene No: 13

In specific embodiments, polypeptides of the invention comprise the following amino acid sequence: LCAALIS-PLWKCSPPSPPTSGPGTRRAAGT (SEQ ID NO:179), and/or SRALILVADSAKETNKMILAWTRTLNLR-RVSLNHSNHYLK GHGAQNKV (SEQ ID NO:180). Polynucleotides encoding these polypeptides are also encompassed by the invention. The gene encoding the disclosed cDNA is thought to reside on chromosome 2. Accordingly, polynucleotides related to this invention are useful as a marker in linkage analysis for chromosome 2.

This gene is expressed primarily in fetal tissues, such as fetal lung tissue.

Therefore, polynucleotides and polypeptides of the invention are useful as reagents for differential identification of the tissue(s) or cell type(s) present in a biological sample and for diagnosis of diseases and conditions which include, but are not limited to, developmental abnormalities, or disorders characterized by proliferating tissues, as well as pulmonary disorders. Similarly, polypeptides and antibodies directed to these polypeptides are useful in providing immunological probes for differential identification of the tissue(s) or cell type(s). For a number of disorders of the above tissues or cells, particularly of the reproductive system, lungs, and developing tissues, expression of this gene at significantly higher or lower levels may be routinely detected in certain tissues or cell types (e.g., developing, proliferating, lungs, or cancerous and wounded tissues) or bodily fluids (e.g. amniotic fluid, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:99 as residues: Gly-26 to Arg-37.

Expression within embryonic tissue and other cellular sources marked by proliferating cells indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus this protein may also be involved in apoptosis or tissue differentiation and could again be useful in cancer therapy.

Furthermore, the tissue distribution indicates that polynucleotides and polypeptides corresponding to this gene are useful for the detection and treatment of disorders associated with developing lungs, particularly in premature infants where the lungs are the last tissues to develop. The tissue distribution indicates that polynucleotides and polypeptides corresponding to this gene are useful for the diagnosis and intervention of lung tumors, since the gene may be involved in the regulation of cell division, particularly since it is expressed in fetal tissue. Protein, as well as, antibodies directed against the protein may show utility as a tumor marker and immunotherapy targets for the above listed tumors and tissues. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:23 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 633 of SEQ ID NO:23, b is an integer of 15 to 647, where both a and b correspond to the positions of nucleotide residues shown in SEQ ID NO:23, and where b is greater than or equal to a+14.

Features of Protein Encoded by Gene No: 14

The gene encoding the disclosed cDNA is believed to reside on chromosome 19. Accordingly, polynucleotides related to this invention are useful as a marker in linkage analysis for chromosome 19.

This gene is expressed primarily in epididymus tissue.

Therefore, polynucleotides and polypeptides of the invention are useful as reagents for differential identification of the tissue(s) or cell type(s) present in a biological sample and for diagnosis of diseases and conditions which include, but are not limited to, male infertility and reproductive disorders. Similarly, polypeptides and antibodies directed to these polypeptides are useful in providing immunological probes for differential identification of the tissue(s) or cell type(s). For a number of disorders of the above tissues or cells, particularly of the male reproductive system, expression of this gene at significantly higher or lower levels may be routinely detected in certain tissues or cell types (e.g., epididymus, reproductive, or cancerous and wounded tissues) or bodily fluids (e.g.seminal fluid, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in epididymus tissue indicates that polynucleotides and polypeptides corresponding to this gene are useful for the treatment of male infertility, possibly related to low sperm motility. Similarly, expression of this gene product in the epididymus may implicate this gene product in playing a vital role in maintaining normal testicular function. As such, this gene product may find utility as a male contraceptive. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:24 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 811 of SEQ ID NO:24, b is an integer of 15 to 825, where both a and b correspond to the positions of nucleotide residues shown in SEQ ID NO:24, and where b is greater than or equal to a+14.

Features of Protein Encoded by Gene No: 15

In specific embodiments, polypeptides of the invention comprise the following amino acid sequence: QWEFLYSQSLLSVALILFCVSFQGSDLDSYLSCSPKRGC (SEQ ID NO:181). Polynucleotides encoding these polypeptides are also encompassed by the invention.

This gene is expressed primarily in IL5-induced eosinophils.

Therefore, polynucleotides and polypeptides of the invention are useful as reagents for differential identification of the tissue(s) or cell type(s) present in a biological sample and for diagnosis of diseases and conditions which include, but are not limited to, acute inflammation, or other immune disorders such as asthma. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., inflamed, blood cells, immune, hematopoietic, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in eosinophils indicates that polynucleotides and polypeptides corresponding to this gene are useful for the diagnosis and/or treatment of a variety of immune system disorders. Expression of this gene product in eosinophils indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, sepsis, acne, and psoriasis, asthma, and inflammatory disorders, such as inflammatory bowel disease. In addition, this gene product may have commercial utility in the expansion of stem cells and committed progenitors of various blood lineages, and in the differentiation and/or proliferation of various cell types. Furthermore, expression of this gene product in eosinophils also strongly indicates a role for this protein in immune function and immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:25 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 527 of SEQ ID NO:25, b is an integer of 15 to 541, where both a and b correspond to the positions of nucleotide residues shown in SEQ ID NO:25, and where b is greater than or equal to a+14.

Features of Protein Encoded by Gene No: 16

The gene encoding the disclosed cDNA is thought to reside on chromosome 8. Accordingly, polynucleotides related to this invention are useful as a marker in linkage analysis for chromosome 8.

This gene is expressed primarily in induced endothelial cells, as well as a number of vascular tissues such as fetal heart tissue, smooth muscle tissue, synovial fibroblasts, and microvascular endothelial cells.

Therefore, polynucleotides and polypeptides of the invention are useful as reagents for differential identification of the tissue(s) or cell type(s) present in a biological sample and for diagnosis of diseases and conditions which include, but are not limited to, arteriosclerosis, or other vasculature disorders, particularly microvascular disease and stroke. Similarly, polypeptides and antibodies directed to these polypeptides are useful in providing immunological probes for differential identification of the tissue(s) or cell type(s). For a number of disorders of the above tissues or cells, particularly of the circulatory system, expression of this gene at significantly higher or lower levels may be routinely detected in certain tissues or cell types (e.g., cardiovascular, vascular, or cancerous and wounded tissues) or bodily fluids (e.g. serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:102 as residues: Ser-33 to Arg-48, Gln-64 to Val-71, Pro-121 to Thr-132, Gln-167 to Lys-181.

The tissue distribution in vascular tissues indicates that polynucleotides and polypeptides corresponding to this gene are useful for the treatment of endothelial inflammation or occlusion due to arteriosclerosis. Similarly, the protein product of this gene may also show utility in the detection, treatment, or prevention of stroke, aneurysms, or other vascular disorders. The tissue distribution in smooth muscle, fetal heart, and microvascular endothelial cell tissue indicates that the protein product of this gene is useful for the diagnosis and treatment of conditions and pathologies of the cardiovascular system, such as heart disease, restenosis, atherosclerosis, angina, thrombosis, and wound healing. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:26 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 838 of SEQ ID NO:26, b is an integer of 15 to 852, where both a and b correspond to the positions of nucleotide residues shown in SEQ ID NO:26, and where b is greater than or equal to a+14.

Features of Protein Encoded by Gene No: 17

In specific embodiments, polypeptides of the invention comprise the following amino acid sequence: NYRNSN-LKKTLKETKKYSTILSALLTFSIVSCDLCLVLC SIDDE-HLI (SEQ ID NO:182). Polynucleotides encoding these polypeptides are also encompassed by the invention.

This gene is expressed primarily in ovarian cancer, and to a lesser extent in infant brain tissue, 12 Week old early stage embryonic tissue, and synovial hypoxia.

Therefore, polynucleotides and polypeptides of the invention are useful as reagents for differential identification of the tissue(s) or cell type(s) present in a biological sample and for diagnosis of diseases and conditions which include, but are not limited to, developmental or proliferative disorders, particularly ovarian cancer. Similarly, polypeptides and antibodies directed to these polypeptides are useful in providing immunological probes for differential identification of the tissue(s) or cell type(s). For a number of disorders of the above tissues or cells, particularly of the reproductive or neural systems, expression of this gene at significantly higher or lower levels may be routinely detected in certain tissues or cell types (e.g., neural, developmental, skeletal, or cancerous and wounded tissues) or bodily fluids (e.g., lymph, amniotic fluid, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:103 as residues: Ser-7 to Gly-17.

The tissue distribution within embryonic tissue and other cellular sources marked by proliferating cells indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus this protein may also be involved in apoptosis or tissue differentiation and could again be useful in cancer therapy. The tissue distribution of the translation product of this gene in ovarian cancer tissues indicates that the translation product of this gene is useful for the detection and/or treatment of ovarian cancer, as well as cancers of other tissues where expression has been observed.

Alternatively, expression within infant brain tissue indicates that the protein product of this gene is useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:27 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 4584 of SEQ ID NO:27, b is an integer of 15 to 4598, where both a and b correspond to the positions of nucleotide residues shown in SEQ ID NO:27, and where b is greater than or equal to a+14.

Features of Protein Encoded by Gene No: 18

When tested against PC12sensory neuron cell lines, supernatants removed from cells containing this gene activated the EGR1 (early growth response gene 1) pathway. Thus, it is likely that this gene activates sensory neuron cells, and to a lesser extent other neuronal cells, through the EGR1 signal transduction pathway. EGR1 is a separate signal transduction pathway from Jaks-STAT, genes containing the EGR1 promoter are induced in various tissues and cell types upon activation, leading the cells to undergo differentiation and proliferation. In specific embodiments, polypeptides of the invention comprise the following amino acid sequence: NSARGEVAFLIKKKKS SSIVYGKFFQATIPS (SEQ ID NO:183). Polynucleotides encoding these polypeptides are also encompassed by the invention.

This gene is expressed primarily in fetal brain tissue.

Therefore, polynucleotides and polypeptides of the invention are useful as reagents for differential identification of the tissue(s) or cell type(s) present in a biological sample and for diagnosis of diseases and conditions which include, but are not limited to, degenerative neural disorders or developmental disorders, particularly proliferative abnormalities. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., brain, neural, developing, or cancerous and wounded tissues) or bodily fluids (e.g. lymph, amniotic fluid, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:104 as residues: Val-16 to Asn-24.

The tissue distribution in infant brain tissue, combined with the detected biological EGR1 activity in sensory neuron cells, indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:28 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 571 of SEQ ID NO:28, b is an integer of 15 to 585, where both a and b correspond to the positions of nucleotide residues shown in SEQ ID NO:28, and where b is greater than or equal to a+14.

Features of Protein Encoded by Gene No: 19

The translation product of this gene was shown to have homology to the human zinc finger 91 which is thought to important in the regulation of gene expression (See Genbank Accession No. Q05481). The gene encoding the disclosed cDNA is believed to reside on chromosome 19. Accordingly, polynucleotides related to this invention are useful as a marker in linkage analysis for chromosome 19.

This gene is expressed primarily in uterine cancer tissue, and to a lesser extent in melanocytes.

Therefore, polynucleotides and polypeptides of the invention are useful as reagents for differential identification of the tissue(s) or cell type(s) present in a biological sample and for diagnosis of diseases and conditions which include, but are not limited to, reproductive disorders, particularly uterine cancer. Similarly, polypeptides and antibodies directed to these polypeptides are useful in providing immunological probes for differential identification of the tissue(s) or cell type(s). For a number of disorders of the above tissues or cells, particularly of the reproductive or integumentary system, expression of this gene at significantly higher or lower levels may be routinely detected in certain tissues or cell types (e.g., reproductive, epithelial, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in tumors of uterine origins indicates that polynucleotides and polypeptides corresponding to this gene are useful for the diagnosis and/or intervention of these tumors, in addition to other tumors where expression has been indicated. Alternatively, considering the expression within melanocytes, it is suggested that polynucleotides and polypeptides corresponding to this gene are useful for the treatment, diagnosis, and/or prevention of various skin disorders including congenital disorders (i.e. nevi, moles, freckles, Mongolian spots, hemangiomas, port-wine syndrome), integumentary tumors (i.e. keratoses, Bowen's disease, basal cell carcinoma, squamous cell carcinoma, malignant melanoma, Paget's disease, mycosis fungoides, and Kaposi's sarcoma), injuries and inflammation of the skin (i.e.wounds, rashes, prickly heat disorder, psoriasis, dermatitis), atherosclerosis, uticaria, eczema, photosensitivity, autoimmune disorders (i.e. lupus erythematosus, vitiligo, dermatomyositis, morphea, scleroderma, pemphigoid, and pemphigus), keloids, striae, erythema, petechiae, purpura, and xanthelasma.

Moreover, such disorders may predispose increased susceptibility to viral and bacterial infections of the skin (i.e. cold sores, warts, chickenpox, molluscum contagiosum, herpes zoster, boils, cellulitis, erysipelas, impetigo, tinea, althletes foot, and ringworm). Protein, as well as, antibodies directed against the protein may show utility as a tissue-specific marker and/or immunotherapy target for the above listed tissues.

Many polynucleotide sequences, such as EST sequences, are publicly available and accessible through sequence databases. Some of these sequences are related to SEQ ID NO:29 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 810 of SEQ ID NO:29, b is an integer of 15 to 824, where both a and b correspond to the positions of nucleotide residues shown in SEQ ID NO:29, and where b is greater than or equal to a+14.

Features of Protein Encoded by Gene No: 20

The translation product of this gene was shown to have homology to the human RAMP2 protein which is thought to be important in calcitonin regulation (See Genbank Accession No. gnl|PID|e1295011 (AJ00105)). In specific embodiments, polypeptides of the invention comprise the following amino acid sequence: RAGGPRLPRTRVG RPAALR-LLLLLGAVLNPHEALAQXLPTTGTPG-SEGGTVKNXETAVQFCWNH YKDQM DPIEKDWCD-WAMISRPYSTLRDCLEHFAELFDLGFPNPLAERIIFETHQI HFANCSLVQPTFSDPPEDVL LA (SEQ ID NO:184), CWNHYKDQMDPIEKDW CDWAMISRPYSTLRDCLE-HFAELFDLGFPNPLAERIIFETHQIH (SEQ ID NO:185), FANCSLVQPTFSDPPEDVLLAMIIAPI-CLIPFLITLVVWRSKDSEAQA (SEQ ID NO:186), RAG-GPRLPRT (SEQ ID NO:187), and/or NPHEALAQ (SEQ ID NO:188). Polynucleotides encoding these polypeptides are also encompassed by the invention.

This gene is expressed primarily in fetal kidney and spleen tissue, and to a lesser extent in chronic synovitis and lung tissues.

Therefore, polynucleotides and polypeptides of the invention are useful as reagents for differential identification of the tissue(s) or cell type(s) present in a biological sample and for diagnosis of diseases and conditions which include, but are not limited to, kidney, endocrine, urogenital, pulmonary, or hematopoietic disorders. Similarly, polypeptides and antibodies directed to these polypeptides are useful in providing immunological probes for differential identification of the tissue(s) or cell type(s). For a number of disorders of the above tissues or cells, particularly of the endocrine, pulmonary, renal, urogenital or haemopoietic system, expression of this gene at significantly higher or lower levels may be routinely detected in certain tissues or cell types (e.g., lungs, kidney, endocrine, urogenital, skeletal, cardiovascular, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:106 as residues: Arg-13 to Gly-20, Trp-69 to Asp-85, Thr-137 to Glu-143, Arg-167 to Gln-174.

The tissue distribution in kidney tissue indicates that this gene or gene product could be used in the treatment and/or detection of kidney diseases including renal failure, nephritus, renal tubular acidosis, proteinuria, pyuria, edema, pyelonephritis, hydronephritis, nephrotic syndrome, crush syndrome, glomerulonephritis, hematuria, renal colic and kidney stones, in addition to Wilms Tumor Disease, and congenital kidney abnormalities such as horseshoe kidney, polycystic kidney, and Falconi's syndrome.

Similarly, considering the homology to the RAMP2 protein, it is suggested that polynucleotides and polypeptides corresponding to this gene are useful for the detection, treatment, and/or prevention of various endocrine disorders and cancers, particularly Addison's disease, Cushing's Syndrome, and disorders and/or cancers of the pancrease (e.g. diabetes mellitus), adrenal cortex, ovaries, pituitary (e.g., hyper-, hypopituitarism), thyroid (e.g. hyper-, hypothyroidism), parathyroid (e.g. hyper-, hypoparathyroidism), hypothallamus, and testes.

Furthermore, the tissue distribution in fetal lung tissue indicates that polynucleotides and polypeptides corresponding to this gene are useful for the detection and treatment of disorders associated with developing lungs, particularly in premature infants where the lungs are the last tissues to develop. The tissue distribution indicates that polynucleotides and polypeptides corresponding to this gene are useful for the diagnosis and intervention of lung tumors, since the gene may be involved in the regulation of cell division, particularly since it is expressed in fetal tissue. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:30 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 737 of SEQ ID NO:30, b is an integer of 15 to 751, where both a and b correspond to the positions of nucleotide residues shown in SEQ ID NO:30, and where b is greater than or equal to a+14.

Features of Protein Encoded by Gene No: 21

In specific embodiments, polypeptides of the invention comprise the following amino acid sequence: ARGRLFSFLYQSSPDQVIDVAPELLRICSLILAET-IQGLGAASAQFVSRLLPVLLSTAQEADPEVRSNAIFG (SEQ ID NO:189), Polynucleotides encoding these polypeptides are also encompassed by the invention. The gene encoding the disclosed cDNA is thought to reside on chromosome 14. Accordingly, polynucleotides related to this invention are useful as a marker in linkage analysis for chromosome 14. The translation product of this gene shares sequence homology with human karyopherin beta 3 (See Genbank Accession No.: gi|2102696).

This gene is expressed primarily in infant brain and testes tissues.

Therefore, polynucleotides and polypeptides of the invention are useful as reagents for differential identification of the tissue(s) or cell type(s) present in a biological sample and for diagnosis of diseases and conditions which include, but are not limited to, neurodegenerative and reproductive disorders. Similarly, polypeptides and antibodies directed to these polypeptides are useful in providing immunological probes for differential identification of the tissue(s) or cell type(s). For a number of disorders of the above tissues or cells, particularly of the central nervous system and male reproductive system, expression of this gene at significantly higher or lower levels may be routinely detected in certain tissues or cell types (e.g., reproductive, testes, brain, neural, developing, or cancerous and wounded tissues) or bodily fluids (e.g. lymph, amniotic fluid, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:107 as residues: Arg-29 to Ile-39, Pro-51 to Pro-57.

The tissue distribution in brain tissue indicates that polynucleotides and polypeptides corresponding to this gene are useful for the detection and/or treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system.

Alternatively, the tissue distribution in testes tissue indicates that polynucleotides and polypeptides corresponding to this gene are useful for the treatment and diagnosis of conditions concerning proper testicular function (e.g. endocrine function, sperm maturation), as well as cancer. Therefore, this gene product is useful in the treatment of male infertility and/or impotence. This gene product is also useful in assays designed to identify binding agents, as such agents (antagonists) are useful as male contraceptive agents. Similarly, the protein is believed to be useful in the treatment and/or diagnosis of testicular cancer. The testes are also a site of active gene expression of transcripts that may be expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:31 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 803 of SEQ ID NO:31, b is an integer of 15 to 817, where both a and b correspond to the positions of nucleotide residues shown in SEQ ID NO:31, and where b is greater than or equal to a+14.

Features of Protein Encoded by Gene No: 22

The gene encoding the disclosed cDNA is believed to reside on chromosome 12. Accordingly, polynucleotides related to this invention are useful as a marker in linkage analysis for chromosome 12.

This gene is expressed primarily in infant and adult brain tissues.

Therefore, polynucleotides and polypeptides of the invention are useful as reagents for differential identification of the tissue(s) or cell type(s) present in a biological sample and for diagnosis of diseases and conditions which include, but are not limited to, neurodegenerative or developmental disorders. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., brain, neural, developing, proliferative, or cancerous and wounded tissues) or bodily fluids (e.g., lymph, amniotic fluid, lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:108 as residues: Arg-13 to Glu-22, Ser-34 to Phe-44, Ser-46 to Thr-52.

The tissue distribution in brain tissues indicates that polynucleotides and polypeptides corresponding to this gene are useful for the detection and/or treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:32 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1341 of SEQ ID NO:32, b is an integer of 15 to 1355, where both a and b correspond to the positions of nucleotide residues shown in SEQ ID NO:32, and where b is greater than or equal to a+14.

Features of Protein Encoded by Gene No: 23

In specific embodiments, polypeptides of the invention comprise the following amino acid sequence: RGLPSTLI-CLVESFGSKWAPLWEGGRTHHWGPRHHWH VAS-CVSLFSCCK (SEQ ID NO:190), Polynucleotides encoding these polypeptides are also encompassed by the invention.

This gene is expressed primarily in fetal dura mater.

Therefore, polynucleotides and polypeptides of the invention are useful as reagents for differential identification of the tissue(s) or cell type(s) present in a biological sample and for diagnosis of diseases and conditions which include, but are not limited to, neurodegenerative disorders, particularly spina bifita. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., neural, developmental, proliferative, or cancerous and wounded tissues) or bodily fluids (e.g., lymph, amniotic fluid, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:109 as residues: Lys-15 to His-21.

The tissue distribution in fetal dura mater tissue indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, spina bifita, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:33 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 522 of SEQ ID NO:33, b is an integer of 15 to 536, where both a and b correspond to the positions of nucleotide residues shown in SEQ ID NO:33, and where b is greater than or equal to a+14.

Features of Protein Encoded by Gene No: 24

The gene encoding the disclosed cDNA is believed to reside on chromosome 3. Accordingly, polynucleotides related to this invention are useful as a marker in linkage analysis for chromosome 3.

This gene is expressed primarily in fetal liver and spleen tissues, and to a lesser extent in ovary and glioblastoma tissue.

Therefore, polynucleotides and polypeptides of the invention are useful as reagents for differential identification of the tissue(s) or cell type(s) present in a biological sample and for diagnosis of diseases and conditions which include, but are not limited to, hepatic, immune, or hematopoietic disorders. Similarly, polypeptides and antibodies directed to these polypeptides are useful in providing immunological probes for differential identification of the tissue(s) or cell type(s). For a number of disorders of the above tissues or cells, particularly of the hematopoietic or hepatic system, expression of this gene at significantly higher or lower levels may be routinely detected in certain tissues or cell types (e.g., hepatic, blood cells, immune, hematopoietic, or cancerous and wounded tissues) or bodily fluids (e.g., lymph, bile, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in fetal liver tissue indicates that polynucleotides and polypeptides corresponding to this gene are useful for the detection and/or treatment of liver disorders and cancers (e.g. hepatoblastoma, jaundice, hepatitis, liver metabolic diseases and conditions that are attributable to the differentiation of hepatocyte progenitor cells). In addition, the expression in fetus would suggest a useful role for the protein product in developmental abnormalities, fetal deficiencies, pre-natal disorders and various would-healing models and/or tissue trauma.

Alternatively, expression within spleen tissue indicates that the protein product of this gene is useful for the diagnosis and treatment of a variety of immune system disorders. Expression of this gene product in fetal liver/spleen tissue indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:34 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1109 of SEQ ID NO:34, b is an integer of 15 to 1123, where both a and b correspond to the positions of nucleotide residues shown in SEQ ID NO:34, and where b is greater than or equal to a+14.

Features of Protein Encoded by Gene No: 25

This gene is expressed primarily in brain frontal cortex tissue.

Therefore, polynucleotides and polypeptides of the invention are useful as reagents for differential identification of the tissue(s) or cell type(s) present in a biological sample and for diagnosis of diseases and conditions which include, but are not limited to, neurodegenerative disorders, particularly those afflicting the frontal cortex. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cells (e.g., brain, neural, cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:111 as residues: Ser-5 to Thr-11, Tyr-90 to Arg-96.

The tissue distribution in frontal cortex tissue indicates that the protein product of this gene is useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception.

Moreover, elevated expression of this gene product within the frontal cortex of the brain indicates that it may be involved in neuronal survival; synapse formation; conductance; neural differentiation, etc. Such involvement may impact many processes, such as learning and cognition. It may also be useful in the treatment of such neurodegenerative disorders as schizophrenia; ALS; or Alzheimer's. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:35 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 573 of SEQ ID NO:35, b is an integer of 15 to 587, where both a and b correspond to the positions of nucleotide residues shown in SEQ ID NO:35, and where b is greater than or equal to a+14.

Features of Protein Encoded by Gene No: 26

This gene is expressed primarily in brain frontal cortex tissue.

Therefore, polynucleotides and polypeptides of the invention are useful as reagents for differential identification of the tissue(s) or cell type(s) present in a biological sample and for diagnosis of diseases and conditions which include, but are not limited to, neurodegenerative disorders, particularly of the frontal cortex. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cells (e.g., brain, neural, cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in frontal cortex tissue indicates that polynucleotides and polypeptides corresponding to this gene are useful for the detection and/or treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception.

Moreover, elevated expression of this gene product within the frontal cortex of the brain indicates that it may be involved in neuronal survival; synapse formation; conductance; neural differentiation, etc. Such involvement may impact many processes, such as learning and cognition. It may also be useful in the treatment of such neurodegenerative disorders as schizophrenia; ALS; or Alzheimer's. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:36 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 828 of SEQ ID NO:36, b is an integer of 15 to 842, where both a and b correspond to the positions of nucleotide residues shown in SEQ ID NO:36, and where b is greater than or equal to a+14.

Features of Protein Encoded by Gene No: 27

In specific embodiments, polypeptides of the invention comprise the following amino acid sequence: GILICN-FFFSVELAIVRFWCI (SEQ ID NO:191). Polynucleotides encoding these polypeptides are also encompassed by the invention.

This gene is expressed primarily in brain frontal cortex tissue, and to a lesser extent in the epididymus.

Therefore, polynucleotides and polypeptides of the invention are useful as reagents for differential identification of the tissue(s) or cell type(s) present in a biological sample and for diagnosis of diseases and conditions which include, but are not limited to, neurodegenerative disorders, particularly of the frontal cortex, or reproductive disorders. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cells (e.g., brain, neural, urogenital, reproductive, or cancerous and wounded tissues) or bodily fluids (e.g. lymph, seminal fluid, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in frontal cortex tissue indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception.

Moreover, elevated expression of this gene product within the frontal cortex of the brain indicates that it may be involved in neuronal survival; synapse formation; conductance; neural differentiation, etc. Such involvement may impact many processes, such as learning and cognition. It may also be useful in the treatment of such neurodegenerative disorders as schizophrenia; ALS; or Alzheimer's. In addition, the gene or gene product may also play a role in the treatment and/or detection of developmental disorders associated with the developing embryo, sexually-linked disorders, or disorders of the cardiovascular system. Alternatively, the expression within the epididymus may suggest that the protein product of this gene is useful for the detection, treatment, and/or prevention of various reproductive disorders, particularly male infertility. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:37 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 939 of SEQ ID NO:37, b is an integer of 15 to 953, where both a and b correspond to the positions of nucleotide residues shown in SEQ ID NO:37, and where b is greater than or equal to a+14.

Features of Protein Encoded by Gene No: 28

The translation product of this gene shares sequence homology with the human placental DIFF33-LIKE protein, in addition to the Diff33 gene product (See Genbank Accession Nos. gnl|PID|e1310269 dJ425C14.2 and gi|1293563, respectively). Both of these proteins are thought to be important in the regulation of cell-cycle control and growth within reproductive tissues and cells. In specific embodiments, polypeptides of the invention comprise the following amino acid sequence: AQERSCLHLVCIRCSCD VVEMGSVLGLCSMASWIPCLCGSAP-CLLCRCCPSGNNSTVTRLIYALFLLVGV CVACVM-LIPGMEEQLNKIPGFCENEKGVVPCNIL-VGYKAVYRLCFGLA (SEQ ID NO:192), IPCLCGSAPCLLCRCCPSGNNSTVTR-LIYALFLLVGVCVACVM LIPGMEEQLNKIPG-FCENEKGVVPCNILVGY (SEQ ID NO:193), ARS-DGSLEDG DDVHRAVDNERDGVTYSYSFFHFM-LFLASLYIMMTLTNWYRYEPSREMKSQ WTAVWVKISS SWIGIVLYVWTLVAPLVLTNRDFD (SEQ ID NO:194), NEKGVVP CNILVGYKAVYRLCF-GLAMFY (SEQ ID NO:195), MIKVKSSSDPRAAVH-NGFW (SEQ ID NO:196), GMAGAFCFILIQLVLLIDFAH (SEQ ID NO:197), YAALLSAT ALNYLLSLVAIVLFFV (SEQ ID NO:198), PSLLSIIGYNTTSTVPKEGQS (SEQ ID NO:199), YSSIRTSNNSQVNKLTLTSDES (SEQ ID NO:200), DNERDGVTYSYS FFHFMLFL (SEQ ID NO:201), and/or IVLYVWTLVAPLVLTNRD (SEQ ID NO:202). Polynucleotides encoding these polypeptides are also encompassed by the invention. The gene encoding the disclosed cDNA is believed to reside on chromosome 6. Accordingly, polynucleotides related to this invention are useful as a marker in linkage analysis for chromosome 6.

This gene is expressed primarily in thymus stromal cells, and to a lesser extent in human T-cell lymphoma.

Therefore, polynucleotides and polypeptides of the invention are useful as reagents for differential identification of the tissue(s) or cell type(s) present in a biological sample and for diagnosis of diseases and conditions which include, but are not limited to, reproductive disorders, particularly those involving proliferative cells, such as cancer and tumor growth. Similarly, polypeptides and antibodies directed to these polypeptides are useful in providing immunological probes for differential identification of the tissue(s) or cell type(s). For a number of disorders of the above tissues or cells, particularly of the immune system and tumor growth in various tissues, expression of this gene at significantly higher or lower levels may be routinely detected in certain tissues or cells (e.g., reproductive, immune, cancerous and wounded tissues) or bodily fluids (e.g., lymph, seminal fluid, amniotic fluid, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:114 as residues: Lys-87 to Cys-95, Ala-126 to Asn-131, Ile-154 to Gly-162, Thr-182 to Asn-190, Ser-203 to Gln-210, Ser-234 to Asn-244, Gly-259 to Ser-266, Asp-278 to Val-284, Glu-313 to Gln-321.

The tissue distribution in rapidly proliferating tissues, and the homology to the Diff33 gene product, indicates that polynucleotides and polypeptides corresponding to this gene are useful for identifying and/or designing drugs targeted against tumors where unregulated growth is due, in part, to the overexpression of this gene product. The Diff33 gene product is 2–15 fold overexpressed in testicular tumors from polyomavirus large T-antigen transgenic mice, and thus may play a regulatory role in cell growth. Due to its strong homology to Diff33, this gene may have a similar regulatory role, not only in testicular or placental cancers, but within reproductive tissues, in general.

The secreted protein can also be used to determine biological activity, to raise antibodies, as tissue markers, to isolate cognate ligands or receptors, to identify agents that modulate their interactions and as nutritional supplements. It may also have a very wide range of biological acitivities. Typical of these are cytokine, cell proliferation/differentiation modulating activity or induction of other cytokines; immunostimulating/immunosuppressant activities (e.g. for treating human immunodeficiency virus infection, cancer, autoimmune diseases and allergy); regulation of hematopoiesis (e.g. for treating anaemia or as adjunct to chemotherapy); stimulation or growth of bone, cartilage, tendons, ligaments and/or nerves (e.g. for treating wounds, stimulation of follicle stimulating hormone (for control of fertility); chemotactic and chemokinetic activities (e.g. for treating infections, tumors); hemostatic or thrombolytic activity (e.g. for treating haemophilia, cardiac infarction etc.); anti-inflammatory activity (e.g. for treating septic shock, Crohn's disease); as antimicrobials; for treating psoriasis or other hyperproliferative diseases; for regulation of metabolism, and behaviour. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:38 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2197 of SEQ ID NO:38, b is an integer of 15 to 2211, where both a and b correspond to the positions of nucleotide residues shown in SEQ ID NO:38, and where b is greater than or equal to a+14.

Features of Protein Encoded by Gene No: 29

In specific embodiments, polypeptides of the invention comprise the following amino acid sequence: FESLRTG-SEGPHG (SEQ ID NO:203). Polynucleotides encoding these polypeptides are also encompassed by the invention. The gene encoding the disclosed cDNA is thought to reside on chromosome 20. Accordingly, polynucleotides related to this invention are useful as a marker in linkage analysis for chromosome 20.

This gene is expressed primarily in breast tissue, and to a lesser extent in placental tissue, keratinocytes and epithelial cells.

Therefore, polynucleotides and polypeptides of the invention are useful as reagents for differential identification of the tissue(s) or cell type(s) present in a biological sample and for diagnosis of diseases and conditions which include, but are not limited to, reproductive disorders, particularly breast cancer. Similarly, polypeptides and antibodies directed to these polypeptides are useful in providing immunological probes for differential identification of the tissue(s) or cell type(s). For a number of disorders of the above tissues or cells, particularly of the metabolic and female reproductive systems, expression of this gene at significantly higher or lower levels may be routinely detected in certain tissues or cells (e.g., breast, reproductive, or cancerous and wounded tissues) or bodily fluids (e.g., lymph, breast milk, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:115 as residues: Gly-13 to Pro-19, Pro-38 to Pro-46, Thr-49 to Gly-57.

The tissue distribution in tumors of breast origins indicates that polynucleotides and polypeptides corresponding to this gene are useful for the diagnosis and/or intervention of these tumors, in addition to other tumors where expression has been indicated. Expression within cellular sources marked by proliferating cells indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:39 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 668 of SEQ ID NO:39, b is an integer of 15 to 682, where both a and b correspond to the positions of nucleotide residues shown in SEQ ID NO:39, and where b is greater than or equal to a+14.

Features of Protein Encoded by Gene No: 30

The translation product of this gene shares sequence homology with the human ZN-alpha-2-glycoprotein, which is thought to important in the modulation of the immune response and possibly in the regulation of cell division (See Genbank Accession No. gi|467671). In specific embodiments, polypeptides of the invention comprise the following amino acid sequence: DPRVRADTMVR (SEQ ID NO:204), GPAVPQENQDGRYSLTYIYTGLSKHVED-VPAFQALGSLNDLQFFR (SEQ ID NO:205), YNSKDRK-SQPMGLWRQVEGME (SEQ ID NO:206), FMETLKDI-VEY YNDSNGSHVLQ (SEQ ID NO:207), and/or NRSSGAFWKYYYDGKDYIEF (SEQ ID NO:208). Polynucleotides encoding these polypeptides are also encompassed by the invention. The gene encoding the disclosed cDNA is believed to reside on chromosome 7. Accordingly, polynucleotides related to this invention are useful as a marker in linkage analysis for chromosome 7.

This gene is expressed primarily in liver and breast tissues, and to a lesser extent in spleen tissue.

Therefore, polynucleotides and polypeptides of the invention are useful as reagents for differential identification of the tissue(s) or cell type(s) present in a biological sample and for diagnosis of diseases and conditions which include, but are not limited to, reproductive or immune disorders, liver disorders, particularly those involving cancer, such as of the breast. Similarly, polypeptides and antibodies directed to these polypeptides are useful in providing immunological probes for differential identification of the tissue(s) or cell type(s). For a number of disorders of the above tissues or cells, particularly of the hepatic, immune, hematopoietic, or reproductive systems, expression of this gene at significantly higher or lower levels may be routinely detected in certain tissues or cells (e.g., hepatic, immune, reproductive, hematopoietic, or cancerous and wounded tissues) or bodily fluids (e.g., lymph, breast milk, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:116 as residues: Val-16 to Tyr-25, Tyr-58 to Gln-66, Met-77 to Arg-90, Tyr-104 to Gly-110, Glu-123 to Ser-128, Tyr-135 to Asp-140, Ile-160 to Trp-165.

The tissue distribution in immune tissues indicates that polynucleotides and polypeptides corresponding to this gene are useful for the diagnosis and/or treatment of a variety of immune system disorders. Expression of this gene product in spleen tissue indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types.

Alternatively, expression within the liver indicates that the protein product of this gene is useful for the detection and treatment of liver disorders and cancers (e.g. hepatoblastoma, jaundice, hepatitis, liver metabolic diseases and conditions that are attributable to the differentiation of hepatocyte progenitor cells). In addition the expression in fetus would suggest a useful role for the protein product in developmental abnormalities, fetal deficiencies, pre-natal disorders and various would-healing models and/or tissue trauma. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:40 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 671 of SEQ ID NO:40, b is an integer of 15 to 685, where both a and b correspond to the positions of nucleotide residues shown in SEQ ID NO:40, and where b is greater than or equal to a+14.

Features of Protein Encoded by Gene No: 31

When tested against human Jurkat T-cell lines, supernatants removed from cells containing this gene activated the NF-kB (Nuclear Factor kB) transcription pathway. Thus, it is likely that this gene activates T-cells, or more generally, immune or hematopoietic cells, in addition to other cells or cell-types, through the NF-kB pathway. NF-kB is a transcription factor activated by a wide variety of agents, leading to cell activation, differentiation, or apoptosis. Reporter constructs utilizing the NF-kB promoter element are used to screen supernatants for such activity.

This gene is expressed primarily in synovial sarcoma.

Therefore, polynucleotides and polypeptides of the invention are useful as reagents for differential identification of the tissue(s) or cell type(s) present in a biological sample and for diagnosis of diseases and conditions which include, but are not limited to, immune or musculo-skeletal disorders, particularly synovial sarcoma. Similarly, polypeptides and antibodies directed to these polypeptides are useful in providing immunological probes for differential identification of the tissue(s) or cell type(s). For a number of disorders of the above tissues or cells, particularly of the immune or skeletal system, expression of this gene at significantly higher or lower levels may be routinely detected in certain tissues or cells (e.g., skeletal, immune, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:117 as residues: Cys-7 to Ser-13.

The tissue distribution of this gene product in synovium would suggest a role in the detection and/or treatment of disorders and conditions affecting the skeletal system, in particular osteoporosis, as well as disorders afflicting connective tissues (e.g. arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, andspecific joint abnormalities as well as chondrodysplasias ie. spondyloepiphyseal dysplasia congenita, familial osteoarthritis, Atelosteogenesis type II, metaphyseal chondrodysplasia type Schmid. The detected NF-Kb biological activity in T-cells is consistent with the described uses for this protein. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:41 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 536 of SEQ ID NO:41, b is an integer of 15 to 550, where both a and b correspond to the positions of nucleotide residues shown in SEQ ID NO:41, and where b is greater than or equal to a+14.

Features of Protein Encoded by Gene No: 32

The translation product of this gene shares sequence homology with the elastin like protein from *Drosophila melanogaster* which is believed to important in the maintainance of the extracellular matrix of tissues (See Genbank Accession No. gi|762925). When tested against K562 cell lines, supernatants removed from cells containing this gene activated the ISRE (interferon-sensitive responsive element) pathway. Thus, it is likely that this gene activates leukemia cells through the Jaks-STAT signal transduction pathway. ISRE is a promoter element found upstream in many genes which are involved in the Jaks-STAT pathway.

The Jaks-STAT pathway is a large, signal transduction pathway involved in the differentiation and proliferation of cells. Therefore, activation of the Jaks-STATs pathway, reflected by the binding of the ISRE element, can be used to indicate proteins involved in the proliferation and differentiation of cells. The gene encoding the disclosed cDNA is believed to reside on chromosome 2. Accordingly, polynucleotides related to this invention are useful as a marker in linkage analysis for chromosome 2.

This gene is expressed in synovial sarcoma.

Therefore, polynucleotides and polypeptides of the invention are useful as reagents for differential identification of the tissue(s) or cell type(s) present in a biological sample and for diagnosis of diseases and conditions which include, but are not limited to, skeletal disorders, particularly synovial sarcoma. Similarly, polypeptides and antibodies directed to these polypeptides are useful in providing immunological probes for differential identification of the tissue(s) or cell type(s). For a number of disorders of the above tissues or cells, particularly of the immune or skeletal system, expression of this gene at significantly higher or lower levels may be routinely detected in certain tissues or cells (e.g., immune, musculo-skeletal, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution of this gene product in synovium, combined with its homology to elastin and its biological activity data, indicates a role in the detection and/or treatment of disorders and conditions affecting the skeletal system, in particular osteoporosis, as well as disorders afflicting connective tissues (e.g. arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias ie. spondyloepiphyseal dysplasia congenita, familial osteoarthritis, Atelosteogenesis type II, metaphyseal chondrodysplasia type Schmid. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:42 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 588 of SEQ ID NO:42, b is an integer of 15 to 602, where both a and b correspond to the positions of nucleotide residues shown in SEQ ID NO:42, and where b is greater than or equal to a+14.

Features of Protein Encoded by Gene No: 33

The translation product of this gene shares sequence homology with the cell division control protein CDC91 from the yeast, Saccharomyces cerevisiae (See Genbank Accession No.: gi|717072).

This gene is expressed in testes, colon, embryonic, and retinal tissues. It is also present in several cancerous tissues such as glioblastoma and Wilm's tumor.

Therefore, polynucleotides and polypeptides of the invention are useful as reagents for differential identification of the tissue(s) or cell type(s) present in a biological sample and for diagnosis of diseases and conditions which include, but are not limited to, cancers, including glioblastoma and Wilm's tumor, in addition to reproductive disorders. Similarly, polypeptides and antibodies directed to these polypeptides are useful in providing immunological probes for differential identification of the tissue(s) or cell type(s). For a number of disorders of the above tissues or cells, particularly of the immune or reproductive system, expression of this gene at significantly higher or lower levels may be routinely detected in certain tissues or cells (e.g., immune, reproductive, or cancerous and wounded tissues) or bodily fluids (e.g., lymph, seminal fluid, vitreous humor, aqueous humor, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:119 as residues: Arg-131 to Leu-136.

The tissue distribution in cancerous tissues, and the homology to a yeast cell division control protein CDC91, indicates that this protein may play a role in the regulation of cellular division, and may show utility in the diagnosis and/or treatment of cancer and other proliferative disorders. Similarly, embryonic development also involves decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:43 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1613 of SEQ ID NO:43, b is an integer of 15 to 1627, where both a and b correspond to the positions of nucleotide residues shown in SEQ ID NO:43, and where b is greater than or equal to a+14.

Features of Protein Encoded by Gene No: 34

The gene encoding the disclosed cDNA is believed to reside on chromosome 16. Accordingly, polynucleotides related to this invention are useful as a marker in linkage analysis for chromosome 16.

This gene is expressed primarily in brain tissues, such as whole brain, cerebellum, and hypothalmus.

Therefore, polynucleotides and polypeptides of the invention are useful as reagents for differential identification of the tissue(s) or cell type(s) present in a biological sample and for diagnosis of diseases and conditions which include, but are not limited to, neural and neurodegenerative disorders, particularly Alzheimer's and Parkinson's diseases. Similarly, polypeptides and antibodies directed to these polypeptides are useful in providing immunological probes for differential identification of the tissue(s) or cell type(s). For a number of disorders of the above tissues or cells, particularly of the disorders of the brain and central nervous system, expression of this gene at significantly higher or lower levels may be routinely detected in certain tissues or cells (e.g., neural, cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in tissues of the brain and neural system indicates that polynucleotides and polypeptides corresponding to this gene are useful for the detection and/or treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Furthermore, this gene product may be involved in neuronal survival; synapse formation; conductance; neural differentiation, etc. Such involvement may impact many processes, such as learning and cognition. It may also be useful in the treatment of such neurodegenerative disorders as schizophrenia; ALS; or Alzheimer's. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:44 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1443 of SEQ ID NO:44, b is an integer of 15 to 1457, where both a and b correspond to the positions of nucleotide residues shown in SEQ ID NO:44, and where b is greater than or equal to a+14.

Features of Protein Encoded by Gene No: 35

The translation product of this gene shares sequence homology with the human ADAM 21 protein, a testis-specific metalloprotease-like protein which is thought to be important in egg recognition during fertilization, and possibly in a more general role in integrin-mediated cell-cell recognition, adhesion or signalling (See Genbank Accession No. gi|2739137 (AF029900)). In specific embodiments, polypeptides of the invention comprise the following amino acid sequence: FCYLCILLLIVLFILLCCLYRLCKKSK PXKKQQXVQTPSAKEEEKIQRRPHELP-PQSQPWVMPSQSQPPVTPSQSHPQ VMPSQSQP-PVTPSQSQPRVMPSQSQPPVMPSQSH-PQLTPSQSQPPVTPSQRQP Q LMPSQSQPPVTPS (SEQ ID NO:211), IRHETECGIDHICIHRHCVHITILNSNC SPAFCNKRGICNNKHHCHCNYLWDPPNC-LIKGYGGSVDSGPPP (SEQ ID NO:209), and/or GICNN-KHHCHC (SEQ ID NO:210). Polynucleotides encoding these polypeptides are also encompassed by the invention.

This gene is expressed primarily in human testes tissue.

Therefore, polynucleotides and polypeptides of the invention are useful as reagents for differential identification of the tissue(s) or cell type(s) present in a biological sample and for diagnosis of diseases and conditions which include, but are not limited to, reproductive disorders, particularly of the testes, or allergy, infectious and inflammatatory diseases. Similarly, polypeptides and antibodies directed to these polypeptides are useful in providing immunological probes for differential identification of the tissue(s) or cell type(s). For a number of disorders of the above tissues or cells, particularly of the immune and reproductive systems, expression of this gene at significantly higher or lower levels may be routinely detected in certain tissues or cells (e.g., immune, reproductive, or cancerous and wounded tissues) or bodily fluids (e.g., lymph, seminal fluid, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:121 as residues: Arg-12 to Ser-18.

The tissue distribution in testes tissue indicates that polynucleotides and polypeptides corresponding to this gene are useful for the diagnosis and/or treatment of a variety of immune system or reproductive disorders. The homology of this gene product to a human metalloproteinase indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types.

Alternatively, the tissue distribution within testes, combined with its homology to a testes-specific metalloproteinase, indicates that the protein product of this gene may show utility in the detection, treatment, and/or prevention of various reproductive disorders, particularly male infertility. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:45 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 874 of SEQ ID NO:45, b is an integer of 15 to 888, where both a and b correspond to the positions of nucleotide residues shown in SEQ ID NO:45, and where b is greater than or equal to a+14.

Features of Protein Encoded by Gene No: 36

The translation product of this gene shares sequence homology with the human lysozyme, which is thought to be important in the hydrolysis of proteins specific to bacteriolysis (See Genbank Accession No.: P90343). As such, the protein product of this gene may be useful in antibiotic applications.

This gene is expressed primarily in testes tissue and neutrophils induced by IL-1 and LPS.

Therefore, polynucleotides-and polypeptides of the invention are useful as reagents for differential identification of the tissue(s) or cell type(s) present in a biological sample and for diagnosis of diseases and conditions which include, but are not limited to, immune disorders and afflications, particularly in bacteria infections, and reproductive disorders, such as male infertility. Similarly, polypeptides and antibodies directed to these polypeptides are useful in providing immunological probes for differential identification of the tissue(s) or cell type(s). For a number of disorders of the above tissues or cells, particularly of the reproductive and immune system, expression of this gene at significantly higher or lower levels may be routinely detected in certain tissues or cells (e.g., immune, reproductive, or cancerous and wounded tissues) or bodily fluids (e.g., lymph, seminal fluid, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:122 as residues: Lys-30 to Gly-35, Glu-64 to Gly-69.

The tissue distribution in activated neutrophils, combined with the homology to the human lysozyme protein, indicates that polynucleotides and polypeptides corresponding to this gene are useful for the diagnosis and/or treatment of a variety of immune system disorders, particularly bacterial infections. Expression of this gene product in neutrophils indicates a role in the regulation of the proliferation; survival; differentiation; and/or activation of potentially all hematopoietic cell lineages, including blood stem cells. Expression of this gene product in neutrophils also strongly indicates a role for this protein in immune function and immune surveillance. This gene product may be involved in the regulation of cytokine production, antigen presentation, or other processes that may also suggest a usefulness in the treatment of cancer (e.g. by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:46 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 738 of SEQ ID NO:46, b is an integer of 15 to 752, where both a and b correspond to the positions of nucleotide residues shown in SEQ ID NO:46, and where b is greater than or equal to a+14.

Features of Protein Encoded by Gene No: 37

The translation product of this gene shares sequence homology with human ApoE4L1 protease which is thought to be important in Alzheimer's disease. When tested against PC12 sensory neuron cell lines, supernatants removed from cells containing this gene activated the EGR1 (early growth response gene 1) pathway. Thus, it is likely that this gene activates sensory neuron cells, and to a lesser extent other neuronal cells, through the EGR1 signal transduction pathway. EGR1 is a separate signal transduction pathway from Jaks-STAT, genes containing the EGR1 promoter are induced in various tissues and cell types upon activation, leading the cells to undergo differentiation and proliferation.

This gene is expressed primarily in small intestine, and to a lesser extent in T-cells and thymus tissue.

Therefore, polynucleotides and polypeptides of the invention are useful as reagents for differential identification of the tissue(s) or cell type(s) present in a biological sample and for diagnosis of diseases and conditions which include, but are not limited to, Alzheimer's disease, Downs syndrome, Parkinson's diseases and cardiovascular disease, or gastrointestinal or immune disorders. Similarly, polypeptides and antibodies directed to these polypeptides are useful in providing immunological probes for differential identification of the tissue(s) or cell type(s). For a number of disorders of the above tissues or cells, particularly of the neural and immune systems, expression of this gene at significantly higher or lower levels may be routinely detected in certain tissues or cells (e.g., immune, gastrointestinal, neural, or cancerous and wounded tissues) or bodily fluids (e.g., lymph, bile, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The homology to ApoE4L1, combined with the detected EGR1 biological activity, indicates that polynucleotides and polypeptides corresponding to this gene are useful for the detection and/or treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Alternatively, the expression within T-cells and thymus tissue indicates a role in the regulation of the proliferation; survival; differentiation; and/or activation of potentially all hematopoietic cell lineages, including blood stem cells.

This gene product may be involved in the regulation of cytokine production, antigen presentation, or other processes that may also suggest a usefulness in the treatment of cancer (e.g. by boosting immune responses). Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:47 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1774 of SEQ ID NO:47, b is an integer of 15 to 1788, where both a and b correspond to the positions of nucleotide residues shown in SEQ ID NO:47, and where b is greater than or equal to a+14.

Features of Protein Encoded by Gene No: 38

In specific embodiments, polypeptides of the invention comprise the following amino acid sequence: IRHEEMH-MALNNQATGLLNLKKDIRGVLDQ-MEDIQLEILRERAQCRTRARKEKQMAS (SEQ ID NO:212). Polynucleotides encoding these polypeptides are also encompassed by the invention.

This gene is expressed primarily in human adult testes tissue.

Therefore, polynucleotides and polypeptides of the invention are useful as reagents for differential identification of the tissue(s) or cell type(s) present in a biological sample and for diagnosis of diseases and conditions which include, but are not limited to, reproductive or endocrine disorders, particularly male infertility. Similarly, polypeptides and antibodies directed to these polypeptides are useful in providing immunological probes for differential identification of the tissue(s) or cell type(s). For a number of disorders of the above tissues or cells, particularly of the male reproductive system, expression of this gene at significantly higher or lower levels may be routinely detected in certain tissues or cells (e.g., endocrine, reproductive, or cancerous and wounded tissues) or bodily fluids (e.g., lymph, seminal fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:124 as residues: Met-1 to Ser-10.

The tissue distribution in testes tissue indicates that polynucleotides and polypeptides corresponding to this gene are useful for the detection, treatment, and/or prevention of various endocrine disorders and cancers, particularly Addison's disease, Cushing's Syndrome, and disorders and/or cancers of the pancrease (e.g. diabetes mellitus), adrenal cortex, ovaries, pituitary (e.g., hyper-, hypopituitarism), thyroid (e.g. hyper-, hypothyroidism), parathyroid (e.g. hyper-, hypoparathyroidism), hypothallamus, and testes.

Alternatively, expression within testes tissue indicates that polynucleotides and polypeptides corresponding to this gene are useful for the detection, treatment, and/or prevention of a variety of male reproductive disorders, particularly male infertility. This gene product is also useful in assays designed to identify binding agents, as such agents (antagonists) are useful as male contraceptive agents. Similarly, the protein is believed to be useful in the treatment and/or diagnosis of testicular cancer. The testes are also a site of active gene expression of transcripts that may be expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:48 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 646 of SEQ ID NO:48, b is an integer of 15 to 660, where both a and b correspond to the positions of nucleotide residues shown in SEQ ID NO:48, and where b is greater than or equal to a+14.

Features of Protein Encoded by Gene No: 39

The translation product of this gene shares sequence homology with ankyrin which is thought to be important in cell-cell interactions and other cellular functions, such as maintanance of the cytoskeleton, etc. (See Genbank Accession No.: gi|2447128).

This gene is expressed in osteoblasts and tonsils.

Therefore, polynucleotides and polypeptides of the invention are useful as reagents for differential identification of the tissue(s) or cell type(s) present in a biological sample and for diagnosis of diseases and conditions which include, but are not limited to, disorders affecting the skeletal or immune systems. Similarly, polypeptides and antibodies directed to these polypeptides are useful in providing immunological probes for differential identification of the tissue(s) or cell type(s). For a number of disorders of the above tissues or cells, particularly of the skeletal and immune systems, expression of this gene at significantly higher or lower levels may be routinely detected in certain tissues or cells (e.g., immune, skeletal, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:125 as residues: Lys-41 to Gln-46.

The tissue distribution in tonsils indicates that polynucleotides and polypeptides corresponding to this gene are useful for the diagnosis and/or treatment of a variety of immune system disorders. Expression of this gene product in tonsils indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types.

Alternatively, expression within osteoblasts indicates a role in the detection and treatment of disorders and conditions affecting the skeletal system, in particular osteoporosis as well as disorders afflicting connective tissues (e.g. arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (ie. spondyloepiphyseal dysplasia congenita, familial osteoarthritis, Atelosteogenesis type II, metaphyseal chondrodysplasia type Schmid). Elevated levels of expression of this gene product in osteoblasts indicates that it may play a role in the survival, proliferation, and/or growth of osteoblasts. Therefore, it may be useful in influencing bone mass in such conditions as osteoporosis. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:49 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1307 of SEQ ID NO:49, b is an integer of 15 to 1321, where both a and b correspond to the positions of nucleotide residues shown in SEQ ID NO:49, and where b is greater than or equal to a+14.

Features of Protein Encoded by Gene No: 40

In specific embodiments, polypeptides of the invention comprise the following amino acid sequence: WIPRAA-GIRHERNLRLWQIEIMAGPESDAQYQFTGIKKYF NSYTLTGR (SEQ ID NO:213). Polynucleotides encoding these polypeptides are also encompassed by the invention.

The gene encoding the disclosed cDNA is thought to reside on chromosome 10. Accordingly, polynucleotides related to this invention are useful as a marker in linkage analysis for chromosome 10.

This gene is expressed in bone marrow, testes, liver, and retinal tissues.

Therefore, polynucleotides and polypeptides of the invention are useful as reagents for differential identification of the tissue(s) or cell type(s) present in a biological sample and for diagnosis of diseases and conditions which include, but are not limited to, disorders affecting the immune, reproductive, or hepatic systems, such as AIDS, infertility, or cirrhosis. Similarly, polypeptides and antibodies directed to these polypeptides are useful in providing immunological probes for differential identification of the tissue(s) or cell type(s). For a number of disorders of the above tissues or cells, particularly of the immune, hepatic, and reproductive systems, expression of this gene at significantly higher or lower levels may be routinely detected in certain tissues or cells (e.g., immune, reproductive, hepatic, or cancerous and wounded tissues) or bodily fluids (e.g., lymph, bile, seminal fluid, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:126 as residues: Leu-20 to Pro-26.

The tissue distribution in liver tissue indicates that polynucleotides and polypeptides corresponding to this gene are useful for the detection and/or treatment of liver disorders and cancers (e.g. hepatoblastoma, jaundice, hepatitis, liver metabolic diseases and conditions that are attributable to the differentiation of hepatocyte progenitor cells). Alternatively, the secreted protein can also be used to determine biological activity, to raise antibodies, as tissue markers, to isolate cognate ligands or receptors, to identify agents that modulate their interactions and as nutritional supplements.

Moreover, the protein may also have a very wide range of biological acitivities. Typical of these are cytokine, cell proliferation/differentiation modulating activity or induction of other cytokines; immunostimulating/immunosuppressant activities (e.g. for treating human immunodeficiency virus infection, cancer, autoimmune diseases and allergy); regulation of hematopoiesis (e.g. for treating anaemia or as an adjunct to chemotherapy); stimulation or growth of bone, cartilage, tendons, ligaments and/or nerves (e.g. for treating wounds, stimulation of follicle stimulating hormone (for control of fertility); chemotactic and chemokinetic activities (e.g. for treating infections, tumors); hemostatic or thrombolytic activity (e.g. for treating haemophilia, cardiac infarction etc.); anti-inflammatory activity (e.g. for treating septic shock, Crohn's disease); as antimicrobials; for treating psoriasis or other hyperproliferative diseases; for regulation of metabolism, and behaviour. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:50 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 534 of SEQ ID NO:50, b is an integer of 15 to 548, where both a and b correspond to the positions of nucleotide residues shown in SEQ ID NO:50, and where b is greater than or equal to a+14.

Features of Protein Encoded by Gene No: 41

This gene is expressed primarily in T cells.

Therefore, polynucleotides and polypeptides of the invention are useful as reagents for differential identification of the tissue(s) or cell type(s) present in a biological sample and for diagnosis of diseases and conditions which include, but are not limited to, disorders affecting the immune or hematopoietic system, particularly immunodeficiencies such as AIDS. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cells (e.g., immune, hematopoietic, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in T-cells indicates that polynucleotides and polypeptides corresponding to this gene are useful for the diagnosis and/or treatment of a variety of immune system disorders. Expression of this gene product in T-cells indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:51 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 644 of SEQ ID NO:51, b is an integer of 15 to 658, where both a and b correspond to the positions of nucleotide residues shown in SEQ ID NO:51, and where b is greater than or equal to a+14.

Features of Protein Encoded by Gene No: 42

This gene is expressed in T cells.

Therefore, polynucleotides and polypeptides of the invention are useful as reagents for differential identification of the tissue(s) or cell type(s) present in a biological sample and for diagnosis of diseases and conditions which include, but are not limited to, disorders of the immune system, particularly immunodeficiencies such as AIDS. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cells (e.g., immune, hematopoietic, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:128 as residues: Thr-6 to Leu-11, Pro-13 to Cys-27, Pro-65 to Met-72.

The tissue distribution in T-cells indicates that polynucleotides and polypeptides corresponding to this gene are useful for the diagnosis and/or treatment of a variety of immune system disorders. Expression of this gene product in T-cells indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:52 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 608 of SEQ ID NO:52, b is an integer of 15 to 622, where both a and b correspond to the positions of nucleotide residues shown in SEQ ID NO:52, and where b is greater than or equal to a+14.

Features of Protein Encoded by Gene No: 43

In specific embodiments, polypeptides of the invention comprise the following amino acid sequence: AFESLPKYHLLKCSFSLLLNFIVPHQCT (SEQ ID NO:214), and/or FFFVCLFIVFLPHKSKVYMNRELVCFVYYCIPYAGTYYVISVC (SEQ ID NO:215). Polynucleotides encoding these polypeptides are also encompassed by the invention.

This gene is expressed in T cells.

Therefore, polynucleotides and polypeptides of the invention are useful as reagents for differential identification of the tissue(s) or cell type(s) present in a biological sample and for diagnosis of diseases and conditions which include, but are not limited to, disorders of the immune system, particularly immunodeciencies such as AIDS. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cells (e.g., immune, hematopoietic, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in T-cells indicates that polynucleotides and polypeptides corresponding to this gene are useful for the diagnosis and/or treatment of a variety of immune system disorders. Expression of this gene product in T-cells indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis, and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:53 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 709 of SEQ ID NO:53, b is an integer of 15 to 723, where both a and b correspond to the positions of nucleotide residues shown in SEQ ID NO:53, and where b is greater than or equal to a+14.

Features of Protein Encoded by Gene No: 44

The translation product of this gene shares sequence homology with calmodulin, which is known to be important in intracellular signalling.

This gene is expressed in activated T cells.

Therefore, polynucleotides and polypeptides of the invention are useful as reagents for differential identification of the tissue(s) or cell type(s) present in a biological sample and for diagnosis of diseases and conditions which include, but are not limited to, disorders of the immune system, particularly immunodeficienceis such as AIDS. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cells (e.g., immune, hematopoietic, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in activated T-cells indicates that polynucleotides and polypeptides corresponding to this gene are useful for the diagnosis and/or treatment of a variety of immune system disorders. Expression of this gene product in T-cells indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:54 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 894 of SEQ ID NO:54, b is an integer of 15 to 908, where both a and b correspond to the positions of nucleotide residues shown in SEQ ID NO:54, and where b is greater than or equal to a+14.

Features of Protein Encoded by Gene No: 45

In specific embodiments, polypeptides of the invention comprise the following amino acid sequence: RKKYYLRCENYSPKYCSFQA (SEQ ID NO:216). Polynucleotides encoding these polypeptides are also encompassed by the invention. The gene encoding the disclosed cDNA is thought to reside on chromosome 5. Accordingly, polynucleotides related to this invention are useful as a marker in linkage analysis for chromosome 5.

This gene is expressed primarily in fetal lung tissue and olfactory epithelium, as well as in ovary tissue.

Therefore, polynucleotides and polypeptides of the invention are useful as reagents for differential identification of the tissue(s) or cell type(s) present in a biological sample and for diagnosis of diseases and conditions which include, but are not limited to, cardiopulmonary, endocrine or reproductive disorders, including cancer. Similarly, polypeptides and antibodies directed to these polypeptides are useful in providing immunological probes for differential identification of the tissue(s) or cell type(s). For a number of disorders of the above tissues or cells, particularly of the pulmonary, immune and reproductive systems, expression of this gene at significantly higher or lower levels may be routinely detected in certain tissues or cell types (e.g., cardiopulmonary, endocrine, reproductive, or cancerous and wounded tissues) or bodily fluids (e.g. lymph, amniotic fluid, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution indicates that polynucleotides and polypeptides corresponding to this gene are useful for diagnosis, treatment, or prevention of various lung and reproductive disorders, including cancer. Similarly, The tissue distribution indicates that polynucleotides and polypeptides corresponding to this gene are useful for the detection and treatment of disorders associated with developing lungs, particularly in premature infants where the lungs are the last tissues to develop.

Moreover, the tissue distribution indicates that polynucleotides and polypeptides corresponding to this gene are useful for the diagnosis and intervention of lung tumors, since the gene may be involved in the regulation of cell division, particularly since it is expressed in fetal tissue. Alternatively, expression within the ovaries indicates that polynucleotides and polypeptides corresponding to this gene are useful for the detection, treatment, and/or prevention of various endocrine disorders and cancers, particularly Addison's disease, Cushing's Syndrome, and disorders and/or cancers of the pancrease (e.g. diabetes mellitus), adrenal cortex, ovaries, pituitary (e.g., hyper-, hypopituitarism), thyroid (e.g. hyper-, hypothyroidism), parathyroid (e.g. hyper-, hypoparathyroidism), hypothallamus, and testes. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:55 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 808 of SEQ ID NO:55, b is an integer of 15 to 822, where both a and b correspond to the positions of nucleotide residues shown in SEQ ID NO:55, and where b is greater than or equal to a+14.

Features of Protein Encoded by Gene No: 46

The translation product of this gene was shown to have homology to the human 150 kDa oxygen-regulated protein ORP150, which may be involved in metabolic processes (See Genbank Accession No. AA004278). In specific embodiments, polypeptides of the invention comprise the following amino acid sequence: GSFRGTG RGRDGAQH-PLLYVKLLIQVGHEPMPPTLGTNV-LGRKVLYLPSFFTYAKYIVQ VDGKIGLFRGLSPRLM-SNALSTVTRGSMKKVFPPDEIEQVSNKDDMKTSLKK V VKETSYEMMMQCVSRMLAHPLHVISMRC-MVQFVGREAKYSGVLSSIGKIF KEEGLLG-FFVGLIPHLLGDVVFLWGCNLLAHFI-NAYLVDDSVSDTPGGLGND QNPGSQFSQALAIRSYTKFV (SEQ ID NO:217), GSFRGTGRGRDGAQHPLLY VKLLIQVGHEP-MPPTLGTNVLGRKVLYLP (SEQ ID NO:218), SFFTY-AKYIVQ VDGKIGLFRGLSPRLMSNAL-STVTRGSMKKVFPPDEI (SEQ ID NO:219), EQVSNKDDMKTSLKKVVKETSYEMMM-QCVSRMLAHPLHVISMRCM (SEQ ID NO:220), VQFVGREAKYSGVLSSIGKIFKEEGLLG-FFVGLIPHLLGDVVFLWG CNLL (SEQ ID NO:221), and/or AHFINAYLVDDSVSDTPGGLGNDQNPGSQFSQ ALAIRSYTKFV (SEQ ID NO:222). Polynucleotides encoding these polypeptides are also encompassed by the invention.

This gene is expressed primarily in breast, brain, and bone marrow tissues.

Therefore, polynucleotides and polypeptides of the invention are useful as reagents for differential identification of the tissue(s) or cell type(s) present in a biological sample and for diagnosis of diseases and conditions which include, but are not limited to, disorders of the reproductive, neural, or hematopoietic system, including cancers. Similarly, polypeptides and antibodies directed to these polypeptides are useful in providing immunological probes for differential identification of the tissue(s) or cell type(s). For a number of disorders of the above tissues or cells, particularly of the immune, skeletal, and central nervous systems, expression of this gene at significantly higher or lower levels may be routinely detected in certain tissues or cell types (e.g., reproductive, neural, skeletal, or cancerous and wounded tissues) or bodily fluids (e.g., lymph, breast milk, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in brain tissue indicates that the protein product of this gene is useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system.

Alternatively, expression within the bone marrow indicates that the protein product of this gene is useful for the treatment and diagnosis of hematopoetic related disorders such as anemia, pancytopenia, leukopenia, thrombocytopenia or leukemia since stromal cells are important in the production of cells of hematopoietic lineages. The uses include bone marrow cell ex vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the abovelisted tissues.

Many polynucleotide sequences, such as EST sequences, are publicly available and accessible through sequence databases. Some of these sequences are related to SEQ ID NO:56 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1937 of SEQ ID NO:56, b is an integer of 15 to 1951, where both a and b correspond to the positions of nucleotide residues shown in SEQ ID NO:56, and where b is greater than or equal to a+14.

Features of Protein Encoded by Gene No: 47

In specific embodiments, polypeptides of the invention comprise the following amino acid sequence: LILSAL-RELLMLLCPPVHMLIAKKKMSMSEPKAAETFCVY ATSLPSIQGRWFHCLV (SEQ ID NO:223), and/or DHFQPNVHLAGIWLSQNNI (SEQ ID NO:224). Polynucleotides encoding these polypeptides are also encompassed by the invention. The gene encoding the disclosed cDNA is thought to reside on chromosome 11. Accordingly, polynucleotides related to this invention are useful as a marker in linkage analysis for chromosome 11.

This gene is expressed primarily in placental tissue, and to a lesser extent in cartilage ans synovial tissue.

Therefore, polynucleotides and polypeptides of the invention are useful as reagents for differential identification of the tissue(s) or cell type(s) present in a biological sample and for diagnosis of diseases and conditions which include, but are not limited to, reproductive and connective tissue disorders. Similarly, polypeptides and antibodies directed to these polypeptides are useful in providing immunological probes for differential identification of the tissue(s) or cell type(s). For a number of disorders of the above tissues or cells, particularly of the reproductive system and connective tissues, expression of this gene at significantly higher or lower levels may be routinely detected in certain tissues or cells (e.g., musculo-skeletal, reproductive, developing, or cancerous and wounded tissues) or bodily fluids (e.g., lymph, amniotic fluid, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:133 as residues: Ser-49 to Cys-54.

Expression within embryonic tissue and other cellular sources marked by proliferating cells indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus this protein may also be involved in apoptosis or tissue differentiation and could again be useful in cancer therapy.

Alternatively, the expression of this gene product in synovium and cartilage indicates a role in the detection and treatment of disorders and conditions affecting the skeletal system, in particular osteoporosis as well as disorders afflicting connective tissues (e.g. arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (ie. spondyloepiphyseal dysplasia congenita, familial arthritis, Atelosteogenesis type II, metaphyseal chondrodysplasia type Schmid). Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:57 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 649 of SEQ ID NO:57, b is an integer of 15 to 663, where both a and b correspond to the positions of nucleotide residues shown in SEQ ID NO:57, and where b is greater than or equal to a+14.

Features of Protein Encoded by Gene No: 48

In specific embodiments, polypeptides of the invention comprise the following amino acid sequence: IKHISTQFCHPRESTNCR-PLLQLKEDPTENGIESGDRTL HRTLEHSQDFIHTFG-SCVLYRRLSYELLSKSQSLEANPVTRPS-SEESDLKRSRD LTAKPHHPHRFFCDTERSNPRPGLCLSRDIII (SEQ ID NO:225), IKHISTQFCHPR ESTNCRPLLQLKEDPTENG-IESGDRTLHRTL (SEQ ID NO:226), EHSQDFIHTF GSCVLYRRLSYELLSKSQSLEANPVTRPSSE (SEQ ID NO:227), and/or ESDLKR SRDLTAKPHHPHRFFCDTER-SNPRPGLCLSRDIII (SEQ ID NO:228). Polynucleotides encoding these polypeptides are also encompassed by the invention. The gene encoding the disclosed cDNA is believed to reside on chromosome 18. Accordingly, polynucleotides related to this invention are useful as a marker in linkage analysis for chromosome 18.

This gene is expressed primarily in tissues of the brain, such as the amygdala.

Therefore, polynucleotides and polypeptides of the invention are useful as reagents for differential identification of the tissue(s) or cell type(s) present in a biological sample and for diagnosis of diseases and conditions which include, but are not limited to, disorders affecting the brain and central nervous system, particularly neurodegenerative disorders. Similarly, polypeptides and antibodies directed to these polypeptides are useful in providing immunological probes for differential identification of the tissue(s) or cell type(s). For a number of disorders of the above tissues or cells, particularly of the brain and central nervous system, expression of this gene at significantly higher or lower levels may be routinely detected in certain tissues or cells (e.g., neural, cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in brain tissue indicates that polynucleotides and polypeptides corresponding to this gene are useful for the detection and/or treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:58 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 764 of SEQ ID NO:58, b is an integer of 15 to 778, where both a and b correspond to the positions of nucleotide residues shown in SEQ ID NO:58, and where b is greater than or equal to a+14.

Features of Protein Encoded by Gene No: 49

The translation product of this gene shares sequence homology with pigment epithelium derived factor, which is thought to be important in enhancing neuronal cell survival and inhibiting glial cell proliferation, and is useful for example in CNS cell culture, or to treat neuro-degenerative diseases. In specific embodiments, polypeptides of the invention comprise the following amino acid sequence: NSARAYVQVLPCLAP RNTVPRT (SEQ ID NO:229). Polynucleotides encoding these polypeptides are also encompassed by the invention.

This gene is expressed primarily in epithelial cells.

Therefore, polynucleotides and polypeptides of the invention are useful as reagents for differential identification of the tissue(s) or cell type(s) present in a biological sample and for diagnosis of diseases and conditions which include, but are not limited to, neural or integumentary disorders, particularly those affecting epithelial cells, such as cancer. Similarly, polypeptides and antibodies directed to these polypeptides are useful in providing immunological probes for differential identification of the tissue(s) or cell type(s). For a number of disorders of the above tissues or cells, particularly of the immune, neural, or integumentary system, expression of this gene at significantly higher or lower levels may be routinely detected in certain tissues or cell types (e.g., neural, integumentary, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in epithelium,. combined with the homology to the PEDF protein, indicates that polynucleotides and polypeptides corresponding to this gene are useful for the treatment, diagnosis, and/or prevention of various skin disorders including congenital disorders (i.e. nevi, moles, freckles, Mongolian spots, hemangiomas, port-wine syndrome), integumentary tumors (i.e. keratoses, Bowen's disease, basal cell carcinoma, squamous cell carcinoma, malignant melanoma, Paget's disease, mycosis fungoides, and Kaposi's sarcoma), injuries and inflammation of the skin (i.e. wounds, rashes, prickly heat disorder, psoriasis, dermatitis), atherosclerosis, uticaria, eczema, photosensitivity, autoimmune disorders (i.e. lupus erythematosus, vitiligo, dermatomyositis, morphea, scleroderma, pemphigoid, and pemphigus), keloids, striae, erythema, petechiae, purpura, and xanthelasma. Moreover, such disorders may predispose increased susceptibility to viral and bacterial infections of the skin (i.e. cold sores, warts, chickenpox, molluscum contagiosum, herpes zoster, boils, cellulitis, erysipelas, impetigo, tinea, althletes foot, and ringworm).

Alternatively, the homology to the PDEF protein also indicates that polynucleotides and polypeptides corresponding to this gene are useful for the detection and/or treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:59 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 968 of SEQ ID NO:59, b is an integer of 15 to 982, where both a and b correspond to the positions of nucleotide residues shown in SEQ ID NO:59, and where b is greater than or equal to a+14.

Features of Protein Encoded by Gene No: 50

In specific embodiments, polypeptides of the invention comprise the following amino acid sequence: VSYAHEPSLFFFNLVPATFLT (SEQ ID NO:230). Polynucleotides encoding these polypeptides are also encompassed by the invention.

This gene is expressed primarily in the ovary and placental tissue.

Therefore, polynucleotides and polypeptides of the invention are useful as reagents for differential identification of the tissue(s) or cell type(s) present in a biological sample and for diagnosis of diseases and conditions which include, but are not limited to, disorders of the reproductive system, including developing tissues. Similarly, polypeptides and antibodies directed to these polypeptides are useful in providing immunological probes for differential identification of the tissue(s) or cell type(s). For a number of disorders of the above tissues or cells, particularly of the reproductive system, expression of this gene at significantly higher or lower levels may be routinely detected in certain tissues or cell types (e.g., reproductive, developing, or cancerous and wounded tissues) or bodily fluids (e.g., lymph, amniotic fluid, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:136 as residues: Cys-43 to Lys-49.

The tissue distribution in ovaries and placental tissues indicates that polynucleotides and polypeptides corresponding to this gene are useful for the diagnosis, treatment, and/or prevention of a variety of reproductive disorders, particularly infertility. In addition, expression within placental tissue and other cellular sources marked by proliferating cells indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:60 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 392 of SEQ ID NO:60, b is an integer of 15 to 406, where both a and b correspond to the positions of nucleotide residues shown in SEQ ID NO:60, and where b is greater than or equal to a+14.

Features of Protein Encoded by Gene No: 51

In specific embodiments, polypeptides of the invention comprise the following amino acid sequence: FTPSWPLFITVKVHPSFDL (SEQ ID NO:231). Polynucleotides encoding these polypeptides are also encompassed by the invention.

This gene is expressed primarily in immune cells, including B cells.

Therefore, polynucleotides and polypeptides of the invention are useful as reagents for differential identification of the tissue(s) or cell type(s) present in a biological sample and for diagnosis of diseases and conditions which include, but are not limited to, immune disorders, particularly B cell lymphomas. Similarly, polypeptides and antibodies directed to these polypeptides are useful in providing immunological probes for differential identification of the tissue(s) or cell type(s). For a number of disorders of the above tissues or cells, particularly of the immune or hematopoietic system, expression of this gene at significantly higher or lower levels may be routinely detected in certain tissues or cells (e.g., immune, hematopoietic, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:137 as residues: Thr-15 to Cys-21, Pro-60 to His-65, Pro-68 to Asp-74.

The tissue distribution in immune system cells indicates that polynucleotides and polypeptides corresponding to this gene are useful for the diagnosis and treatment of a variety of immune system disorders. Expression of this gene product in B-cells indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:61 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 799 of SEQ ID NO:61, b is an integer of 15 to 813, where both a and b correspond to the positions of nucleotide residues shown in SEQ ID NO:61, and where b is greater than or equal to a+14.

Features of Protein Encoded by Gene No: 52

In specific embodiments, polypeptides of the invention comprise the following amino acid sequence: RNYKKCIS-LLRD (SEQ ID NO:232). Polynucleotides encoding these polypeptides are also encompassed by the invention. The translation product of this gene shares sequence homology with C. elegans protein F11A10.5, the function of which is unknown (See Genbank Accession No.: gi|2393734).

This gene is expressed primarily in pineal gland and epididymus tissue, and to a lesser extent in bone marrow, melanocyte and CD34 positive cells.

Therefore, polynucleotides and polypeptides of the invention are useful as reagents for differential identification of the tissue(s) or cell type(s) present in a biological sample and for diagnosis of diseases and conditions which include, but are not limited to, endocrine, reproductive, or immune disorders. Similarly, polypeptides and antibodies directed to these polypeptides are useful in providing immunological probes for differential identification of the tissue(s) or cell type(s). For a number of disorders of the above tissues or cells, particularly of the endocrine and immune system, expression of this gene at significantly higher or lower levels may be routinely detected in certain tissues or cells (e.g., reproductive, endocrine, immune, hematopoietic, or cancerous and wounded tissues) or bodily fluids (e.g., lymph, seminal fluid, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in pineal gland tissue indicates that polynucleotides and polypeptides corresponding to this gene are useful for the detection, treatment, and/or prevention of various endocrine disorders and cancers, particularly Addison's disease, Cushing's Syndrome, and disorders and/or cancers of the pancrease (e.g. diabetes mellitus), adrenal cortex, ovaries, pituitary (e.g., hyper-, hypopituitarism), thyroid (e.g. hyper-, hypothyroidism), parathyroid (e.g. hyper-, hypoparathyroidism), hypothallamus, and testes. Alternatively, the expression in a variety of immune and hematopoietic disordes indicates that polynucleotides and polypeptides corresponding to this gene are useful for the treatment and/or diagnosis of hematopoietic related disorders such as anemia, pancytopenia, leukopenia, thrombocytopenia or leukemia since stromal cells are important in the production of cells of hematopoietic lineages.

The uses include bone marrow cell ex vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:62 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 832 of SEQ ID NO:62, b is an integer of 15 to 846, where both a and b correspond to the positions of nucleotide residues shown in SEQ ID NO:62, and where b is greater than or equal to a+14.

Features of Protein Encoded by Gene No: 53

When tested against U937 cell lines, supernatants removed from cells containing this gene activated the GAS (gamma activation site) promoter. Thus, it is likely that this gene activates promyelocytic cells, or more generally, immune or hematopoietic cells, in addition to other cells or cell types, through the Jaks-STAT signal transduction pathway. GAS is a promoter element found upstream in many genes which are involved in the Jaks-STAT pathway. The Jaks-STAT pathway is a large, signal transduction pathway involved in the differentiation and proliferation of cells.

Therefore, activation of the Jaks-STATs pathway, reflected by the binding of the GAS element, can be used to indicate proteins involved in the proliferation and differentiation of cells.

This gene is expressed primarily in frontal cortex and cerebellum tissues.

Therefore, polynucleotides and polypeptides of the invention are useful as reagents for differential identification of the tissue(s) or cell type(s) present in a biological sample and for diagnosis of diseases and conditions which include, but are not limited to, neural or hematopoietic disorders. Similarly, polypeptides and antibodies directed to these polypeptides are useful in providing immunological probes for differential identification of the tissue(s) or cell type(s). For a number of disorders of the above tissues or cells, particularly of the neural system, expression of this gene at significantly higher or lower levels may be routinely detected in certain tissues or cell types (e.g., neural, hematopoietic, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in frontal cortex and cerebellum tissues indicates that polynucleotides and polypeptides corresponding to this gene are useful for the detection and/or treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:63 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1428 of SEQ ID NO:63, b is an integer of 15 to 1442, where both a and b correspond to the positions of nucleotide residues shown in SEQ ID NO:63, and where b is greater than or equal to a+14.

Features of Protein Encoded by Gene No: 54

This gene is expressed primarily in T-cell activated by PHA.

Therefore, polynucleotides and polypeptides of the invention are useful as reagents for differential identification of the tissue(s) or cell type(s) present in a biological sample and for diagnosis of diseases and conditions which include, but are not limited to, immune disorders, particularly those imvolving T lymphocytes, such as immunodeficiency disorders and AIDS. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cells (e.g., immune, hematopoietic, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:140 as residues: Ser-17 to Met-22, Cys-25 to Thr-37.

The tissue distribution in T cells indicates that polynucleotides and polypeptides corresponding to this gene are useful for the diagnosis and/or treatment of a variety of immune system disorders. Expression of this gene product in T-cells indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses). Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:64 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 990 of SEQ ID NO:64, b is an integer of 15 to 1004, where both a and b correspond to the positions of nucleotide residues shown in SEQ ID NO:64, and where b is greater than or equal to a+14.

Features of Protein Encoded by Gene No: 55

The translation product of this gene shares sequence homology with a murine transmembrane protein which is thought to be important in tumorigenesis (See Genbank Accession No. gi|535682). In specific embodiments, polypeptides of the invention comprise the following amino acid sequence: ARAAPRLLLLFLVPLLWAPAAVRAG PDEDLSHRNKEPPAPAQQLQPQPVAVQG-PEPARVEDPYGVAVGGTVGHCLC T GLAVIGGRMI-AQKISVRTVTIIGGIVFLAFAFSALFISPDSGF (SEQ ID NO:233). Polynucleotides encoding these polypeptides are also encompassed by the invention.

This gene is expressed primarily in skin tumor tissue, colorectal tumor tissue, placental tissue and synovial fibroblasts and to a lesser extent in mutiple sclerosis, lymphoma, hypothalmus and spinal cord tissues.

Therefore, polynucleotides and polypeptides of the invention are useful as reagents for differential identification of the tissue(s) or cell type(s) present in a biological sample and for diagnosis of diseases and conditions which include, but are not limited to, integumentary disorders, particularly tumors, sclerosis, or reproductive or neural disorders, such as schizophrenia. Similarly, polypeptides and antibodies directed to these polypeptides are useful in providing immunological probes for differential identification of the tissue(s) or cell type(s). For a number of disorders of the above tissues or cells, particularly of the neural and immune system, expression of this gene at significantly higher or lower levels may be routinely detected in certain tissues or cells (e.g., skeletal, reproductive, integumentary, neural, or cancerous and wounded tissues) or bodily fluids (e.g., lymph, amniotic fluid, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:141 as residues: Gly-7 to Pro-15.

The tissue distribution in a number of tumor tissues as well as in placental tissue, combined with its homology to a putative tumorigenic protein, indicates that polynucleotides and polypeptides corresponding to this gene are useful for the diagnosis and/or treatment of cancer and other proliferative disorders. Expression within skin and colon tumors, in addition to placental tissue, and other cellular sources marked by proliferating cells indicates that this protein may play a role in the regulation of cellular division. Additionally, the expression in hematopoietic cells and tissues indicates that this protein may play a role in the proliferation, differentiation, and/or survival of hematopoietic cell lineages. In such an event, this gene may be useful in the treatment of lymphoproliferative disorders, and in the maintenance and differentiation of various hematopoietic lineages from early hematopoietic stem and committed progenitor cells. Similarly, embryonic development also involves decisions involving cell differentiation and/or apoptosis in pattern formation. Thus this protein may also be involved in apoptosis or tissue differentiation and could again be useful in cancer therapy.

Many polynucleotide sequences, such as EST sequences, are publicly available and accessible through sequence databases. Some of these sequences are related to SEQ ID NO:65 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1669 of SEQ ID NO:65, b is an integer of 15 to 1683, where both a and b correspond to the positions of nucleotide residues shown in SEQ ID NO:65, and where b is greater than or equal to a+14.

Features of Protein Encoded by Gene No: 56

The translation product of this gene was shown to have homology to the human hMed7 protein, which is thought to play a pivotal role in the regulation of the human RNA polymerase II C-terminal domain (See Genbank Accession No.gi|2736290 (AF031383)). In specific embodiments, polypeptides of the invention comprise the following amino acid sequence: FRIAWLLCLMICLIQKQECRVKTEPMDADDSNN CTGQNEHQRENSGHRRDQIIEKDAALCVLIDEMNERP (SEQ ID NO:234), RVK TEPMDADDSNNCTGQNEHQRENSGHRRDQIIEKDAALCV LIDEMNERP (SEQ ID NO:235), QVSALPPPPMQYIKEYTDENIQEGLA (SEQ ID NO:236), SQGIERL HPMQFDHKKELRKLNMS (SEQ ID NO:237), and/or LETAERFQKHLERVIEMI QNCLASLPDDLPH (SEQ ID NO:238). Polynucleotides encoding these polypeptides are also encompassed by the invention. The gene encoding the disclosed cDNA is thought to reside on chromosome 5. Accordingly, polynucleotides related to this invention are useful as a marker in linkage analysis for chromosome 5.

This gene is expressed primarily in fetal and placental tissues, as well as in various tumors.

Therefore, polynucleotides and polypeptides of the invention are useful as reagents for differential identification of the tissue(s) or cell type(s) present in a biological sample and for diagnosis of diseases and conditions which include, but are not limited to, developmental disorders and tumors. Similarly, polypeptides and antibodies directed to these polypeptides are useful in providing immunological probes for differential identification of the tissue(s) or cell type(s). For a number of disorders of the above tissues or cells, particularly of the immune system and developing tissues, expression of this gene at significantly higher or lower levels may be routinely detected in certain tissues or cells (e.g., developmental, reproductive, or cancerous and wounded tissues) or bodily fluids (e.g., lymph, amniotic fluid, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in fetal and placental tissues, as well as in tumor tissues, combined with the homology to the human hMed7 protein, indicates that polynucleotides and polypeptides corresponding to this gene are useful for the diagnosis and/or treatment of cancer and other proliferative disorders. Expression within embryonic tissue and other cellular sources marked by proliferating cells indicates that this protein may play a role in the regulation of cellular division.

Additionally, the expression in hematopoietic cells and tissues indicates that this protein may play a role in the proliferation, differentiation, and/or survival of hematopoietic cell lineages. In such an event, this gene may be useful in the treatment of lymphoproliferative disorders, and in the maintenance and differentiation of various hematopoietic lineages from early hematopoietic stem and committed progenitor cells. Similarly, embryonic development also involves decisions involving cell differentiation and/or apoptosis in pattern formation. Thus this protein may also be involved in apoptosis or tissue differentiation and could again be useful in cancer therapy Protein, as well as, antibodies directed against the protein may show utility as a tumor marker and/or immunotherapy targets for the abovelisted tissues.

Many polynucleotide sequences, such as EST sequences, are publicly available and accessible through sequence databases. Some of these sequences are related to SEQ ID NO:66 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1427 of SEQ ID NO:66, b is an integer of 15 to 1441, where both a and b correspond to the positions of nucleotide residues shown in SEQ ID NO:66, and where b is greater than or equal to a+14.

Features of Protein Encoded by Gene No: 57

In specific embodiments, polypeptides of the invention comprise the following amino acid sequence: NSAR-GALSSADSCHFSRPPLSEETRRWETG (SEQ ID NO:239). Polynucleotides encoding these polypeptides are also encompassed by the invention.

This gene is expressed primarily in human early stage brain tissue.

Therefore, polynucleotides and polypeptides of the invention are useful as reagents for differential identification of the tissue(s) or cell type(s) present in a biological sample and for diagnosis of diseases and conditions which include, but are not limited to, developmental or neural disorders, particularly maliganant fibrous histiocytoma and related cancers. Similarly, polypeptides and antibodies directed to these polypeptides are useful in providing immunological probes for differential identification of the tissue(s) or cell type(s). For a number of disorders of the above tissues or cells, particularly of the neural system, expression of this gene at significantly higher or lower levels may be routinely detected in certain tissues or cells (e.g., neural, developmental, or cancerous and wounded tissues) or bodily fluids (e.g., lymph, amniotic fluid, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in brain tissue indicates that polynucleotides and polypeptides corresponding to this gene are useful for the detection and/or treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Alternatively, the tissue distribution in an early stage human tissue indicates that polynucleotides and polypeptides corresponding to this gene are useful for the diagnosis and treatment of cancer and other proliferative disorders. Expression within embryonic tissue and other cellular sources marked by proliferating cells indicates that this protein may play a role in the regulation of cellular division.

Additionally, the expression in hematopoietic cells and tissues indicates that this protein may play a role in the proliferation, differentiation, and/or survival of hematopoietic cell lineages. In such an event, this gene may be useful in the treatment of lymphoproliferative disorders, and in the maintenance and differentiation of various hematopoietic lineages from early hematopoietic stem and committed progenitor cells. Similarly, embryonic development also involves decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the abovelisted tissues.

Many polynucleotide sequences, such as EST sequences, are publicly available and accessible through sequence databases. Some of these sequences are related to SEQ ID NO:67 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 608 of SEQ ID NO:67, b is an integer of 15 to 622, where both a and b correspond to the positions of nucleotide residues shown in SEQ ID NO:67, and where b is greater than or equal to a+14.

Features of Protein Encoded by Gene No: 58

The translation product of this gene was shown to have homology to an R47650 Interferon induced 1-8 gene encoded polypeptide, which is known to be able to inhibit retroviral protein synthesis and/or assembly of retroviral structural proteins. The polypeptide can be used for treating or preventing retroviral infection, e.g. HIV; HTLV; bovine leukaemia virus, or can be used to assay the efficacy of interferon therapy. They can also be used for extracorporeal treatment of a host's cells or for inhibiting retroviral replication in the cell. In specific embodiments, polypeptides of the invention comprise the following amino acid sequence:

MTMITPSSKLTLTKGNKSWSSTAVAAALE LVDP-PGCRNSPPPPHTPFSYAFGVLDGNLG-GERKDRSGLPQPLLLLSPRVRIAG APPSWFLRTRPFS-FCLYLLRILSLLMWLTPLPPLPAGGWPGGQVPAGAVNR XCAFVLVCACAVFLCFDRS (SEQ ID NO:240), LTLT-KGNKSWSSTAVAAALELV DPPGCR (SEQ ID NO:241), ADNNFTQETAMTMITPSSKLTLTKGNKSWSSTAV AAALELVDPPGCR (SEQ ID NO:242), NSPPPHT-PFSYAFGVLDGNLGGERKD RSGLPQPLLLL-SPRVRIAGAPP (SEQ ID NO:243), and/or PSWFLRTR-PFSFCLYL
LRILSLLMWLTPLPPLPAGGWPGGQVPAGAVNR (SEQ ID NO:244). Polynucleotides encoding these polypeptides are also encompassed by the invention.

This gene is expressed primarily in eosinophils and neutrophils, fetal liver tissue, and small intestine tissue.

Therefore, polynucleotides and polypeptides of the invention are useful as reagents for differential identification of the tissue(s) or cell type(s) present in a biological sample and for diagnosis of diseases and conditions which include, but are not limited to, hepatic, developmental, or immune disorders, particularly inflammation. Similarly, polypeptides and antibodies directed to these polypeptides are useful in providing immunological probes for differential identification of the tissue(s) or cell type(s). For a number of disorders of the above tissues or cells, particularly of the immune or hepatic system, expression of this gene at significantly higher or lower levels may be routinely detected in certain tissues or cell types (e.g., hepatic, immune, developmental, or cancerous and wounded tissues) or bodily fluids (e.g., lymph, bile, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:144 as residues: Glu-12 to Gln-18.

The tissue distribution in immune tissues and leukocytes (neutrophils, eosinophils) indicates that polynucleotides and polypeptides corresponding to this gene are useful for the diagnosis and/or treatment of a variety of immune system disorders. Expression of this gene product in eosinophils and neutrophils indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types. Furthermore, expression of this gene product in neutrophils and eosinophils also strongly indicates a role for this protein in immune function and immune surveillance.

Alternatively, expression within infant liver tissue indicates that polynucleotides and polypeptides corresponding to this gene are useful for the detection and/or treatment of liver disorders and cancers (e.g. hepatoblastoma, jaundice, hepatitis, liver metabolic diseases and conditions that are attributable to the differentiation of hepatocyte progenitor cells). In addition the expression in fetus would suggest a useful role for the protein product in developmental abnormalities, fetal deficiencies, pre-natal disorders and various would-healing models and/or tissue trauma.

Many polynucleotide sequences, such as EST sequences, are publicly available and accessible through sequence databases. Some of these sequences are related to SEQ ID NO:68 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 602 of SEQ ID NO:68, b is an integer of 15 to 616, where both a and b correspond to the positions of nucleotide residues shown in SEQ ID NO:68, and where b is greater than or equal to a+14.

Features of Protein Encoded by Gene No: 59

The gene encoding the disclosed cDNA is believed to reside on chromosome 8. Accordingly, polynucleotides related to this invention are useful as a marker in linkage analysis for chromosome 8. In specific embodiments, polypeptides of the invention comprise the following amino acid sequence: RAPERSSAGRVPPPEPAAPMAG GYGV (SEQ ID NO:245). Polynucleotides encoding these polypeptides are also encompassed by the invention.

This gene is expressed primarily in infant brain tissue.

Therefore, polynucleotides and polypeptides of the invention are useful as reagents for differential identification of the tissue(s) or cell type(s) present in a biological sample and for diagnosis of diseases and conditions which include, but are not limited to, neural or developmental disorders, particularly ischemic damage to the CNS. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., neural, developmental, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:145 as residues: Met-1 to Ser-6, Pro-51 to Ser-57, Ser-78 to Asp-93.

The tissue distribution in infant brain tissue indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:69 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1005 of SEQ ID NO:69, b is an integer of 15 to 1019, where both a and b correspond to the positions of nucleotide residues shown in SEQ ID NO:69, and where b is greater than or equal to a+14.

Features of Protein Encoded by Gene No: 60

The gene encoding the disclosed cDNA is believed to reside on chromosome 7. Accordingly, polynucleotides related to this invention are useful as a marker in linkage analysis for chromosome 7. In specific embodiments, polypeptides of the invention comprise the following amino acid sequence: TFGLLLSFGYYECYKYLCTSICVD (SEQ ID NO:246). Polynucleotides encoding these polypeptides are also encompassed by the invention.

This gene is expressed primarily in the immune system including T helper II cells, neutrophils, CD34 (+) buffy coat cells and lymph nodes.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders, particularly inflamation, autoimmunity, and immunodeficiencies such as AIDS. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in immune system cells and tissues indicates that polynucleotides and polypeptides corresponding to this gene are useful for the diagnosis and/or treatment of a variety of immune system disorders. Expression of this gene product in T-cells indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types.

Furthermore, the tissue distribution in helper T-cells indicates that polynucleotides and polypeptides corresponding to this gene are useful for the diagnosis and/or treatment of a variety of disorders of the immune system. Elevated or specific expression of this gene product in T cells, notably helper T cells, indicates that it may play key roles in the regulation and coordination of immune responses. For example, it may be involved in the regulation of the activation state of T cells, or the activation/differentiation of other key hematopoietic lineages, including neutrophils, B cells, monocytes, and macrophages. Therefore, this gene product may have clinical relevance in the treatment of impaired immunity; in the correction of autoimmunity; in immune modulation; in the treatment of allergy; and in the regulation of inflammation. It may also play a role in influencing differentiation of specific hematopoietic lineages, and may even affect the hematopoietic stem cell. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:70 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 817 of SEQ ID NO:70, b is an integer of 15 to 831, where both a and b correspond to the positions of nucleotide residues shown in SEQ ID NO:70, and where b is greater than or equal to a+14.

Features of Protein Encoded by Gene No: 61

In specific embodiments, polypeptides of the invention comprise the following amino acid sequence: EHCFLRPD-CLFAWRFLSQHPAGLGEDDTSIPLTLQGLL (SEQ ID NO:247). Polynucleotides encoding these polypeptides are also encompassed by the invention.

This gene is expressed in the medulla region of the kidney.

Therefore, polynucleotides and polypeptides of the invention are useful as reagents for differential identification of the tissue(s) or cell type(s) present in a biological sample and for diagnosis of diseases and conditions which include, but are not limited to, urogenital or renal disorders, particularly kidney failure. Similarly, polypeptides and antibodies directed to these polypeptides are useful in providing immunological probes for differential identification of the tissue(s) or cell type(s). For a number of disorders of the above tissues or cells, particularly of the renal system, expression of this gene at significantly higher or lower levels may be routinely detected in certain tissues or cell types (e.g., urogenital, renal, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:147 as residues: Lys-8 to Thr-13, Glu-39 to Gly-46.

The tissue distribution in kidney tissue indicates that this gene or gene product could be used in the treatment and/or detection of kidney diseases including renal failure, nephritus, renal tubular acidosis, proteinuria, pyuria, edema, pyelonephritis, hydronephritis, nephrotic syndrome, crush syndrome, glomerulonephritis, hematuria, renal colic and kidney stones, in addition to Wilms Tumor Disease, and congenital kidney abnormalities such as horseshoe kidney, polycystic kidney, and Falconi's syndrome. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:71 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 736 of SEQ ID NO:71, b is an integer of 15 to 750, where both a and b correspond to the positions of nucleotide residues shown in SEQ ID NO:71, and where b is greater than or equal to a+14.

Features of Protein Encoded by Gene No: 62

In specific embodiments, polypeptides of the invention comprise the following amino acid sequence: FRPSPDI-CARECGMVQSSRSSATEKRVTPIHHGQSTQSG SALD-PARQMQPLNRVCASKLDDDRRNPVASEK-TPNPRMKASGSIPRNSCRGC CGIFFKRTKQGKTKFNRVEQPGV-VGHACNLSNLGGQGRISAIWEAKAGRSLE PRSSRPA-WAT (SEQ ID NO:248), FRPSPDICAREECGMVQSSRS- SATEKRVTPIHH GQSTQSGSA (SEQ ID NO:249), LDPARQMQPLNRVCASKLDDDRRNPVASEKT PNPRMKAS (SEQ ID NO:250), GSIPRNSCRGC-CGIFFKRTKQGKTKFNRVEQP GVVGHACNLS (SEQ ID NO: 251), and/or NLGGQGRISAIWEAKAGRSLEPRS SRPAWAT (SEQ ID NO: 252). Polynucleotides encoding these polypeptides are also encompassed by the invention.

This gene is expressed primarily in prostate cells and testes tissue.

Therefore, polynucleotides and polypeptides of the invention are useful as reagents for differential identification of the tissue(s) or cell type(s) present in a biological sample and for diagnosis of diseases and conditions which include, but are not limited to, reproductive disorders, particularly prostatic hyperplasia, prostatic cancer and testes cancer. Similarly, polypeptides and antibodies directed to these polypeptides are useful in providing immunological probes for differential identification of the tissue(s) or cell type(s). For a number of disorders of the above tissues or cells, particularly of the reproductive system, expression of this gene at significantly higher or lower levels may be routinely detected in certain tissues or cell types (e.g., reproductive, urogenital, endocrine, or cancerous and wounded tissues) or bodily fluids (e.g., lymph, seminal fluid, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:148 as residues: Lys-19 to Asn-32.

The tissue distribution in testes tissue indicates that polynucleotides and polypeptides corresponding to this gene are useful for the treatment, diagnosis, and/or prevention of various disorders of the reproductive system, including cancers of the prostate or testes. Alternatively, the expression within testes may suggest that polynucleotides and polypeptides corresponding to this gene are useful for the detection, treatment, and/or prevention of various endocrine disorders and cancers, particularly Addison's disease, Cushing's Syndrome, and disorders and/or cancers of the pancrease (e.g. diabetes mellitus), adrenal cortex, ovaries, pituitary (e.g., hyper-, hypopituitarism), thyroid (e.g. hyper-, hypothyroidism), parathyroid (e.g. hyper-, hypoparathyroidism), hypothallamus, and testes.

Similarly, the tissue distribution indicates that polynucleotides and polypeptides corresponding to this gene are useful for the treatment and diagnosis of conditions concerning proper testicular function (e.g. endocrine function, sperm maturation), as well as cancer. Therefore, this gene product is useful in the treatment of male infertility and/or impotence. This gene product is also useful in assays designed to identify binding agents, as such agents (antagonists) are useful as male contraceptive agents. Similarly, the protein is believed to be useful in the treatment and/or diagnosis of testicular cancer. The testes are also a site of active gene expression of transcripts that may be expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:72 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 700 of SEQ ID NO:72, b is an integer of 15 to 714, where both a and b correspond to the positions of nucleotide residues shown in SEQ ID NO:72, and where b is greater than or equal to a+14.

Features of Protein Encoded by Gene No: 63

In specific embodiments, polypeptides of the invention comprise the following amino acid sequence: GYLLIAETQ (SEQ ID NO:253). Polynucleotides encoding these polypeptides are also encompassed by the invention.

This gene is expressed primarily in hepatocellular tumors, skin tumors, and osteoclastoma, and to a lesser extent in kidney and lung tissues.

Therefore, polynucleotides and polypeptides of the invention are useful as reagents for differential identification of the tissue(s) or cell type(s) present in a biological sample and for diagnosis of diseases and conditions which include, but are not limited to, tumors, particularly of the hepatic, integumentary and/or skeletal systems. Similarly, polypeptides and antibodies directed to these polypeptides are useful in providing immunological probes for differential identification of the tissue(s) or cell type(s). For a number of disorders of the above tissues or cells, particularly of the skin and hepatic system, expression of this gene at significantly higher or lower levels may be routinely detected in certain tissues or cell types (e.g., integumentary, hepatic, skeletal, or cancerous and wounded tissues) or bodily fluids (e.g., lymph, bile, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:149 as residues: Pro-10 to Pro-17.

The tissue distribution in skin tissue indicates that polynucleotides and polypeptides corresponding to this gene are useful for the treatment, diagnosis, and/or prevention of various skin disorders including congenital disorders (i.e. nevi, moles, freckles, Mongolian spots, hemangiomas, port-wine syndrome), integumentary tumors (i.e. keratoses, Bowen's disease, basal cell carcinoma, squamous cell carcinoma, malignant melanoma, Paget's disease, mycosis fungoides, and Kaposi's sarcoma), injuries and inflammation of the skin (i.e. wounds, rashes, prickly heat disorder, psoriasis, dermatitis), atherosclerosis, uticaria, eczema, photosensitivity, autoimmune disorders (i.e. lupus erythematosus, vitiligo, dermatomyositis, morphea, scleroderma, pemphigoid, and pemphigus), keloids, striae, erythema, petechiae, purpura, and xanthelasma.

Moreover, such disorders may predispose increased susceptibility to viral and bacterial infections of the skin (i.e. cold sores, warts, chickenpox, molluscum contagiosum, herpes zoster, boils, cellulitis, erysipelas, impetigo, tinea, althletes foot, and ringworm). Alternatively, expression within bone tissue would suggest a role in the detection and treatment of disorders and conditions affecting the skeletal system, in particular osteoporosis as well as disorders afflicting connective tissues (e.g. arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (ie. spondyloepiphyseal dysplasia congenita, familial osteoarthritis, Atelosteogenesis type II, metaphyseal chondrodysplasia type Schmid). Elevated levels of expression of this gene product in osteoclastoma indicates that it may play a role in the survival, proliferation, and/or growth of osteoclasts. Therefore, it may be useful in influencing bone mass in such conditions as osteoporosis. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:73 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1391 of SEQ ID NO:73, b is an integer of 15 to 1405, where both a and b correspond to the positions of nucleotide residues shown in SEQ ID NO:73, and where b is greater than or equal to a+14.

Features of Protein Encoded by Gene No: 64

In specific embodiments, polypeptides of the invention comprise the following amino acid sequence: HSXIXPHPPLLIDSRFTQLVNLSSEPSPKLICPQNSTPSP SLSLPTHASDSPGSTSEMSAK-TLLIQAVFPVQKRGSTFSLALFELNMQLPGVT (SEQ ID NO:254). Polynucleotides encoding these polypeptides are also encompassed by the invention.

This gene is expressed primarily in meningima tissue.

Therefore, polynucleotides and polypeptides of the invention are useful as reagents for differential identification of the tissue(s) or cell type(s) present in a biological sample and for diagnosis of diseases and conditions which include, but are not limited to, meningioma. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., neural, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in meningima tissue indicates that polynucleotides and polypeptides corresponding to this gene are useful for the diagnosis and/or treatment of tumors of the meninges, as well as tumors of other tissues where expression has been observed. Similarly, the tissue distribution indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:74 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 893 of SEQ ID NO:74, b is an integer of 15 to 907, where both a and b correspond to the positions of nucleotide residues shown in SEQ ID NO:74, and where b is greater than or equal to a+14.

Features of Protein Encoded by Gene No: 65

This gene is expressed primarily in Wilm's tumor tissue.

Therefore, polynucleotides and polypeptides of the invention are useful as reagents for differential identification of the tissue(s) or cell type(s) present in a biological sample and for diagnosis of diseases and conditions which include, but are not limited to, urogenital or renal disorders, particularly tumors of the kidney. Similarly, polypeptides and antibodies directed to these polypeptides are useful in providing immunological probes for differential identification of the tissue(s) or cell type(s). For a number of disorders of the above tissues or cells, particularly of the renal, expression of this gene at significantly higher or lower levels may be routinely detected in certain tissues or cell types (e.g., renal, urogenital, or cancerous and wounded tissues) or bodily fluids (e.g., lymph, bile, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:151 as residues: Glu-6 to Cys-12.

The tissue distribution in Wilm's tumor tissue of the kidney indicates that this gene or gene product could be used in the treatment and/or detection of kidney diseases including renal failure, nephritis, renal tubular acidosis, proteinuria, pyuria, edema, pyelonephritis, hydronephritis, nephrotic syndrome, crush syndrome, glomerulonephritis, hematuria, renal colic and kidney stones, in addition to Wilms Tumor Disease, and congenital kidney abnormalities such as horseshoe kidney, polycystic kidney, and Falconi's syndrome. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:75 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 673 of SEQ ID NO:75, b is an integer of 15 to 687, where both a and b correspond to the positions of nucleotide residues shown in SEQ ID NO:75, and where b is greater than or equal to a+14.

Features of Protein Encoded by Gene No: 66

In specific embodiments, polypeptides of the invention comprise the following amino acid sequence: KVRTENSENNQNKIYSYFSLKSWKNFG-FXLRFLSPTHAF TNYVFVYSMSAAQAEGASLHG-MRG (SEQ ID NO:255). Polynucleotides encoding these polypeptides are also encompassed by the invention.

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders, such as autoimmune diseases or inflammatory diseases. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The tissue distribution in neutrophils indicates that polynucleotides and polypeptides corresponding to this gene are useful for the diagnosis and/or treatment of a variety of immune system disorders. Expression of this gene product in neutrophils indicates a role in the regulation of the proliferation; survival; differentiation; and/or activation of potentially all hematopoietic cell lineages, including blood stem cells. This gene product may be involved in the regulation of cytokine production, antigen presentation,. or other processes that may also suggest a usefulness in the treatment of cancer (e.g. by boosting immune responses).

Moreover, since the gene is expressed in cells of lymphoid origin, the natural gene product may be involved in immune functions. Therefore it may also be used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Expression of this gene product in neutrophils also strongly indicates a role for this protein in immune function and immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:76 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 778 of SEQ ID NO:76, b is an integer of 15 to 792, where both a and b correspond to the positions of nucleotide residues shown in SEQ ID NO:76, and where b is greater than or equal to a+14.

Features of Protein Encoded by Gene No: 67

In specific embodiments, polypeptides of the invention comprise the following amino acid sequence: SSTLKSSC-CCFQPRKFS (SEQ ID NO:256). Polynucleotides encoding these polypeptides are also encompassed by the invention.

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders, such as diseases resulting from chronic or acute inflammatory response. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:153 as residues: Pro-43 to Ser-49, Met-56 to Gly-66, Gln-69 to Pro-75.

The tissue distribution in neutrophils indicates that polynucleotides and polypeptides corresponding to this gene are useful for the diagnosis and/or treatment of a variety of immune system disorders. Expression of this gene product in neutrophils indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types. Expression of this gene product in neutrophils also strongly indicates a role for this protein in immune function and immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:77 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 742 of SEQ ID NO:77, b is an integer of 15 to 756, where both a and b correspond to the positions of nucleotide residues shown in SEQ ID NO:77, and where b is greater than or equal to a+14.

Features of Protein Encoded by Gene No: 68

In specific embodiments, polypeptides of the invention comprise the following amino acid sequence: AAMVTM-VTGSQPETT (SEQ ID NO:257). Polynucleotides encoding these polypeptides are also encompassed by the invention.

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders, such as inflammation or autoimmune diseases. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:154 as residues: Pro-24 to Glu-29, Glu-31 to Pro-37, Pro-48 to Asp-55, Arg-87 to Pro-93, Pro-100 to Ser-106.

The tissue distribution in neutrophils indicates that polynucleotides and polypeptides corresponding to this gene are useful for the diagnosis and/or treatment of a variety of immune system disorders. Expression of this gene product in neutrophils indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types. Expression of this gene product in neutrophils also strongly indicates a role for this protein in immune function and immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:78 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 737 of SEQ ID NO:78, b is an integer of 15 to 751, where both a and b correspond to the positions of nucleotide residues shown in SEQ ID NO:78, and where b is greater than or equal to a+14.

Features of Protein Encoded by Gene No: 69

The gene encoding the disclosed cDNA is believed to reside on chromosome 12. Accordingly, polynucleotides related to this invention are useful as a marker in linkage analysis for chromosome 12.

This gene is expressed primarily in fetal ear tissue, and to a lesser extent in osteoclastoma.

Therefore, polynucleotides and polypeptides of the invention are useful as reagents for differential identification of the tissue(s) or cell type(s) present in a biological sample and for diagnosis of diseases and conditions which include, but are not limited to, skeletal or developmental disorders, particularly abnormal bone formation such as bone tumors. Similarly, polypeptides and antibodies directed to these polypeptides are useful in providing immunological probes for differential identification of the tissue(s) or cell type(s). For a number of disorders of the above tissues or cells, particularly of the skeletal system, expression of this gene at significantly higher or lower levels may be routinely detected in certain tissues or cell types (e.g., skeletal, or cancerous and wounded tissues) or bodily fluids (e.g., lymph, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

The expression of this gene product in osteoclasts would suggest a role in the detection and/or treatment of disorders and conditions affecting the skeletal system, in particular osteoporosis as well as disorders afflicting connective tissues (e.g. arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (ie. spondyloepiphyseal dysplasia congenita, familial osteoarthritis, Atelosteogenesis type II, metaphyseal chondrodysplasia type Schmid). Elevated levels of expression of this gene product in osteoclastoma indicates that it may play a role in the survival, proliferation, and/or growth of osteoclasts. Therefore, it may be useful in influencing bone mass in such conditions as osteoporosis. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:79 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1397 of SEQ ID NO:79, b is an integer of 15 to 1411, where both a and b correspond to the positions of nucleotide residues shown in SEQ ID NO:79, and where b is greater than or equal to a+14.

Features of Protein Encoded by Gene No: 70

The translation product of this gene was found to have homology to the human kidney epidermal growth factor precursor (See Genbank Accession No. R51437). The gene encoding the disclosed cDNA is believed to reside on chromosome 3. Accordingly, polynucleotides related to this invention are useful as a marker in linkage analysis for chromosome 3.

This gene is expressed primarily in brain, and to a lesser extent, in prostate.

Therefore, polynucleotides and polypeptides of the invention are useful as reagents for differential identification of the tissue(s) or cell type(s) present in a biological sample and for diagnosis of diseases and conditions which include, but are not limited to, neural or reproductive disorders, particularly prostate disease such as tumors of the prostate and benign prostatic hypertrophy. Similarly, polypeptides and antibodies directed to these polypeptides are useful in providing immunological probes for differential identification of the tissue(s) or cell type(s). For a number of disorders of the above tissues or cells, particularly of the endocrine, neural or reproductive systems, expression of this gene at significantly higher or lower levels may be routinely detected in certain tissues or cells (e.g. reproductive, neural, or cancerous and wounded tissues) or bodily fluids (e.g. lymph, seminal fluid, serum, plasma, urine, synovial fluid and spinal fluid) or another tissue or cell sample taken from anindividual having such a disorder, relative to the standard gene expression level, i.e., the expression level in healthy tissue or bodily fluid from an individual not having the disorder.

Preferred epitopes include those comprising a sequence shown in SEQ ID NO:156 as residues: Pro-31 to Thr-48, Arg-62 to Gly-70, Ala-74 to Glu-87, Lys-123 to Asp-129, Pro-162 to Gly-167, Glu-170 to Gly-189, Arg-220 to Asn-228.

The tissue distribution indicates that the protein product of this gene is useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered bahaviors, including disorders in feeding, sleep patterns, balance, and preception. In addition, the gene or gene product may also play a role in the treatment and/or detection of developmental disorders associated with the developing embryo, sexually-linked disorders, or disorders of the cardiovascular system. Alternatively, expression within the prostate indicates that the translation product of this gene is useful for the detection, treatment, and/or prevention of a variety of reproductive disorders, including prostate cancer, and infertility. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:80 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1761 of SEQ ID NO:80, b is an integer of 15 to 1775, where both a and b correspond to the positions of nucleotide residues shown in SEQ ID NO:80, and where b is greater than or equal to a+14.

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 1 | HCUDK80 | 209178 Jul. 24, 1997 | ZAP Express | 11 | 392 | 1 | 392 | 80 | 80 | 87 | 1 | 26 | 27 | 29 |
| 2 | HCWFV11 | 209178 Jul. 24, 1997 | ZAP Express | 12 | 465 | 1 | 465 | 126 | 126 | 88 | 1 | 33 | 34 | 33 |
| 3 | HCWHN10 | 209178 Jul. 24, 1997 | ZAP Express | 13 | 674 | 1 | 674 | 85 | 85 | 89 | 1 | 25 | 26 | 65 |
| 4 | HCWHT35 | 209178 Jul. 24, 1997 | ZAP Express | 14 | 297 | 1 | 297 | 36 | 36 | 90 | 1 | 16 | 17 | 26 |
| 5 | HDTAE40 | 209178 Jul. 24, 1997 | pCMVSport 2.0 | 15 | 604 | 1 | 604 | 110 | 110 | 91 | 1 | 34 | 35 | 48 |
| 6 | HE2BX71 | 209178 Jul. 24, 1997 | Uni-ZAP XR | 16 | 1146 | 203 | 1146 | 276 | 276 | 92 | 1 | 27 | 28 | 32 |
| 7 | HE2EO70 | 209178 Jul. 24, 1997 | Uni-ZAP XR | 17 | 678 | 1 | 678 | 150 | 150 | 93 | 1 | 15 | 16 | 22 |
| 8 | HE8DY08 | 209178 Jul. 24, 1997 | Uni-ZAP XR | 18 | 1305 | 393 | 1305 | 734 | 734 | 94 | 1 | 23 | 24 | 54 |
| 9 | HE9NB19 | 209178 Jul. 24, 1997 | Uni-ZAP XR | 19 | 1060 | 1 | 1060 | 174 | 174 | 95 | 1 | 26 | 27 | 38 |
| 10 | HE9ND27 | 209178 Jul. 24, 1997 | Uni-ZAP XR | 20 | 1170 | 95 | 1170 | 353 | 353 | 96 | 1 | 27 | 28 | 52 |

-continued

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 11 | HCE3G69 | 209878 May 18, 1998 | Uni-ZAP XR | 21 | 2084 | 1 | 2084 | 165 | 165 | 97 | 1 | 19 | 20 | 336 |
| 11 | HEAAA85 | 209178 Jul. 24, 1997 | Uni-ZAP XR | 81 | 2078 | 1290 | 2065 | 1295 | 1295 | 157 | 1 | 58 | 59 | 118 |
| 12 | HEAAX57 | 209178 Jul. 24, 1997 | Uni-ZAP XR | 22 | 643 | 1 | 643 | 127 | 127 | 98 | 1 | 38 | 39 | 48 |
| 13 | HEEAG93 | 209178 Jul. 24, 1997 | Uni-ZAP XR | 23 | 647 | 1 | 647 | 334 | 334 | 99 | 1 | 21 | 22 | 37 |
| 14 | HEGAI91 | 209178 Jul. 24, 1997 | Uni-ZAP XR | 24 | 825 | 1 | 825 | 179 | 179 | 100 | 1 | 18 | 19 | 28 |
| 15 | HEIAU93 | 209178 Jul. 24, 1997 | Uni-ZAP XR | 25 | 541 | 1 | 541 | 96 | 96 | 101 | 1 | 24 | 25 | 35 |
| 16 | HEMGD15 | 209178 Jul. 24, 1997 | Uni-ZAP XR | 26 | 852 | 1 | 711 | 20 | 20 | 102 | 1 | 31 | 32 | 181 |
| 17 | HEQBR95 | 209178 Jul. 24, 1997 | pCMVSport 3.0 | 27 | 4598 | 2673 | 3242 | 2767 | 2767 | 103 | 1 | 50 | 51 | 83 |
| 18 | HFCEW42 | 209178 Jul. 24, 1997 | Uni-ZAP XR | 28 | 585 | 1 | 585 | 95 | 95 | 104 | 1 | 18 | 19 | 24 |
| 19 | HFIXC91 | 209178 Jul. 24, 1997 | pSport1 | 29 | 824 | 1 | 824 | 244 | 244 | 105 | 1 | 19 | 20 | 31 |
| 20 | HFKFN45 | 209178 Jul. 24, 1997 | Uni-ZAP XR | 30 | 751 | 211 | 751 | 20 | 20 | 106 | 1 | 42 | 43 | 175 |
| 20 | HFKFN45 | 209178 Jul. 24, 1997 | Uni-ZAP XR | 82 | 773 | 153 | 721 | 428 | 428 | 158 | 1 | 25 | 26 | 27 |
| 21 | HFKGE44 | 209178 Jul. 24, 1997 | Uni-ZAP XR | 31 | 817 | 1 | 817 | 218 | 218 | 107 | 1 | 30 | 31 | 119 |
| 21 | HFKGE44 | 209178 Jul. 24, 1997 | Uni-ZAP XR | 83 | 969 | 141 | 969 | 363 | 363 | 159 | 1 | 29 | 30 | 86 |
| 22 | HFPCY39 | 209178 Jul. 24, 1997 | Uni-ZAP XR | 32 | 1355 | 1 | 606 | 362 | 362 | 108 | 1 | 14 | 15 | 127 |
| 23 | HFTBS49 | 209178 Jul. 24, 1997 | Uni-ZAP XR | 33 | 536 | 1 | 362 | 232 | 232 | 109 | 1 | 30 | 31 | 30 |
| 24 | HFVHE58 | 209178 Jul. 24, 1997 | pBluescript | 34 | 1123 | 594 | 1123 | 762 | 762 | 110 | 1 | 17 | 18 | 31 |
| 25 | HFXDX75 | 209178 Jul. 24, 1997 | Lambda ZAP II | 35 | 587 | 1 | 587 | 300 | 300 | 111 | 1 | 29 | 30 | 96 |
| 26 | HFXFZ81 | 209178 Jul. 24, 1997 | Lambda ZAP II | 36 | 842 | 1 | 842 | 129 | 129 | 112 | 1 | 16 | 17 | 21 |
| 27 | HFXJC53 | 209178 Jul. 24, 1997 | Lambda ZAP II | 37 | 953 | 1 | 953 | 707 | 707 | 113 | 1 | 42 | 43 | 46 |
| 28 | HFXJW48 | 209178 Jul. 24, 1997 | Lambda ZAP II | 38 | 2211 | 63 | 635 | 356 | 356 | 114 | 1 | 17 | 18 | 355 |
| 29 | HGBGO11 | 209178 Jul. 24, 1997 | Uni-ZAP XR | 39 | 682 | 1 | 682 | 58 | 58 | 115 | 1 | 36 | 37 | 70 |
| 30 | HGBHM10 | 209178 Jul. 24, 1997 | Uni-ZAP XR | 40 | 685 | 18 | 665 | 36 | 36 | 116 | 1 | 17 | 18 | 170 |
| 31 | HSSAO72 | 209194 Aug. 1, 1997 | Uni-ZAP XR | 41 | 550 | 1 | 550 | 28 | 28 | 117 | 1 | 34 | 35 | 35 |
| 32 | HSSEO83 | 209194 Aug. 1, 1997 | Uni-ZAP XR | 42 | 602 | 1 | 602 | 233 | 233 | 118 | 1 | | | 13 |
| 33 | HSWAY58 | 209194 Aug. 1, 1997 | pCMVSport 3.0 | 43 | 1627 | 702 | 1627 | 815 | 815 | 119 | 1 | 18 | 19 | 155 |
| 34 | HSXAR64 | 209194 Aug. 1, 1997 | Uni-ZAP XR | 44 | 1457 | 1000 | 1457 | 1191 | 1191 | 120 | 1 | 24 | 25 | 38 |
| 35 | HTECE72 | 209194 Aug. 1, 1997 | Uni-ZAP XR | 45 | 888 | 1 | 888 | 184 | 184 | 121 | 1 | 46 | 47 | 45 |
| 36 | HTEIM65 | 209194 Aug. 1, 1997 | Uni-ZAP XR | 46 | 752 | 1 | 752 | 109 | 109 | 122 | 1 | 19 | 20 | 146 |
| 37 | HTHBX95 | 209194 Aug. 1, 1997 | Uni-ZAP XR | 47 | 1788 | 1025 | 1788 | 1054 | 1054 | 123 | 1 | 25 | 26 | 43 |
| 38 | HTLDQ56 | 209194 Aug. 1, 1997 | Uni-ZAP XR | 48 | 660 | 1 | 660 | 174 | 174 | 124 | 1 | 36 | 37 | 80 |
| 39 | HTOFU06 | 209194 Aug. 1, 1997 | Uni-ZAP XR | 49 | 1321 | 300 | 1321 | 255 | 255 | 125 | 1 | 16 | 17 | 98 |
| 39 | HTOFU06 | 209194 Aug. 1, 1997 | Uni-ZAP XR | 84 | 1064 | 15 | 1064 | 227 | 227 | 160 | 1 | 27 | 28 | 27 |
| 40 | HTPDX06 | 209194 Aug. 1, 1997 | Uni-ZAP XR | 50 | 548 | 1 | 548 | 216 | 216 | 126 | 1 | 21 | 22 | 31 |
| 41 | HTWCE16 | 209194 Aug. 1, 1997 | pSport1 | 51 | 658 | 1 | 658 | 208 | 208 | 127 | 1 | 19 | 20 | 21 |
| 42 | HTWEE31 | 209194 Aug. 1, 1997 | pSport1 | 52 | 622 | 1 | 622 | 27 | 27 | 128 | 1 | 41 | 42 | 121 |

-continued

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 43 | HTWEL91 | 209194 Aug. 1, 1997 | pSport1 | 53 | 723 | 1 | 723 | 154 | 154 | 129 | 1 | 23 | 24 | 25 |
| 44 | HTXDE07 | 209194 Aug. 1, 1997 | Uni-ZAP XR | 54 | 908 | 1 | 908 | 207 | 207 | 130 | 1 | 21 | 22 | 34 |
| 45 | HUFBO40 | 209194 Aug. 1, 1997 | pSport1 | 55 | 822 | 1 | 816 | 172 | 172 | 131 | 1 | 24 | 25 | 38 |
| 46 | HUSAO56 | 209194 Aug. 1, 1997 | Lambda ZAP II | 56 | 1951 | 839 | 1947 | 922 | 922 | 132 | 1 | 26 | 27 | 73 |
| 47 | HUSIJ08 | 209194 Aug. 1, 1997 | pSport1 | 57 | 663 | 1 | 663 | 351 | 351 | 133 | 1 | 50 | 51 | 54 |
| 48 | HAGBD57 | 209194 Aug. 1, 1997 | Uni-ZAP XR | 58 | 778 | 1 | 778 | 221 | 221 | 134 | 1 | 29 | 30 | 43 |
| 49 | HAICJ56 | 209194 Aug. 1, 1997 | Uni-ZAP XR | 59 | 982 | 1 | 982 | 68 | 68 | 135 | 1 | 24 | 25 | 36 |
| 50 | HBAFA04 | 209194 Aug. 1, 1997 | pSport1 | 60 | 406 | 1 | 406 | 96 | 96 | 136 | 1 | 33 | 34 | 49 |
| 51 | HBJES16 | 209194 Aug. 1, 1997 | Uni-ZAP XR | 61 | 813 | 1 | 813 | 309 | 309 | 137 | 1 | 56 | 57 | 84 |
| 52 | HBMTA15 | 209194 Aug. 1, 1997 | Uni-ZAP XR | 62 | 846 | 1 | 846 | 116 | 116 | 138 | 1 | 19 | 20 | 22 |
| 53 | HCEFZ05 | 209194 Aug. 1, 1997 | Uni-ZAP XR | 63 | 1442 | 548 | 1442 | 587 | 587 | 139 | 1 | 15 | 16 | 44 |
| 54 | HCFMX95 | 209194 Aug. 1, 1997 | pSport1 | 64 | 1004 | 1 | 1004 | 186 | 186 | 140 | 1 | 16 | 17 | 46 |
| 55 | HLYHA71 | 209852 05/07/98 | pSport1 | 65 | 1683 | 156 | 1683 | 55 | 55 | 141 | 1 | 25 | 26 | 288 |
| 55 | HDTAR09 | 209194 Aug. 1, 1997 | pCMVSport 2.0 | 85 | 1126 | 355 | 1126 | 602 | 602 | 161 | 1 | 15 | 16 | 45 |
| 56 | HE9FC17 | 209194 Aug. 1, 1997 | Uni-ZAP XR | 66 | 1441 | 590 | 1087 | 780 | 780 | 142 | 1 | 17 | 18 | 23 |
| 57 | HEBAL06 | 209194 Aug. 1, 1997 | Uni-ZAP XR | 67 | 622 | 1 | 622 | 93 | 93 | 143 | 1 | 18 | 19 | 53 |
| 58 | HEIAB33 | 209195 Aug. 1, 1997 | Uni-ZAP XR | 68 | 616 | 1 | 616 | 269 | 269 | 144 | 1 | 43 | 44 | 60 |
| 59 | HEPBC02 | 209195 Aug. 1, 1997 | Uni-ZAP XR | 69 | 1019 | 15 | 829 | 137 | 137 | 145 | 1 | 36 | 37 | 100 |
| 60 | HFTBY96 | 209195 Aug. 1, 1997 | Uni-ZAP XR | 70 | 831 | 1 | 831 | 150 | 150 | 146 | 1 | 17 | 18 | 41 |
| 61 | HKMMM61 | 209195 Aug. 1, 1997 | pBluescript | 71 | 750 | 1 | 750 | 130 | 130 | 147 | 1 | 37 | 38 | 62 |
| 62 | HL3AA35 | 209195 Aug. 1, 1997 | Uni-ZAP XR | 72 | 714 | 1 | 714 | 56 | 56 | 148 | 1 | 24 | 25 | 32 |
| 63 | HLQBQ38 | 209195 Aug. 1, 1997 | Lambda ZAP II | 73 | 1405 | 453 | 1405 | 472 | 472 | 149 | 1 | 39 | 40 | 41 |
| 64 | HMKCP66 | 209195 Aug. 1, 1997 | pSport1 | 74 | 907 | 1 | 907 | 353 | 353 | 150 | 1 | 19 | 20 | 40 |
| 65 | HWTAL40 | 209195 Aug. 1, 1997 | Uni-ZAP XR | 75 | 687 | 51 | 687 | 124 | 124 | 151 | 1 | 31 | 32 | 43 |
| 66 | HNHDR03 | 209195 Aug. 1, 1997 | Uni-ZAP XR | 76 | 792 | 1 | 792 | 184 | 184 | 152 | 1 | 45 | 46 | 54 |
| 67 | HNHFH41 | 209195 Aug. 1, 1997 | Uni-ZAP XR | 77 | 756 | 1 | 756 | 52 | 52 | 153 | 1 | 24 | 25 | 165 |
| 68 | HNHFI81 | 209195 Aug. 1, 1997 | Uni-ZAP XR | 78 | 751 | 1 | 751 | 46 | 46 | 154 | 1 | 18 | 19 | 113 |
| 69 | HOSFQ28 | 209195 Aug. 1, 1997 | Uni-ZAP XR | 79 | 1411 | 219 | 987 | 304 | 304 | 155 | 1 | 20 | 21 | 39 |
| 70 | HPRAL78 | 209195 Aug. 1, 1997 | Uni-ZAP XR | 80 | 1775 | 1038 | 1775 | 70 | 70 | 156 | 1 | 29 | 30 | 392 |
| 70 | HPRAL78 | 209195 Aug. 1, 1997 | Uni-ZAP XR | 86 | 866 | 128 | 866 | 148 | 148 | 162 | 1 | 42 | 43 | 63 |

Table 1 summarizes the information corresponding to each "Gene No." described above. The nucleotide sequence identified as "NT SEQ ID NO:X" was assembled from partially homologous ("overlapping") sequences obtained from the "cDNA clone ID" identified in Table 1 and, in some cases, from additional related DNA clones. The overlapping sequences were assembled into a single contiguous sequence of high redundancy (usually three to five overlapping sequences at each nucleotide position), resulting in a final sequence identified as SEQ ID NO:X.

The cDNA Clone ID was deposited on the date and given the corresponding deposit number listed in "ATCC Deposit No:Z and Date." Some of the deposits contain multiple different clones corresponding to the same gene. "Vector" refers to the type of vector contained in the cDNA Clone ID.

"Total NT Seq." refers to the total number of nucleotides in the contig identified by "Gene No." The deposited clone may contain all or most of these sequences, reflected by the nucleotide position indicated as "5' NT of Clone Seq." and the "3' NT of Clone Seq." of SEQ ID NO:X. The nucleotide position of SEQ ID NO:X of the putative start codon (methionine) is identified as "5' NT of Start Codon." Similarly, the nucleotide position of SEQ ID NO:X of the predicted signal sequence is identified as "5' NT of First AA of Signal Pep."

The translated amino acid sequence, beginning with the methionine, is identified as "AA SEQ ID NO:Y," although other reading frames can also be easily translated using known molecular biology techniques. The polypeptides produced by these alternative open reading frames are specifically contemplated by the present invention.

The first and last amino acid position of SEQ ID NO:Y of the predicted signal peptide is identified as "First AA of Sig Pep" and "Last AA of Sig Pep." The predicted first amino acid position of SEQ ID NO:Y of the secreted portion is identified as "Predicted First AA of Secreted Portion." Finally, the amino acid position of SEQ ID NO:Y of the last amino acid in the open reading frame is identified as "Last AA of ORF."

SEQ ID NO:X and the translated SEQ ID NO:Y are sufficiently accurate and otherwise suitable for a variety of uses well known in the art and described further below. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used to generate antibodies which bind specifically to the secreted proteins encoded by the cDNA clones identified in Table 1.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:X and the predicted translated amino acid sequence identified as SEQ ID NO:Y, but also a sample of plasmid DNA containing a human cDNA of the invention deposited with the ATCC, as set forth in Table 1. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited human cDNA, collecting the protein, and determining its sequence.

The present invention also relates to the genes corresponding to SEQ ID NO:X, SEQ ID NO:Y, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs. Species homologs may be isolated and identified by making suitable probes or primers from the sequences provided herein and screening a suitable nucleic acid source for the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the secreted protein, including the mature form, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, including the secreted polypeptide, can be substantially purified by the one-step method described in Smith and Johnson, Gene 67:31–40 (1988). Polypeptides of the invention also can be purified from natural or recombinant sources using antibodies of the invention raised against the secreted protein in methods which are well known in the art.

Signal Sequences

Methods for predicting whether a protein has a signal sequence, as well as the cleavage point for that sequence, are available. For instance, the method of McGeoch, Virus Res. 3:271–286 (1985), uses the information from a short N-terminal charged region and a subsequent uncharged region of the complete (uncleaved) protein. The method of von Heinje, Nucleic Acids Res. 14:4683–4690 (1986) uses the information from the residues surrounding the cleavage site, typically residues –13 to +2, where +1 indicates the amino terminus of the secreted protein. The accuracy of predicting the cleavage points of known mammalian secretory proteins for each of these methods is in the range of 75–80%. (von Heinje, supra.) However, the two methods do not always produce the same predicted cleavage point(s) for a given protein.

In the present case, the deduced amino acid sequence of the secreted polypeptide was analyzed by a computer program called SignalP (Henrik Nielsen et al., Protein Engineering 10:1–6 (1997)), which predicts the cellular location of a protein based on the amino acid sequence. As part of this computational prediction of localization, the methods of McGeoch and von Heinje are incorporated. The analysis of the amino acid sequences of the secreted proteins described herein by this program provided the results shown in Table 1.

As one of ordinary skill would appreciate, however, cleavage sites sometimes vary from organism to organism and cannot be predicted with absolute certainty. Accordingly, the present invention provides secreted polypeptides having a sequence shown in SEQ ID NO:Y which have an N-terminus beginning within 5 residues (i.e., + or −5 residues) of the predicted cleavage point. Similarly, it is also recognized that in some cases, cleavage of the signal sequence from a secreted protein is not entirely uniform, resulting in more than one secreted species. These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. These polypeptides, and the polynucleotides encoding such polypeptides, are contemplated by the present invention.

Polynucleotide and Polypeptide Variants

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown in Table 1, the ORF (open reading frame), or any fragement specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determing the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identiy are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the lenght of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequences shown in Table 1 or to the amino acid sequence encoded by deposited DNA clone can be determined conventionally using known computer programs. A preferred method for determing the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is becuase the FASTDB program does not account for N- and C-terminal truncations of the subject sequence when calculating global percent identity. For subject sequences truncated at the N- and C-termini, relative to the the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred. Polynucleotide variants can be produced for a variety of reasons, e.g., to optimize codon expression for a particular host (change codons in the human mRNA to those preferred by a bacterial host such as *E. coli*).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the secreted protein without substantial loss of biological function. The authors of Ron et al., J. Biol. Chem. 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein. (Dobeli et al., J. Biotechnology 7:199–216 (1988).)

Moreover, ample evidence demonstrates that variants often retain a biological activity similar to that of the naturally occurring protein. For example, Gayle and coworkers (J. Biol. Chem 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes polypeptide variants which show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie, J. U. et al., Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function.

Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Besides conservative amino acid substitution, variants of the present invention include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1–5, 5–10, 5–25, 5–50, 10–50 or 50–150, conservative amino acid substitutions are preferable.

Polynucleotide and Polypeptide Fragments

In the present invention, a "polynucleotide fragment" refers to a short polynucleotide having a nucleic acid sequence contained in the deposited clone or shown in SEQ ID NO:X. The short nucleotide fragments are preferably at least about 15 nt, and more preferably at least about 20 nt, still more preferably at least about 30 nt, and even more preferably, at least about 40 nt in length. A fragment "at least 20 nt in length," for example, is intended to include 20 or more contiguous bases from the cDNA sequence contained in the deposited clone or the nucleotide sequence shown in SEQ ID NO:X. These nucleotide fragments are useful as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments having a sequence from about nucleotide number 1–50, 51–100, 101–150, 151–200, 201–250, 251–300, 301–350, 351–400, 401-450, 451–500, 501–550, 551–600, 651–700, 701–750, 751–800, 800–850, 851–900, 901-950, 951–1000, 1001–1050, 1051–1100, 1101–1150, 1151–1200, 1201–1250, 1251-1300, 1301–1350, 1351–1400, 1401–1450, 1451–1500, 1501–1550, 1551–1600, 1601-1650, 1651–1700, 1701–1750, 1751–1800, 1801–1850, 1851–1900, 1901–1950, 1951-2000, or 2001 to the end of SEQ ID NO:X or the cDNA contained in the deposited clone. In this context "about" includes the particularly recited ranges, larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein.

In the present invention, a "polypeptide fragment" refers to a short amino acid sequence contained in SEQ ID NO:Y or encoded by the cDNA contained in the deposited clone. Protein fragments may be "free-standing," or comprised within a larger polypeptide of which the fragment forms a part or region, most preferably as a single continuous region. Representative examples of polypeptide fragments of the invention, include, for example, fragments from about amino acid number 1–20, 21–40, 41–60, 61–80, 81–100, 102–120, 121–140, 141–160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes.

Preferred polypeptide fragments include the secreted protein as well as the mature form. Further preferred polypeptide fragments include the secreted protein or the mature form having a continuous series of deleted residues from the amino or the carboxy terminus, or both. For example, any number of amino acids, ranging from 1–60, can be deleted from the amino terminus of either the secreted polypeptide or the mature form. Similarly, any number of amino acids, ranging from 1–30, can be deleted from the carboxy terminus of the secreted protein or mature form. Furthermore, any combination of the above amino and carboxy terminus deletions are preferred. Similarly, polynucleotide fragments encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:Y falling within conserved domains are specifically contemplated by the present invention. Moreover, polynucleotide fragments encoding these domains are also contemplated.

Other preferred fragments are biologically active fragments. Biologically active fragments are those exhibiting activity similar, but not necessarily identical, to an activity of the polypeptide of the present invention. The biological activity of the fragments may include an improved desired activity, or a decreased undesirable activity.

Epitopes & Antibodies

In the present invention, "epitopes" refer to polypeptide fragments having antigenic or immunogenic activity in an animal, especially in a human. A preferred embodiment of the present invention relates to a polypeptide fragment comprising an epitope, as well as the polynucleotide encoding this fragment. A region of a protein molecule to which an antibody can bind is defined as an "antigenic epitope." In contrast, an "immunogenic epitope" is defined as a part of a protein that elicits an antibody response. (See, for instance, Geysen et al., Proc. Natl. Acad. Sci. USA 81:3998–4002 (1983).)

Fragments which function as epitopes may be produced by any conventional means. (See, e.g., Houghten, R. A., Proc. Natl. Acad. Sci. USA 82:5131–5135 (1985) further described in U.S. Pat. No. 4,631,211.)

In the present invention, antigenic epitopes preferably contain a sequence of at least seven, more preferably at least nine, and most preferably between about 15 to about 30 amino acids. Antigenic epitopes are useful to raise antibodies, including monoclonal antibodies, that specifically bind the epitope. (See, for instance, Wilson et al., Cell 37:767–778 (1984); Sutcliffe, J. G. et al., Science 219: 660–666 (1983).)

Similarly, immunogenic epitopes can be used to induce antibodies according to methods well known in the art. (See, for instance, Sutcliffe et al., supra; Wilson et al., supra; Chow, M. et al., Proc. Natl. Acad. Sci. USA 82:910–914; and Bittle, F. J. et al., J. Gen. Virol. 66:2347–2354 (1985).) A preferred immunogenic epitope includes the secreted protein. The immunogenic epitopes may be presented together with a carrier protein, such as an albumin, to an animal system (such as rabbit or mouse) or, if it is long enough (at least about 25 amino acids), without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting.)

As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody. (Wahl et al., J. Nucl. Med. 24:316–325 (1983).) Thus, these fragments are preferred, as well as the products of a FAB or other immunoglobulin expression library. Moreover, antibodies of the present invention include chimeric, single chain, and humanized antibodies.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because secreted proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Also, peptide moieties may be added to the polypeptide to facilitate purification. Such regions may be removed prior to final preparation of the polypeptide. The addition of peptide moieties to facilitate handling of polypeptides are familiar and routine techniques in the art.

Moreover, polypeptides of the present invention, including fragments, and specifically epitopes, can be combined with parts of the constant domain of immunoglobulins (IgG), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331: 84-86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).)

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270: 9459–9471 (1995).)

Moreover, the polypeptides of the present invention can be fused to marker sequences, such as a peptide which facilitates purification of the fused polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, *Streptomyces* and *Salmonella typhimurium* cells; fungal cells, such as yeast cells; insect cells such as *Drosophila* S2 and *Spodoptera* Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435-438 (1989), the disclosures of each of which are incorporated by reference in their entireties).

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15–25 bp) from the sequences shown in SEQ ID NO:X. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:X will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on fine through Johns Hopkins University Welch Medical Library).) Assuming 1 megabase mapping resolution and one gene per 20 kb, a cDNA precisely localized to a chromosomal region associated with the disease could be one of 50–500 potential causative genes.

Thus, once coinheritance is established, differences in the polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using polynucleotides of the present invention. Any of these alterations (altered expression, chromosomal rearrangement, or mutation) can be used as a diagnostic or prognostic marker.

In addition to the foregoing, a polynucleotide can be used to control gene expression through triple helix formation or antisense DNA or RNA. Both methods rely on binding of the polynucleotide to DNA or RNA. For these techniques, preferred polynucleotides are usually 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991) ) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat disease.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell.

The polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once an unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, polynucleotides of the present invention can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell. Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (121In), and technetium (99mTc), and fluorescent labels, such as fluorescein and rhodamine, and biotin.

In addition to assaying secreted protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder.

Moreover, polypeptides of the present invention can be used to treat disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B), to inhibit the activity of a polypeptide (e.g., an oncogene), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth).

Similarly, antibodies directed to a polypeptide of the present invention can also be used to treat disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Biological Activities

The polynucleotides and polypeptides of the present invention can be used in assays to test for one or more biological activities. If these polynucleotides and polypeptides do exhibit activity in a particular assay, it is likely that these molecules may be involved in the diseases associated with the biological activity. Thus, the polynucleotides and polypeptides could be used to treat the associated disease.

Immune Activity

A polypeptide or polynucleotide of the present invention may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, a polynucleotide or polypeptide of the present invention can be used as a marker or detector of a particular immune system disease or disorder.

A polynucleotide or polypeptide of the present invention may be useful in treating or detecting deficiencies or disorders of hematopoietic cells. A polypeptide or polynucleotide of the present invention could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polypeptide or polynucleotide of the present invention could also be used to modulate hemostatic (the stopping of bleeding) or thrombolytic activity (clot formation). For example, by increasing hemostatic or thrombolytic activity, a polynucleotide or polypeptide of the present invention could be used to treat blood coagulation disorders (e.g., afibrinogenemia, factor deficiencies), blood platelet disorders (e.g. thrombocytopenia), or wounds resulting from trauma, surgery, or other causes. Alternatively, a polynucleotide or polypeptide of the present invention that can decrease hemostatic or thrombolytic activity could be used to inhibit or dissolve clotting. These molecules could be important in the treatment of heart attacks (infarction), strokes, or scarring.

A polynucleotide or polypeptide of the present invention may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of a polypeptide or polynucleotide of the present invention that inhibits an immune response, particularly the proliferation, differentiation, or chemotaxis of T-cells, may be an effective therapy in preventing autoimmune disorders.

Examples of autoimmune disorders that can be treated or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated by a polypeptide or polynucleotide of the present invention. Moreover, these molecules can be used to treat anaphylaxis, hypersensitivity to an antigenic molecule, or blood group incompatibility.

A polynucleotide or polypeptide of the present invention may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polypeptide or polynucleotide of the present invention that inhibits an immune response, particularly the proliferation, differentiation, or chemotaxis of T-cells, may be an effective therapy in preventing organ rejection or GVHD.

Similarly, a polypeptide or polynucleotide of the present invention may also be used to modulate inflammation. For example, the polypeptide or polynucleotide may inhibit the proliferation and differentiation of cells involved in an inflammatory response. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polypeptide or polynucleotide can be used to treat or detect hyperproliferative disorders, including neoplasms. A polypeptide or polynucleotide of the present invention may inhibit the proliferation of the disorder through direct or indirect interactions. Alternatively, a polypeptide or polynucleotide of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by a polynucleotide or polypeptide of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by a polynucleotide or polypeptide of the present invention. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Infectious Disease

A polypeptide or polynucleotide of the present invention can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, the polypeptide or polynucleotide of the present invention may also directly inhibit the infectious agent, without necessarily eliciting an immune response.

Viruses are one example of an infectious agent that can cause disease or symptoms that can be treated or detected by a polynucleotide or polypeptide of the present invention. Examples of viruses, include, but are not limited to the following DNA and RNA viral families: Arbovirus, Adenoviridae, Arenaviridae, Arterivirus, Bimaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. A polypeptide or polynucleotide of the present invention can be used to treat or detect any of these symptoms or diseases.

Similarly, bacterial or fungal agents that can cause disease or symptoms and that can be treated or detected by a polynucleotide or polypeptide of the present invention include, but not limited to, the following Gram-Negative and Gram-positive bacterial families and fungi: Actinomycetales (e.g., *Corynebacterium, Mycobacterium, Norcardia*), Aspergillosis, Bacillaceae (e.g., Anthrax, *Clostridium*), Bacteroidaceae, Blastomycosis, Bordetella, *Borrelia*, Brucellosis, Candidiasis, *Campylobacter*, Coccidioidomycosis, Cryptococcosis, Dermatocycoses, Enterobacteriaceae (*Klebsiella, Salmonella, Serratia, Yersinia*), Erysipelothrix, *Helicobacter*, Legionellosis, Leptospirosis, *Listeria*, Mycoplasmatales, Neisseriaceae (e.g., Acinetobacter, Gonorrhea, Menigococcal), Pasteurellacea Infections (e.g., Actinobacillus, Heamophilus, Pasteurella), *Pseudomonas*, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. A polypeptide or polynucleotide of the present invention can be used to treat or detect any of these symptoms or diseases.

Moreover, parasitic agents causing disease or symptoms that can be treated or detected by a polynucleotide or polypeptide of the present invention include, but not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. A polypeptide or polynucleotide of the present invention can be used to treat or detect any of these symptoms or diseases.

Preferably, treatment using a polypeptide or polynucleotide of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide of the present invention can be used to differentiate, proliferate, and attract cells, leading to the regeneration of tissues. (See, Science 276: 59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide of the present invention may increase regeneration of tissues difficult to heal. For example, increased tendon/ligament regeneration would quicken recovery time after damage. A polynucleotide or polypeptide of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide of the present invention to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the polynucleotide or polypeptide of the present invention.

Chemotaxis

A polynucleotide or polypeptide of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polynucleotide or polypeptide of the present invention may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. Chemotactic molecules of the present invention can also attract fibroblasts, which can be used to treat wounds.

It is also contemplated that a polynucleotide or polypeptide of the present invention may inhibit chemotactic activity. These molecules could also be used to treat disorders. Thus, a polynucleotide or polypeptide of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2): Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, *Drosophila*, or *E. coli*. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

All of these above assays can be used as diagnostic or prognostic markers. The molecules discovered using these assays can be used to treat disease or to bring about a particular result in a patient (e.g., blood vessel growth) by activating or inhibiting the polypeptide/molecule. Moreover, the assays can discover agents which may inhibit or enhance the production of the polypeptide from suitably manipulated cells or tissues.

Therefore, the invention includes a method of identifying compounds which bind to a polypeptide of the invention comprising the steps of: (a) incubating a candidate binding compound with a polypeptide of the invention; and (b) determining if binding has occurred. Moreover, the invention includes a method of identifying agonists/antagonists comprising the steps of: (a) incubating a candidate compound with a polypeptide of the invention, (b) assaying a biological activity , and (b) determining if a biological activity of the polypeptide has been altered.

Other Activities

A polypeptide or polynucleotide of the present invention may also increase or decrease the differentiation or proliferation of embryonic stem cells, besides, as discussed above, hematopoietic lineage.

A polypeptide or polynucleotide of the present invention may also be used to modulate mammalian characteristics, such as body height, weight, hair color, eye color, skin, percentage of adipose tissue, pigmentation, size, and shape (e.g., cosmetic surgery). Similarly, a polypeptide or polynucleotide of the present invention may be used to modulate mammalian metabolism affecting catabolism, anabolism, processing, utilization, and storage of energy.

A polypeptide or polynucleotide of the present invention may be used to change a mammal's mental state or physical state by influencing biorhythms, caricadic rhythms, depression (including depressive disorders), tendency for violence, tolerance for pain, reproductive capabilities (preferably by Activin or Inhibin-like activity), hormonal or endocrine levels, appetite, libido, memory, stress, or other cognitive qualities.

A polypeptide or polynucleotide of the present invention may also be used as a food additive or preservative, such as to increase or decrease storage capabilities, fat content, lipid, protein, carbohydrate, vitamins, minerals, cofactors or other nutritional components.

Other Preferred Embodiments

Other preferred embodiments of the claimed invention include an isolated nucleic acid molecule comprising a nucleotide sequence which is at least 95% identical to a sequence of at least about 50 contiguous nucleotides in the nucleotide sequence of SEQ ID NO:X wherein X is any integer as defined in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Clone Sequence and ending with the nucleotide at about the position of the 3' Nucleotide of the Clone Sequence as defined for SEQ ID NO:X in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Start Codon and ending with the nucleotide at about the position of the 3' Nucleotide of the Clone Sequence as defined for SEQ ID NO:X in Table 1.

Similarly preferred is a nucleic acid molecule wherein said sequence of contiguous nucleotides is included in the nucleotide sequence of SEQ ID NO:X in the range of positions beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

Also preferred is an isolated nucleic acid molecule comprising a nucleotide sequence which is at least 95% identical to a sequence of at least about 150 contiguous nucleotides in the nucleotide sequence of SEQ ID NO:X.

Further preferred is an isolated nucleic acid molecule comprising a nucleotide sequence which is at least 95% identical to a sequence of at least about 500 contiguous nucleotides in the nucleotide sequence of SEQ ID NO:X.

A further preferred embodiment is a nucleic acid molecule comprising a nucleotide sequence which is at least 95% identical to the nucleotide sequence of SEQ ID NO:X beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

A further preferred embodiment is an isolated nucleic acid molecule comprising a nucleotide sequence which is at least 95% identical to the complete nucleotide sequence of SEQ ID NO:X.

Also preferred is an isolated nucleic acid molecule which hybridizes under stringent hybridization conditions to a nucleic acid molecule, wherein said nucleic acid molecule which hybridizes does not hybridize under stringent hybridization conditions to a nucleic acid molecule having a nucleotide sequence consisting of only A residues or of only T residues.

Also preferred is a composition of matter comprising a DNA molecule which comprises a human cDNA clone identified by a cDNA Clone Identifier in Table 1, which DNA molecule is contained in the material deposited with the American Type Culture Collection and given the ATCC Deposit Number shown in Table 1 for said cDNA Clone Identifier.

Also preferred is an isolated nucleic acid molecule comprising a nucleotide sequence which is at least 95% identical to a sequence of at least 50 contiguous nucleotides in the nucleotide sequence of a human cDNA clone identified by a cDNA Clone Identifier in Table 1, which DNA molecule is contained in the deposit given the ATCC Deposit Number shown in Table 1.

Also preferred is an isolated nucleic acid molecule, wherein said sequence of at least 50 contiguous nucleotides is included in the nucleotide sequence of the complete open reading frame sequence encoded by said human cDNA clone.

Also preferred is an isolated nucleic acid molecule comprising a nucleotide sequence which is at least 95% identical to sequence of at least 150 contiguous nucleotides in the nucleotide sequence encoded by said human cDNA clone.

A further preferred embodiment is an isolated nucleic acid molecule comprising a nucleotide sequence which is at least 95% identical to sequence of at least 500 contiguous nucleotides in the nucleotide sequence encoded by said human cDNA clone.

A further preferred embodiment is an isolated nucleic acid molecule comprising a nucleotide sequence which is at least 95% identical to the complete nucleotide sequence encoded by said human cDNA clone.

A further preferred embodiment is a method for detecting in a biological sample a nucleic acid molecule comprising a nucleotide sequence which is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1; which method comprises a step of comparing a nucleotide sequence of at least one nucleic acid molecule in said sample with a sequence selected from said group and determining whether the sequence of said nucleic acid molecule in said sample is at least 95% identical to said selected sequence.

Also preferred is the above method wherein said step of comparing sequences comprises determining the extent of nucleic acid hybridization between nucleic acid molecules in said sample and a nucleic acid molecule comprising said sequence selected from said group. Similarly, also preferred is the above method wherein said step of comparing sequences is performed by comparing the nucleotide sequence determined from a nucleic acid molecule in said sample with said sequence selected from said group. The nucleic acid molecules can comprise DNA molecules or RNA molecules.

A further preferred embodiment is a method for identifying the species, tissue or cell type of a biological sample which method comprises a step of detecting nucleic acid molecules in said sample, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for identifying the species, tissue or cell type of a biological sample can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a method for diagnosing in a subject a pathological condition associated with abnormal structure or expression of a gene encoding a secreted protein identified in Table 1, which method comprises a step of detecting in a biological sample obtained from said subject nucleic acid molecules, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for diagnosing a pathological condition can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a composition of matter comprising isolated nucleic acid molecules wherein the nucleotide sequences of said nucleic acid molecules comprise a panel of at least two nucleotide sequences, wherein at least one sequence in said panel is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1. The nucleic acid molecules can comprise DNA molecules or RNA molecules.

Also preferred is an isolated polypeptide comprising an amino acid sequence at least 90% identical to a sequence of at least about 10 contiguous amino acids in the amino acid sequence of SEQ ID NO:Y wherein Y is any integer as defined in Table 1.

Also preferred is a polypeptide, wherein said sequence of contiguous amino acids is included in the amino acid sequence of SEQ ID NO:Y in the range of positions beginning with the residue at about the position of the First Amino Acid of the Secreted Portion and ending with the residue at about the Last Amino Acid of the Open Reading Frame as set forth for SEQ ID NO:Y in Table 1.

Also preferred is an isolated polypeptide comprising an amino acid sequence at least 95% identical to a sequence of at least about 30 contiguous amino acids in the amino acid sequence of SEQ ID NO:Y.

Further preferred is an isolated polypeptide comprising an amino acid sequence at least 95% identical to a sequence of at least about 100 contiguous amino acids in the amino acid sequence of SEQ ID NO:Y.

Further preferred is an isolated polypeptide comprising an amino acid sequence at least 95% identical to the complete amino acid sequence of SEQ ID NO:Y.

Further preferred is an isolated polypeptide comprising an amino acid sequence at least 90% identical to a sequence of at least about 10 contiguous amino acids in the complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is a polypeptide wherein said sequence of contiguous amino acids is included in the amino acid sequence of a secreted portion of the secreted protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 30 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 100 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Further preferred is an isolated antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Further preferred is a method for detecting in a biological sample a polypeptide comprising an amino acid sequence which is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1; which method comprises a step of comparing an amino acid sequence of at least one polypeptide molecule in said sample with a sequence selected from said group and determining whether the sequence of said polypeptide molecule in said sample is at least 90% identical to said sequence of at least 10 contiguous amino acids.

Also preferred is the above method wherein said step of comparing an amino acid sequence of at least one polypeptide molecule in said sample with a sequence selected from said group comprises determining the extent of specific binding of polypeptides in said sample to an antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Also preferred is the above method wherein said step of comparing sequences is performed by comparing the amino acid sequence determined from a polypeptide molecule in said sample with said sequence selected from said group.

Also preferred is a method for identifying the species, tissue or cell type of a biological sample which method comprises a step of detecting polypeptide molecules in said sample, if any, comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is the above method for identifying the species, tissue or cell type of a biological sample, which method comprises a step of detecting polypeptide molecules comprising an amino acid sequence in a panel of at least two amino acid sequences, wherein at least one sequence in said panel is at least 90% identical to a sequence of at least 10 contiguous amino acids in a sequence selected from the above group.

Also preferred is a method for diagnosing in a subject a pathological condition associated with abnormal structure or expression of a gene encoding a secreted protein identified in Table 1, which method comprises a step of detecting in a biological sample obtained from said subject polypeptide molecules comprising an amino acid sequence in a panel of at least two amino acid sequences, wherein at least one sequence in said panel is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

In any of these methods, the step of detecting said polypeptide molecules includes using an antibody.

Also preferred is an isolated nucleic acid molecule comprising a nucleotide sequence which is at least 95% identical to a nucleotide sequence encoding a polypeptide wherein said polypeptide comprises an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is an isolated nucleic acid molecule, wherein said nucleotide sequence encoding a polypeptide has been optimized for expression of said polypeptide in a prokaryotic host.

Also preferred is an isolated nucleic acid molecule, wherein said polypeptide comprises an amino acid sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Further preferred is a method of making a recombinant vector comprising inserting any of the above isolated nucleic acid molecule into a vector. Also preferred is the recombinant vector produced by this method. Also preferred is a method of making a recombinant host cell comprising introducing the vector into a host cell, as well as the recombinant host cell produced by this method.

Also preferred is a method of making an isolated polypeptide comprising culturing this recombinant host cell under conditions such that said polypeptide is expressed and recovering said polypeptide. Also preferred is this method of making an isolated polypeptide, wherein said recombinant host cell is a eukaryotic cell and said polypeptide is a secreted portion of a human secreted protein comprising an amino acid sequence selected from the group consisting of: an amino acid sequence of SEQ ID NO:Y beginning with the residue at the position of the First Amino Acid of the Secreted Portion of SEQ ID NO:Y wherein Y is an integer set forth in Table 1 and said position of the First Amino Acid of the Secreted Portion of SEQ ID NO:Y is defined in Table 1; and an amino acid sequence of a secreted portion of a protein encoded by a human cDNA clone identified by a cDNA Clone Identifier in Table 1 and contained in the deposit with the ATCC Deposit Number shown for said cDNA clone in Table 1. The isolated polypeptide produced by this method is also preferred.

Also preferred is a method of treatment of an individual in need of an increased level of a secreted protein activity, which method comprises administering to such an individual a pharmaceutical composition comprising an amount of an isolated polypeptide, polynucleotide, or antibody of the claimed invention effective to increase the level of said protein activity in said individual.

Having generally described the invention, the same will be more readily understood by reference to the following examples, which are provided by way of illustration and are not intended as limiting.

EXAMPLES

Example 1

Isolation of a Selected cDNA Clone from the Deposited Sample

Each cDNA clone in a cited ATCC deposit is contained in a plasmid vector. Table 1 identifies the vectors used to construct the cDNA library from which each clone was isolated. In many cases, the vector used to construct the library is a phage vector from which a plasmid has been excised. The table immediately below correlates the related plasmid for each phage vector used in constructing the cDNA library. For example, where a particular clone is identified in Table 1 as being isolated in the vector "Lambda Zap," the corresponding deposited clone is in "pBluescript."

| Vector Used to Construct Library | Corresponding Deposited Plasmid |
|---|---|
| Lambda Zap | pBluescript (pBS) |
| Uni-Zap XR | pBluescript (pBS) |
| Zap Express | pBK |
| lafmid BA | plafmid BA |
| pSport1 | pSport1 |
| pCMVSport 2.0 | pCMVSport 2.0 |
| pCMVSport 3.0 | pCMVSport 3.0 |
| pCR ® 2.1 | pCR ® 2.1 |

Vectors Lambda Zap (U.S. Pat. Nos. 5,128,256 and 5,286,636), Uni-Zap XR (U.S. Pat. Nos. 5,128,256 and 5,286,636), Zap Express (U.S. Pat. Nos. 5,128,256 and 5,286,636), pBluescript (pBS) (Short, J. M. et al., Nucleic Acids Res. 16:7583–7600 (1988); Alting-Mees, M. A. and Short, J. M., Nucleic Acids Res. 17:9494 (1989)) and pBK (Alting-Mees, M. A. et al., Strategies 5:58–61 (1992)) are commercially available from Stratagene Cloning Systems, Inc., 11011 N. Torrey Pines Road, La Jolla, Calif., 92037. pBS contains an ampicillin resistance gene and pBK contains a neomycin resistance gene. Both can be transformed into E. coli strain XL-1 Blue, also available from Stratagene. pBS comes in 4 forms SK+, SK−, KS+ and KS. The S and K refers to the orientation of the polylinker to the T7 and T3 primer sequences which flank the polylinker region ("S" is for SacI and "K" is for KpnI which are the first sites on each respective end of the linker). "+" or "−" refer to the orientation of the f1 origin of replication ("ori"), such that in one orientation, single stranded rescue initiated from the f1 ori generates sense strand DNA and in the other, antisense.

Vectors pSport1, pCMVSport 2.0 and pCMVSport 3.0, were obtained from Life Technologies, Inc., P. O. Box 6009, Gaithersburg, Md. 20897. All Sport vectors contain an ampicillin resistance gene and may be transformed into E.

*coli* strain DH10B, also available from Life Technologies. (See, for instance, Gruber, C. E., et al., Focus 15:59 (1993).) Vector lafmid BA (Bento Soares, Columbia University, NY) contains an ampicillin resistance gene and can be transformed into *E. coli* strain XL-1 Blue. Vector pCR®2.1, which is available from Invitrogen, 1600 Faraday Avenue, Carlsbad, Calif. 92008, contains an ampicillin resistance gene and may be transformed into *E. coli* strain DH10B, available from Life Technologies. (See, for instance, Clark, J. M., Nuc. Acids Res. 16:9677–9686 (1988) and Mead, D. et al., Bio/Technology 9: (1991).) Preferably, a polynucleotide of the present invention does not comprise the phage vector sequences identified for the particular clone in Table 1, as well as the corresponding plasmid vector sequences designated above.

The deposited material in the sample assigned the ATCC Deposit Number cited in Table 1 for any given cDNA clone also may contain one or more additional plasmids, each comprising a cDNA clone different from that given clone. Thus, deposits sharing the same ATCC Deposit Number contain at least a plasmid for each cDNA clone identified in Table 1. Typically, each ATCC deposit sample cited in Table 1 comprises a mixture of approximately equal amounts (by weight) of about 50 plasmid DNAs, each containing a different cDNA clone; but such a deposit sample may include plasmids for more or less than 50 cDNA clones, up to about 500 cDNA clones.

Two approaches can be used to isolate a particular clone from the deposited sample of plasmid DNAs cited for that clone in Table 1. First, a plasmid is directly isolated by screening the clones using a polynucleotide probe corresponding to SEQ ID NO:X.

Particularly, a specific polynucleotide with 30–40 nucleotides is synthesized using an Applied Biosystems DNA synthesizer according to the sequence reported. The oligonucleotide is labeled, for instance, with $^{32}$P-γ-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ ID NO:X (i.e., within the region of SEQ ID NO:X bounded by the 5' NT and the 3' NT of the clone defined in Table 1) are synthesized and used to amplify the desired cDNA using the deposited cDNA plasmid as a template. The polymerase chain reaction is carried out under routine conditions, for instance, in 25 μl of reaction mixture with 0.5 ug of the above cDNA template. A convenient reaction mixture is 1.5–5 mM MgCl$_2$, 0.01% (w/v) gelatin, 20 μM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of a gene which may not be present in the deposited clone. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript. (Fromont-Racine et al., Nucleic Acids Res. 21(7): 1683–1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full length gene.

This above method starts with total RNA isolated from the desired source, although poly-A+ RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene.

Example 2

Isolation of Genomic Clones Corresponding to a Polynucleotide

A human genomic P1 library (Genomic Systems, Inc.) is screened by PCR using primers selected for the cDNA sequence corresponding to SEQ ID NO:X., according to the method described in Example 1. (See also, Sambrook.)

Example 3

Tissue Distribution of Polypeptide

Tissue distribution of mRNA expression of polynucleotides of the present invention is determined using protocols for Northern blot analysis, described by, among others, Sambrook et al. For example, a cDNA probe produced by the method described in Example 1 is labeled with $P^{32}$ using the rediprime™ DNA labeling system (Amersham Life Science), according to manufacturer's instructions. After labeling, the probe is purified using CHROMA SPIN-100™ column (Clontech Laboratories, Inc.), according to manufacturer's protocol number PT1200-1. The purified labeled probe is then used to examine various human tissues for mRNA expression.

Multiple Tissue Northern (MTN) blots containing various human tissues (H) or human immune system tissues (IM) (Clontech) are examined with the labeled probe using ExpressHyb™ hybridization solution (Clontech) according to manufacturer's protocol number PT1190-1. Following hybridization and washing, the blots are mounted and exposed to film at −70° C. overnight, and the films developed according to standard procedures.

Example 4

Chromosomal Mapping of the Polynucleotides

An oligonucleotide primer set is designed according to the sequence at the 5' end of SEQ ID NO:X. This primer preferably spans about 100 nucleotides. This primer set is then used in a polymerase chain reaction under the following set of conditions: 30 seconds, 95° C.; 1 minute, 56° C.; 1 minute, 70° C. This cycle is repeated 32 times followed by one 5 minute cycle at 70° C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 5

Bacterial Expression of a Polypeptide

A polynucleotide encoding a polypeptide of the present invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Amp$^r$); a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the *E. coli* strain M15/rep4 (Qiagen, Inc.) which contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3–4 hours at 4° C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

In addition to the above expression vector, the present invention further includes an expression vector comprising phage operator and promoter elements operatively linked to a polynucleotide of the present invention, called pHE4a. (ATCC Accession Number 209645, deposited on Feb. 25, 1998.) This vector contains: 1) a neomycinphosphotransferase gene as a selection marker, 2) an *E. coli* origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LTI, Gaithersburg, Md.). The promoter sequence and operator sequences are made synthetically.

DNA can be inserted into the pHEa by restricting the vector with NdeI and XbaI, BamHI, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 6

Purification of a Polypeptide from an Inclusion Body

The following alternative method can be used to purify a polypeptide expressed in *E coli* when it is present in the form of inclusion bodies. Unless otherwise specified, all of the following steps are conducted at 4–10° C.

Upon completion of the production phase of the *E. coli* fermentation, the cell culture is cooled to 4–10° C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the polypeptide containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to ftrther purification steps.

To clarify the refolded polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Commassie blue stained 16% SDS-PAGE gel when 5 μg of purified protein is loaded. The purified protein can also be tested for endotoxin/LPS contamination, and typically the LPS content is less than 0.1 ng/ml according to LAL assays.

Example 7

Cloning and Expression of a Polypeptide in a Baculovirus Expression System

In this example, the plasmid shuttle vector pA2 is used to insert a polynucleotide into a baculovirus to express a polypeptide. This expression vector contains the strong polyhedrin promoter of the *Autographa californica* nuclear polyhedrosis virus (AcMNPV) followed by convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

Specifically, the cDNA sequence contained in the deposited clone, including the AUG initiation codon and the naturally associated leader sequence identified in Table 1, is amplified using the PCR protocol described in Example 1. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five μg of a plasmid containing the polynucleotide is co-transfected with 1.0 μg of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413–7417 (1987). One μg of BaculoGold™ virus DNA and 5 μg of the plasmid are mixed in a sterile well of a microtiter plate containing 50 μl of serum-free Grace's medium (Life Technologies Inc., Gaithersburg, Md.). Afterwards, 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later the supernatants of these culture dishes are harvested and then they are stored at 4° C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 µCi of $^{35}$S-methionine and 5 µCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 8

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1–3 cells, mouse L cells and Chinese hamster ovary (CHO) cells.

Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357–1370 (1978); Hamlin, J. L. and Ma, C., Biochem. et Biophys. Acta, 1097:107–143 (1990); Page, M. J. and Sydenham, M. A., Biotechnology 9:64–68 (1991).) Another useful selection marker is the enzyme glutamine synthase (GS) (Murphy et al., Biochem J. 227:277–279 (1991); Bebbington et al., Bio/Technology 10:169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-dhfr (ATCC Accession No. 37146), the expression vectors pC4 (ATCC Accession No. 209646) and pC6 (ATCC Accession No. 209647) contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985).) Multiple cloning sites, e.g., with the restriction enzyme cleavage sites BamHI, XbaI and Asp718, facilitate the cloning of the gene of interest. The vectors also contain the 3' intron, the polyadenylation and termination signal of the rat preproinsulin gene, and the mouse DHFR gene under control of the SV40 early promoter.

Specifically, the plasmid pC6, for example, is digested with appropriate restriction enzymes and then dephosphorylated using calf intestinal phosphates by procedures known in the art. The vector is then isolated from a 1% agarose gel.

A polynucleotide of the present invention is amplified according to the protocol outlined in Example 1. If the naturally occurring signal sequence is used to produce the secreted protein, the vector does not need a second signal peptide. Alternatively, if the naturally occurring signal sequence is not used, the vector can be modified to include a heterologous signal sequence. (See, e.g., WO 96/34891.)

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transfection. Five µg of the expression plasmid pC6 is cotransfected with 0.5 µg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 µM, 2 µM, 5 µM, 10 mM, 20 mM). The same procedure is repeated until clones are obtained which grow at a concentration of 100–200 µM. Expression of the desired gene product is analyzed, for instance, by SDS-PAGE and Western blot or by reversed phase HPLC analysis.

Example 9

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example 5; see also EP A 394,827; Traunecker, et al., Nature 331:84–86 (1988).) Similarly, fusion to IgG-1, IgG-3, and albumin increases the halflife time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 5.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide of the present invention, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

```
Human IgG Fc region:              (SEQ ID NO:1)
GGGATCCGGAGCCCAAATCTTCTGACAAAACTCACACATGCCCACCGTGC

CCAGCACCTGAATTCGAGGGTGCACCGTCAGTCTTCCTCTTCCCCCCAAAA

CCCAAGGACACCCTCATGATCTCCCGGACTCCTGAGGTCACATGCGTGGT
```

-continued

```
GGTGGACGTAAGCCACGAAGACCCTGAGGTCAAGTTCAACTGGTACGTGG

ACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

ACCCCCATCGAGAAAACCATCTCCAAAGCCAAAGGGCAGCCCCGAGAAC

CACAGGTGTACACCCTGCCCCCATCCCGGGATGAGCTGACCAAGAACCAG

GTCAGCCTGACCTGCCTGGTCAAAGGCTTCTATCCAAGCGACATCGCCGT

GGAGTGGGAGAGCAATGGGCAGCCGGAGAACAACTACAAGACCACGCCT

CCCGTGCTGGACTCCGACGGCTCCTTCTTCCTCTACAGCAAGCTCACCGTG

GACAAGAGCAGGTGGCAGCAGGGGAACGTCTTCTCATGCTCCGTGATGCA

TGAGGCTCTGCACAACCACTACACGCAGAAGAGCCTCTCCCTGTCTCCGG

GTAAATGAGTGCGACGGCCGCGACTCTAGAGGAT
```

Example 10

Production of an Antibody from a Polypeptide

The antibodies of the present invention can be prepared by a variety of methods. (See, Current Protocols, Chapter 2.) For example, cells expressing a polypeptide of the present invention is administered to an animal to induce the production of sera containing polyclonal antibodies. In a preferred method, a preparation of the secreted protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with polypeptide or, more preferably, with a secreted polypeptide-expressing cell. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al. (Gastroenterology 80:225–232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., Bio-Techniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Example 11

Production of Secreted Protein for
High-Throughput Screening Assays

The following protocol produces a supernatant containing a polypeptide to be tested. This supernatant can then be used in the Screening Assays described in Examples 13–20.

First, dilute Poly-D-Lysine (644 587 Boehringer-Mannheim) stock solution (1 mg/ml in PBS) 1:20 in PBS (w/o calcium or magnesium 17–516F Biowhittaker) for a working solution of 50 ug/ml. Add 200 ul of this solution to each well (24 well plates) and incubate at RT for 20 minutes. Be sure to distribute the solution over each well (note: a 12-channel pipetter may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at $2 \times 10^5$ cells/well in 0.5 ml DMEM(Dulbecco's Modified Eagle Medium)(with 4.5 G/L glucose and L-glutamine (12–604F Biowhittaker))/10% heat inactivated FBS(14–503F Biowhittaker)/1× Penstrep(17–602E Biowhittaker). Let the cells grow overnight.

The next day, mix together in a sterile solution basin: 300 ul Lipofectamine (18324–012 Gibco/BRL) and 5 ml Optimem I (31985070 Gibco/BRL)/96-well plate. With a small volume multi-channel pipetter, aliquot approximately 2 ug of an expression vector containing a polynucleotide insert, produced by the methods described in Examples 8 or 9, into an appropriately labeled 96-well round bottom plate. With a multi-channel pipetter, add 50 ul of the Lipofectamine/Optimem I mixture to each well. Pipette up and down gently to mix. Incubate at RT 15–45 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5–1 ml PBS. Person A then aspirates off PBS rinse, and person B, using a 12-channel pipetter with tips on every other channel, adds the 200 ul of DNA/Lipofectamine/Optimem I complex to the odd wells first, then to the even wells, to each row on the 24-well plates. Incubate at 37° C. for 6 hours.

While cells are incubating, prepare appropriate media, either 1% BSA in DMEM with 1× penstrep, or CHO-5 media (116.6 mg/L of CaCl2 (anhyd); 0.00130 mg/L $CuSO_{4-5}H_2O$; 0.050 mgL of $Fe(NO_3)_{3-9}H_2O$; 0.417 mg/L of $FeSO_{4-7}H_2O$; 311.80 mg/L of Kcl; 28.64 mg/L of $MgCl_2$; 48.84 mg/L of $MgSO_4$; 6995.50 mg/L of NaCl; 2400.0 mg/L of $NaHCO_3$; 62.50 mg/L of $NaH_2PO_4$-$H_2O$; 71.02 mg/L of $Na_2HPO4$; 0.4320 mg/L of $ZnSO_{4-7}H_2O$; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Stearic Acid; 2.20 mg/L of Tween 80; 4551 mg/L of D-Glucose; 130.85 mg/ml of L-Alanine; 147.50 mg/ml of L-Arginine-HCL; 7.50 mg/ml of L-Asparagine-$H_2O$; 6.65 mg/ml of L-Aspartic Acid; 29.56 mg/ml of L-Cystine-2HCL-$H_2O$; 31.29 mg/ml of L-Cystine-2HCL; 7.35 mg/ml of L-Glutamic Acid; 365.0 mg/ml of L-Glutamine; 18.75 mg/ml of Glycine; 52.48 mg/ml of L-Histidine-HCL-$H_2O$; 106.97 mg/ml of L-Isoleucine; 111.45 mg/ml of L-Leucine; 163.75 mg/ml of L-Lysine HCL; 32.34 mg/ml of L-Methionine; 68.48 mg/ml of L-Phenylalainine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na-2$H_2O$; 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; and 0.680 mg/L of Vitamin $B_{12}$; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 20 uM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; and 10 mg/L of Methyl-B-Cyclodextrin complexed with Retinal) with 2 mm glutamine and 1× penstrep. (BSA (81-068-3 Bayer) 100 gm dissolved in 1 L DMEM for a 10% BSA stock solution). Filter the media and collect 50 ul for endotoxin assay in 15 ml polystyrene conical.

The transfection reaction is terminated, preferably by tag-teaming, at the end of the incubation period. Person A aspirates off the transfection media, while person B adds 1.5 ml appropriate media to each well. Incubate at 37° C. for 45 or 72 hours depending on the media used: 1% BSA for 45 hours or CHO-5 for 72 hours.

On day four, using a 300 ul multichannel pipetter, aliquot 600 ul in one 1 ml deep well plate and the remaining supernatant into a 2 ml deep well. The supernatants from each well can then be used in the assays described in Examples 13–20.

It is specifically understood that when activity is obtained in any of the assays described below using a supernatant, the activity originates from either the polypeptide directly (e.g., as a secreted protein) or by the polypeptide inducing expression of other proteins, which are then secreted into the supernatant. Thus, the invention further provides a method of identifying the protein in the supernatant characterized by an activity in a particular assay.

Example 12

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table below. (Adapted from review by Schidler and Darnell, Ann. Rev. Biochem. 64:621–51 (1995).) A cytokine receptor family, capable of activating Jaks, is divided into two groups: (a) Class 1 includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proximal region encoding Trp-Ser-Xxx-Trp-Ser (SEQ ID NO:2)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table below.) Thus, by using GAS elements linked to reporter molecules, activators of the Jaks-STATs pathway can be identified.

| Ligand | JAKs | | | | STATS | GAS(elements) or ISRE |
| --- | --- | --- | --- | --- | --- | --- |
| | tyk2 | Jak1 | Jak2 | Jak3 | | |
| IFN family | | | | | | |
| IFN-a/B | + | + | – | – | 1, 2, 3 | ISRE |
| IFN-g | | + | + | – | 1 | GAS (IRF1 > Lys6 > IFP) |
| Il-10 | + | ? | ? | – | 1, 3 | |
| gp130 family | | | | | | |
| IL-6 (Pleiotrophic) | + | + | + | ? | 1, 3 | GAS (IRF1 > Lys6 > IFP) |
| Il-11(Pleiotrophic) | ? | + | ? | ? | 1, 3 | |
| OnM(Pleiotrophic) | ? | + | + | ? | 1, 3 | |
| LIF(Pleiotrophic) | ? | + | + | ? | 1, 3 | |
| CNTF(Pleiotrophic) | –/+ | + | + | ? | 1, 3 | |
| G-CSF(Pleiotrophic) | ? | + | ? | ? | 1, 3 | |
| IL-12(Pleiotrophic) | + | – | + | + | 1, 3 | |
| g-C family | | | | | | |
| IL-2 (lymphocytes) | – | + | – | + | 1, 3, 5 | GAS |
| IL-4 (lymph/myeloid) | – | + | – | + | 6 | GAS (IRF1 = IFP >> Ly6)(IgH) |
| IL-7 (lymphocytes) | – | + | – | + | 5 | GAS |
| IL-9 (lymphocytes) | – | + | – | + | 5 | GAS |
| IL-13 (lymphocyte) | – | + | ? | ? | 6 | GAS |
| IL-15 | ? | + | ? | + | 5 | GAS |
| gp140 family | | | | | | |
| IL-3 (myeloid) | – | – | + | – | 5 | GAS (IRF1 > IFP >> Ly6) |
| IL-5 (myeloid) | – | – | + | – | 5 | GAS |
| GM-CSF (myeloid) | – | – | + | – | 5 | GAS |
| Growth hormone family | | | | | | |
| GH | ? | – | + | – | 5 | |

-continued

| | | JAKs | | | | |
|---|---|---|---|---|---|---|
| Ligand | tyk2 | Jak1 | Jak2 | Jak3 | STATS | GAS(elements) or ISRE |
| PRL | ? | +/− | + | − | 1, 3, 5 | |
| EPO | ? | − | + | − | 5 | GAS(B − CAS > IRF1 = IFP >> Ly6) |
| Receptor Tyrosine Kinases | | | | | | |
| EGF | ? | + | + | − | 1, 3 | GAS (IRF1) |
| PDGF | ? | + | + | − | 1, 3 | |
| CSF-1 | ? | + | + | − | 1, 3 | GAS (not IRF1) |

To construct a synthetic GAS containing promoter element, which is used in the Biological Assays described in Examples 13–14, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., Immunity 1:457–468 (1994).), although other GAS or ISRE elements can be used instead. The 5' primer also contains 18bp of sequence complementary to the SV40 early promoter sequence and is flanked with an XhoI site. The sequence of the 5' primer is:

(SEQ ID NO:3)
5':
GCGCCTCGAGATTTCCCCGAAATCTAGATTTCCCCGAAATGATTTCCCC

GAAATGATTTCCCCGAAATATCTGCCATCTCAATTAG:3'

The downstream primer is complementary to the SV40 promoter and is flanked with a Hind III site: 5':GCG-GCAAGCTTTTTGCAAAGCCTAGGC:3' (SEQ ID NO:4)

PCR amplification is performed using the SV40 promoter template present in the B-gal:promoter plasmid obtained from Clontech. The resulting PCR fragment is digested with XhoI/Hind III and subcloned into BLSK2-. (Stratagene.) Sequencing with forward and reverse primers confirms that the insert contains the following sequence:

(SEQ ID NO:5)
5':
CTCGAGATTTCCCCGAAATCTAGATTTCCCCGAAATGATTTCCCCGAAA

TGATTTCCCCGAAATATCTGCCATCTCAATTAGTCAGCAACCATAGTCCCG

CCCCTAACTCCGCCCATCCCGCCCCTAACTCCGCCCAGTTCCGCCCATTCT

CCGCCCCATGGCTGACTAATTTTTTTTATTTATGCAGAGGCCGAGGCCGCC

TCGGCCTCTGAGCTATTCCAGAAGTAGTGAGGAGGCTTTTTTGGAGGCCT

AGGCTTTTGCAAAAAGCTT:3'

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is subcloned into the pSEAP-Promoter vector obtained from Clontech using HindIII and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding as described in Examples 13–14.

Other constructs can be made using the above description and replacing GAS with a different promoter sequence. For example, construction of reporter molecules containing NFK-B and EGR promoter sequences are described in Examples 15 and 16. However, many other promoters can be substituted using the protocols described in these Examples. For instance, SRE, IL-2, NFAT, or Osteocalcin promoters can be substituted, alone or in combination (e.g., GAS/NF-KB/EGR, GAS/NF-KB, II-2/NDAT, or NF-KB/GAS). Similarly other cell lines can be used to test reporter construct activity, such as HELA (epithelial), HUVEC (endothelial), Reh (B-cell), Saos-2 (osteoblast), HUVAC (aortic), or Cardiomyocyte.

Example 13

High-Throughput Screening Assay for T-cell Activity

The following protocol is used to assess T-cell activity by identifying factors, such as growth factors and cytokines, that may proliferate or differentiate T-cells. T-cell activity is assessed using the GAS/SEAP/Neo construct produced in Example 12. Thus, factors that increase SEAP activity indicate the ability to activate the Jaks-STATS signal transduction pathway. The T-cell used in this assay is Jurkat T-cells (ATCC Accession No. TIB-152), although Molt-3 cells (ATCC Accession No. CRL-1552) and Molt-4 cells (ATCC Accession No. CRL-1582) cells can also be used.

Jurkat T-cells are lymphoblastic CD4+ Th1 helper cells. In order to generate stable cell lines, approximately 2 million Jurkat cells are transfected with the GAS-SEAP/neo vector using DMRIE-C (Life Technologies)(transfection procedure described below). The transfected cells are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI+10% serum with 1% Pen-Strep. Combine 2.5 mls of OPTI-MEM (Life Technologies) with 10 ug of plasmid DNA in a T25 flask. Add 2.5 ml OPTI-MEM containing 50 ul of DMRIE-C and incubate at room temperature for 15–45 mins.

During the incubation period, count cell concentration, spin down the required number of cells ($10^7$ per transfection), and resuspend in OPTI-MEM to a final concentration of $10^7$ cells/ml. Then add 1 ml of $1 \times 10^7$ cells in OPTI-MEM to T25 flask and incubate at 37° C. for 6 hrs. After the incubation, add 10 ml of RPMI+15% serum.

The Jurkat:GAS-SEAP stable reporter lines are maintained in RPMI+10% serum, 1 mg/ml Genticin, and 1% Pen-Strep. These cells are treated with supernatants containing a polypeptide as produced by the protocol described in Example 11.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100,000 cells per well).

After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48–72 hrs). 35 ul samples from each well are then transferred to an opaque 96 well plate using a 12 channel pipette. The opaque plates should be covered (using sellophene covers) and stored at −20° C. until SEAP assays are performed according to Example 17. The plates containing the remaining treated cells are placed at 4° C. and serve as a source of material for repeating the assay on a specific well if desired.

As a positive control, 100 Unit/ml interferon gamma can be used which is known to activate Jurkat T cells. Over 30 fold induction is typically observed in the positive control wells.

The above protocol may be used in the generation of both transient, as well as, stable transfected cells, which would be apparent to those of skill in the art.

Example 14

High-Throughput Screening Assay Identifying Myeloid Activity

The following protocol is used to assess myeloid activity by identifying factors, such as growth factors and cytokines, that may proliferate or differentiate myeloid cells. Myeloid cell activity is assessed using the GAS/SEAP/Neo construct produced in Example 12. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 12, a DEAE-Dextran method (Kharbanda et. al., 1994, Cell Growth & Differentiation, 5:259–265) is used. First, harvest $2 \times 10e^7$ U937 cells and wash with PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 ug GAS-SEAP2 plasmid DNA, 140 mM NaCl, 5 mM KCl, 375 uM $Na_2HPO_4 \cdot 7H_2O$, 1 mM $MgCl_2$, and 675 uM $CaCl_2$. Incubate at 37° C. for 45 min.

Wash the cells with RPMI 1640 medium containing 10% FBS and then resuspend in 10 ml complete medium and incubate at 37° C. for 36 hr.

The GAS-SEAP/U937 stable cells are obtained by growing the cells in 400 ug/ml G418. The G418-free medium is used for routine growth but every one to two months, the cells should be re-grown in 400 ug/ml G418 for couple of passages.

These cells are tested by harvesting $1 \times 10^8$ cells (this is enough for ten 96-well plates assay) and wash with PBS. Suspend the cells in 200 ml above described growth medium, with a final density of $5 \times 10^5$ cells/ml. Plate 200 ul cells per well in the 96-well plate (or $1 \times 10^5$ cells/well).

Add 50 ul of the supernatant prepared by the protocol described in Example 11. Incubate at 37° C. for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 17.

Example 15

High-Throughput Screening Assay Identifying Neuronal Activity

When cells undergo differentiation and proliferation, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed.

Particularly, the following protocol is used to assess neuronal activity in PC12 cell lines. PC12 cells (rat phenochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC12 cells can be assessed.

The EGR/SEAP reporter construct can be assembled by the following protocol. The EGR-1 promoter sequence (−633 to +1)(Sakamoto K et al., Oncogene 6:867–871 (1991)) can be PCR amplified from human genomic DNA using the following primers:

```
                                                      (SEQ ID NO:6)
   5' GCGCTCGAGGGATGACAGCGATAGAACCCCGG -3'

(SEQ ID NO:7)
   5' GCGAAGCTTCGCGACTCCCCGGATCCGCCTC-3'
```

Using the GAS:SEAP/Neo vector produced in Example 12, EGR1 amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1promoter.

To prepare 96 well-plates for cell culture, two mls of a coating solution (1:30 dilution of collagen type I (Upstate Biotech Inc. Cat#08-115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIO-SCIENCES, Cat. # 12449-78P), 5% heat-inactivated fetal bovine serum (FBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC12 using the Lipofectamine protocol described in Example 11. EGR-SEAP/PC12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as $5 \times 10^5$ cells/ml.

Add 200 ul of the cell suspension to each well of 96-well plate (equivalent to $1 \times 10^5$ cells/well). Add 50 ul supernatant produced by Example 11, 37° C. for 48 to 72 hr. As a positive control, a growth factor known to activate PC12 cells through EGR can be used, such as 50 ng/ul of Neuronal Growth Factor (NGF). Over fifty-fold induction of SEAP is typically seen in the positive control wells. SEAP assay the supernatant according to Example 17.

Example 16

High-Throughput Screening Assay for T-cell Activity

NF-κB (Nuclear Factor κB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-κB regulates the expression of genes involved in immune cell activation, control of apoptosis (NF-κB appears to shield cells from apoptosis), B and T-cell development, anti-viral and antimicrobial responses, and multiple stress responses.

In non-stimulated conditions, NF-κB is retained in the cytoplasm with I-κB (Inhibitor κB). However, upon stimulation, I-κB is phosphorylated and degraded, causing NF-κB to shuttle to the nucleus, thereby activating transcription of target genes. Target genes activated by NF-κB include IL-2, IL-6, GM-CSF, ICAM-1 and class 1 MHC.

Due to its central role and ability to respond to a range of stimuli, reporter constructs utilizing the NF-κB promoter element are used to screen the supernatants produced in Example 11. Activators or inhibitors of NF-κB would be useful in treating diseases. For example, inhibitors of NF-κB could be used to treat those diseases related to the acute or chronic activation of NF-κB, such as rheumatoid arthritis.

To construct a vector containing the NF-κB promoter element, a PCR based strategy is employed. The upstream primer contains four tandem copies of the NF-κB binding site (GGGGACTTTCCC) (SEQ ID NO:8), 18 bp of sequence complementary to the 5' end of the SV40 early promoter sequence, and is flanked with an XhoI site:

```
                                                      (SEQ ID NO:9)
   5':
   GCGGCCTCGAGGGGACTTTCCCGGGGACTTTCCGGGGACTTTCCGGGAC

TTTCCATCCTGCCATCTCAATTAG:3'
```

The downstream primer is complementary to the 3' end of the SV40 promoter and is flanked with a Hind III site:

```
   5':GCGGCAAGCTTTTTGCAAAGCCTAGGC:3'        (SEQ ID NO:4)
```

PCR amplification is performed using the SV40 promoter template present in the pB-gal:promoter plasmid obtained from Clontech. The resulting PCR fragment is digested with XhoI and Hind III and subcloned into BLSK2-. (Stratagene) Sequencing with the T7 and T3 primers confirms the insert contains the following sequence:

```
                                                      (SEQ ID NO:10)
   5':
   CTCGAGGGGACTTTCCCGGGGACTTTCCGGGGACTTTCCGGGACTTTCC

ATCTGCCATCTCAATTAGTCAGCAACCATAGTCCCGCCCCTAACTCCGCCC

ATCCCGCCCCTAACTCCGCCCAGTTCCGCCCATTCTCCGCCCCATGGCTGA

CTAATTTTTTTTATTTATGCAGAGGCCGAGGCCGCCTCGGCCTCTGAGCTA

TTCCAGAAGTAGTGAGGAGGCTTTTTTGGAGGCCTAGGCTTTTGCAAAAA

GCTT:3'
```

Next, replace the SV40 minimal promoter element present in the pSEAP2-promoter plasmid (Clontech) with this NF-κB/SV40 fragment using XhoI and HindIII. However, this vector does not contain a neomycin resistance gene, and therefore, is not preferred for mammalian expression systems.

In order to generate stable mammalian cell lines, the NF-κB/SV40/SEAP cassette is removed from the above NF-κB/SEAP vector using restriction enzymes SalI and NotI, and inserted into a vector containing neomycin resistance. Particularly, the NF-κB/SV40/SEAP cassette was inserted into pGFP-1 (Clontech), replacing the GFP gene, after restricting pGFP-1 with SalI and NotI.

Once NF-κB/SV40/SEAP/Neo vector is created, stable Jurkat T-cells are created and maintained according to the protocol described in Example 13. Similarly, the method for assaying supernatants with these stable Jurkat T-cells is also described in Example 13. As a positive control, exogenous TNF alpha (0.1, 1, 10 ng) is added to wells H9, H10, and H11, with a 5–10 fold activation typically observed.

Example 17

Assay for SEAP Activity

As a reporter molecule for the assays described in Examples 13–16, SEAP activity is assayed using the Tropix Phospho-light Kit (Cat. BP-400) according to the following general procedure. The Tropix Phospho-light Kit supplies the Dilution, Assay, and Reaction Buffers used below.

Prime a dispenser with the 2.5× Dilution Buffer and dispense 15 µl of 2.5× dilution buffer into Optiplates containing 35 µl of a supernatant. Seal the plates with a plastic sealer and incubate at 65° C. for 30 min. Separate the Optiplates to avoid uneven heating.

Cool the samples to room temperature for 15 minutes. Empty the dispenser and prime with the Assay Buffer. Add 50 µl Assay Buffer and incubate at room temperature 5 min. Empty the dispenser and prime with the Reaction Buffer (see the table below). Add 50 µl Reaction Buffer and incubate at room temperature for 20 minutes. Since the intensity of the chemiluminescent signal is time dependent, and it tkes about 10 minutes to read 5 plates on luminometer, one should treat 5 plates at each time and start the second set 10 minutes later.

Read the relative light unit in the luminometer. Set H12 as blank, and print the results. An increase in chemiluminescence indicates reporter activity.

| Reaction Buffer Formulation: | | |
|---|---|---|
| # of plates | Rxn buffer diluent (ml) | CSPD (ml) |
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 18

High-Throughput Screening Assay Identifying Changes in Small Molecules Conentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measures changes in fluorescent molecules (Molecular Probes) that bind small molecules clearly, any fluorescent molecule detecting a small molecule can be used instead of calcium fluorescent molecule, fluo-4 (Molecular Probes, Inc.; catalog no. F-14202), used here.

For adherent cells, seed the cells at 10,000–20,000 cells/well in a Co-star black 96-well plate with clear bottom. The plate is incubated in a $CO_2$ incubator for 20 hours. The adherent cells are washed two times in Biotek washer with 200 ul of HBSS (Hank's Balanced Salt Solution) leaving 100 ul of buffer after the final wash.

A stock solution of 1 mg/ml fluo-4 is made in 10% pluronic acid DMSO. To load the cells with fluo-4, 50 ul of 12 ug/ml fluo-4 is added to each well. The plate is incubated at 37° C. in a $CO_2$ incubator for 60 min. The plate is washed four times in the Biotek washer with HBSS leaving 100 ul of buffer.

For non-adherent cells, the cells are spun down from culture media. Cells are re-suspended to $2-5 \times 10^6$ cells/ml with HBSS in a 50-ml conical tube. 4 ul of 1 mg/ml fluo-4 solution in 10% pluronic acid DMSO is added to each ml of cell suspension. The tube is then placed in a 37° C. water bath for 30–60 min. The cells are washed twice with HBSS, resuspended to $1 \times 10^6$ cells/ml, and dispensed into a microplate, 100 ul/well. The plate is centrifuged at 1000 rpm for 5 min. The plate is then washed once in Denley CellWash with 200 ul, followed by an aspiration step to 100 ul final volume.

For a non-cell based assay, each well contains a fluorescent molecule, such as fluo-4. The supernatant is added to the well, and a change in fluorescence is detected.

To measure the fluorescence of intracellular calcium, the FLIPR is set for the following parameters: (1) System gain is 300–800 mW; (2) Exposure time is 0.4 second; (3)

Camera F/stop is F/2; (4) Excitation is 488 nm; (5) Emission is 530 nm; and (6) Sample addition is 50 ul. Increased emission at 530 nm indicates an extracellular signaling event which has resulted in an increase in the intracellular Ca++ concentration.

Example 19

High-Throughput Screening Assay Identifying Tyrosine Kinase Activity

The Protein Tyrosine Kinases (PTK) represent a diverse group of transmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, lck, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, the identification of novel human secreted proteins capable of activating tyrosine kinase signal transduction pathways are of interest. Therefore, the following protocol is designed to identify those novel human secreted proteins capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or polylysine (50 mg/ml), all of which can be purchased from Sigma Chemicals (St. Louis, Mo.) or 10% Matrigel purchased from Becton Dickinson (Bedford, Mass.), or calf serum, rinsed with PBS and stored at 4° C. Cell growth on these plates is assayed by seeding 5,000 cells/well in growth medium and indirect quantitation of cell number through use of alamarBlue as described by the manufacturer Alamar Biosciences, Inc. (Sacramento, Calif.) after 48 hr. Falcon plate covers #3071 from Becton Dickinson (Bedford, Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200 ml/well) and cultured overnight in complete medium. Cells are quiesced by incubation in serum-free basal medium for 24 hr. After 5–20 minutes treatment with EGF (60 ng/ml) or 50 ul of the supernatant produced in Example 11, the medium was removed and 100 ml of extraction buffer ((20 mM HEPES pH 7.5, 0.15 M NaCl, 1% Triton X-100, 0.1% SDS, 2 mM Na3VO4, 2 mM Na4P2O7 and a cocktail of protease inhibitors (# 1836170) obtained from Boeheringer Mannheim (Indianapolis, Ind.) is added to each well and the plate is shaken on a rotating shaker for 5 minutes at 4° C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4° C. at 16,000×g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSK1 (corresponding to amino acids 6–20 of the cell division kinase cdc2-p34) and PSK2 (corresponding to amino acids 1–17 of gastrin). Both peptides are substrates for a range of tyrosine kinases and are available from Boehringer Mannheim.

The tyrosine kinase reaction is set up by adding the following components in order. First, add 10 ul of 5 uM Biotinylated Peptide, then 10 ul ATP/Mg$_{2+}$ (5 mM ATP/50 mM MgCl$_2$), then 10 ul of 5× Assay Buffer (40 mM imidazole hydrochloride, pH7.3, 40 mM beta-glycerophosphate, 1 mM EGTA, 100 mM MgCl$_2$, 5 mM MnCl$_2$, 0.5 mg/ml BSA), then 5 ul of Sodium Vanadate(1 mM), and then 5 ul of water. Mix the components gently and preincubate the reaction mix at 30° C. for 2 min. Initial the reaction by adding 10 ul of the control enzyme or the filtered supernatant.

The tyrosine kinase assay reaction is then terminated by adding 10 ul of 120 mm EDTA and place the reactions on ice.

Tyrosine kinase activity is determined by transferring 50 ul aliquot of reaction mixture to a microtiter plate (MTP) module and incubating at 37° C. for 20 min. This allows the streptavadin coated 96 well plate to associate with the biotinylated peptide. Wash the MTP module with 300 ul/well of PBS four times. Next add 75 ul of anti-phospotyrosine antibody conjugated to horse radish peroxidase (anti-P-Tyr-POD(0.5 u/ml)) to each well and incubate at 37° C. for one hour. Wash the well as above.

Next add 100 ul of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 20

High-Throughput Screening Assay Identifying Phosphorylation Activity

As a potential alternative and/or compliment to the assay of protein tyrosine kinase activity described in Example 19, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, JNK, p38 MAP, Map kinase kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSA/PBS for 1 hr at RT. The protein G plates are then treated with 2 commercial monoclonal antibodies (100 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3–5 rinses with PBS, the plates are stored at 4° C. until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 ul of the supernatants obtained in Example 11 for 5–20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (1 ug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFIA instrument (time-resolved fluorescence). An increased fluorescent signal over background indicates a phosphorylation.

Example 21

Method of Determining Alterations in a Gene Corresponding to a Polynucleotide

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:X. Suggested PCR conditions consist of 35 cycles at 95° C. for 30 seconds; 60–120 seconds at 52–58° C.; and 60–120 seconds at 70° C., using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products is cloned into T-tailed vectors as described in Holton, T. A. and Graham, M. W., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to Example 2 are nick-translated with digoxigenindeoxy-uridine 5'-triphosphate (Boehringer Manheim), and FISH performed as described in Johnson, Cg. et al., Methods Cell Biol. 35:73–99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 22

Method of Detecting Abnormal Levels of a Polypeptide in a Biological Sample

A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described in Example 10. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 23

Formulating a Polypeptide

The secreted polypeptide composition will be formulated and dosed in a fashion consistent with good medical practice, taking into account the clinical condition of the individual patient (especially the side effects of treatment with the secreted polypeptide alone), the site of delivery, the method of administration, the scheduling of administration, and other factors known to practitioners. The "effective amount" for purposes herein is thus determined by such considerations.

As a general proposition, the total pharmaceutically effective amount of secreted polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the secreted polypeptide is typically administered at a dose rate of about 1 µg/kg/hour to about 50 µg/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the secreted protein of the invention are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The secreted polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547–556 (1983)), poly (2-hydroxyethyl methacrylate) (R. Langer et al., J. Biomed. Mater. Res. 15:167–277 (1981), and R. Langer, Chem. Tech. 12:98–105 (1982)), ethylene vinyl acetate (R. Langer et al.) or poly-D-(−)-3-hydroxybutyric acid (EP 133,988). Sustained-release compositions also include liposomally entrapped polypeptides. Liposomes containing the secreted polypeptide are prepared by methods known per se: DE 3,218,121; Epstein et al., Proc. Natl. Acad. Sci. USA 82:3688–3692 (1985); Hwang et al., Proc. Natl. Acad. Sci. USA 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal secreted polypeptide therapy.

For parenteral administration, in one embodiment, the secreted polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The secreted polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any polypeptide to be used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

Polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous polypeptide solution, and the resulting mixture is lyophilized. The infusion solution is prepared by reconstituting the lyophilized polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Example 24

Method of Treating Decreased Levels of the Polypeptide

It will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a pharmaceutical composition comprising an amount of the polypeptide to increase the activity level of the polypeptide in such an individual.

For example, a patient with decreased levels of a polypeptide receives a daily dose 0.1–100 ug/kg of the polypeptide for six consecutive days. Preferably, the polypeptide is in the secreted form. The exact details of the dosing scheme, based on administration and formulation, are provided in Example 23.

Example 25

Method of Treating Increased Levels of the Polypeptide

Antisense technology is used to inhibit production of a polypeptide of the present invention. This technology is one example of a method of decreasing levels of a polypeptide, preferably a secreted form, due to a variety of etiologies, such as cancer.

For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 23.

Example 26

Method of Treatment Using Gene Therapy

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRi and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 1. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Example 27

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) sequences into an animal to increase or decrease the expression of the polypeptide. The polynucleotide of the present invention may be operatively linked to a promoter or any other genetic elements necessary for the expression of the polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata H. et al. (1997) Cardiovasc. Res. 35(3):470–479, Chao J et al. (1997) Pharmacol. Res. 35(6):517–522, Wolff J. A. (1997) Neuromuscul. Disord. 7(5):314–318, Schwartz B. et al. (1996) Gene Ther. 3(5):405–411, Tsurumi Y. et al. (1996) Circulation 94(12):3281–3290 (incorporated herein by reference).

The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the polynucleotides of the present invention may also be delivered in liposome formulations (such as those taught in Felgner P. L. et al. (1995) Ann. NY Acad. Sci. 772:126–139 and Abdallah B. et al. (1995) Biol. Cell 85(1):1–7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using naked DNA.

Example 28

Transgenic Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (NY) 11:1263–1270 (1993); Wright et al., Biotechnology (NY) 9:830–834 (1991); and Hoppe et al., U.S. Pat. No. 4,873,191 (1989)); retrovirus mediated gene transfer into germ lines (Van der Putten et al., Proc. Natl. Acad. Sci., USA 82:6148–6152 (1985)), blastocysts or embryos; gene targeting in embryonic stem cells (Thompson et al., Cell 56:313–321 (1989)); electroporation of cells or embryos (Lo, 1983, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989); etc. For a review of such techniques, see Gordon, "Transgenic Animals," Intl. Rev. Cytol. 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64–66 (1996); Wilmut et al., Nature 385:810-813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

Example 29

Knock-Out Animals

Endogenous gene expression can also be reduced by inactivating or "knocking out" the gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (eg., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

What is claimed is:

1. An isolated antibody or fragment thereof that specifically binds to a polypeptide selected from the group consisting of:
   (a) a polypeptide encoded by SEQ ID NO:38, wherein said polypeptide comprises the amino acid sequence of SEQ ID NO:114; and,
   (b) a polypeptide whose amino acid sequence consists of amino acid residues 1 to 74 of SEQ ID NO:193;

2. The antibody or fragment thereof of claim 1 that specifically binds polypeptide (a).

3. The antibody or fragment thereof of claim 1 which is a polyclonal antibody.

4. The antibody or fragment thereof of claim 1 which is a monoclonal antibody.

5. The antibody or fragment thereof of claim 1 which is selected from the group consisting of:
   (a) a chimeric antibody;
   (b) a humanized antibody;
   (c) a single chain antibody; and
   (d) a Fab fragment.

6. The antibody or fragment thereof of claim 1 which is labeled.

7. The antibody or fragment thereof of claim 1 wherein said polypeptide bound by said antibody or fragment thereof is glycosylated.

8. The antibody or fragment thereof of claim 1 wherein said antibody or fragment thereof specifically binds to said polypeptide in a Western blot.

9. The antibody or fragment thereof of claim 1 wherein said antibody or fragment thereof specifically binds to said polypeptide in an ELISA.

10. An isolated cell that produces the antibody or fragment thereof of claim 1.

11. A hybridoma that produces the antibody or fragment thereof of claim 1.

12. A method of detecting the polypeptide of claim 1 in a biological sample comprising:
    (a) contacting the biological sample with the antibody or fragment thereof of claim 1;
    (b) allowing a complex to form between said polypeptide and said antibody of claim 1; and,
    (c) detecting said complex.

13. The antibody or fragment thereof of claim 1 that specifically binds polypeptide (b).

14. The antibody or fragment thereof of claim 13 which is a polyclonal antibody.

15. The antibody or fragment thereof of claim 13 which is a monoclonal antibody.

16. The antibody or fragment thereof of claim 13 which is selected from the group consisting of:
    (a) a chimeric antibody;
    (b) a humanized antibody;
    (c) a single chain antibody; and
    (d) a Fab fragment.

17. The antibody or fragment thereof of claim 13 which is labeled.

18. The antibody or fragment thereof of claim 13 wherein said polypeptide bound by said antibody or fragment thereof is glycosylated.

19. The antibody or fragment thereof of claim 13 wherein said antibody or fragment thereof specifically binds to said polypeptide in a Western blot.

20. The antibody or fragment thereof of claim 13 wherein said antibody or fragment thereof specifically binds to said polypeptide in an ELISA.

21. An isolated cell that produces the antibody or fragment thereof of claim 13.

22. A hybridoma that produces the antibody or fragment thereof of claim 13.

* * * * *

UNITED STATES PATENT AND TRADEMARK OFFICE
CERTIFICATE OF CORRECTION

| | | |
|---|---|---|
| PATENT NO. | : 7,217,528 B2 | Page 1 of 1 |
| APPLICATION NO. | : 10/866831 | |
| DATED | : May 15, 2007 | |
| INVENTOR(S) | : Ruben et al. | |

It is certified that error appears in the above-identified patent and that said Letters Patent is hereby corrected as shown below:

On the Title Page: item (60)

Under "Related U.S. Application Data," in the second paragraph, line 3, delete "filed on June 16, 1998, provisional application No. 60/056,555" and insert -- filed on June 16, 1998, provisional application No. 60/056,629, filed on Aug. 19, 1997, provisional application No. 60/056,555 --.

Signed and Sealed this

Eleventh Day of September, 2007

JON W. DUDAS
*Director of the United States Patent and Trademark Office*